US011230591B2

(12) United States Patent
Fu et al.

(10) Patent No.: US 11,230,591 B2
(45) Date of Patent: Jan. 25, 2022

(54) CMV NEUTRALIZING ANTIGEN BINDING PROTEINS

(71) Applicants: Merck Sharp & Dohme Corp., Rahway, NJ (US); The Board of Regents, The University of Texas System, Austin, TX (US)

(72) Inventors: Tong-Ming Fu, Ambler, PA (US); Aimin Tang, Lansdale, PA (US); Dai Wang, Blue Bell, PA (US); Zhiqiang An, Pearland, TX (US); Ningyan Zhang, Pearland, TX (US); Sha Ha, Blue Bell, PA (US)

(73) Assignees: Merck Sharp & Dohme Corp., Rahway, NJ (US); The Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 16/094,624

(22) PCT Filed: Apr. 18, 2017

(86) PCT No.: PCT/US2017/028062
§ 371 (c)(1),
(2) Date: Oct. 18, 2018

(87) PCT Pub. No.: WO2017/184562
PCT Pub. Date: Oct. 26, 2017

(65) Prior Publication Data
US 2019/0106481 A1    Apr. 11, 2019

Related U.S. Application Data

(60) Provisional application No. 62/324,952, filed on Apr. 20, 2016.

(51) Int. Cl.
*C07K 16/08* (2006.01)
*A61P 31/22* (2006.01)
*C07K 16/06* (2006.01)
*C12N 15/62* (2006.01)

(52) U.S. Cl.
CPC .......... *C07K 16/088* (2013.01); *A61P 31/22* (2018.01); *C07K 16/065* (2013.01); *C12N 15/62* (2013.01); *C07K 2317/21* (2013.01); *C07K 2317/34* (2013.01); *C07K 2317/51* (2013.01); *C07K 2317/524* (2013.01); *C07K 2317/72* (2013.01); *C07K 2317/76* (2013.01); *C07K 2317/92* (2013.01); *C07K 2317/94* (2013.01)

(58) Field of Classification Search
CPC ............... C07K 16/088; C07K 16/065; C07K 2317/524; C07K 2317/76; C07K 2317/21; C07K 2317/92; C07K 2317/72; C07K 2317/94; C07K 2317/34; C07K 2317/51; A61P 31/22; C12N 15/62; Y02P 20/54
See application file for complete search history.

(56) References Cited

U.S. PATENT DOCUMENTS 6,331,415 B1    12/2001    Cabily et al.
2017/0081391 A1   3/2017    Lanzavecchia et al.

FOREIGN PATENT DOCUMENTS

| EP | 1382615 A1 | 1/2004 |
| WO | 2008084410 A3 | 7/2008 |
| WO | 2009114560 A2 | 9/2009 |
| WO | 2010007533 A9 | 1/2010 |
| WO | 2014200898 A2 | 12/2014 |
| WO | 2015170287 A1 | 11/2015 |
| WO | 2017044895 A2 | 3/2017 |

OTHER PUBLICATIONS

Genini E, Percivalle E, Sarasini A, Revello MG, Baldanti F, Gerna G. Serum antibody response to the gH/gL/pUL128-131 five-protein complex of human cytomegalovirus (HCMV) in primary and reactivated HCMV infections. J Clin Virol. Oct. 2011;52(2): 113-8. Epub Aug. 4, 2011. (Year: 2011).*
Lilleri D, Kabanova A, Lanzavecchia A, Gerna G. Antibodies against neutralization epitopes of human cytomegalovirus gH/gL/pUL128-130-131 complex and virus spreading may correlate with virus control in vivo. J Clin Immunol. Dec. 2012;32(6): 1324-31. Epub Jul. 27, 2012. (Year: 2012).*
Bowie JU, Reidhaar-Olson JF, Lim WA, Sauer RT. Deciphering the message in protein sequences: tolerance to amino acid substitutions. Science. Mar. 16, 1990;247(4948):1306-10 (Year: 1990).*
Winkler K, Kramer A, Küttner G, Seifert M, Scholz C, Wessner H, Schneider-Mergener J, Höhne W. Changing the antigen binding specificity by single point mutations of an anti-p24 (HIV-1) antibody. J Immunol. Oct. 15, 2000;165(8):4505-14. (Year: 2000).*

(Continued)

*Primary Examiner* — Rachel B Gill
(74) *Attorney, Agent, or Firm* — Nichole M. Valeyko; Alysia A. Finnegan

(57) ABSTRACT

The present invention is directed to antigen binding proteins including, but not limited to, monoclonal antibodies and antigen binding fragments thereof, that specifically bind to and preferably neutralize human cytomegalovirus (CMV). The antigen binding proteins of the invention are useful as a prophylactic and/or therapeutic agent for preventing and/or treating CMV infections in a patient in need thereof. Also encompassed by the invention are pharmaceutical compositions comprising the antigen binding proteins of the invention and a pharmaceutically acceptable carrier. The invention further relates to methods of using the antigen binding proteins and pharmaceutical compositions of the invention for the prevention or treatment of CMV infection in patients in need thereof.

17 Claims, 11 Drawing Sheets

Specification includes a Sequence Listing.

(56) References Cited

OTHER PUBLICATIONS

Kussie PH, Parhami-Seren B, Wysocki LJ, Margolies MN. A single engineered amino acid substitution changes antibody fine specificity. J Immunol. Jan. 1, 1994;152(1): 146-52. (Year: 1994).*
Chen Z, Wang J, Bao L, Guo L, Zhang W, Xue Y, Zhou H, Xiao Y, Wang J, Wu F, Deng Y, Qin C, Jin Q. Human monoclonal antibodies targeting the haemagglutinin glycoprotein can neutralize H7N9 influenza virus. Nat Commun. Mar. 30, 2015;6:6714. (Year: 2015).*
Sela-Culang I, Kunik V, Ofran Y. The structural basis of antibody-antigen recognition. Front Immunol. Oct. 8, 2013;4:302. (Year: 2013).*
Sirin S, Apgar JR, Bennett EM, Keating AE. AB-Bind: Antibody binding mutational database for computational affinity predictions. Protein Sci. Feb. 2016;25(2):393-409. Epub Nov. 6, 2015. (Year: 2016).*
Tsuchiya Y, Mizuguchi K. The diversity of H3 loops determines the antigen-binding tendencies of antibody CDR loops. Protein Sci. Apr. 2016;25(4):815-25. Epub Jan. 20, 2016. (Year: 2016).*
Collis AV, Brouwer AP, Martin AC. Analysis of the antigen combining site: correlations between length and sequence composition of the hypervariable loops and the nature of the antigen. J Mol Biol. Jan. 10, 2003;325(2):337-54. (Year: 2003).*
Adler, et al., Human CMV vaccine trials: What if CMV caused a rash?, Journal of Clinical Virology, 2008, 231-236, 41.
Amanna, Ian J. et al., Quantitation of rare memory B cell populations by two independent and complementary approaches, Journal of Immunological Methods, 2006, 175-185, 317.
Arvin, et al., Vaccine Development to Prevent Cytomegalovirus Disease: Report from the National Vaccine Advisory Committee, Clinical Infectious Diseases, 2004, 233-239, 39.
Burke, Heidi G., Crystal Structure of the Human Cytomegalovirus Glycoprotein B, Plos Pathogens, 2015, 1-21, 11:e1005227.
Ciferri, Claudio et al., Antigenic Characterization of the HCMV gH/gL/gO and Pentamer Cell Entry Complexes Reveals Binding Sites for Potently Neutralizing Human Antibodies, PLOS Pathogens, 2015, 1-20, 11:e1005230.
Cui, et al., Cytomegalovirus vaccines fail to induce epithelial entry neutralizing antibodies comparable to natural infection, Vaccine, 2008, 5760-5766, 26.
Dall'Acqua, William F. et al., Properties of Human IgG1s Engineered for Enhanced Binding to the Neonatal Fc Receptor (FcRn), Journal of Biological Chemistry, 2006, 23514-23524, 281(33).
Dargan, et al., Sequential mutations associated with adaptation of human cytomegalovirus to growth in cell culture, Journal of General Virology, 2010, 1535-1546, 91.
Elek, et al., Development of a vaccine against mental retardation caused by cytomegalovirus infection in utero, Lancet, 1974, 1-5, 1.
Ettinger, Rachel et al., IL-21 Induces Differentiation of Human Naive and Memory B Cells into Antibody-Secreting Plasma Cells1, The Journal of Immunology, 2005, 7867-7879, 176.
Freed, et al., Pentameric complex of viral glycoprotein H is the primary target for potent neutralization by a human cytomegalovirus vaccine, Proc. Natl. Acad. Sci. USA, 2013, E4997-E5005, 1.
Gerna, et al., Dendritic-cell infection by human cytomegalovirus is restricted to strains carrying functional UL131-128 genes and mediates efficient viral antigen presentation to CD8+ T cells, Journal of General Virology, 2005, 275-284, 86.
Gerna, et al., Human cytomegalovirus serum neutralizing antibodies block virus infection of endothelial/epithelial cells, but not fibroblasts, early during primary infection, Journal of General Virology, 2008, 853-865, 89.
Gerna, et al., Rescue of human cytomegalovirus strain AD 169 tropism for both leukocytes and human endothelial cells, Journal of General Virology, 2003, 1431-1436, 84.
Gerna, et al., The attenuated Towne strain of human cytomegalovirus may revert to both endothelial cell tropism and leuko- (neutrophiland monocyte-) tropism in vitro, Journal of General Virology, 2002, 1993-2000, 83.
Ha, Sha et al., Neutralizationof Diverse Human Cytomegalovirus Strains Conferred by Antibodies TargetingViral gH/gL/pUL128-131 Pentameric Complex, Journal of Virology, 2017, 1-15, 99(7).
Hahn, et al., Human Cytomegalovirus UL131-128 Genes Are Indispensable for Virus Growth in Endothelial Cells and Virus Transfer to Leukocytes, Journal of Virology, 2004, 10023-10033, 78(18).
Huang, Jinghe et al., Isolation of human monoclonal antibodies from peripheral blood B cells, Nature Protocols, 2013, 1907-1915, 8(10).
Loughney, John W. et al., Soluble Human Cytomegalovirus gH/gL/pUL128 -131 Pentameric Complex, but Not gH/gL, Inhibits Viral Entry to Epithelial Cells and Presents Dominant Native Neutralizing Epitopes*, The Journal of Biological Chemistry, 2015, 15985-15995, 290(26).
Macagno, A. et al., Isolation of Human Monoclonal Antibodies That Potently Neutralize Human Cytomegalovirus Infection by Targeting Different Epitopes on the gH/gL/UL128-131A Complex, Journal of Virology, 2010, 1005-1013, 84 (2).
Meyer, H. et al., Glycoprotein gpII6 of human cytomegalovirus contains epitopes for strain-common and strain-specific antibodies, Journal of General Virology, 1992, 2375-2383, 73.
Mocarski, et al., Cytomegaloviruses, Fields Virology, 2007, 2701-2772, Editors: Knipe, David M.; Howley, Peter M.
Plachter, et al., Cell Types Involved In Replicaton and Distribution of Human Cytomegalovirus, Advances in Virus Research, 1996, 195-261, 46.
Plotkin et al., Candidate Cytomegalovirus Strain for Human Vaccination, Infection and Immunity, 1975, 521-527, 12(3).
Revello, et al., Molecular Epidemiology of Primary Human Cytomegalovirus Infection in Pregnant Women and Their Families, Journal of Medical Virology, 2008, 1415-1425, 80.
Ryckman, et al., Characterization of the Human Cytomegalovirus gH/gL/UL128-131 Complex That Mediates Entry into Epithelial and Endothelial Cells, Journal of Virology, 2008, 60-70, 82(1).
Scheid, Johannes F. et al., Broad diversity of neutralizing antibodies isolated from memory B cells in HIV-infected individuals, Nature, 2009, 636-640, 458.
Spaete, R. R., A Recombinant Subunit Vaccine Approach to HCMV Vaccine Development, Transplantation Proceedings, 1991, 90-96, vol. 23, No. 3, Suppl 3.
Spaete, Richard R. et al., Sequence Requirements for Proteolytic Processing of Glycoprotein B of Human Cytomegalovirus Strain Towne, Journal of Virology, 1990, 2922-2931, 64(6).
Stern-Ginossar, Naom et al., Decoding Human Cytomegalovirus, Science, 2012, 1088-1092, 338.
Tang, et al., A novel high-throughput neutralization assay for supporting clinical evaluations of human cytomegalovirus vaccines, Vaccine, 2011, 8350-8356, 29.
Urban, M. et al., The Dominant Linear Neutralizing Antibody-Binding Site ofGlycoprotein gp86 of Human Cytomegalovirus is Strain Specific, Journal of Virology, 1992, 1303-1311, 66(3).
Vanarsdall, Adam L et al., Human cytomegalovirus entry into cells, Current Opinion in Virology, 2012, 37-42, 2.
Varnum et al., Identification of Proteins in Human Cytomegalovirus (HCMV) Particles: the HCMV Proteome, Journal of Virology, 2004, 10960-10966, 78.
Wang, Dai et al., Quantitative analysis of neutralizing antibody response to human cytomegalovirus in natural infection, Vaccine, 2011, 9075-9080, 29.
Wang, et al., Human Cytomegalovirus UL131 Open Reading Frame is Required for Epithelial Cell Tropism, Journal of Virology, 2005, 10330-10338, 79(16).
Wang, et al., Human cytomegalovirus virion protein complex required for epithelial and endothelial cell tropism, Proc. Natl. Acad. Sci. USA, 2005, 18153-18158, 102(50).
Wille, Paul et al., Human Cytomegalovirus (HCMV) Glycoprotein gB Promotes Virus Entry in Trans Acting as the Viral Fusion Protein Rather than as a Receptor-Binding Protein, MBIO, 2013, 1-9, 4(3).
Wille, Paul T. et al., A Human Cytomegalovirus gO-Null Mutant Fails to Incorporate gH/gL into the Virion Envelope and is Unable to Enter Fibroblasts and Epithelial and Endothelial CellsV, Journal of Virology, 2010, 2585-2596, 84(5).

(56) References Cited

OTHER PUBLICATIONS

Zhou, Momei et al., Human Cytomegalovirus gH/gL/gO Promotes the Fusion Step of Entry into All Cell Types, whereas gH/gL/UL128-131 Broadens Virus Tropism through a Distinct Mechanism, Journal of Virology, 2015, 8999-9009, 89(17).

* cited by examiner

| Memory B-cell isolation | | |
|---|---|---|
| 1. | Donor identification | Three donors were identified with CMV neutralizing titers greater than 1:5000 |
| 2. | PBMC for memory B-cell enrichment | |
| Short-term B-cell culture and screening | | |
| 3. | B-cell culture in 96-well plates | After 14-day in culture, the supernatant was harvested and stored at −70 °C. The cells in plates were preserved in 100 mL/well RNAlater® solution (Ambion) and stored at −70 °C. |
| 4. | Screening for CMV-specific antibodies | Culture supernatant (~100 mL) was split for screening in assays for viral neutralization and binding to virions |
| Isolation of IgG gene and confirmation of antibody activity | | |
| 5. | RNA extraction and cDNA conversion | Total RNA purified from lysed B-cell cultures and converted to cDNA by reverse transcription with oligo-dT primer. |
| 6. | PCR amplification of IgG genes | Variable region genes were amplified in one round of PCR reaction with VH, VK, Vλ family-leader region specific primers. PCR products with the expected sizes were extracted, ligated into pCR2.1 TA-clone vectors, and plated for the selection. Five colonies per clone were independently picked from multiple colony pools, and sequence from each colony was confirmed from both directions. |
| 7. | IgG heavy and light chain pairing | Bioinformatic analysis of IgG genes and 1H1L antibody pairing; cloning of all plausible combination to expression vectors. |
| 8. | Recombinant expression for functional verification | Transient transfection for production of antibody candidates; purified antibodies were tested in viral neutralization assay and virion-binding ELISA for verification of their functions. |

FIG.2

| Ab ID | EC50 neutralizing ng/mL (Epithelial) | EC50 neutralizing ng/mL (Fibroblast) | Antigen specifity | IgG type |
|---|---|---|---|---|
| 2-25 | 0.08 (0.06-0.11) | - 0 - | Pentamer, IR1 | IgG1λ |
| 1-85 | 0.13 (0.09-0.17) | - 0 - | Pentamer, IR1 | IgG1λ |
| 2-18 | 0.18 | - 0 - | Pentamer, IR1 | IgG1κ |
| 1-125 | 0.19 (0.11-0.27) | - 0 - | Pentamer, IR1 | IgG1λ |
| 1-15 | 0.23 (0.17-0.34) | - 0 - | Pentamer, IR1 | IgG1λ |
| 1-103 | 0.88 | - 0 - | Pentamer, IR1 | IgG1κ |
|  |  |  |  |  |
| 3-16 | 17 | 37-81 | Pentamer, IR3 | IgG1κ |
| 3-7 | 9.5 | 20-100 | Pentamer, IR3 | IgG1κ |
| 3-25 | 37-100 | 100-120 | gB | IgG1κ |
| 2-59 | 22-76 | 34-370 | gB | IgG1λ |
| 2-48 | 1.2 | 200-2300 | gB | IgG1κ |
| CytoGam | 380-630 | 1200-7100 | many | n/a |

FIG.5

CMV NEUTRALIZING ANTIGEN BINDING PROTEINS

FIELD OF INVENTION

The present invention relates to anti-CMV antigen binding proteins including, but not limited to, monoclonal antibodies. The invention also relates to use of the antigen binding proteins of the present invention in the diagnosis, prevention and/or treatment of CMV infection. Compositions comprising the antigen binding proteins of the invention are also encompassed by the present invention.

REFERENCE TO SEQUENCE LISTING SUBMITTED ELECTRONICALLY

The sequence listing of the present application is submitted electronically via EFS-Web as an ASCII formatted sequence listing with a file name 24320USPCT-SEQTXT-18DEC2019, creation date of Dec. 18, 2019, and a size of 114 kB. This sequence listing submitted via EFS-Web is part of the specification and is herein incorporated by reference in its entirety.

BACKGROUND OF THE INVENTION

Cytomegalovirus (CMV) is a herpes virus classified as being a member of the beta subfamily of herpesviridae. The species infecting humans is also known as human CMV or herpesvirus 5 (HHV-5). According to the Centers for Disease Control and Prevention, CMV infection is found fairly ubiquitously in the human population, with an estimated 40-80% of the United States adult population having been infected. The virus is spread primarily through bodily fluids and is frequently passed from pregnant mothers to the fetus or newborn. In most individuals, CMV infection is latent, although virus activation can result in high fever, chills, fatigue, headaches, nausea, and splenomegaly.

Although most human CMV infections are asymptomatic, CMV infections in immunocompromised individuals, (such as HIV-positive patients, allogeneic transplant patients and cancer patients) or persons whose immune system has yet fully developed (such as newborns) can be particularly problematic See Mocarski et al., Cytomegalovirus, in Field Virology, 2701-2772, Editor: Knipes and Howley, 2007. CMV infection in such individuals can cause severe morbidity, including pneumonia, hepatitis, encephalitis, colitis, uveitis, retinitis, blindness, and neuropathy, among other deleterious conditions. In addition, CMV infection during pregnancy is a leading cause of birth defects. See Adler, 2008, J. Clin Virol, 41:231; Arvin et al., 2004, Clin Infect Dis 39:233; and Revello et al., 2008, J Med Virol 80:1415.

CMV antibodies have been described in, for example, International Patent Application Publication Nos. WO 2008/084410 and WO 2010/007533.

There is a need for a vaccine or therapy to prevent or treat CMV infection.

SUMMARY OF THE INVENTION

The present invention relates to anti-CMV antigen binding proteins comprising the structural and functional features specified below, including having one or more desirable properties, including specific binding to and, preferably, neutralization of CMV. The invention also relates to use of the antigen binding proteins of the present invention in the treatment and/or prevention of CMV infection.

In particular embodiments, the antigen binding proteins as disclosed herein specifically bind to and, preferably, neutralize CMV. In more particular embodiments, the antigen binding proteins as disclosed herein block/decrease CMV virions from binding to a cell, fusing with the cellular membrane and/or releasing viral genetic material into the cell.

In one embodiment, the invention provides an antibody or antigen binding fragment thereof that binds to human CMV, wherein the antibody or antigen binding fragment is selected from the group consisting of:

A. an antibody or antigen binding fragment that binds to the pentameric gH complex site 1 comprising:
 a. a heavy chain variable domain complementary determining region (CDR) 1 comprising the amino acid sequence of SEQ ID NO: 1 or SEQ ID NO: 7, a heavy chain variable domain CDR2 comprising the amino acid sequence of SEQ ID NO: 2 or SEQ ID NO: 8, and a heavy chain variable domain CDR3 comprising the amino acid sequence of SEQ ID NO: 3 or SEQ ID NO: 9, optionally with the proviso that the heavy chain variable domain does not comprise the amino acid sequence of SEQ ID NO: 77 or SEQ ID NO: 78; and
 b. a light chain variable domain CDR1 comprising the amino acid sequence of SEQ ID NO: 4 or SEQ ID NO: 10, a light chain variable domain CDR2 comprising the amino acid sequence of SEQ ID NO: 5 or SEQ ID NO: 11, and a light chain variable domain CDR3 comprising the amino acid sequence of SEQ ID NO: 6 or SEQ ID NO: 12, optionally with the proviso that the light chain variable domain does not comprise the amino acid sequence of SEQ ID NO: 102 or SEQ ID NO: 103;

B. an antibody or antigen binding fragment that binds to the pentameric gH complex site 2 comprising:
 a. a heavy chain variable domain CDR1 comprising the amino acid sequence of SEQ ID NO: 13, SEQ ID NO: 19, SEQ ID NO: 24, or SEQ ID NO: 28, a heavy chain variable domain CDR2 comprising the amino acid sequence of SEQ ID NO: 14, SEQ ID NO: 20, SEQ ID NO: 25, SEQ ID NO: 29, or SEQ ID NO: 32, and a heavy chain variable domain CDR3 comprising the amino acid sequence of SEQ ID NO: 15, SEQ ID NO: 26, SEQ ID NO: 30, or SEQ ID NO: 33, optionally with the proviso that the heavy chain variable domain does not comprise the amino acid sequence of any of SEQ ID NOS: 79 to 84; and
 b. a light chain variable domain CDR1 comprising the amino acid sequence of SEQ ID NO: 16, or SEQ ID NO: 21, a light chain variable domain CDR2 comprising the amino acid sequence of SEQ ID NO: 17, or SEQ ID NO: 22, and a light chain variable domain CDR3 comprising the amino acid sequence of SEQ ID NO: 18, SEQ ID NO: 23, SEQ ID NO: 27, SEQ ID NO: 31 or SEQ ID NO: 34, optionally with the proviso that the light chain variable domain does not comprise the amino acid sequence of any of SEQ ID NOS: 104 to 108;

C. an antibody or antigen binding fragment that binds to the pentameric gH complex site 3 comprising:
 a. a heavy chain variable domain CDR1 comprising the amino acid sequence of SEQ ID NO: 35, a heavy chain variable domain CDR2 comprising the amino acid sequence of SEQ ID NO: 36, and a heavy chain variable domain CDR3 comprising the amino acid sequence of SEQ ID NO: 37, optionally with the proviso that the heavy chain variable domain does not comprise the amino acid sequence of SEQ ID NO: 85; and
b. a light chain variable domain CDR1 comprising the amino acid sequence of SEQ ID NO: 38, a light chain variable domain CDR2 comprising the amino acid sequence of SEQ ID NO: 39, and a light chain variable domain CDR3 comprising the amino acid sequence of SEQ ID NO: 40, optionally with the proviso that the light chain variable domain does not comprise the amino acid sequence of SEQ ID NO: 109;

D. an antibody or antigen binding fragment that binds to the pentameric gH complex site 5 comprising:
a. a heavy chain variable domain CDR1 comprising the amino acid sequence of SEQ ID NO: 41, a heavy chain variable domain CDR2 comprising the amino acid sequence of SEQ ID NO: 42, and a heavy chain variable domain CDR3 comprising the amino acid sequence of SEQ ID NO: 43, optionally with the proviso that the heavy chain variable domain does not comprise the amino acid sequence of SEQ ID NO: 86; and b. a light chain variable domain CDR1 comprising the amino acid sequence of SEQ ID NO: 44, a light chain variable domain CDR2 comprising the amino acid sequence of SEQ ID NO: 5, and a light chain variable domain CDR3 comprising the amino acid sequence of SEQ ID NO: 45, optionally with the proviso that the light chain variable domain does not comprise the amino acid sequence of SEQ ID NO: 110;

E. an antibody or antigen binding protein that binds to the pentameric gH complex site 7 comprising:
a. a heavy chain variable domain CDR1 comprising the amino acid sequence of SEQ ID NO: 46 or SEQ ID NO: 52, a heavy chain variable domain CDR2 comprising the amino acid sequence of SEQ ID NO: 47 or SEQ ID NO: 53, and a heavy chain variable domain CDR3 comprising the amino acid sequence of SEQ ID NO: 48 or SEQ ID NO: 54, optionally with the proviso that the heavy chain variable domain does not comprise the amino acid sequence of SEQ ID NO: 87 or SEQ ID NO: 88; and
b. a light chain variable domain CDR1 comprising the amino acid sequence of SEQ ID NO: 49 or SEQ ID NO: 55, a light chain variable domain CDR2 comprising the amino acid sequence of SEQ ID NO: 50 or SEQ ID NO: 56, and a light chain variable domain CDR3 comprising the amino acid sequence of SEQ ID NO: 51 or SEQ ID NO: 57, optionally with the proviso that the light chain variable domain does not comprise the amino acid sequence of SEQ ID NO: 111 or SEQ ID NO: 112;

F. an antibody or antigen binding fragment that binds gB comprising:
a. a heavy chain variable domain CDR1 comprising the amino acid sequence of SEQ ID NO: 58, a heavy chain variable domain CDR2 comprising the amino acid sequence of SEQ ID NO: 59, and a heavy chain variable domain CDR3 comprising the amino acid sequence of SEQ ID NO: 60, optionally with the proviso that the heavy chain variable domain does not comprise the amino acid sequence of SEQ ID NO: 89; and
b. a light chain variable domain CDR1 comprising the amino acid sequence of SEQ ID NO: 61, a light chain variable domain CDR2 comprising the amino acid sequence of SEQ ID NO: 62, and a light chain variable domain CDR3 comprising the amino acid sequence of SEQ ID NO: 63, optionally with the proviso that the light chain variable domain does not comprise the amino acid sequence of SEQ ID NO: 113.

In another embodiment, the invention provides an antibody or antigen binding fragment that binds to human CMV, wherein the antibody or antigen binding fragment is selected from the group consisting of:

A. an antibody or antigen binding fragment that binds to the pentameric gH complex site 1 comprising:
a. a heavy chain variable domain CDR1 comprising the amino acid sequence of SEQ ID NO: 1, a heavy chain variable domain CDR2 comprising the amino acid sequence of SEQ ID NO: 2, a heavy chain variable domain CDR3 comprising the amino acid sequence of SEQ ID NO: 3, a light chain variable domain CDR1 comprising the amino acid sequence of SEQ ID NO: 4, a light chain variable domain CDR2 comprising the amino acid sequence of SEQ ID NO: 5, and a light chain variable domain CDR3 comprising the amino acid sequence of SEQ ID NO: 6, optionally with the proviso that the heavy chain variable domain does not comprise the amino acid sequence of SEQ ID NO: 77 or the light chain variable domain does not comprise the amino acid sequence of SEQ ID NO: 102; and
b. a heavy chain variable domain CDR1 comprising the amino acid sequence of SEQ ID NO: 7, a heavy chain variable domain CDR2 comprising the amino acid sequence of SEQ ID NO: 8, a heavy chain variable domain CDR3 comprising the amino acid sequence of SEQ ID NO: 9, a light chain variable domain CDR1 comprising the amino acid sequence of SEQ ID NO: 10, a light chain variable domain CDR2 comprising the amino acid sequence of SEQ ID NO: 11, and a light chain variable domain CDR3 comprising the amino acid sequence of SEQ ID NO: 12, optionally with the proviso that the heavy chain variable domain does not comprise the amino acid sequence of SEQ ID NO: 78 or the light chain variable domain does not comprise the amino acid sequence of SEQ ID NO: 103;

B. an antibody or antigen binding fragment that binds to the pentameric gH complex site 2 comprising:
a. a heavy chain variable domain CDR1 comprising the amino acid sequence of SEQ ID NO: 13, a heavy chain variable domain CDR2 comprising the amino acid sequence of SEQ ID NO: 14, a heavy chain variable domain CDR3 comprising the amino acid sequence of SEQ ID NO: 15, a light chain variable domain CDR1 comprising the amino acid sequence of SEQ ID NO: 16, a light chain variable domain CDR2 comprising the amino acid sequence of SEQ ID NO: 17, and a light chain variable domain CDR3 comprising the amino acid sequence of SEQ ID NO: 18, optionally with the proviso that the heavy chain variable domain does not comprise the amino acid sequence of SEQ ID NO: 79 or the light chain variable domain does not comprise the amino acid sequence of SEQ ID NO: 104;
b. a heavy chain variable domain CDR1 comprising the amino acid sequence of SEQ ID NO: 19, a heavy chain variable domain CDR2 comprising the amino acid sequence of SEQ ID NO: 14, a heavy chain variable domain CDR3 comprising the amino acid sequence of SEQ ID NO: 15, a light chain variable domain CDR1 comprising the amino acid sequence of SEQ ID NO: 16, a light chain variable domain CDR2 comprising the amino acid sequence of SEQ ID NO: 17, and a light chain variable domain CDR3 comprising the amino acid sequence of SEQ ID NO: 18, optionally with the proviso that the heavy chain variable domain does not comprise the amino acid sequence of SEQ ID NO: 80 or the light chain variable domain does not comprise the amino acid sequence of SEQ ID NO: 104;

c. a heavy chain variable domain CDR1 comprising the amino acid sequence of SEQ ID NO: 19, a heavy chain variable domain CDR2 comprising the amino acid sequence of SEQ ID NO: 20, a heavy chain variable domain CDR3 comprising the amino acid sequence of SEQ ID NO: 15, a light chain variable domain CDR1 comprising the amino acid sequence of SEQ ID NO: 21, a light chain variable domain CDR2 comprising the amino acid sequence of SEQ ID NO: 22, and a light chain variable domain CDR3 comprising the amino acid sequence of SEQ ID NO: 23, optionally with the proviso that the heavy chain variable domain does not comprise the amino acid sequence of SEQ ID NO: 81 or the light chain variable domain does not comprise the amino acid sequence of SEQ ID NO: 105;

d. a heavy chain variable domain CDR1 comprising the amino acid sequence of SEQ ID NO: 24, a heavy chain variable domain CDR2 comprising the amino acid sequence of SEQ ID NO: 25, a heavy chain variable domain CDR3 comprising the amino acid sequence of SEQ ID NO: 26, a light chain variable domain CDR1 comprising the amino acid sequence of SEQ ID NO: 16, a light chain variable domain CDR2 comprising the amino acid sequence of SEQ ID NO: 17, and a light chain variable domain CDR3 comprising the amino acid sequence of SEQ ID NO: 27, optionally with the proviso that the heavy chain variable domain does not comprise the amino acid sequence of SEQ ID NO: 82 or the light chain variable domain does not comprise the amino acid sequence of SEQ ID NO: 106;

e. a heavy chain variable domain CDR1 comprising the amino acid sequence of SEQ ID NO: 28, a heavy chain variable domain CDR2 comprising the amino acid sequence of SEQ ID NO: 29, a heavy chain variable domain CDR3 comprising the amino acid sequence of SEQ ID NO: 30, a light chain variable domain CDR1 comprising the amino acid sequence of SEQ ID NO: 16, a light chain variable domain CDR2 comprising the amino acid sequence of SEQ ID NO: 22, and a light chain variable domain CDR3 comprising the amino acid sequence of SEQ ID NO: 31, optionally with the proviso that the heavy chain variable domain does not comprise the amino acid sequence of SEQ ID NO: 83 or the light chain variable domain does not comprise the amino acid sequence of SEQ ID NO: 107;

f. a heavy chain variable domain CDR1 comprising the amino acid sequence of SEQ ID NO: 19, a heavy chain variable domain CDR2 comprising the amino acid sequence of SEQ ID NO: 32, a heavy chain variable domain CDR3 comprising the amino acid sequence of SEQ ID NO: 33, a light chain variable domain CDR1 comprising the amino acid sequence of SEQ ID NO: 21, a light chain variable domain CDR2 comprising the amino acid sequence of SEQ ID NO: 22, and a light chain variable domain CDR3 comprising the amino acid sequence of SEQ ID NO: 34, optionally with the proviso that the heavy chain variable domain does not comprise the amino acid sequence of SEQ ID NO: 84 or the light chain variable domain does not comprise the amino acid sequence of SEQ ID NO: 108;

C. an antibody or antigen binding fragment that binds to the pentameric gH complex site 3 comprising:
  a. a heavy chain variable domain CDR1 comprising the amino acid sequence of SEQ ID NO: 35, a heavy chain variable domain CDR2 comprising the amino acid sequence of SEQ ID NO: 36, and a heavy chain variable domain CDR3 comprising the amino acid sequence of SEQ ID NO: 37, a light chain variable domain CDR1 comprising the amino acid sequence of SEQ ID NO: 38, a light chain variable domain CDR2 comprising the amino acid sequence of SEQ ID NO: 39, and a light chain variable domain CDR3 comprising the amino acid sequence of SEQ ID NO: 40, optionally with the proviso that the heavy chain variable domain does not comprise the amino acid sequence of SEQ ID NO: 85 or the light chain variable domain does not comprise the amino acid sequence of SEQ ID NO: 109;

D. an antibody or antigen binding fragment that binds to the pentameric gH complex site 5 comprising:
  a. a heavy chain variable domain CDR1 comprising the amino acid sequence of SEQ ID NO: 41, a heavy chain variable domain CDR2 comprising the amino acid sequence of SEQ ID NO: 42, and a heavy chain variable domain CDR3 comprising the amino acid sequence of SEQ ID NO: 43, a light chain variable domain CDR1 comprising the amino acid sequence of SEQ ID NO: 44, a light chain variable domain CDR2 comprising the amino acid sequence of SEQ ID NO: 5, and a light chain variable domain CDR3 comprising the amino acid sequence of SEQ ID NO: 45, optionally with the proviso that the heavy chain variable domain does not comprise the amino acid sequence of SEQ ID NO: 86 or the light chain variable domain does not comprise the amino acid sequence of SEQ ID NO: 110;

E. an antibody or antigen binding protein that binds to the pentameric gH complex site 7 comprising:
  a. a heavy chain variable domain CDR1 comprising the amino acid sequence of SEQ ID NO: 46, a heavy chain variable domain CDR2 comprising the amino acid sequence of SEQ ID NO: 47, a heavy chain variable domain CDR3 comprising the amino acid sequence of SEQ ID NO: 48, a light chain variable domain CDR1 comprising the amino acid sequence of SEQ ID NO: 49, a light chain variable domain CDR2 comprising the amino acid sequence of SEQ ID NO: 50, and a light chain variable domain CDR3 comprising the amino acid sequence of SEQ ID NO: 51, optionally with the proviso that the heavy chain variable domain does not comprise the amino acid sequence of SEQ ID NO: 87 or the light chain variable domain does not comprise the amino acid sequence of SEQ ID NO: 111;
  b. a heavy chain variable domain CDR1 comprising the amino acid sequence of SEQ ID NO: 52, a heavy chain variable domain CDR2 comprising the amino acid sequence of SEQ ID NO: 53, and a heavy chain variable domain CDR3 comprising the amino acid sequence of SEQ ID NO: 54, a light chain variable domain CDR1 comprising the amino acid sequence of SEQ ID NO: 55, a light chain variable domain CDR2 comprising the amino acid sequence of SEQ ID NO: 56, and a light chain variable domain CDR3 comprising the amino acid sequence of SEQ ID NO: 57, optionally with the proviso that the heavy chain variable domain does not comprise the amino acid sequence of SEQ ID NO: 88 or the light chain variable domain does not comprise the amino acid sequence of SEQ ID NO: 112;

F. an antibody or antigen binding fragment that binds gB comprising:
  a. a heavy chain variable domain CDR1 comprising the amino acid sequence of SEQ ID NO: 58, a heavy chain variable domain CDR2 comprising the amino acid sequence of SEQ ID NO: 59, and a heavy chain variable domain CDR3 comprising the amino acid sequence of SEQ ID NO: 60, a light chain variable domain CDR1 comprising the amino acid sequence of SEQ ID NO: 61, a light chain variable domain CDR2 comprising the amino acid sequence of SEQ ID NO: 62, and a light chain variable domain CDR3 comprising the amino acid sequence of SEQ ID NO: 63, optionally with the proviso that the heavy chain variable domain does not comprise the amino acid sequence of SEQ ID NO: 89 or the light chain variable domain does not comprise the amino acid sequence of SEQ ID NO: 113.

In another embodiment, the invention provides an antibody or antigen binding fragment that binds to human CMV wherein the antibody or antigen binding fragment is selected from the group consisting of:
  a. an antibody or antigen binding fragment comprising: a heavy chain variable domain CDR1 comprising the amino acid sequence of SEQ ID NO: 1, a heavy chain variable domain CDR2 comprising the amino acid sequence of SEQ ID NO: 2, a heavy chain variable domain CDR3 comprising the amino acid sequence of SEQ ID NO: 3, a light chain variable domain CDR1 comprising the amino acid sequence of SEQ ID NO: 4, a light chain variable domain CDR2 comprising the amino acid sequence of SEQ ID NO: 5, and a light chain variable domain CDR3 comprising the amino acid sequence of SEQ ID NO: 6, optionally with the proviso that the heavy chain variable domain does not comprise the amino acid sequence of SEQ ID NO: 77 or the light chain variable domain does not comprise the amino acid sequence of SEQ ID NO: 102;
  b. an antibody or antigen binding fragment comprising: a heavy chain variable domain CDR1 comprising the amino acid sequence of SEQ ID NO: 19, a heavy chain variable domain CDR2 comprising the amino acid sequence of SEQ ID NO: 20, a heavy chain variable domain CDR3 comprising the amino acid sequence of SEQ ID NO: 15, a light chain variable domain CDR1 comprising the amino acid sequence of SEQ ID NO: 21, a light chain variable domain CDR2 comprising the amino acid sequence of SEQ ID NO: 22, and a light chain variable domain CDR3 comprising the amino acid sequence of SEQ ID NO: 23, optionally with the proviso that the heavy chain variable domain does not comprise the amino acid sequence of SEQ ID NO: 81 or the light chain variable domain does not comprise the amino acid sequence of SEQ ID NO: 105; and
  c. an antibody or antigen binding fragment that binds gB comprising: a heavy chain variable domain CDR1 comprising the amino acid sequence of SEQ ID NO: 58, a heavy chain variable domain CDR2 comprising the amino acid sequence of SEQ ID NO: 59, and a heavy chain variable domain CDR3 comprising the amino acid sequence of SEQ ID NO: 60, a light chain variable domain CDR1 comprising the amino acid sequence of SEQ ID NO: 61, a light chain variable domain CDR2 comprising the amino acid sequence of SEQ ID NO: 62, and a light chain variable domain CDR3 comprising the amino acid sequence of SEQ ID NO: 63, optionally with the proviso that the heavy chain variable domain does not comprise the amino acid sequence of SEQ ID NO: 89 or the light chain variable domain does not comprise the amino acid sequence of SEQ ID NO: 113.

In another embodiment, the invention provides an antibody or antigen binding fragment that binds to human CMV comprising a light chain immunoglobulin, a heavy chain immunoglobulin or both a light chain and a heavy chain immunoglobulin selected from the group consisting of:
  A. an antibody or antigen binding fragment that binds to the pentameric gH complex site 1 comprising:
    a. a variable heavy chain comprising the amino acid sequence of SEQ ID NO: 77 and/or a variable light chain comprising the amino acid sequence of SEQ ID NO: 102;
    b. a variable heavy chain comprising the amino acid sequence of SEQ ID NO: 78 and/or a variable light chain comprising the amino acid sequence of SEQ ID NO: 103;
    c. a variable heavy chain comprising the amino acid sequence of SEQ ID NO: 115 and/or a variable light chain comprising the amino acid sequence of SEQ ID NO: 117;
    d. a variable heavy chain comprising at least 90%, 95%, 96%, 97%, 98% or 99% identity to SEQ ID NO: 77, SEQ ID NO: 78, or SEQ ID NO: 115 and/or a variable light chain comprising at least 90%, 95%, 96%, 97%, 98% or 99% identity to SEQ ID NO: 102, SEQ ID NO: 103, or SEQ ID NO: 117, optionally with the proviso that the variable heavy chain does not comprise the amino acid sequence of SEQ ID NO: 77 or SEQ ID NO: 78 or the variable light chain does not comprise the amino acid sequence of SEQ ID NO: 102 or SEQ ID NO: 103;
    e. a variable heavy chain comprising at least 90%, 95%, 96%, 97%, 98% or 99% identity to SEQ ID NO: 77, SEQ ID NO: 78, or SEQ ID NO: 115 and/or a variable light chain comprising at least 90%, 95%, 96%, 97%, 98% or 99% identity to SEQ ID NO: 102, SEQ ID NO: 103, or SEQ ID NO: 117, wherein any sequence variations occur in the framework regions of the antibody, optionally with the proviso that the variable heavy chain does not comprise the amino acid sequence of SEQ ID NO: 77 or SEQ ID NO: 78 or the variable light chain does not comprise the amino acid sequence of SEQ ID NO: 102 or SEQ ID NO: 103;
  B. an antibody or antigen binding fragment that binds to the pentameric gH complex site 2 comprising:
    a. a variable heavy chain comprising the amino acid sequence of SEQ ID NO: 79 and/or a variable light chain comprising the amino acid sequence of SEQ ID NO: 104;

b. a variable heavy chain comprising the amino acid sequence of SEQ ID NO: 80 and/or a variable light chain comprising the amino acid sequence of SEQ ID NO: 104;

c. a variable heavy chain comprising the amino acid sequence of SEQ ID NO: 81 and/or a variable light chain comprising the amino acid sequence of SEQ ID NO: 105;

d. a variable heavy chain comprising the amino acid sequence of SEQ ID NO: 82 and/or a variable light chain comprising the amino acid sequence of SEQ ID NO: 106;

e. a variable heavy chain comprising the amino acid sequence of SEQ ID NO: 83 and/or a variable light chain comprising the amino acid sequence of SEQ ID NO: 107;

f. a variable heavy chain comprising the amino acid sequence of SEQ ID NO: 84 and/or a variable light chain comprising the amino acid sequence of SEQ ID NO: 108;

g. a variable heavy chain comprising the amino acid sequence of SEQ ID NO: 119 and/or a variable light chain comprising the amino acid sequence of SEQ ID NO: 121;

h. a variable heavy chain comprising at least 90%, 95%, 96%, 97%, 98% or 99% identity to any one of SEQ ID NOS: 79 to 84 and 119 and/or a variable light chain comprising at least 90%, 95%, 96%, 97%, 98% or 99% identity to any one of SEQ ID NOS: 104 to 108 and 121, optionally with the proviso that the variable heavy chain does not comprise the amino acid sequence of any of SEQ ID NOS: 79 to 84 or the variable light chain does not comprise the amino acid sequence of any one of SEQ ID NOS: 104 to 108;

i. a variable heavy chain comprising at least 90%, 95%, 96%, 97%, 98% or 99% identity to any one of SEQ ID NOS: 79 to 84 and 119 and/or a variable light chain comprising at least 90%, 95%, 96%, 97%, 98% or 99% identity to any one of SEQ ID NOS: 104 to 108 and 121, wherein any sequence variations occur in the framework regions of the antibody, optionally with the proviso that the variable heavy chain does not comprise the amino acid sequence of any of SEQ ID NOS: 79 to 84 or the variable light chain does not comprise the amino acid sequence of any one of SEQ ID NOS: 104 to 108;

C. an antibody or antigen binding fragment that binds to the pentameric gH complex site 3 comprising:

a. a variable heavy chain comprising the amino acid sequence of SEQ ID NO: 85 and/or a variable light chain comprising the amino acid sequence of SEQ ID NO: 109;

b. a variable heavy chain comprising at least 90%, 95%, 96%, 97%, 98% or 99% identity to SEQ ID NO: 85 and/or a variable light chain comprising at least 90%, 95%, 96%, 97%, 98% or 99% identity to SEQ ID NO: 109, optionally with the proviso that the variable heavy chain does not comprise the amino acid sequence of SEQ ID NO: 85 or the variable light chain does not comprise the amino acid sequence of SEQ ID NO: 109;

c. a variable heavy chain comprising at least 90%, 95%, 96%, 97%, 98% or 99% identity to SEQ ID NO: 85 and/or a variable light chain comprising at least 90%, 95%, 96%, 97%, 98% or 99% identity to SEQ ID NO: 109, wherein any sequence variations occur in the framework regions of the antibody, optionally with the proviso that the variable heavy chain does not comprise the amino acid sequence of SEQ ID NO: 85 or the variable light chain does not comprise the amino acid sequence of SEQ ID NO: 109;

D. an antibody or antigen binding fragment that binds to the pentameric gH complex site 5 comprising:

a. a variable heavy chain comprising the amino acid sequence of SEQ ID NO: 86 and/or a variable light chain comprising the amino acid sequence of SEQ ID NO: 110;

b. a variable heavy chain comprising at least 90%, 95%, 96%, 97%, 98% or 99% identity to SEQ ID NO: 86 and/or a variable light chain comprising at least 90%, 95%, 96%, 97%, 98% or 99% identity to SEQ ID NO: 110, optionally with the proviso that the variable heavy chain does not comprise the amino acid sequence of SEQ ID NO: 86 or the variable light chain does not comprise the amino acid sequence of SEQ ID NO: 110;

c. a variable heavy chain comprising at least 90%, 95%, 96%, 97%, 98% or 99% identity to SEQ ID NO: 86 and/or a variable light chain comprising at least 90%, 95%, 96%, 97%, 98% or 99% identity to SEQ ID NO: 110, wherein any sequence variations occur in the framework regions of the antibody, optionally with the proviso that the variable heavy chain does not comprise the amino acid sequence of SEQ ID NO: 86 or the variable light chain does not comprise the amino acid sequence of SEQ ID NO: 110;

E. an antibody or antigen binding protein that binds to the pentameric gH complex site 7 comprising:

a. a variable heavy chain comprising the amino acid sequence of SEQ ID NO: 87 and/or a variable light chain comprising the amino acid sequence of SEQ ID NO: 111;

b. a variable heavy chain comprising the amino acid sequence of SEQ ID NO: 88 and/or a variable light chain comprising the amino acid sequence of SEQ ID NO: 112;

c. a variable heavy chain comprising at least 90%, 95%, 96%, 97%, 98% or 99% identity to SEQ ID NO: 87 or SEQ ID NO: 88 and/or a variable light chain comprising at least 90%, 95%, 96%, 97%, 98% or 99% identity to SEQ ID NO: 111 or SEQ ID NO: 112, optionally with the proviso that the variable heavy chain does not comprise the amino acid sequence of SEQ ID NO: 87 or SEQ ID NO: 88 or the variable light chain does not comprise the amino acid sequence of SEQ ID NO: 111 or SEQ ID NO: 112;

d. a variable heavy chain comprising at least 90%, 95%, 96%, 97%, 98% or 99% identity to SEQ ID NO: 87 or SEQ ID NO: 88 and/or a variable light chain comprising at least 90%, 95%, 96%, 97%, 98% or 99% identity to SEQ ID NO: 111 or SEQ ID NO: 112, wherein any sequence variations occur in the framework regions of the antibody, optionally with the proviso that the variable heavy chain does not comprise the amino acid sequence of SEQ ID NO: 87 or SEQ ID NO: 88 or the variable light chain does not comprise the amino acid sequence of SEQ ID NO: 111 or SEQ ID NO: 112;

F. an antibody or antigen binding fragment that binds gB comprising:
 a. a variable heavy chain comprising the amino acid sequence of SEQ ID NO: 89 and/or a variable light chain comprising the amino acid sequence of SEQ ID NO: 113;
 b. a variable heavy chain comprising the amino acid sequence of SEQ ID NO: 123 and/or a variable light chain comprising the amino acid sequence of SEQ ID NO: 125;
 c. a variable heavy chain comprising at least 90%, 95%, 96%, 97%, 98% or 99% identity to SEQ ID NO: 89 or SEQ ID NO: 123 and/or a variable light chain comprising at least 90%, 95%, 96%, 97%, 98% or 99% identity to SEQ ID NO: 113 or SEQ ID NO: 125, optionally with the proviso that the variable heavy chain does not comprise the amino acid sequence of SEQ ID NO: 89 or the variable light chain does not comprise the amino acid sequence of SEQ ID NO: 113;
 d. a variable heavy chain comprising at least 90%, 95%, 96%, 97%, 98% or 99% identity to SEQ ID NO: 89 or SEQ ID NO: 123 and/or a variable light chain comprising at least 90%, 95%, 96%, 97%, 98% or 99% identity to SEQ ID NO: 113 or SEQ ID NO: 125, wherein any sequence variations occur in the framework regions of the antibody, optionally with the proviso that the variable heavy chain does not comprise the amino acid sequence of SEQ ID NO: 89 or the variable light chain does not comprise the amino acid sequence of SEQ ID NO: 113.

In another embodiment, the invention provides an antibody or antigen binding fragment that binds to human CMV comprising a variable heavy chain comprising the amino acid sequence of SEQ ID NO: 77 and a variable light chain comprising the amino acid sequence of SEQ ID NO: 102, optionally with the proviso that the heavy chain and/or the light chain do not comprise a naturally-occurring human constant region.

In another embodiment, the invention provides an antibody or antigen binding fragment that binds to human CMV comprising a variable heavy chain comprising the amino acid sequence of SEQ ID NO: 115 and a variable light chain comprising the amino acid sequence of SEQ ID NO: 117. In one aspect of this embodiment, the invention provides an antibody or antigen binding fragment, wherein the heavy chain comprises the amino acid sequence of SEQ ID NO: 127 or SEQ ID NO: 131 and the light chain comprises the amino acid sequence of SEQ ID NO: 129 or SEQ ID NO: 133.

In another embodiment, the invention provides an antibody or antigen binding fragment that binds to human CMV comprising a variable heavy chain comprising the amino acid sequence of SEQ ID NO: 81 and a variable light chain comprising the amino acid sequence of SEQ ID NO: 105, optionally with the proviso that the heavy chain and/or the light chain do not comprise a naturally-occurring human constant region.

In another embodiment, the invention provides an antibody or antigen binding fragment that binds to human CMV comprising a variable heavy chain comprising the amino acid sequence of SEQ ID NO: 119 and a variable light chain comprising the amino acid sequence of SEQ ID NO: 121. In one aspect of this embodiment, the invention provides an antibody or antigen binding fragment, wherein the heavy chain comprises the amino acid sequence of SEQ ID NO: 135 or SEQ ID NO: 139 and the light chain comprises the amino acid sequence of SEQ ID NO: 137 or SEQ ID NO: 141.

In another embodiment, the invention provides an antibody or antigen binding fragment that binds to human CMV comprising a variable heavy chain comprising the amino acid sequence of SEQ ID NO: 89 and a variable light chain comprising the amino acid sequence of SEQ ID NO: 113, optionally with the proviso that the heavy chain and/or the light chain do not comprise a naturally-occurring human constant region.

In another embodiment, the invention provides an antibody or antigen binding fragment that binds to human CMV comprising a variable heavy chain comprising the amino acid sequence of SEQ ID NO: 123 and a variable light chain comprising the amino acid sequence of SEQ ID NO: 125. In one aspect of this embodiment, the invention provides an antibody or antigen binding fragment, wherein the heavy chain comprises the amino acid sequence of SEQ ID NO: 143 or SEQ ID NO: 147 and the light chain comprises the amino acid sequence of SEQ ID NO: 145 or SEQ ID NO: 149.

In any of the above embodiments, the antibody or antigen binding fragment thereof is isolated, a recombinant antibody, or a full-length antibody.

The invention also provides isolated nucleic acids encoding anyone of the anti-CMV antibodies or antigen binding fragments of the invention. In one embodiment, the invention provides isolated nucleic acids comprising a sequence of nucleotides as set forth in any of SEQ ID NOS: 64-76 or SEQ ID NOS: 90-101, in any of SEQ ID NOS: 114, 116, 118, 120, 122, or 124, or in any of SEQ ID NOS: 126, 128, 130, 132, 134, 136, 138, 140, 142, 144, 146, or 148, wherein said nucleic acids can optionally comprise a leader sequence. The invention also provides expression vectors comprising a nucleic acid encoding a sequence of nucleotides as set forth in any of SEQ ID NOS: 64-76 or SEQ ID NOS: 90-101, in any of SEQ ID NOS: 114, 116, 118, 120, 122, or 124, or in any of SEQ ID NOS: 126, 128, 130, 132, 134, 136, 138, 140, 142, 144, 146, or 148, wherein said nucleic acids can optionally comprise a leader sequence. These isolated nucleic acids and the expression vectors comprising them may be used to express the antibodies of the invention or antigen binding fragments thereof in recombinant host cells. Thus, the invention also provides host cells comprising isolated nucleic acids comprising a sequence of nucleotides as set forth in any of SEQ ID NOS: 64-76 or SEQ ID NOS: 90-101, in any of SEQ ID NOS: 114, 116, 118, 120, 122, or 124, or in any of SEQ ID NOS: 126, 128, 130, 132, 134, 136, 138, 140, 142, 144, 146, or 148, wherein said nucleic acids can optionally comprise a leader sequence. In one embodiment, the host cell is Chinese hamster ovary cell. In one embodiment, the host cell is a yeast cell, for example a *Pichia* cell or a *Pichia pastoris* host cell.

The invention also provides pharmaceutical compositions comprising an antibody or antigen binding fragment of the invention and a pharmaceutically acceptable carrier or diluent.

The invention also provides a method of preventing or treating CMV infection, or conferring passive immunity, in a subject in need thereof, comprising administering to the subject an effective amount of an anti-CMV antibody or antigen binding fragment of the invention. In one embodiment, the subject been treated is a human subject. In one embodiment, the anti-CMV antibody or antigen binding fragment of the invention comprises: (i) a heavy chain variable region CDR1 comprising the amino acid sequence of SEQ ID NO: 1; (ii) a heavy chain variable region CDR2 comprising the amino acid sequence of SEQ ID NO: 2; (iii) a heavy chain variable region CDR3 comprising the amino acid sequence of SEQ ID NO: 3; (iv) a light chain variable region CDR1 comprising the amino acid sequence of SEQ ID NO: 4; (v) a light chain variable region CDR2 comprising the amino acid sequence of SEQ ID NO: 5; and (vi) a light chain variable region CDR3 comprising the amino acid sequence of SEQ ID NO: 6. In one embodiment, the anti-CMV antibody or antigen binding fragment thereof comprises: (i) a heavy chain variable region CDR1 comprising the amino acid sequence of SEQ ID NO: 19; (ii) a heavy chain variable region CDR2 comprising the amino acid sequence of SEQ ID NO: 20; (iii) a heavy chain variable region CDR3 comprising the amino acid sequence of SEQ ID NO: 15; (iv) a light chain variable region CDR1 comprising the amino acid sequence of SEQ ID NO: 21; (v) a light chain variable region CDR2 comprising the amino acid sequence of SEQ ID NO: 22; and (vi) a light chain variable region CDR3 comprising the amino acid sequence of SEQ ID NO: 23. In one embodiment, the anti-CMV antibody or antigen binding fragment thereof comprises: (i) a heavy chain variable region CDR1 comprising the amino acid sequence of SEQ ID NO: 58; (ii) a heavy chain variable region CDR2 comprising the amino acid sequence of SEQ ID NO: 59; (iii) a heavy chain variable region CDR3 comprising the amino acid sequence of SEQ ID NO: 60; (iv) a light chain variable region CDR1 comprising the amino acid sequence of SEQ ID NO: 61; (v) a light chain variable region CDR2 comprising the amino acid sequence of SEQ ID NO: 62; and (vi) a light chain variable region CDR3 comprising the amino acid sequence of SEQ ID NO: 63.

In one embodiment, the antibody or antigen binding fragment, comprises a variable heavy chain comprising the amino acid sequence of SEQ ID NO: 77 and a variable light chain comprising the amino acid sequence of SEQ ID NO: 102, optionally with the proviso that the heavy chain and/or the light chain do not comprise a naturally-occurring human constant region.

In another embodiment, the invention provides an antibody or antigen binding fragment that binds to human CMV comprising a variable heavy chain comprising the amino acid sequence of SEQ ID NO: 115 and a variable light chain comprising the amino acid sequence of SEQ ID NO: 117. In one aspect of this embodiment, the invention provides an antibody or antigen binding fragment, wherein the heavy chain comprises the amino acid sequence of SEQ ID NO: 127 or SEQ ID NO: 131 and the light chain comprises the amino acid sequence of SEQ ID NO: 129 or SEQ ID NO: 133.

In another embodiment, the invention provides an antibody or antigen binding fragment that binds to human CMV comprising a variable heavy chain comprising the amino acid sequence of SEQ ID NO: 81 and a variable light chain comprising the amino acid sequence of SEQ ID NO: 105, optionally with the proviso that the heavy chain and/or the light chain do not comprise a naturally-occurring human constant region.

In another embodiment, the invention provides an antibody or antigen binding fragment that binds to human CMV comprising a variable heavy chain comprising the amino acid sequence of SEQ ID NO: 119 and a variable light chain comprising the amino acid sequence of SEQ ID NO: 121. In one aspect of this embodiment, the invention provides an antibody or antigen binding fragment, wherein the heavy chain comprises the amino acid sequence of SEQ ID NO: 135 or SEQ ID NO: 139 and the light chain comprises the amino acid sequence of SEQ ID NO: 137 or SEQ ID NO: 141.

In another embodiment, the invention provides an antibody or antigen binding fragment that binds to human CMV comprising a variable heavy chain comprising the amino acid sequence of SEQ ID NO: 89 and a variable light chain comprising the amino acid sequence of SEQ ID NO: 113, optionally with the proviso that the heavy chain and/or the light chain do not comprise a naturally-occurring human constant region.

In another embodiment, the invention provides an antibody or antigen binding fragment that binds to human CMV comprising a variable heavy chain comprising the amino acid sequence of SEQ ID NO: 123 and a variable light chain comprising the amino acid sequence of SEQ ID NO: 125. In one aspect of this embodiment, the invention provides an antibody or antigen binding fragment, wherein the heavy chain comprises the amino acid sequence of SEQ ID NO: 143 or SEQ ID NO: 147 and the light chain comprises the amino acid sequence of SEQ ID NO: 145 or SEQ ID NO: 149.

In yet additional embodiments, the present invention provides for an antibody or antigen binding fragment according to the invention for use in the preparation of a medicament to treat a CMV infection or confer passive immunity to CMV infection. In yet other embodiments, the present invention provides for the use of an antibody or antigen binding fragment according to the invention for the manufacture of a medicament for the treatment of CMV infection or conferring passive immunity to CMV infection in a subject.

The invention also provides a method of producing an anti-CMV antibody or antigen binding fragment of the invention comprising: culturing a host cell comprising a polynucleotide encoding a heavy chain and/or light chain of an antibody of the invention (or an antigen binding fragment thereof) under conditions favorable to expression of the polynucleotide; and optionally, recovering the antibody or antigen binding fragment from the host cell and/or culture medium. In one embodiment, the polynucleotide encoding the heavy chain and the polynucleotide encoding the light chain are in a single vector. In another embodiment, the polynucleotide encoding the heavy chain and the polynucleotide encoding the light chain are in different vectors.

BRIEF DESCRIPTION OF THE DRAWINGS

FIG. 2 provides an outline of the procedures used for the isolation and confirmation of human antibodies specific for CMV derived from memory B-cells (see Example 2).

FIG. 5 shows that the antibodies with potent neutralizing activity in ARPE-19 cells have poor neutralizing activity in MRC-5 fibroblast cells. However, the antibodies specific to the pentamer but with less potency in ARPE-19 cells have antiviral activity in MRC-5 cells. Some antibodies of gB specificity can also neutralize virus in both ARPE-19 and MRC-5 cells.

DETAILED DESCRIPTION

Figure 1A:
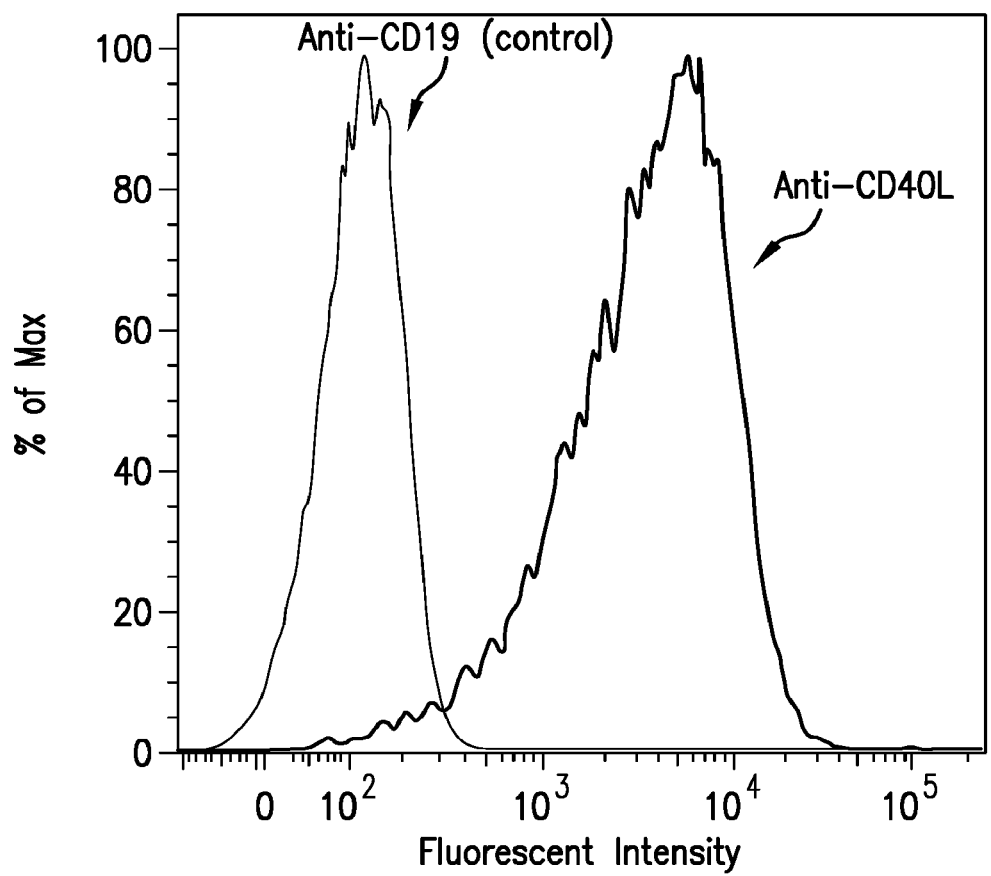
FIG. 1 (A) shows the expression of a feeder cell line, which was established to constitutively express human CD40L. The expression is shown by flow cytometry (PE-conjugated mouse anti-human CD154 (CD40L), Cat. No. 555700; and PE-conjugated mouse anti-human CD19 (control), Cat. No. 555413; both are from BD Pharmingen). (B) Human memory B-cells were enriched from PBMC using a commercial kit designed for purification of human memory B-cells (Miltenyi Biotec). The purity of the enriched fraction was demonstrated by flow cytometry, with the gating strategy shown below the histograms. The purities of human memory B-cells range from ~50%. (C) An ELISA was developed to assess human IgG concentration using capturing ELISA format, using goat-anti-human IgG capturing antibodies and goat-anti-human IgG Fc conjugated with HRP as detection antibody (Southern Biotech). (D) Fraction of wells positive for IgG after human memory B-cell culture for 14-day at 37° C. Enriched memory B-cells were seeded in 96-well plates at 0.5-1.5 cell/well with a cocktail of cytokines, along with gamma-irradiated 4×10⁴ CD40L feeder cells, in total 200 μL complete RPM11640 medium supplemented with 10% FBS. The supernatant from each well was harvested after 14-day culture, and assessed in human IgG ELISA.

The present invention provides isolated anti-CMV antigen binding proteins and methods of use of the antigen binding proteins in the treatment and/or prevention of CMV infection. Specifically, the antigen binding proteins described herein bind to the HCMV gB glycoprotein or the pentameric gH complex (gH/gL/pUL128-131).

Abbreviations Throughout the detailed description and examples of the invention the following abbreviations will be used:
ADCC Antibody-dependent cellular cytotoxicity
ASC Antibody secreting cells
BCR B-cell receptor
CDC Complement-dependent cytotoxicity
CDR Complementarity determining region in the immunoglobulin variable regions, defined using the Kabat numbering system
CHO Chinese hamster ovary
CMV Cytomegalovirus
EC₅₀ concentration resulting in 50% efficacy of binding or neutralization
ELISA Enzyme-linked immunosorbant assay
FR Antibody framework region: the immunoglobulin variable regions excluding the CDR regions.
HRP Horseradish peroxidase
IFN interferon
IC50 concentration resulting in 50% inhibition
IgG Immunoglobulin G
Kabat An immunoglobulin alignment and numbering system pioneered by Elvin A. Kabat ((1991) Sequences of Proteins of Immunological Interest, 5th Ed. Public Health Service, National Institutes of Health, Bethesda, Md.)
mAb or Mab or MAb Monoclonal antibody
PBMC Peripheral blood mononuclear cells.
SEB *Staphylococcus* Enterotoxin B
TT Tetanus toxoid
V region The segment of IgG chains which is variable in sequence between different antibodies. It extends to Kabat residue 109 in the light chain and 113 in the heavy chain.
VH Immunoglobulin heavy chain variable region
VK Immunoglobulin kappa light chain variable region
VL Immunoglobulin light chain variable region Definitions So that the invention may be more readily understood, certain technical and scientific terms are specifically defined below. Unless specifically defined elsewhere in this document, all other technical and scientific terms used herein have the meaning commonly understood by one of ordinary skill in the art to which this invention belongs.

As used herein, including the appended claims, the singular forms of words such as "a," "an," and "the," include their corresponding plural references unless the context clearly dictates otherwise.

"Administration" and "treatment," as it applies to an animal, human, experimental subject, cell, tissue, organ, or biological fluid, refers to contact of an exogenous pharmaceutical, therapeutic, diagnostic agent, or composition to the animal, human, subject, cell, tissue, organ, or biological fluid. Treatment of a cell encompasses contact of a reagent to the cell, as well as contact of a reagent to a fluid, where the fluid is in contact with the cell. "Administration" and "treatment" also means in vitro and ex vivo treatments, e.g., of a cell, by a reagent, diagnostic, binding compound, or by another cell.

Anti-CMV Antigen Binding Proteins

An anti-CMV antigen binding protein refers to an antigen binding protein that specifically binds to CMV. An antigen binding protein that "specifically binds to CMV," is an antigen binding protein that exhibits preferential binding to CMV as compared to other viruses, but this specificity does not require absolute binding specificity. The anti-CMV antigen binding protein has an affinity for CMV that is at least two fold greater, preferably at least ten fold greater, more preferably at least 20 fold greater, and most preferably at least 100 fold greater than the affinity with any other antigen. In certain embodiments of the invention, an anti-CMV antigen binding protein binds to the human CMV (HCMV) or human herpesvirus-5.

The antigen binding protein that binds CMV can comprise one, two, three, four, five, or six of the complementarity determining regions (CDRs) of the antigen binding proteins disclosed herein. The one, two, three, four, five, or six CDRs may be independently selected from the CDR sequences of the antigen binding proteins disclosed herein (e.g., Tables 1 and 2). Alternatively, the one, two, three, four, five, or six CDRs may be selected from the CDR sequences of a single described antigen binding protein of the invention.

The recombinant antigen binding protein that binds CMV can comprise at least one light chain variable ($V_L$) domain comprising one or more of CDR1, CDR2 and CDR3 of any antigen binding protein of the invention (see Table 2). In specific embodiments, the antigen binding protein comprises a $V_L$ domain comprising three CDRs of an antigen binding protein of the invention.

In an embodiment, the antigen binding protein comprises a $V_L$ domain comprising the CDR1 of SEQ ID NO: 4, CDR2 of SEQ ID NO: 5 and CDR3 of SEQ ID NO: 6. In an aspect of this embodiment, the antigen binding protein does not comprise SEQ ID NO: 102. In another aspect of this embodiment, the antigen binding protein comprises any of SEQ ID NOS: 117, 129 and 133.

In an embodiment, the antigen binding protein comprises a $V_L$ domain comprising the CDR1 of SEQ ID NO: 10, CDR2 of SEQ ID NO: 11 and CDR3 of SEQ ID NO: 12. In an aspect of this embodiment, the antigen binding protein does not comprise SEQ ID NO: 103.

In an embodiment, the antigen binding protein comprises a $V_L$ domain comprising the CDR1 of SEQ ID NO: 16, CDR2 of SEQ ID NO: 17 and CDR3 of SEQ ID NO: 18. In an aspect of this embodiment, the antigen binding protein does not comprise SEQ ID NO: 104.

In an embodiment, the antigen binding protein comprises a $V_L$ domain comprising the CDR1 of SEQ ID NO: 21, CDR2 of SEQ ID NO: 22 and CDR3 of SEQ ID NO: 23. In an aspect of this embodiment, the antigen binding protein does not comprise SEQ ID NO: 105. In another aspect of this embodiment, the antigen binding protein comprises any of SEQ ID NOS: 121, 137 and 141.

In an embodiment, the antigen binding protein comprises a $V_L$ domain comprising the CDR1 of SEQ ID NO: 16, CDR2 of SEQ ID NO: 17 and CDR3 of SEQ ID NO: 27. In an aspect of this embodiment, the antigen binding protein does not comprise SEQ ID NO: 106.

In an embodiment, the antigen binding protein comprises a $V_L$ domain comprising the CDR1 of SEQ ID NO: 16, CDR2 of SEQ ID NO: 22 and CDR3 of SEQ ID NO: 31. In an aspect of this embodiment, the antigen binding protein does not comprise SEQ ID NO: 107.

In an embodiment, the antigen binding protein comprises a $V_L$ domain comprising the CDR1 of SEQ ID NO: 21, CDR2 of SEQ ID NO: 22 and CDR3 of SEQ ID NO: 34. In an aspect of this embodiment, the antigen binding protein does not comprise SEQ ID NO: 108.

In an embodiment, the antigen binding protein comprises a $V_L$ domain comprising the CDR1 of SEQ ID NO: 38, CDR2 of SEQ ID NO: 39 and CDR3 of SEQ ID NO: 40. In an aspect of this embodiment, the antigen binding protein does not comprise SEQ ID NO: 109.

In an embodiment, the antigen binding protein comprises a $V_L$ domain comprising the CDR1 of SEQ ID NO: 44, CDR2 of SEQ ID NO: 5 and CDR3 of SEQ ID NO: 45. In an aspect of this embodiment, the antigen binding protein does not comprise SEQ ID NO: 110.

In an embodiment, the antigen binding protein comprises a $V_L$ domain comprising the CDR1 of SEQ ID NO: 49, CDR2 of SEQ ID NO: 50 and CDR3 of SEQ ID NO: 51. In an aspect of this embodiment, the antigen binding protein does not comprise SEQ ID NO: 111.

In an embodiment, the antigen binding protein comprises a $V_L$ domain comprising the CDR1 of SEQ ID NO: 55, CDR2 of SEQ ID NO: 56 and CDR3 of SEQ ID NO: 57. In an aspect of this embodiment, the antigen binding protein does not comprise SEQ ID NO: 112.

In an embodiment, the antigen binding protein comprises a $V_L$ domain comprising the CDR1 of SEQ ID NO: 61, CDR2 of SEQ ID NO: 62 and CDR3 of SEQ ID NO: 63. In an aspect of this embodiment, the antigen binding protein does not comprise SEQ ID NO: 113. In another aspect of this embodiment, the antigen binding protein comprises any of SEQ ID NOS: 125, 145 or 149.

In other embodiments, the antigen binding protein comprises a $V_L$ domain with at least 75%, 80%, 85%, 90%, 95%, 98% or 99% sequence identity with the $V_L$ domains described above, optionally with the proviso that the $V_L$ domain is not a naturally occurring sequence.

In another embodiment, the recombinant antigen binding protein comprises a light chain variable region having the amino acid sequence set forth in any of SEQ ID NOS: 102-113. In certain embodiments of the invention, the recombinant antigen binding protein does not comprise a light chain variable region having the amino acid sequence set forth in any of SEQ ID NOS: 102-113, but comprises CDR sequences as discussed above.

The isolated antigen binding protein that binds CMV can comprise at least one heavy chain variable ($V_H$) domain comprising one or more of CDR1, CDR2 and CDR3 of any of the antigen binding proteins of the invention (see Table 1). In specific embodiments, the antigen binding protein comprises a $V_H$ domain comprising three CDRs of an antigen binding protein of the invention.

In one embodiment, the antigen binding protein comprises a $V_H$ domain comprising the CDR1 of SEQ ID NO: 1, CDR2 of SEQ ID NO: 2 and CDR3 of SEQ ID NO: 3. In an aspect of this embodiment, the antigen binding protein does not comprise SEQ ID NO: 77. In another aspect of this embodiment, the antigen binding protein comprises any of SEQ ID NOS: 115, 127 and 131.

In one embodiment, the antigen binding protein comprises a $V_H$ domain comprising the CDR1 of SEQ ID NO: 7, CDR2 of SEQ ID NO: 8 and CDR3 of SEQ ID NO: 9. In an aspect of this embodiment, the antigen binding protein does not comprise SEQ ID NO: 78.

In one embodiment, the antigen binding protein comprises a $V_H$ domain comprising the CDR1 of SEQ ID NO: 13, CDR2 of SEQ ID NO: 14 and CDR3 of SEQ ID NO: 15. In an aspect of this embodiment, the antigen binding protein does not comprise SEQ ID NO: 79.

In one embodiment, the antigen binding protein comprises a $V_H$ domain comprising the CDR1 of SEQ ID NO: 19, CDR2 of SEQ ID NO: 14 and CDR3 of SEQ ID NO: 15. In an aspect of this embodiment, the antigen binding protein does not comprise SEQ ID NO: 80.

In one embodiment, the antigen binding protein comprises a $V_H$ domain comprising the CDR1 of SEQ ID NO: 19, CDR2 of SEQ ID NO: 20 and CDR3 of SEQ ID NO: 15. In an aspect of this embodiment, the antigen binding protein does not comprise SEQ ID NO: 81. In another aspect of this embodiment, the antigen binding protein comprises any of SEQ ID NOS: 119, 135 or 139.

In one embodiment, the antigen binding protein comprises a $V_H$ domain comprising the CDR1 of SEQ ID NO: 24, CDR2 of SEQ ID NO: 25 and CDR3 of SEQ ID NO: 26. In an aspect of this embodiment, the antigen binding protein does not comprise SEQ ID NO: 82.

In one embodiment, the antigen binding protein comprises a $V_H$ domain comprising the CDR1 of SEQ ID NO: 28, CDR2 of SEQ ID NO: 29 and CDR3 of SEQ ID NO: 30. In an aspect of this embodiment, the antigen binding protein does not comprise SEQ ID NO: 83.

In one embodiment, the antigen binding protein comprises a $V_H$ domain comprising the CDR1 of SEQ ID NO: 19, CDR2 of SEQ ID NO: 32 and CDR3 of SEQ ID NO: 33. In an aspect of this embodiment, the antigen binding protein does not comprise SEQ ID NO: 84.

In one embodiment, the antigen binding protein comprises a $V_H$ domain comprising the CDR1 of SEQ ID NO: 35, CDR2 of SEQ ID NO: 36 and CDR3 of SEQ ID NO: 37. In an aspect of this embodiment, the antigen binding protein does not comprise SEQ ID NO: 85, In one embodiment, the antigen binding protein comprises a $V_H$ domain comprising the CDR1 of SEQ ID NO: 41, CDR2 of SEQ ID NO: 42 and CDR3 of SEQ ID NO: 43. In an aspect of this embodiment, the antigen binding protein does not comprise SEQ ID NO: 86.

In one embodiment, the antigen binding protein comprises a $V_H$ domain comprising the CDR1 of SEQ ID NO: 46, CDR2 of SEQ ID NO: 47 and CDR3 of SEQ ID NO: 48. In an aspect of this embodiment, the antigen binding protein does not comprise SEQ ID NO: 87.

In one embodiment, the antigen binding protein comprises a $V_H$ domain comprising the CDR1 of SEQ ID NO: 52, CDR2 of SEQ ID NO: 53 and CDR3 of SEQ ID NO: 54. In an aspect of this embodiment, the antigen binding protein does not comprise SEQ ID NO: 88.

In one embodiment, the antigen binding protein comprises a $V_H$ domain comprising the CDR1 of SEQ ID NO: 58, CDR2 of SEQ ID NO: 59 and CDR3 of SEQ ID NO: 60. In an aspect of this embodiment, the antigen binding protein does not comprise SEQ ID NO: 89. In another aspect of this embodiment, the antigen binding protein comprises any of SEQ ID NOS: 123, 143 or 147.

In other embodiments, the antigen binding protein comprises a $V_H$ domain with at least 75%, 80%, 85%, 90%, 95%, 98% or 99% sequence identity with the $V_H$ domains described above, optionally with the proviso that the $V_L$ domain is not a naturally occurring sequence.

In another embodiment, the recombinant antigen binding protein comprises a heavy chain variable region having the amino acid sequence set forth in any of SEQ ID NOS: 77-89. In certain embodiments of the invention, the recombinant antigen binding protein does not comprise a heavy chain variable region having the amino acid sequence set forth in any of SEQ ID NOS: 77-89, but comprises CDR sequences as discussed above.

In a further particular embodiment, the recombinant antigen binding protein comprises a light chain variable region and a heavy chain variable region comprising the amino acid sequences set forth in: (a) SEQ ID NO: 102 and SEQ ID NO:77; (b) SEQ ID NO:103 and SEQ ID NO:78; (c) SEQ ID NO:104 and SEQ ID NO:79; (d) SEQ ID NO:104 and SEQ ID NO: 80; (e) SEQ ID NO:105 and SEQ ID NO:81; (f) SEQ ID NO:106 and SEQ ID NO:82; (g) SEQ ID NO: 107 and SEQ ID NO:83; (h) SEQ ID NO:108 and SEQ ID NO:84; (i) SEQ ID NO:109 and SEQ ID NO:85; (j) SEQ ID NO:110 and SEQ ID NO:86; (k) SEQ ID NO:111 and SEQ ID NO: 87; (l) SEQ ID NO:112 and SEQ ID NO:88; and (m) SEQ ID NO:113 and SEQ ID NO:89. In certain embodiments, the recombinant antigen binding protein does not comprise a light chain variable region and a heavy chain variable region comprising the amino acid sequences set forth in: (a) SEQ ID NO:102 and SEQ ID NO:77; (b) SEQ ID NO:103 and SEQ ID NO:78; (c) SEQ ID NO:104 and SEQ ID NO:79; (d) SEQ ID NO:104 and SEQ ID NO:80; (e) SEQ ID NO:105 and SEQ ID NO:81; (f) SEQ ID NO:106 and SEQ ID NO:82; (g) SEQ ID NO: 107 and SEQ ID NO:83; (h) SEQ ID NO:108 and SEQ ID NO:84; (i) SEQ ID NO:109 and SEQ ID NO:85; (j) SEQ ID NO:110 and SEQ ID NO:86; (k) SEQ ID NO: 111 and SEQ ID NO:87; (l) SEQ ID NO:112 and SEQ ID NO:88; and (m) SEQ ID NO:113 and SEQ ID NO:89, but comprises CDR sequences as discussed above.

In yet another particular embodiment, the recombinant antigen binding protein comprises a light chain variable region and a heavy chain variable region comprising the amino acid sequences set forth in: (a) SEQ ID NO: 102 and SEQ ID NO:77; (e) SEQ ID NO:105 and SEQ ID NO:81; or (m) SEQ ID NO:113 and SEQ ID NO:89.

In an embodiment, the recombinant antigen binding protein comprises a heavy chain comprising the amino acid sequences set forth in SEQ ID NO: 115 and a light chain comprising the amino acid sequences set forth in SEQ ID NO: 117. In an embodiment, the recombinant antigen binding protein comprises a heavy chain comprising the amino acid sequences set forth in SEQ ID NO: 127 or SEQ ID NO: 131 and a light chain comprising the amino acid sequences set forth in SEQ ID NO: 129 or SEQ ID NO: 133.

In an embodiment, the recombinant antigen binding protein comprises a heavy chain comprising the amino acid sequences set forth in SEQ ID NO: 119 and a light chain comprising the amino acid sequences set forth in SEQ ID NO: 121. In an embodiment, the recombinant antigen binding protein comprises a heavy chain comprising the amino acid sequences set forth in SEQ ID NO: 135 or SEQ ID NO: 139 and a light chain comprising the amino acid sequences set forth in SEQ ID NO: 137 or SEQ ID NO: 141.

In an embodiment, the recombinant antigen binding protein comprises a heavy chain comprising the amino acid sequences set forth in SEQ ID NO: 123 and a light chain comprising the amino acid sequences set forth in SEQ ID NO: 125. In an embodiment, the recombinant antigen binding protein comprises a heavy chain comprising the amino acid sequences set forth in SEQ ID NO: 143 or SEQ ID NO: 147 and a light chain comprising the amino acid sequences set forth in SEQ ID NO: 145 or SEQ ID NO: 149.

In other embodiments, the antigen binding protein comprises a $V_L$ and/or $V_H$ domain with at least 75%, 80%, 85%, 90%, 95%, 98% or 99% sequence identity with the $V_L$ and $V_H$ domains described above, provided that the CDR regions comprise or consist of a sequence of amino acids as set forth herein or comprise or consist of the CDR sequences set forth herein with one amino acid residue modification. Accordingly, in one embodiment, the antigen binding protein comprises a $V_L$ and/or $V_H$ domain, wherein the framework regions share at least 75%, 80%, 85%, 90%, 95%, 98% or 99% sequence identity with the $V_L$ and $V_H$ domains described above and the CDR regions comprise or consist of the CDR sequences as set forth herein. In alternative embodiment, the antigen binding protein comprises a $V_L$ and/or $V_H$ domain, wherein the framework regions share at least 75%, 80%, 85%, 90%, 95%, 98% or 99% sequence identity with the $V_L$ and $V_H$ domains described above and the CDR regions comprise or consist of the CDR sequences as set forth herein with one amino acid modification relative to the CDR sequences defined herein.

As used herein, the term "antigen binding protein" refers to a protein comprising a portion that binds to an antigen and, optionally, a scaffold or framework portion that allows the antigen binding portion to adopt a conformation that promotes binding of the antigen binding protein to the antigen. Examples of antigen binding proteins include antibodies and antigen binding fragments thereof including, but not limited to, recombinant antibodies, monoclonal antibodies, chimeric antibodies, bispecific antibodies, single chain antibodies, diabodies, triabodies, tetrabodies, Fv fragments, scFv fragments, Fab fragments, Fab' fragments, F(ab')$_2$ fragments and camelized single domain antibodies. The antigen binding protein can comprise, for example, an antibody-derived protein scaffold or an alternative protein scaffold or artificial scaffold with grafted CDRs or CDR derivatives. Such scaffolds include, but are not limited to, antibody-derived scaffolds comprising mutations introduced to, for example, stabilize the three-dimensional structure of the antigen binding protein as well as wholly synthetic scaffolds comprising, for example, a biocompatible polymer. See, e.g., Korndorfer et al., 2003, Proteins: Structure, Function, and Bioinformatics 53(1):121-129 (2003); Roque et al., 2004, Biotechnol. Prog. 20:639-654. In addition, peptide antibody mimetics ("PAMs") can be used, as well as scaffolds based on antibody mimetics utilizing fibronectin components as a scaffold.

As used herein, the term "antibody" refers to a protein including at least one or two, heavy (H) chain variable regions (abbreviated herein as $V_H$), and at least one or two light (L) chain variable regions (abbreviated herein as $V_L$). The $V_H$ and $V_L$ regions can be further subdivided into regions of hypervariability, termed "complementarity determining regions" ("CDR"), interspersed with regions that are more conserved, termed "framework regions" (FR). The extent of the framework region and CDRs has been precisely defined (see, Kabat, E. A., et al. Sequences of Proteins of Immunological Interest, Fifth Edition, U.S. Department of Health and Human Services, NIH Publication No. 91-3242, 1991, and Chothia, C. et al., 1987, J. Mol. Biol. 196:901-917, which are incorporated herein by reference). Preferably, each $V_H$ and $V_L$ is composed of three CDRs and four FRs, arranged from amino-terminus to carboxy-terminus in the following order: FR1, CDR1, FR2, CDR2, FR3, CDR3 and FR4.

The $V_H$ or $V_L$ chain of the antibody can further include all or part of a heavy or light chain constant region. In one embodiment, the antibody is a tetramer of two heavy immunoglobulin chains and two light immunoglobulin chains, wherein the heavy and light immunoglobulin chains are inter-connected by, e.g., disulfide bonds. The heavy chain constant region includes three domains, CH1, CH2 and CH3. The light chain constant region is comprised of one domain, CL. The variable region of the heavy and light chains contains a binding domain that interacts with an antigen. The constant regions of the antibodies typically mediate the binding of the antibody to host tissues or factors, including various cells of the immune system (e.g., effector cells) and the first component (C1q) of the classical complement system. The term "antibody" includes intact immunoglobulins of types IgA, IgG, IgE, IgD, IgM (as well as subtypes thereof), wherein the light chains of the immunoglobulin may be of types kappa or lambda.

Within light and heavy chains, the variable and constant regions are joined by a "J" region of about 12 or more amino acids, with the heavy chain also including a "D" region of about 10 more amino acids. See generally, *Fundamental Immunology* Ch. 7 (Paul, W., ed., 2nd ed. Raven Press, N.Y. (1989).

As used herein, the term "monoclonal antibody" refers to a population of substantially homogeneous antibodies, i.e., the antibody molecules comprising the population are identical in amino acid sequence except for possible naturally occurring mutations that may be present in minor amounts. In contrast, conventional (polyclonal) antibody preparations typically include a multitude of different antibodies having different amino acid sequences in their variable domains, particularly their CDRs, which are often specific for different epitopes. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., 1975, *Nature* 256:495, or may be made by recombinant DNA methods (see, e.g., U.S. Pat. No. 4,816,567). The "monoclonal antibodies" may also be isolated from phage antibody libraries using the techniques described in Clackson et al., 1991, *Nature* 352:624-628 and Marks et al., 1991, *J. Mol. Biol.* 222:581-597, for example. See also Presta, 2005, *J. Allergy Clin. Immunol.* 116:731.

As used herein, a "chimeric antibody" is an antibody having the variable domain from a first antibody and the constant domain from a second antibody, where the first and second antibodies are from different species. See e.g., U.S. Pat. No. 4,816,567; and Morrison et al., 1984, *Proc. Natl. Acad. Sci. USA* 81:6851-6855). Typically the variable domains are obtained from an antibody from an experimental animal (the "parental antibody"), such as a rodent, and the constant domain sequences are obtained from human antibodies, so that the resulting chimeric antibody will be less likely to elicit an adverse immune response in a human subject than the parental (e.g. rodent) antibody.

As used herein, the terms "antibody fragment" or "antigen binding fragment" refer to antigen binding fragments of antibodies, i.e., antibody fragments that retain the ability to bind specifically to the antigen bound by the full-length antibody, e.g., fragments that retain one or more CDR regions. Examples of antibody binding fragments include, but are not limited to, Fab, Fab', F(ab')$_2$, Fv fragments, diabodies, linear antibodies, single-chain antibody molecules, e.g., scFv, and multispecific antibodies formed from antibody fragments.

A "Fab fragment" is comprised of one light chain and the $C_H1$ and variable regions of one heavy chain. The heavy chain of a Fab molecule cannot form a disulfide bond with another heavy chain molecule. A "Fab fragment" can be the product of papain cleavage of an antibody.

A "Fab' fragment" contains one light chain and a portion or fragment of one heavy chain that contains the $V_H$ domain and the $C_H1$ domain and also the region between the $C_H1$ and $C_H2$ domains, such that an interchain disulfide bond can be formed between the two heavy chains of two Fab' fragments to form a $F(ab')_2$ molecule.

A "$F(ab')_2$ fragment" contains two light chains and two heavy chains containing a portion of the constant region between the $C_H1$ and $C_H2$ domains, such that an interchain disulfide bond is formed between the two heavy chains. A $F(ab')_2$ fragment thus is composed of two Fab' fragments that are held together by a disulfide bond between the two heavy chains. An "$F(ab')_2$ fragment" can be the product of pepsin cleavage of an antibody.

The "Fv region" comprises the variable regions from both the heavy and light chains, but lacks the constant regions.

As used herein, the term "camelized antibody" refers to single domain antibodies derived from Camelidae heavy chain Ig (see, e.g., Muyldermans et al., 2001, Trends Biochem. Sci. 26: 230; Nuttall et al., 2000, Cur. Pharm. Biotech. 1:253; Reichmann and Muyldermans, 1999, J. Immunol. Meth. 231:25; International Patent Application Publication Nos. WO 94/04678 and WO 94/25591; and U.S. Pat. No. 6,005,079).

As used herein, the term "single-chain Fv" or "scFv" antibody refers to antibody fragments comprising the $V_H$ and $V_L$ domains of an antibody, wherein these domains are present in a single polypeptide chain. Generally, the Fv polypeptide further comprises a polypeptide linker between the $V_H$ and $V_L$ domains which enables the scFv to form the desired structure for antigen binding. For a review of scFv, see Pluckthun (1994) THE PHARMACOLOGY OF MONOCLONAL ANTIBODIES, vol. 113, Rosenburg and Moore eds. Springer-Verlag, New York, pp. 269-315. See also, International Patent Application Publication No. WO 88/01649 and U.S. Pat. Nos. 4,946,778 and 5,260,203.

As used herein, the term "domain antibody" is an immunologically functional immunoglobulin fragment containing only the variable region of a heavy chain or the variable region of a light chain. In some instances, two or more $V_H$ regions are covalently joined with a peptide linker to create a bivalent domain antibody. The two $V_H$ regions of a bivalent domain antibody may target the same or different antigens.

As used herein, the term "bivalent antibody" comprises two antigen binding sites. In some instances, the two binding sites have the same antigen specificities. However, bivalent antibodies may be "bispecific" such that each antigen binding site has different antigen specificity. The different antigen specificities may be different antigens on the same molecule or they may be directed to antigens on different molecules.

As used herein, the term "diabody" refers to small antibody fragments with two antigen binding sites, which fragments comprise a heavy chain variable domain ($V_H$) connected to a light chain variable domain ($V_L$) in the same polypeptide chain ($V_H$—$V_L$ or $V_L$—$V_H$). By using a linker that is too short to allow pairing between the two domains on the same chain, the domains are forced to pair with the complementary domains of another chain and create two antigen binding sites. Diabodies are described more fully in, e.g., European Patent Application No. EP 404,097; International Patent Application Publication No. WO 93/11161; and Holliger et al., 1993, Proc. Natl. Acad. Sci. USA 90:6444-6448. For a review of engineered antibody variants generally see Holliger and Hudson, 2005, Nat. Biotechnol. 23:1126-1136.

As used herein, the term "recombinant" antibody refers to antibodies that are prepared, expressed, created, or isolated by recombinant means, such as antibodies expressed using a recombinant expression vector transfected into a host cell, antibodies isolated from a recombinant, combinatorial antibody library, antibodies isolated from an animal (e.g., a mouse) that is transgenic for human immunoglobulin genes or antibodies prepared, expressed, created, or isolated by any other means that involves splicing of human immunoglobulin gene sequences to other DNA sequences. Such recombinant antibodies can be humanized, CDR grafted, chimeric, in vitro generated (e.g., by phage display) antibodies, and may optionally include constant regions derived from human germline immunoglobulin sequences. A recombinant polynucleotide generally includes two or more nucleotide sequences that are present together in a longer polynucleotide sequence, wherein the two sequences are not found together (e.g., attached or fused) in nature, e.g., a promoter and a heterologous nucleotide sequence encoding a polypeptide that are normally not found together in nature or a vector and a heterologous nucleotide sequence.

As used herein, the terms "isolated" or "purified" refer to a molecule (e.g., antibody, nucleic acid, etc.) that is at least partially separated from other molecules normally associated with it in its native state. An "isolated or purified nucleic acid" is at least partially separated from nucleic acids which normally flank the polynucleotide in its native state. Thus, polynucleotides fused to regulatory or coding sequences with which they are not normally associated, for example as the result of recombinant techniques, are considered isolated herein. Such molecules are considered isolated even when present, for example in the chromosome of a host cell, or in a nucleic acid solution. Generally, the terms "isolated" and "purified" are not intended to refer to a complete absence of such material or to an absence of water, buffers, or salts or other components of a pharmaceutical formulation that includes the isolated or purified molecule. Antigen binding proteins of the invention and nucleic acids that encode antigen binding proteins of the invention are isolated/purified.

As used herein, "homology" refers to sequence similarity between two polynucleotide sequences or between two polypeptide sequences when they are optimally aligned. When a position in both of the two compared sequences is occupied by the same base or amino acid monomer subunit, e.g., if a position in each of two DNA molecules is occupied by adenine, then the molecules are homologous at that position. The percent of homology is the number of homologous positions shared by the two sequences divided by the total number of positions compared×100. For example, if 6 of 10 of the positions in two sequences are matched or homologous when the sequences are optimally aligned then the two sequences are 60% homologous. Generally, the comparison is made when two sequences are aligned to give maximum percent homology.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that not all progeny will have precisely identical DNA content, due to deliberate or inadvertent mutations. Mutant progeny that have the same function or biological activity as screened for in the originally transformed cell are included. Where distinct designations are intended, it will be clear from the context.

As used herein, "germline sequence" refers to a sequence of unrearranged immunoglobulin DNA sequences. Any suitable source of unrearranged immunoglobulin sequences may be used. Human germline sequences may be obtained, for example, from JOINSOLVER® germline databases on the website for the National Institute of Arthritis and Musculoskeletal and Skin Diseases of the United States National Institutes of Health. Mouse germline sequences may be obtained, for example, as described in Giudicelli et al., 2005, *Nucleic Acids Res.* 33:D256-D261.

TABLE 1

Heavy Chain Variable Domain CDR Sequences

| Clone ID | HCDR1 Sequence | HCDR1 SEQ ID NO. | HCDR2 Sequence | HCDR2 SEQ ID NO. | HCDR3 Sequence | HCDR3 SEQ ID NO. |
|---|---|---|---|---|---|---|
| Site 1 | | | | | | |
| 2-18 | GFSFSDHD | 1 | SRNKDYSSTT | 2 | ARGPHHSDRSGYYGGTFDI | 3 |
| 2-25 | GYTFTNYA | 7 | INAGRGNT | 8 | ARDESTGDYYYYMDV | 9 |
| Site 2 | | | | | | |
| 1-15 | EFTFSDYY | 13 | ISSSGTTI | 14 | ARDSYSKLVDIEAIEAFDI | 15 |
| 1-64 | GFTFSDYY | 19 | ISSSGTTI | 14 | ARDSYSKLVDIEAIEAFDI | 15 |
| 1-85 | GFTFSDYY | 19 | ISSSGRTI | 20 | ARDSYSKLVDIEAIEAFDI | 15 |
| 1-125 | GFNFKDYY | 24 | 1SSSGQTI | 25 | ARDSYSKLVDIVADEAFDL | 26 |
| 1-150 | GFSFSAYY | 28 | ISSSGNTI | 29 | ARDSYSKLADIEATEAFDV | 30 |
| 1-175 | GFTFSDYY | 19 | ISGSGRTL | 32 | ARDSYSKLVEIEAIEAFDV | 33 |
| Site 3 | | | | | | |
| 1-103 | GDAISGSNYY | 35 | IYHTGST | 36 | ARRIRGYSGTYD | 37 |
| Site 5 | | | | | | |
| 1-32 | GFAFDNYA | 41 | ISLEGRNK | 42 | ARDMRYYYDSNGHYRNRYGMDV | 43 |
| Site 7 | | | | | | |
| 3-7 | GYTFNTYA | 46 | INTYSGST | 47 | ARDGYNWGFLDF | 48 |
| 3-16 | GYRFTIYS | 52 | INTYNGNT | 53 | ARDAENWGFFDD | 54 |
| gB | | | | | | |
| 3-25 | GFTFSNHG | 58 | VSKDGTNE | 59 | AREGYCGDDRCYSGQPDY | 60 |

TABLE 2

Light Chain Variable Domain CDR Sequences

| Clone ID | LCDR1 Sequence | LCDR1 SEQ. ID NO. | LCDR2 Sequence | LCDR2 SEQ ID NO. | LCDR3 Sequence | LCDR3 SEQ ID NO. |
|---|---|---|---|---|---|---|
| Site 1 | | | | | | |
| 2-18 | QGISSW | 4 | DAS | 5 | QQGNMFPLT | 6 |
| 2-25 | RLDDKY | 10 | QDN | 11 | QAWDSDTYV | 12 |
| Site 2 | | | | | | |
| 1-15 | NIGSKS | 16 | FDT | 17 | QVWDRTSDHVV | 18 |
| 1-64 | NIGSKS | 16 | FDT | 17 | QVWDRTSDHVV | 18 |
| 1-85 | NIGGKS | 21 | YDS | 22 | QVWDRHGDHVV | 23 |
| 1-125 | NIGSKS | 16 | FDT | 17 | QVWDSSSARLV | 27 |
| 1-150 | NIGSKS | 16 | YDS | 22 | OVWDSGSDRVV | 31 |
| 1-175 | NIGGKS | 21 | YDS | 22 | QVWDRQTDHVV | 34 |
| Site 3 | | | | | | |
| 1-103 | QDISSY | 38 | SAS | 39 | QQLNN | 40 |
| Site 5 | | | | | | |
| 1-32 | QDINQF | 44 | DAS | 5 | QQYENLFT | 45 |
| Site 7 | | | | | | |
| 3-7 | QGISNY | 49 | AAS | 50 | QKYNSAPLT | 51 |
| 3-16 | OSVGRH | 55 | GAS | 56 | QQYNTWPYT | 57 |
| gB | | | | | | |
| 3-25 | QSVGRY | 61 | DSS | 62 | QQRSHWPPLT | 63 |

Antigen Binding Protein Derivatives

In other embodiments, the invention provides antigen binding proteins that are derivatives of the antigen binding proteins disclosed herein. Antigen binding protein derivatives of the invention specifically bind CMV and have $V_L$ domains and $V_H$ domains with at least 75%, 80%, 85%, 90%, 95%, 98% or 99% sequence identity with the $V_L$ domains and $V_H$ domains of the antibodies disclosed herein (e.g., in Tables 1, 2, 7 and 8) while still exhibiting the desired binding and functional properties (e.g., CMV neutralization). In another embodiment the antigen binding protein derivatives of the present invention comprises $V_L$ and $V_H$ domains having up to 0, 1, 2, 3, 4, 5, 6, 7, 8, 9, 10 or more conservative or non conservative amino acid substitutions, while still exhibiting the desired binding and functional properties. It is preferred that the antigen binding protein derivative have framework regions that share at least 75%, 80%, 85%, 90%, 95%, 98% or 99% sequence identity with the framework regions within the $V_L$ domains and $V_H$ domains of the antigen binding proteins disclosed herein and that the CDR's comprise or consist of a sequence of amino acid residues as set forth therein or said sequences with 1 amino acid difference/modification.

Antigen binding protein derivatives of the invention also encompass those derivatives that specifically bind CMV and have CDRs (i.e., CDR1, CDR2 and CDR3) of a $V_L$ domain and CDRs of a $V_H$ domain with at least 75%, 80%, 85%, 90%, 95%, 98% or 99% sequence identity with the CDRs disclosed herein for the $V_L$ domains and $V_H$ domains of the antigen binding proteins of the invention (e.g., in Tables 1, 2, 7 and 8) while still exhibiting the desired binding and functional properties (e.g., CMV neutralization). In another embodiment the antigen binding protein derivative of the invention comprises CDRs of disclosed $V_L$ and $V_H$ domains having up to 0, 1, 2, 3 or more conservative or non conservative amino acid substitutions, while still exhibiting the desired binding and functional properties.

Sequence identity refers to the degree to which the amino acids of two polypeptides are the same at equivalent positions when the two sequences are optimally aligned. Sequence identity can be determined using a BLAST algorithm wherein the parameters of the algorithm are selected to give the largest match between the respective sequences over the entire length of the respective reference sequences. The following references relate to BLAST algorithms often used for sequence analysis: BLAST ALGORITHMS: Altschul et al., 1990, J. Mol. Biol. 215:403-410; Gish et al., 1993, Nature Genet. 3:266-272; Madden et al., 1996, Meth. Enzymol. 266:131-141; Altschul et al., 1997, Nucleic Acids Res. 25:3389-3402; Zhang et al., 1997, Genome Res. 7:649-656; Wootton et al., 1993, Comput. Chem. 17:149-163; Hancock et al., 1994, Comput. Appl. Biosci. 10:67-70; ALIGNMENT SCORING SYSTEMS: Dayhoff, M. O et al., "A model of evolutionary change in proteins." in Atlas of Protein Sequence and Structure, (1978) vol. 5, suppl. 3. M. O. Dayhoff (ed.), pp. 345-352, Natl. Biomed. Res. Found., Washington, D.C.; Schwartz, R. M., et al., "Matrices for detecting distant relationships." in Atlas of Protein Sequence and Structure, (1978) vol. 5, suppl. 3." M. O. Dayhoff (ed.), pp. 353-358, Natl. Biomed. Res. Found., Washington, D.C.; Altschul, 1991, J. Mol. Biol. 219:555-565; States. et al., 1991, Methods 3:66-70; Henikoff et al., 1992, Proc. Natl. Acad. Sci. USA 89:10915-10919; Altschul et al., 1993, J. Mol. Evol. 36:290-300; ALIGNMENT STATISTICS: Karlin et al., 1990, Proc. Natl. Acad. Sci. USA 87:2264-2268; Karlin et al., 1993, Proc. Natl. Acad. Sci. USA 90:5873-5877; Dembo et al., 1994, Ann. Prob. 22:2022-2039; and Altschul, S. F. "Evaluating the statistical significance of multiple distinct local alignments." in Theoretical and Computational Methods in Genome Research (S. Suhai, ed.), (1997) pp. 1-14, Plenum, New York.

In embodiments of the invention, the antigen binding protein derivatives retain at least 10% of its CMV binding and/or neutralization activity (when compared to the parental antigen binding protein) when that activity is expressed on a molar basis. In preferred embodiments of the invention, an antigen binding protein derivative retains at least 20%, 50%, 70%, 80%, 90%, 95% or 100% of the CMV binding affinity and/or neutralization activity as the parental antigen binding protein.

As used herein, the term "conservative substitution" refers to substitutions of amino acids in a protein with other amino acids having similar characteristics (e.g. charge, side-chain size, hydrophobicity/hydrophilicity, backbone conformation and rigidity, etc.), such that the changes can frequently be made without altering or substantially altering the biological activity of the protein. Those of skill in this art recognize that, in general, single amino acid substitutions in non-essential regions of a polypeptide do not substantially alter biological activity (see, e.g., Watson et al. (1987) *Molecular Biology of the Gene*, The Benjamin/Cummings Pub. Co., p. 224 (4th Ed.)). In addition, substitutions of structurally or functionally similar amino acids are less likely to disrupt biological activity. Various embodiments of the antigen binding proteins of the present invention comprise polypeptide chains with the sequences disclosed herein, e.g. in Tables 1, 2, 7 and 8, or polypeptide chains comprising up to 1, 2, 3, 4, 5, 6, 7, 8, 9, 10, 12, 15, 20 or more conservative amino acid substitutions. Exemplary conservative substitutions are set forth in Table 3.

TABLE 3

Exemplary Conservative Amino Acid Substitutions

| Original residue | Conservative substitution |
|---|---|
| Ala (A) | Gly; Ser |
| Arg (R) | Lys; His |
| Asn (N) | Gln; His |
| Asp (D) | Glu; Asn |
| Cys (C) | Ser; Ala |
| Gln (Q) | Asn |
| Glu (E) | Asp; Gln |
| Gly (G) | Ala |
| His (H) | Asn; Gln |
| Ile (I) | Leu; Val |
| Leu (L) | Ile; Val |
| Lys (K) | Arg; His |
| Met (M) | Leu; Ile; Tyr |
| Phe (F) | Tyr; Met; Leu |
| Pro (P) | Ala |
| Ser (S) | Thr |
| Thr (T) | Ser |
| Trp (W) | Tyr; Phe |
| Tyr (Y) | Trp; Phe |
| Val (V) | Ile; Leu |

Function-conservative derivatives of the antigen binding proteins of the invention are also contemplated by the present invention. As used herein, the term "function-conservative derivative" refers to antigen binding proteins in which one or more amino acid residues have been changed without altering a desired property, such an antigen affinity and/or specificity and/or neutralizing activity. Such variants include, but are not limited to, replacement of an amino acid with one having similar properties, such as the conservative amino acid substitutions of Table 3.

Also provided are recombinant polypeptides comprising the $V_L$ domains of the anti-CMV antigen binding proteins of the invention and recombinant polypeptides comprising the $V_H$ domains of the anti-CMV antigen binding proteins of the invention having up to 1, 2, 3, 4, or 5 or more amino acid substitutions, while still exhibiting the ability to bind to CMV with high affinity and specificity and/or can neutralize CMV.

In another embodiment, provided is an antigen binding protein that has a $V_L$ domain and/or a $V_H$ domain with at least 95%, 90%, 85%, 80%, or 75% sequence homology to one or more of the $V_L$ domains or $V_H$ domains described herein, and exhibits specific binding to CMV and/or can neutralize CMV. In another embodiment the antigen binding protein of the present invention comprises $V_L$ and $V_H$ domains (with and without signal sequence) having up to 1, 2, 3, 4, or 5 or more amino acid substitutions, and exhibits specific binding to CMV and/or can neutralize CMV.

Nucleic Acids

The present invention further comprises the recombinant nucleic acids encoding the anti-CMV antigen binding proteins disclosed herein.

In one embodiment, the recombinant nucleic acid encodes an antigen binding protein comprising a light chain variable ($V_L$) domain comprising the CDR1, CDR2 and CDR3 of any of the antigen binding proteins disclosed herein (SEQ ID NOS: 4, 5, 6, 10, 11, 12, 16, 17, 18, 21, 22, 23, 31, 34, 38, 39, 40, 44, 45, 49, 50, 51, 55, 56, 57, 61, 62, and 63).

In another embodiment, the recombinant nucleic acid encodes antigen binding protein comprising a heavy chain variable ($V_H$) domain comprising the CDR1, CDR2 and CDR3 of any of the antigen binding proteins disclosed herein (SEQ ID NOS: 1, 2, 3, 7, 8, 9, 13, 14, 15, 19, 20, 24, 25, 26, 28, 29, 30, 32, 33, 35, 36, 37, 41, 42, 43, 46, 47, 48, 52, 53, 54, 58, 59, and 60).

In one embodiment, the recombinant nucleic acid encodes an antigen binding protein comprising at least one light chain variable ($V_L$) domain and at least one heavy chain variable ($V_H$) domain, wherein the $V_L$ domain comprises at least three CDRs having a sequence selected from SEQ ID NOS: 4, 5, 6, 10, 11, 12, 16, 17, 18, 21, 22, 23, 31, 34, 38, 39, 40, 44, 45, 49, 50, 51, 55, 56, 57, 61, 62, and 63, and the $V_H$ domain comprises at least at least three CDRs having a sequence selected from SEQ ID NOS: 1, 2, 3, 7, 8, 9, 13, 14, 15, 19, 20, 24, 25, 26, 28, 29, 30, 32, 33, 35, 36, 37, 41, 42, 43, 46, 47, 48, 52, 53, 54, 58, 59, and 60. In one embodiment, the isolated nucleic acid encodes a light chain variable region (See Table 7, SEQ ID NOS: 90-101) and/or a heavy chain variable region (See Table 7, SEQ ID NOS: 64-76) disclosed herein.

In some embodiments, the isolated nucleic acid molecule encodes a light chain variable region and consists, consists essentially of, or comprises a sequence of nucleotides as set forth in any one of SEQ ID NOS: 90-101 (See Table 8). In other embodiments, the isolated nucleic acid molecule encodes a heavy chain variable region and consists, consists essentially of, or comprises a sequence of nucleotides as set forth in any one of SEQ ID NOS: 64-76 (See Table 7).

In some embodiments the isolated nucleic acid encodes both a light chain and a heavy chain on a single nucleic acid molecule, and in other embodiments the light and heavy chains are encoded on separate nucleic acid molecules. In another embodiment the nucleic acids further encodes a signal sequence.

The present invention further comprises nucleic acids which hybridize to nucleic acids encoding the anti-CMV antigen binding proteins disclosed herein. In general, the nucleic acids hybridize under moderate or high stringency conditions to nucleic acids that encode antigen binding proteins disclosed herein and also encode antigen binding proteins that maintain the ability to specifically bind to CMV. A first nucleic acid molecule is "hybridizable" to a second nucleic acid molecule when a single stranded form of the first nucleic acid molecule can anneal to the second nucleic acid molecule under the appropriate conditions of temperature and solution ionic strength (see Sambrook, et al., supra). The conditions of temperature and ionic strength determine the "stringency" of the hybridization. Typical moderate stringency hybridization conditions are 40% formamide, with 5× or 6×SSC and 0.1% SDS at 42° C. High stringency hybridization conditions are 50% formamide, 5× or 6×SSC (0.15M NaCl and 0.015M Na-citrate) at 42° C. or, optionally, at a higher temperature (e.g., 57° C., 59° C., 60° C., 62° C., 63° C., 65° C. or 68° C.). Hybridization requires that the two nucleic acids contain complementary sequences, although, depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the higher the stringency under which the nucleic acids may hybridize. For hybrids of greater than 100 nucleotides in length, equations for calculating the melting temperature have been derived (see Sambrook, et al., supra, 9.50-9.51). For hybridization with shorter nucleic acids, e.g., oligonucleotides, the position of mismatches becomes more important, and the length of the oligonucleotide determines its specificity (see Sambrook, et al., supra, 11.7-11.8).

Also included in the present invention are nucleic acids encoding the anti-CMV antigen binding proteins derivatives.

This present invention also provides expression vectors comprising the recombinant nucleic acids of the invention, wherein the nucleic acid is operably linked to control sequences that are recognized by a host cell when the host cell is transfected with the vector. Also provided are host cells comprising an expression vector of the present invention and methods for producing the antigen binding proteins disclosed herein comprising culturing a host cell harboring an expression vector encoding the antigen binding protein in culture medium, and isolating the antigen binding protein from the host cell or culture medium.

Biological Properties of Anti-CMV Antigen Binding Proteins

The anti-CMV antigen binding proteins of the present invention are capable of binding to and, preferably, neutralizing CMV.

Binding to CMV can be measured by methods known in the art. For example, binding can be measured in antigen-titration ELISA (EIA). The antigen, either recombinant viral proteins or portions thereof or purified recombinant revertant virions, are immobilized on 96-well microtiter plates. Antigen binding protein reactivity to the immobilized antigen is measured in EIA. A strong reactivity signal of a test antigen binding protein as compared to a control antigen binding protein reflects high affinity of the test antigen binding protein to the viral antigen.

Ability of an antigen binding protein to neutralize CMV can be measured by methods known in the art. For example, neutralization can be measured in a viral neutralization assay. The antigen binding protein is mixed with a defined number of infectious CMV virions and the mixture is applied to cells vulnerable to CMV infection (i.e., epithelial cells such as ARPE-19 or MRC-5 cells). Cells that become infected with CMV can be detected by assaying for expression of viral antigens such as the viral immediate early (IE) antigen. Reduction of the number of cells with viral antigen expression as compared to cells infected in the absence of the antigen binding protein reflects neutralizing capacity (i.e, the antigen binding protein can reduce viral infectivity to cells). Reduced viral infectivity can be due to any mechanism including, but not limited to, the ability of the antigen binding protein to decrease binding of CMV to cells, the ability of the antigen binding protein to decrease viral fusion with cellular membranes and/or the ability of the antigen binding protein to decrease the release of viral genetic material into the cell.

Competitive Antigen Binding Proteins

The present invention also encompasses antigen binding proteins that bind to the same epitope or an overlapping epitope on CMV as any of the antigen binding proteins disclosed herein. Such competitive antigen binding proteins are able to cross-block binding of any of the disclosed antigen binding proteins disclosed herein. In one embodiment, the competitive antigen binding proteins can cross-block an antigen binding protein comprising a light chain variable region comprising CDRs disclosed in Table 2 and/or comprising a heavy chain variable region comprising CDRs disclosed in Table 1. In another embodiment, the competitive antigen binding proteins can cross-block an antigen binding protein comprising a light chain variable region disclosed in Table 8 and/or comprising a heavy chain variable region disclosed in Table 7.

A first antigen binding protein is considered to cross-block binding of a second antigen binding protein if pre-binding the target with the first antigen binding protein to saturation increases the concentration of second antigen binding protein needed to achieve half-maximal binding of the target by 2-, 3-, 4-, 5-, 10-, 20-, 50-, 100-, 200-fold or more.

Alternatively, a first antigen binding protein is considered to cross-block binding of a second antigen binding protein if the epitopes to which each bind is the same or significantly overlaps. In one embodiment, determination of epitope binding is conducted by crystallography.

Target

CMV infects various cells in vivo, including monocytes, macrophages, dendritic cells, neutrophils, endothelial cells, epithelial cells, fibroblasts, neurons, smooth muscle cells, hepatocytes, and stromal cells. See Plachter et al., 1996, Adv. Virus Res. 46:195. Although clinical CMV isolates replicate in a variety of cell types, laboratory strains AD169 (Elek et al., 1974, Lancet 1:1) and Towne (Plotkin et al., 1975, Infect. Immun. 12:521) replicate almost exclusively in fibroblasts (Hahn et al., 2004, J. Virol. 78:10023). The restriction in tropism, which results from serial passages and eventual adaptation of the virus in fibroblasts, is stipulated a marker of attenuation. See Gerna et al., 2005, J. Gen. Virol. 86:275; Gerna et al., 2002, J. Gen Virol. 83:1993; Gerna et al., 2003, J. Gen Virol. 84:1431; Dargan et al., 2010, J. Gen Virol. 91:1535.

HCMV is a double-stranded DNA virus with more than 751 translated open reading frames (ORF) and about 20 glycoproteins associated with viral envelope. See Stern-Ginossar et al., 2012, Science 338:1088-1093; and Varnum et al., 2004, J Virol 78:10960-10966. Entry of HCMV requires the concerted efforts of multiple glycoproteins—gB, gH/gL/gO, and gH/gL/pUL128-131. Glycoprotein gB is a class III fusion protein, and its fusogenic activity must be triggered via interaction with gH/gL containing complexes.

See Vanarsdall et al., 2012, Current opinion in virology 2:37-42; Wille et al., 2013, mBio 4:e00332-00313; Burke et al., 2015, PLoS Pathog 11:e1005227. The gH/gL/gO complex mediates viral entry into fibroblasts, and recent reports suggest that the gH/gL/gO might be involved in viral entry into all cell types. See Wille et al., 2010, J. Virol. 84:2585-2596; Zhou et al., 2015, J Virol 89:8999-9009. The pentameric complex gH/gL/pUL128-131 ("pentameric gH complex") determines epithelial and endothelial cell tropism through a receptor mediated endocytosis pathway. See Wang et al., 2005, Proc. Natl. Acad. Sci. USA 102:18153-18158; Ryckman et al., 2008, J. Virol. 82:60-70.

Mutations causing the loss of epithelial cell, endothelial cell, leukocyte, and dendritic cell tropism in human CMV laboratory strains have been mapped to three open reading frames (ORFs): UL128, UL130, and UL131. See Hahn et al., 2004, J. Virol. 78:10023; Wang and Shenk, 2005 J. Virol. 79:10330; Wang and Shenk, 2005 Proc Natl Acad Sci USA. 102:18153.

Loss of endothelial and epithelial tropism has been suspected as a deficiency in the previously evaluated as vaccines such as Towne. See Gerna et al., 2002, J. Gen Virol. 83:1993; Gerna et al., 2003, J. Gen Virol. 84:1431. Neutralizing antibodies in sera from human subjects of natural CMV infection have more than 15-fold higher activity against viral epithelial entry than against fibroblast entry. See Cui et al., 2008, Vaccine 26:5760. Humans with primary infection rapidly develop neutralizing antibodies to viral endothelial and epithelial entry but only slowly develop neutralizing antibodies to viral fibroblast entry. See Gerna et al., 2008, J. Gen. Virol. 89:853. Furthermore, neutralizing activity against viral epithelial and endothelial entry is absent in the immune sera from human subjects who received Towne vaccine. See Cui et al., 2008, Vaccine 26:5760. More recently, a panel of human monoclonal antibodies from four donors with CMV infection was described, and the more potent neutralizing clones from the panel recognized the antigens of the pentameric gH complex. See Macagno et al., 2010, J. Virol. 84:1005.

As used herein, the terms "pentameric gH complex" or "gH complex" refer to a complex of five viral proteins on the surface of the CMV virion. The complex is made up of proteins encoded by UL128, UL130, and UL131 assembled onto a gH/gL scaffold. See Wang and Shenk, 2005, Proc Natl Acad Sci USA. 102:1815; Ryckman et al., 2008, J. Virol. 82:60. The sequences of the complex proteins from CMV strain AD169 are shown at GenBank Accession Nos. NP_783797.1 (UL128), NP 040067 (UL130), CAA35294.1 (UL131), NP_040009 (gH, also known as UL75) and NP_783793 (gL, also known as UL115). Some attenuated CMV strains have one or more mutations in UL131 such that the protein is not expressed and therefore the gH complex is not formed.

As used herein, the terms "revertant virus" or "revertant virion" refer to CMV that has had the gH complex restored and thus expresses the gH complex on its envelope.

Methods of Making Antigen Binding Proteins

Antigen binding proteins that are monoclonal antibodies can be produced by methods commonly known in the art using hybridoma cells that produce parental (e.g., rodent) monoclonal anti-CMV antibodies. These methods include, but are not limited to, the hybridoma technique originally developed by Kohler et al. (1975, Nature 256:495-497), as well as the trioma technique (Hering et al., 1988, Biomed. Biochim. Acta. 47:211-216 and Hagiwara et al., 1993, Hum. Antibod. Hybridomas 4:15), the human B-cell hybridoma technique (Kozbor et al., 1983, Immunology Today 4:72 and Cote et al., 1983, Proc. Natl. Acad. Sci. U.S.A 80:2026-2030), the EBV-hybridoma technique (Cole et al., in *Monoclonal Antibodies and Cancer Therapy*, Alan R. Liss, Inc., pp. 77-96, 1985), and electric field based electrofusion using a Cyto Pulse large chamber cell fusion electroporator (Cyto Pulse Sciences, Inc., Glen Burnie, Md.). Preferably, mouse splenocytes are isolated and fused with PEG or by electrofusion to a mouse myeloma cell line based upon standard protocols. The resulting hybridomas may then be screened for the production of antigen-specific antibodies. For example, single cell suspensions of splenic lymphocytes from immunized mice may by fused to one-sixth the number of P3X63-Ag8.653 nonsecreting mouse myeloma cells (ATCC, CRL 1580) with 50% PEG. Cells may be plated at approximately $2\times10^5$ cells/mL in a flat bottom microtiter plate, followed by a two week incubation in selective medium containing 20% fetal Clone Serum, 18% "653" conditioned media, 5% origen (IGEN), 4 mM L-glutamine, 1 mM L-glutamine, 1 mM sodium pyruvate, 5 mM HEPES, 0.055 mM 2-mercaptoethanol, 50 units/ml penicillin, 50 mg/ml streptomycin, 50 mg/ml gentamycin and 1×HAT (Sigma; the HAT is added 24 hours after the fusion). After two weeks, cells may be cultured in medium in which the HAT is replaced with HT. Individual wells may then be screened by ELISA for anti-X monoclonal IgG antibodies. Once extensive hybridoma growth occurs, medium can be observed usually after 10-14 days. The antibody secreting hybridomas may be replated, screened again, and if still positive for human IgG, anti-CMV monoclonal antibodies, can be subcloned at least twice by limiting dilution. The stable subclones may then be cultured in vitro to generate small amounts of antibody in tissue culture medium for characterization.

The anti-CMV antigen binding proteins disclosed herein may also be produced recombinantly (e.g., in an *E. coli*/T7 expression system as discussed above). In this embodiment, nucleic acids encoding the antigen binding proteins of the invention (e.g., $V_H$ or $V_L$) may be inserted into a pET-based plasmid and expressed in the *E. coli*/T7 system. There are several methods by which to produce recombinant antigen binding proteins which are known in the art. One example of a method for recombinant production of antigen binding proteins is disclosed in U.S. Pat. No. 4,816,567. Transformation can be by any known method for introducing polynucleotides into a host cell. Methods for introduction of heterologous polynucleotides into mammalian cells are well known in the art and include dextran-mediated transfection, calcium phosphate precipitation, polybrene-mediated transfection, protoplast fusion, electroporation, encapsulation of the polynucleotide(s) in liposomes, biolistic injection and direct microinjection of the DNA into nuclei. In addition, nucleic acid molecules may be introduced into mammalian cells by viral vectors. Methods of transforming cells are well known in the art. See, for example, U.S. Pat. Nos. 4,399,216; 4,912,040; 4,740,461 and 4,959,455.

Anti-CMV antigen binding proteins can also be synthesized by the methods set forth in U.S. Pat. No. 6,331,415.

Mammalian cell lines available as hosts for expression of the antigen binding proteins disclosed herein are well known in the art and include many immortalized cell lines available from the American Type Culture Collection (ATCC). These include, inter alia, Chinese hamster ovary (CHO) cells, NSO, SP2 cells, HeLa cells, baby hamster kidney (BHK) cells, monkey kidney cells (COS), human hepatocellular carcinoma cells (e.g., Hep G2), A549 cells, 3T3 cells, HEK-293 cells and a number of other cell lines. Mammalian host cells include human, mouse, rat, dog, monkey, pig, goat, bovine, horse and hamster cells. Cell lines of particular preference are selected through determining which cell lines have high expression levels. Other cell lines that may be used are insect cell lines, such as Sf9 cells, amphibian cells, bacterial cells, plant cells and fungal cells. When recombinant expression vectors encoding the heavy chain or antigen binding portion or fragment thereof, the light chain and/or antigen binding fragment thereof are introduced into mammalian host cells, the antigen binding proteins are produced by culturing the host cells for a period of time sufficient to allow for expression of the antigen binding protein in the host cells or, more preferably, secretion of the antigen binding protein into the culture medium in which the host cells are grown.

Antigen binding proteins can be recovered from the culture medium using standard protein purification methods (e.g., Protein A affinity chromatography). Further, expression of antigen binding proteins of the invention from production cell lines can be enhanced using a number of known techniques. For example, the glutamine synthetase gene expression system (the GS system) is a common approach for enhancing expression under certain conditions. The GS system is discussed in whole or part in connection with European Patent Nos. 0 216 846, 0 256 055, and 0 323 997 and European Patent Application No. 89303964.4.

In general, glycoproteins produced in a particular cell line or transgenic animal will have a glycosylation pattern that is characteristic for glycoproteins produced in the cell line or transgenic animal. Therefore, the particular glycosylation pattern of an antigen binding protein will depend on the particular cell line or transgenic animal used to produce the antigen binding protein. In particular embodiments, antigen binding proteins with a glycosylation pattern comprising only non-fucosylated N-glycans may be advantageous, because these antigen binding proteins have been shown to typically exhibit more potent efficacy than their fucosylated counterparts both in vitro and in vivo. See for example, Shinkawa et al., 2003, J. Biol. Chem. 278: 3466-3473; U.S. Pat. Nos. 6,946,292 and 7,214,775. These antigen binding proteins with non-fucosylated N-glycans are not likely to be immunogenic themselves because their carbohydrate structures are a normal component of the population that exists in human serum IgG.

A bispecific or bifunctional antigen binding protein is an artificial hybrid antigen binding protein having two different heavy/light chain pairs and two different binding sites. Bispecific antigen binding proteins can be produced by a variety of methods including fusion of hybridomas or linking of Fab' fragments. See, e.g., Songsivilai et al., 1990, Clin. Exp. Immunol. 79: 315-321, Kostelny et al., 1992, J Immunol. 148:1547-1553. In addition, bispecific antigen binding proteins may be formed as "diabodies" (Holliger et al., 1993, Proc Natl Acad Sci USA 90:6444-6448) or as "Janusins" (Traunecker et al., 1991, EMBO J. 10:3655-3659 and Traunecker, et al., 1992, Int. J. Cancer Suppl. 7:51-52).

Antigen binding proteins of the present invention include antibody fragments of the anti-CMV antibodies disclosed herein. The antibody fragments include $F(ab)_2$ fragments, which may be produced by enzymatic cleavage of an IgG by, for example, pepsin. Fab fragments may be produced by, for example, reduction of $F(ab)_2$ with dithiothreitol or mercaptoethylamine. A Fab fragment is a $V_L$—$C_L$ chain appended to a $V_H$-$C_H1$ chain by a disulfide bridge. A $F(ab)_2$ fragment is two Fab fragments which, in turn, are appended by two disulfide bridges. The Fab portion of an $F(ab)_2$ molecule includes a portion of the F, region between which disulfide bridges are located. An Fv fragment is a $V_L$ or $V_H$ region.

In some embodiments, different constant domains may be appended to humanized $V_L$ and $V_H$ regions derived from the CDRs provided herein. For example, if a particular intended use of an antigen binding protein of the present invention were to call for altered effector functions, a heavy chain constant domain other than human IgG1 may be used, or hybrid IgG1/IgG4 may be utilized.

Although human IgG1 antibodies provide for long half-life and for effector functions, such as complement activation and antibody-dependent cellular cytotoxicity, such activities may not be desirable for all uses of the antibody. In such instances a human IgG4 constant domain, for example, may be used. In one embodiment, the IgG4 constant domain can differ from the native human IgG4 constant domain (Swiss-Prot Accession No. P01861.1) at a position corresponding to position 228 in the EU system and position 241 in the KABAT system, where the native Ser108 is replaced with Pro, in order to prevent a potential inter-chain disulfide bond between Cys106 and Cys109 (corresponding to positions Cys 226 and Cys 229 in the EU system and positions Cys 239 and Cys 242 in the KABAT system) that could interfere with proper intra-chain disulfide bond formation. See Angal et al. (1993) *Mol. Imunol.* 30:105. In other instances, a modified IgG1 constant domain which has been modified to increase half-life or reduce effector function can be used.

Antigen Binding Protein Engineering

Further included are embodiments in which the anti-CMV antigen binding proteins are engineered to include modifications to framework residues within the variable domains of a parental antigen binding proteins, e.g. to improve the properties of the antigen binding proteins. Typically such framework modifications are made to decrease the immunogenicity of the antigen binding protein. In some cases it is desirable to increase the affinity, or alter the specificity of an engineered antigen binding protein. One approach is to "backmutate" one or more framework residues to the corresponding germline sequence.

More specifically, an antigen binding protein that has undergone somatic mutation can contain framework residues that differ from the germline sequence from which the antigen binding protein is derived. Such residues can be identified by comparing the framework sequences to the germline sequences from which the antigen binding protein is derived. Another approach is to revert to the original parental residue at one or more positions of the engineered antigen binding protein, e.g. to restore binding affinity that may have been lost in the process of replacing the framework residues. See, e.g., U.S. Pat. Nos. 5,693,762, 5,585,089 and 5,530,101. Other mutations may be introduced into the antibody sequence to increase the recombinant expression level in the desired host cell, e.g. to increase expression in CHO cells.

Additionally, the PCR primers used in the direct cloning of antibody encoding genes from memory B cells may introduce mutations in the frame 1 and 4 regions of both heavy and light chains. The mutations introduced during cloning may compromise the antibodies' binding and neutralization activities, as well as expressibility of the antibodies.

Another type of framework modification involves mutating one or more residues within the framework region, or even within one or more CDR regions, to remove T cell epitopes to thereby reduce the potential immunogenicity of the antigen binding protein. This approach is also referred to as "deimmunization" and is described in further detail in U.S. Pat. No. 7,125,689.

In particular embodiments, it will be desirable to change certain amino acids containing exposed side-chains to another amino acid residue in order to provide for greater chemical stability of the final antigen binding protein as follows. The deamidation of asparagine may occur on N-G or D-G sequences and result in the creation of an isoaspartic acid residue that introduces a kink into the polypeptide chain and decreases its stability (isoaspartic acid effect). In certain embodiments, the antigen binding proteins of the present disclosure do not contain asparagine isomerism sites.

For example, an asparagine (Asn) residue may be changed to Gln or Ala to reduce the potential for formation of isoaspartate at any Asn-Gly sequences, particularly within a CDR. A similar problem may occur at an Asp-Gly sequence. See Reissner and Aswad, 2003, *Cell. Mol. Life Sci.* 60:1281. Isoaspartate formation may debilitate or completely abrogate binding of an antibody to its target antigen. See, Presta, 2005, *J. Allergy Clin. Immunol.* 116:731. In one embodiment, the asparagine is changed to glutamine (Gln). It may also be desirable to alter an amino acid adjacent to an asparagine (Asn) or glutamine (Gln) residue to reduce the likelihood of deamidation, which occurs at greater rates when small amino acids occur adjacent to asparagine or glutamine. See Bischoff and Kolbe, 1994, *J. Chromatog.* 662:261. In addition, any methionine residues (typically solvent exposed Met) in CDRs may be changed to Lys, Leu, Ala, or Phe in order to reduce the possibility that the methionine sulfur would oxidize, which could reduce antigen binding affinity and also contribute to molecular heterogeneity in the final antibody preparation. Id. In one embodiment, the methionine is changed to alanine (Ala). Additionally, in order to prevent or minimize potential scissile Asn-Pro peptide bonds, it may be desirable to alter any Asn-Pro combinations found in a CDR to Gln-Pro, Ala-Pro, or Asn-Ala. Antigen binding proteins with such substitutions are subsequently screened to ensure that the substitutions do not decrease the affinity or specificity of the antibody for CMV, or other desired biological activity to unacceptable levels.

TABLE 4

Exemplary stabilizing CDR variants

| CDR Residue | Stabilizing Variant Sequence |
|---|---|
| Asn-Gly | Gln-Gly, Ala-Gly, or Asn-Ala |
| (N-G) | (Q-G), (A-G), or (N-A) |
| Asp-Gly | Glu-Gly, Ala-Gly or Asp-Ala |
| (D-G) | (E-G), (A-G), or (D-A) |
| Met (typically solvent exposed) | Lys, Leu, Ala, or Phe |
| (M) | (K), (L), (A), or (F) |
| Asn | Gln or Ala |
| (N) | (Q) or (A) |
| Asn-Pro | Gln-Pro, Ala-Pro, or Asn-Ala |
| (N-P) | (Q-P), (A-P), or (N-A) |

The variations for the $V_H$ and/or $V_L$ CDRs can be independently selected in any combination. Additionally, any variation described herein can be independently selected in any combination, as long as the desired activity or binding ability is maintained.

Engineering of the Fc Region

The antigen binding proteins disclosed herein can also be engineered to include modifications within the Fc region, typically to alter one or more functional properties of the antigen binding protein, such as serum half-life, complement fixation, Fc receptor binding, and/or effector function (e.g., antigen-dependent cellular cytotoxicity). Furthermore, the antigen binding proteins disclosed herein can be chemically modified (e.g., one or more chemical moieties can be attached to the antigen binding protein) or be modified to alter its glycosylation, again to alter one or more functional properties of the antigen binding protein. Each of these embodiments is described in further detail below. The numbering of residues in the Fc region is that of the EU index of Kabat.

The antigen binding proteins disclosed herein also include antigen binding proteins with modified (or blocked) Fc regions to provide altered effector functions. See, e.g., U.S. Pat. No. 5,624,821; and International Patent Application Publication Nos. WO2003/086310; WO2005/120571; and WO2006/0057702. Such modification can be used to enhance or suppress various reactions of the immune system, with possible beneficial effects in diagnosis and therapy. Alterations of the Fc region include amino acid changes (substitutions, deletions and insertions), glycosylation or deglycosylation, and adding multiple Fc. Changes to the Fc can also alter the half-life of antibodies in therapeutic antigen binding proteins, enabling less frequent dosing and thus increased convenience and decreased use of material. See Presta, 2005, *J. Allergy Clin. Immunol.* 116: 731 at 734-35.

In one embodiment, the antigen binding protein is an antibody or fragment thereof of an IgG4 isotype antibody comprising a Serine to Proline mutation at a position corresponding to position 228 (S228P; EU index) in the hinge region of the heavy chain constant region. This mutation has been reported to abolish the heterogeneity of inter-heavy chain disulfide bridges in the hinge region (Angal et al. supra; position 241 is based on the Kabat numbering system).

In one embodiment, the hinge region of CH1 is modified such that the number of cysteine residues in the hinge region is increased or decreased. This approach is described further in U.S. Pat. No. 5,677,425. The number of cysteine residues in the hinge region of CH1 is altered, for example, to facilitate assembly of the light and heavy chains or to increase or decrease the stability of the antibody.

In another embodiment, the antigen binding protein is modified to increase its biological half-life. Various approaches are possible. For example, one or more of the following mutations can be introduced: T252L, T254S, T256F, as described in U.S. Pat. No. 6,277,375. Alternatively, to increase the biological half-life, the antigen binding protein can be altered within the CH1 or CL region to contain a salvage receptor binding epitope taken from two loops of a CH2 domain of an Fc region of an IgG, as described in U.S. Pat. Nos. 5,869,046 and 6,121,022.

In yet other embodiments, the Fc region is altered by replacing at least one amino acid residue with a different amino acid residue to alter the effector function(s) of the antigen binding proteins. For example, one or more amino acids selected from amino acid residues 234, 235, 236, 237, 297, 318, 320 and 322 can be replaced with a different amino acid residue such that the antigen binding protein has an altered affinity for an effector ligand but retains the antigen binding ability of the parent antigen binding protein. The effector ligand to which affinity is altered can be, for example, an Fc receptor or the C1 component of complement. This approach is described in further detail in U.S. Pat. Nos. 5,624,821 and 5,648,260.

In another example, one or more amino acid residues within amino acid positions 231 and 239 are altered to thereby alter the ability of the antigen binding protein to fix complement. This approach is described further in International Patent Application Publication No. WO 94/29351.

In yet another example, the Fc region is modified to increase or decrease the ability of the antigen binding proteins to mediate antibody dependent cellular cytotoxicity (ADCC) and/or to increase or decrease the affinity of the antigen binding proteins for an Fcγ receptor by modifying one or more amino acids at the following positions: 238, 239, 243, 248, 249, 252, 254, 255, 256, 258, 264, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439. This approach is described further in International Patent Application Publication No. WO 00/42072. Moreover, the binding sites on human IgG1 for FcγR1, FcγRII, FcγRIII and FcRn have been mapped and variants with improved binding have been described (see Shields et al., 2001, *J. Biol. Chem.* 276:6591-6604). Specific mutations at positions 256, 290, 298, 333, 334 and 339 were shown to improve binding to FcγRIII. Additionally, the following combination mutants were shown to improve FcγRIII binding: T256A/S298A, S298A/E333A, S298A/K224A and S298A/E333A/K334A.

In one embodiment, the Fc region is modified to decrease the ability of the antigen binding proteins to mediate effector function and/or to increase anti-inflammatory properties by modifying residues 243 and 264. In one embodiment, the Fc region of the antigen binding protein is modified by changing the residues at positions 243 and 264 to alanine. In one embodiment, the Fc region is modified to decrease the ability of the antibody to mediate effector function and/or to increase anti-inflammatory properties by modifying residues 243, 264, 267 and 328.

In still another embodiment, the antigen binding protein comprises a particular glycosylation pattern. For example, an aglycosylated antigen binding protein can be made (i.e., the antigen binding protein lacks glycosylation). The glycosylation pattern of an antigen binding protein may be altered to, for example, increase the affinity or avidity of the antigen binding protein for an antigen. Such modifications can be accomplished by, for example, altering one or more of the glycosylation sites within the antigen binding protein sequence. For example, one or more amino acid substitutions can be made that result removal of one or more of the variable region framework glycosylation sites to thereby eliminate glycosylation at that site. Such aglycosylation may increase the affinity or avidity of the antibody for antigen. See, e.g., U.S. Pat. Nos. 5,714,350 and 6,350,861.

Production of Antibodies with Modified Glycosylation

An antigen binding protein may also be made in which the glycosylation pattern includes hypofucosylated or afucosylated glycans, such as a hypofucosylated antigen binding proteins or afucosylated antigen binding proteins have reduced amounts of fucosyl residues on the glycan. The antigen binding proteins may also include glycans having an increased amount of bisecting GlcNac structures. Such altered glycosylation patterns have been demonstrated to increase the ADCC ability of antigen binding proteins. Such modifications can be accomplished by, for example, expressing the antigen binding proteins in a host cell in which the glycosylation pathway was been genetically engineered to produce glycoproteins with particular glycosylation patterns. These cells have been described in the art and can be used as host cells in which to express recombinant antigen binding proteins of the invention to thereby produce an antigen binding protein with altered glycosylation. For example, the cell lines Ms704, Ms705, and Ms709 lack the fucosyltransferase gene, FUT8 (α (1,6)-fucosyltransferase), such that antigen binding proteins expressed in the Ms704, Ms705, and Ms709 cell lines lack fucose on their carbohydrates. The Ms704, Ms705, and Ms709 FUT8$^{-/-}$ cell lines were created by the targeted disruption of the FUT8 gene in CHO/DG44 cells using two replacement vectors (see U.S. Patent Application Publication No. 20040110704 and Yamane-Ohnuki et al., 2004, *Biotechnol Bioeng* 87:614-22). As another example, European Patent No. EP 1 176 195 describes a cell line with a functionally disrupted FUT8 gene, which encodes a fucosyl transferase, such that antigen binding proteins expressed in such a cell line exhibit hypofucosylation by reducing or eliminating the α-1,6 bond-related enzyme. EP 1 176 195 also describes cell lines which have a low enzyme activity for adding fucose to the N-acetylglucosamine that binds to the Fc region of the antigen binding protein or does not have the enzyme activity, for example the rat myeloma cell line YB2/0 (ATCC CRL 1662). International Patent Application Publication No. WO 03/035835 describes a variant CHO cell line, Lec13 cells, with reduced ability to attach fucose to Asn(297)-linked carbohydrates, also resulting in hypofucosylation of antigen binding proteins expressed in that host cell (see also Shields et al., 2002, *J. Biol. Chem.* 277:26733-26740). Antigen binding proteins with a modified glycosylation profile can also be produced in chicken eggs, as described in International Patent Application Publication No. WO 06/089231. Alternatively, antigen binding proteins with a modified glycosylation profile can be produced in plant cells, such as *Lemna* (U.S. Pat. No. 7,632,983). Methods for production of antigen binding proteins in a plant system are disclosed in the U.S. Pat. Nos. 6,998,267 and 7,388,081. International Patent Application Publication No. WO 99/54342 describes cell lines engineered to express glycoprotein-modifying glycosyl transferases (e.g., β(1,4)-N-acetylglucosaminyl-transferase III (GnTIII)) such that antigen binding proteins expressed in the engineered cell lines exhibit increased bisecting GlcNac structures which results in increased ADCC activity of the antibodies (see also Umana et al., 1999, *Nat. Biotech.* 17:176-180).

Alternatively, the fucose residues of the antigen binding proteins can be cleaved off using a fucosidase enzyme; e.g., the fucosidase α-L-fucosidase removes fucosyl residues from antibodies. See Tarentino et al., 1975, *Biochem.* 14:5516-23.

Antigen binding proteins disclosed herein further include those produced in lower eukaryote host cells, in particular fungal host cells such as yeast and filamentous fungi have been genetically engineered to produce glycoproteins that have mammalian- or human-like glycosylation patterns. See, for example, Choi et al., 2003, *Proc. Natl. Acad. Sci.* 100:5022-5027; Hamilton et al., 2003, *Science* 301:1244-1246; Hamilton et al., 2006, *Science* 313: 1441-1443. A particular advantage of these genetically modified host cells over currently used mammalian cell lines is the ability to control the glycosylation profile of glycoproteins that are produced in the cells such that compositions of glycoproteins can be produced wherein a particular N-glycan structure predominates (see, e.g., U.S. Pat. Nos. 7,029,872 and 7,449,308). These genetically modified host cells have been used to produce antigen binding proteins that have predominantly particular N-glycan structures (see, for example, Li et al., 2006, *Nat. Biotechnol.* 24:210-215).

In addition, since fungi such as yeast or filamentous fungi lack the ability to produce fucosylated glycoproteins, antigen binding proteins produced in such cells will lack fucose unless the cells are further modified to include the enzymatic pathway for producing fucosylated glycoproteins (See, for example, International Patent Application Publication No. WO2008112092).

In particular embodiments, the antigen binding proteins disclosed herein further include those produced in lower eukaryotic host cells and which comprise fucosylated and non-fucosylated hybrid and complex N-glycans, including bisected and multiantennary species, including but not limited to N-glycans such as $GlcNAc_{(1-4)}Man_3GlcNAc_2$; $Gal_{(1-4)}GlcNAc_{(1-4)}Man_3GlcNAc_2$; $NANA_{(1-4)}Gal_{(1-4)}GlcNAc_{(1-4)}Man_3GlcNAc_2$.

In particular embodiments, the antigen binding protein compositions provided herein may comprise antigen binding proteins having at least one hybrid N-glycan selected from the group consisting of $GlcNAcMan_5GlcNAc_2$; $GalGlcNAcMan_5GlcNAc_2$; and $NANAGalGlcNAcMan_5GlcNAc_2$. In particular aspects, the hybrid N-glycan is the predominant N-glycan species in the composition. In further aspects, the hybrid N-glycan is a particular N-glycan species that comprises about 30%, 40%, 50%, 60%, 70%, 80%, 90%, 95%, 97%, 98%, 99%, or 100% of the hybrid N-glycans in the composition.

In particular embodiments, the antigen binding protein compositions provided herein comprise antigen binding proteins having at least one complex N-glycan selected from the group consisting of $GlcNAcMan_3GlcNAc_2$; $GalGlcNAcMan_3GlcNAc_2$; $NANAGalGlcNAcMan_3GlcNAc_2$; $GlcNAc_2Man_3GlcNAc_2$; $GalGlcNAc_2Man_3GlcNAc_2$; $Gal_2GlcNAc_2Man_3GlcNAc_2$; $NANAGal_2GlcNAc_2Man_3GlcNAc_2$; and $NANA_2Gal_2GlcNAc_2Man_3GlcNAc_2$. In particular aspects, the complex N-glycan is the predominant N-glycan species in the composition. In further aspects, the complex N-glycan is a particular N-glycan species that comprises about 30%, 40%, 50%, 60%, 70%, 80%, 90%, 95%, 97%, 98%, 99%, or 100% of the complex N-glycans in the composition.

In particular embodiments, the N-glycan is fusosylated. In general, the fucose is in an α1,3-linkage with the GlcNAc at the reducing end of the N-glycan, an α1,6-linkage with the GlcNAc at the reducing end of the N-glycan, an α1,2-linkage with the Gal at the non-reducing end of the N-glycan, an α1,3-linkage with the GlcNac at the non-reducing end of the N-glycan, or an α1,4-linkage with a GlcNAc at the non-reducing end of the N-glycan.

Therefore, in particular aspects of the above the glycoprotein compositions, the glycoform is in an α1,3-linkage or α1,6-linkage fucose to produce a glycoform selected from the group consisting of $Man_5GlcNAc_2(Fuc)$, $GlcNAcMan_5GlcNAc_2(Fuc)$, $Man_3GlcNAc_2(Fuc)$, $GlcNAcMan_3GlcNAc_2(Fuc)$, $GlcNAc_2Man_3GlcNAc_2(Fuc)$, $GalGlcNAc_2Man_3GlcNAc_2(Fuc)$, $Gal_2GlcNAc_2Man_3GlcNAc_2(Fuc)$, $NANAGal_2GlcNAc_2Man_3GlcNAc_2(Fuc)$, and $NANA_2Gal_2GlcNAc_2Man_3GlcNAc_2(Fuc)$; in an α1,3-linkage or α1,4-linkage fucose to produce a glycoform selected from the group consisting of $GlcNAc(Fuc)Man_5GlcNAc_2$, $GlcNAc(Fuc)Man_3GlcNAc_2$, $GlcNAc_2(Fuc_{1-2})Man_3GlcNAc_2$, $GalGlcNAc_2(Fuc_{1-2})Man_3GlcNAc_2$, $Gal_2GlcNAc_2(Fuc1-2)Man3GlcNAc2$, $NANAGal2GlcNAc2(Fuc_{1-2})Man_3GlcNAc_2$, and $NANA_2Gal_2GlcNAc_2(Fuc_{1-2})Man_3GlcNAc_2$; or in an α1,2-linkage fucose to produce a glycoform selected from the group consisting of $Gal(Fuc)GlcNAc_2Man_3GlcNAc_2$, $Gal_2$ (Fuc$_{1-2}$)GlcNAc$_2$Man$_3$GlcNAc$_2$, NANAGal$_2$(Fuc$_{1-2}$)GlcNAc$_2$Man$_3$GlcNAc$_2$, and NANA$_2$Gal$_2$(Fuc$_{1-2}$)GlcNAc$_2$Man$_3$GlcNAc$_2$.

In further aspects, the antigen binding proteins comprise high mannose N-glycans, including but not limited to, Man$_8$GlcNAc$_2$, Man$_7$GlcNAc$_2$, Man$_6$GlcNAc$_2$, Man$_5$GlcNAc$_2$, Man$_4$GlcNAc$_2$, or N-glycans that consist of the Man$_3$GlcNAc$_2$ N-glycan structure.

In further aspects of the above, the complex N-glycans further include fucosylated and non-fucosylated bisected and multiantennary species.

As used herein, the terms "N-glycan" and "glycoform" are used interchangeably and refer to an N-linked oligosaccharide, for example, one that is attached by an asparagine-N-acetylglucosamine linkage to an asparagine residue of a polypeptide. N-linked glycoproteins contain an N-acetylglucosamine residue linked to the amide nitrogen of an asparagine residue in the protein. The predominant sugars found on glycoproteins are glucose, galactose, mannose, fucose, N-acetylgalactosamine (GalNAc), N-acetylglucosamine (GlcNAc) and sialic acid (e.g., N-acetyl-neuraminic acid (NANA)). The processing of the sugar groups occurs co-translationally in the lumen of the ER and continues post-translationally in the Golgi apparatus for N-linked glycoproteins.

N-glycans have a common pentasaccharide core of Man$_3$GlcNAc$_2$ ("Man" refers to mannose; "Glc" refers to glucose; and "NAc" refers to N-acetyl; GlcNAc refers to N-acetylglucosamine). Usually, N-glycan structures are presented with the non-reducing end to the left and the reducing end to the right. The reducing end of the N-glycan is the end that is attached to the Asn residue comprising the glycosylation site on the protein. N-glycans differ with respect to the number of branches (antennae) comprising peripheral sugars (e.g., GlcNAc, galactose, fucose and sialic acid) that are added to the Man$_3$GlcNAc$_2$ ("Man3") core structure which is also referred to as the "triammnose core", the "pentasaccharide core" or the "paucimannose core". N-glycans are classified according to their branched constituents (e.g., high mannose, complex or hybrid). A "high mannose" type N-glycan has five or more mannose residues. A "complex" type N-glycan typically has at least one GlcNAc attached to the 1,3 mannose arm and at least one GlcNAc attached to the 1,6 mannose arm of a "trimannose" core. Complex N-glycans may also have galactose ("Gal") or N-acetylgalactosamine ("GalNAc") residues that are optionally modified with sialic acid or derivatives (e.g., "NANA" or "NeuAc", where "Neu" refers to neuraminic acid and "Ac" refers to acetyl). Complex N-glycans may also have intrachain substitutions comprising "bisecting" GlcNAc and core fucose ("Fuc"). Complex N-glycans may also have multiple antennae on the "trimannose core," often referred to as "multiple antennary glycans." A "hybrid" N-glycan has at least one GlcNAc on the terminal of the 1,3 mannose arm of the trimannose core and zero or more mannoses on the 1,6 mannose arm of the trimannose core. The various N-glycans are also referred to as "glycoforms."

With respect to complex N-glycans, the terms "G-2", "G-1", "G0", "G1", "G2", "A1", and "A2" mean the following. "G-2" refers to an N-glycan structure that can be characterized as Man$_3$GlcNAc$_2$; the term "G-1" refers to an N-glycan structure that can be characterized as GlcNAcMan$_3$GlcNAc$_2$; the term "G0" refers to an N-glycan structure that can be characterized as GlcNAc$_2$Man$_3$GlcNAc$_2$; the term "G1" refers to an N-glycan structure that can be characterized as GalGlcNAc$_2$Man$_3$GlcNAc$_2$; the term "G2" refers to an N-glycan structure that can be characterized as Gal$_2$GlcNAc$_2$Man$_3$GlcNAc$_2$; the term "A1" refers to an N-glycan structure that can be characterized as NANAGal$_2$GlcNAc$_2$Man$_3$GlcNAc$_2$; and, the term "A2" refers to an N-glycan structure that can be characterized as NANA$_2$Gal$_2$GlcNAc$_2$Man$_3$GlcNAc$_2$. Unless otherwise indicated, the terms G-2", "G-1", "G0", "G1", "G2", "A1", and "A2" refer to N-glycan species that lack fucose attached to the GlcNAc residue at the reducing end of the N-glycan. When the term includes an "F", the "F" indicates that the N-glycan species contains a fucose residue on the GlcNAc residue at the reducing end of the N-glycan. For example, G0F, G1F, G2F, A1F, and A2F all indicate that the N-glycan further includes a fucose residue attached to the GlcNAc residue at the reducing end of the N-glycan. Lower eukaryotes such as yeast and filamentous fungi do not normally produce N-glycans that produce fucose.

With respect to multiantennary N-glycans, the term "multiantennary N-glycan" refers to N-glycans that further comprise a GlcNAc residue on the mannose residue comprising the non-reducing end of the 1,6 arm or the 1,3 arm of the N-glycan or a GlcNAc residue on each of the mannose residues comprising the non-reducing end of the 1,6 arm and the 1,3 arm of the N-glycan. Thus, multiantennary N-glycans can be characterized by the formulas GlcNAc$_{(2-4)}$Man$_3$GlcNAc$_2$, Gal$_{(1-4)}$GlcNAc$_{(2-4)}$Man$_3$GlcNAc$_2$, or NANA$_{(1-4)}$Gal$_{(1-4)}$GlcNAc$_{(2-4)}$Man$_3$GlcNAc$_2$. The term "1-4" refers to 1, 2, 3, or 4 residues.

With respect to bisected N-glycans, the term "bisected N-glycan" refers to N-glycans in which a GlcNAc residue is linked to the mannose residue at the reducing end of the N-glycan. A bisected N-glycan can be characterized by the formula GlcNAc$_3$Man$_3$GlcNAc$_2$ wherein each mannose residue is linked at its non-reducing end to a GlcNAc residue. In contrast, when a multiantennary N-glycan is characterized as GlcNAc$_3$Man$_3$GlcNAc$_2$, the formula indicates that two GlcNAc residues are linked to the mannose residue at the non-reducing end of one of the two arms of the N-glycans and one GlcNAc residue is linked to the mannose residue at the non-reducing end of the other arm of the N-glycan.

Antigen Binding Protein Conjugates

The anti-CMV antigen binding proteins of the invention may also be conjugated to a chemical moiety. The chemical moiety may be, inter alia, a polymer, a radionuclide or a cytotoxic factor. In particular embodiments, the chemical moiety is a polymer which increases the half-life of the antigen binding protein in the body of a subject. Suitable polymers include, but are not limited to, hydrophilic polymers which include but are not limited to polyethylene glycol (PEG) (e.g., PEG with a molecular weight of 2 kDa, 5 kDa, 10 kDa, 12 kDa, 20 kDa, 30 kDa or 40 kDa), dextran and monomethoxypolyethylene glycol (mPEG). Lee et al. (1999, Bioconj. Chem. 10:973-981) disclose PEG conjugated single-chain antibodies. Wen et al. (2001, Bioconj. Chem. 12:545-553) disclose conjugating antibodies with PEG which is attached to a radiometal chelator (diethylenetriaminpentaacetic acid (DTPA)).

The antigen binding proteins disclosed herein may also be conjugated with labels such as $^{99}$Tc, $^{90}$Y, $^{111}$In, $^{32}$P, $^{14}$C, $^{125}$I, $^{3}$H, $^{131}$I, $^{11}$C, $^{15}$O, $^{13}$N, $^{18}$F, $^{35}$S, $^{51}$C, $^{57}$To, $^{226}$Ra, $^{60}$C, $^{59}$Fe, $^{57}$Se, $^{152}$Eu, $^{67}$CU, $^{217}$Ci, $^{211}$At, $^{212}$Pb, $^{47}$Sc, $^{109}$Pd, $^{234}$Th, and $^{40}$K, $^{157}$Gd, $^{55}$Mn, $^{52}$Tr, and $^{56}$Fe.

The antigen binding proteins disclosed herein may also be pegylated, for example to increase its biological (e.g., serum) half-life. To pegylate an antigen binding protein, the antigen binding protein typically is reacted with a reactive form of polyethylene glycol (PEG), such as a reactive ester or aldehyde derivative of PEG, under conditions in which one or more PEG groups become attached to the antigen binding proteins. In particular embodiments, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antigen binding proteins. Methods for pegylating proteins are known in the art and can be applied to the antigen binding proteins of the invention. See, e.g., European Patent Application Nos. EP 0 154 316 and EP 0 401 384.

The antigen binding proteins disclosed herein may also be conjugated with fluorescent or chemiluminescent labels, including fluorophores such as rare earth chelates, fluorescein and its derivatives, rhodamine and its derivatives, isothiocyanate, phycoerythrin, phycocyanin, allophycocyanin, o-phthaldehyde, fluorescamine, $^{152}$Eu, dansyl, umbelliferone, luciferin, luminal label, isoluminal label, an aromatic acridinium ester label, an imidazole label, an acridimium salt label, an oxalate ester label, an aequorin label, 2,3-dihydrophthalazinediones, biotin/avidin, spin labels and stable free radicals.

Any method known in the art for conjugating the antigen binding proteins to the various moieties may be employed, including those methods described by Hunter et al., 1962, *Nature* 144:945; David et al., 1974, *Biochemistry* 13:1014; Pain et al., 1981, *J. Immunol. Meth.* 40:219; and Nygren, 1982, *Histochem. and Cytochem.* 30:407. Methods for conjugating antibodies are conventional and very well known in the art.

Therapeutic Uses of Anti-CMV Antigen Binding Proteins

Further provided are methods for treating subjects, including human subjects, in need of treatment with the isolated antigen binding proteins disclosed herein. Methods of treatment include administering one or more antigen binding proteins of the invention to a subject to provide passive immunity.

A "subject" refers to a mammal capable of being infected with CMV. In a preferred embodiment, the subject is a human. A subject can be treated prophylactically or therapeutically. Prophylactic treatment provides sufficient protective immunity to reduce the likelihood or severity of a CMV infection, including primary infections, recurrent infections (i.e., those resulting from reactivation of latent CMV) and super-infections (i.e., those resulting from an infection with a different stain of CMV than previously experienced by the patient). Therapeutic treatment can be performed to reduce the severity of a CMV infection or decrease the likelihood/severity of a recurrent or super-infection.

As used herein, the phase "passive immunity" refers to the transfer of active humoral immunity in the form of antigen binding proteins. Passive immunity provides immediate protective effect to the patient from the pathogen recognized by the administered antigen binding proteins and/or ameliorates at least one pathology associated with pathogen infection. However, the patient does not develop an immunological memory to the pathogen and therefore must continue to receive the administered antigen binding proteins for protection from the pathogen to persist. In preferred embodiments, monoclonal antibodies, more preferably human or humanized monoclonal antibodies, are administered to a patient to confer passive immunity.

Treatment can be performed using a pharmaceutical composition comprising one or more antigen binding proteins of the invention or fragments thereof. Pharmaceutical compositions can be administered to the general population, especially to those persons at an increased risk of CMV infection (either primary, recurrent or super) or for whom CMV infection would be particularly problematic (such as immunocompromised individuals, transplant patients or pregnant women). In one embodiment, females of childbearing age, especially pregnant women, are administered one or more antigen binding proteins of the invention to decrease the likelihood of CMV infection (either primary, recurrent or super) CMV during pregnancy.

Those in need of treatment include those already with an infection, as well as those prone to have an infection or in which a reduction in the likelihood of infection is desired. Treatment can ameliorate the symptoms of disease associated with CMV infection and/or shorten the length and/or severity of CMV infection, including infection due to reactivation of latent CMV. Persons with an increased risk of CMV infection (either primary, recurrent or super) include patients with weakened immunity or patients facing therapy leading to a weakened immunity (e.g., undergoing chemotherapy or radiation therapy for cancer or taking immunosuppressive drugs). As used herein, "weakened immunity" refers to an immune system that is less capable of battling infections because of an immune response that is not properly functioning or is not functioning at the level of a normal healthy adult. Examples of patients with weakened immunity are patients that are infants, young children, elderly, pregnant or a patient with a disease that affects the function of the immune system such as HIV infection or AIDS.

In particular embodiments, the antigen binding proteins disclosed herein may be used alone, in combination with each other, or in combination with other agents for treating or preventing CMV infection. In particular embodiments, one or more monoclonal antibodies selected from the group consisting of 2-18, 2-25, 1-15, 1-64, 1-85, 1-125, 1-150, 1-175, 1-103, 1-32, 3-7, 3-16, and 3-25 or antigen binding fragments thereof are administered to a subject to treat or prevent CMV infection. In a more particular embodiment, one or more monoclonal antibodies selected from the group consisting of 2-18, 1-85, or 3-25, or antigen binding fragments thereof are administered to a subject to treat or prevent CMV infection.

The one or more anti-CMV antigen binding proteins of the invention may be co-administered with one or other more therapeutic agents including, but not limited to, ganciclovir (GCV), valganciclovir (VGCV), foscarnet (FOS), cidofovir (CDV), and CytoGam® (CSL, Inc. Melbourne, Australia). The antigen binding protein may be linked to the agent (as an immunocomplex) or can be administered separately from the agent. In the latter case (separate administration), the antigen binding protein can be administered before, after or concurrently with the agent or can be co-administered with other known therapies.

"Treat" or "treating" means to administer a therapeutic agent, such as a composition containing any of the antigen binding proteins of the present invention, internally or externally to a subject having a CMV infection, or being suspected of having a CMV infection. Typically, the agent is administered in an amount effective to alleviate one or more symptoms of CMV infection in the treated subject or population, whether by inducing the regression of or inhibiting the progression of such symptom(s) by any clinically measurable degree. The amount of a therapeutic agent that is effective to alleviate any particular disease symptom (also referred to as the "therapeutically effective amount") may vary according to factors such as the infection state, age, and weight of the patient, and the ability of the therapeutic agent to elicit a desired response in the subject. Whether an infection symptom has been alleviated can be assessed by any clinical measurement typically used by physicians or other skilled healthcare providers to assess the severity or progression status of that symptom. While an embodiment of the present invention (e.g., a treatment method or article of manufacture) may not be effective in alleviating the target infection symptom(s) in every subject, it should alleviate the target infection symptom(s) in a statistically significant number of subjects as determined by any statistical test known in the art such as the Student's t-test, the $chi^2$-test, the U-test according to Mann and Whitney, the Kruskal-Wallis test (H-test), Jonckheere-Terpstra-test and the Wilcoxon-test.

Experimental and Diagnostic Uses

The antigen binding proteins disclosed herein may be used as affinity purification agents. In this process, the antigen binding proteins are immobilized on a solid phase such a Sephadex resin or filter paper, using methods well known in the art. The immobilized antigen binding protein is contacted with a sample containing the CMV to be purified, and thereafter the support is washed with a suitable solvent that will remove substantially all the material in the sample except the CMV, which is bound to the immobilized antigen binding protein. Finally, the support is washed with a solvent which elutes the bound CMV from the column. Such immobilized antibodies form part of the present invention.

Anti-CMV antigen binding proteins disclosed herein may also be useful in diagnostic assays for CMV, e.g., detecting its presence in tissues or serum. Diagnostic assays can use various methods for detection of CMV using the antigen binding proteins of the invention including, but not limited to, ELISA, immunohistochemistry, and Western blots. The antigen binding protein itself can be labeled and therefore detected directly. Alternatively, the antigen binding protein can be bound by a labeled secondary antibody which is then detected.

Purification, diagnostic and detection uses preferably use monoclonal antibodies selected form the group consisting of 2-18, 2-25, 1-15, 1-64, 1-85, 1-125, 1-150, 1-175, 1-103, 1-32, 3-7, 3-16, and 3-25 or antigen binding fragments thereof.

Pharmaceutical Compositions and Administration

The invention also relates to pharmaceutical compositions comprising a therapeutically effective amount of an antigen binding protein as described herein, formulated together with a pharmaceutically acceptable carrier or diluent.

To prepare pharmaceutical or sterile compositions of the anti-CMV antigen binding protein is admixed with a pharmaceutically acceptable carrier or excipient. See, e.g., *Remington's Pharmaceutical Sciences* and *U.S. Pharmacopeia: National Formulary*, Mack Publishing Company, Easton, Pa. (1984). Pharmaceutically acceptable carriers include any and all solvents, dispersion media, isotonic and absorption delaying agents, and the like that are physiologically compatible, i.e. suitable for administration to humans. The carriers can be suitable for intravenous, intramuscular, subcutaneous, parenteral, rectal, spinal, or epidermal administration (e.g., by injection or infusion).

As used herein, the term "pharmaceutically acceptable carrier" refers to a substance, as described above, which is admixed with the antigen binding proteins of the invention that is suitable for administration to humans. In embodiments of the invention, the pharmaceutically acceptable carrier does not occur in nature in the same form, e.g. the substance is man-made, either because it does not exist in nature or the purity and/or sterility of the substance is not the same as the corresponding natural substance. For example, sterile water for injection, which is a sterile, bacteria-free, solute-free preparation of distilled water for injection, does not occur in nature in the same form and is considered a pharmaceutically acceptable carrier. In some embodiments, the pharmaceutical compositions of the invention comprise one or more antigen binding proteins disclosed herein and sterile water for injection. In further embodiments, the pharmaceutically acceptable carrier may be another form of water that is appropriate for pharmaceutical or biological preparations and is not the same as water that occurs in nature, including purified water, water for injection, sterile purified water, and bacteriostatic water for injection.

In additional embodiments, the compositions of the invention include a buffer as a pharmaceutically acceptable carrier. When a buffer is employed, the pH of the buffer is preferably in the range of about 5.5 to about 8.0. In additional embodiments, the pH is about 5.5 to about 7.5, about 5.5 to about 7.0, about 5.5 to about 6.5, about 6.0 to about 8.0, about 6.0 to about 7.5, about 6.0 to about 7.0, about 6.5 to about 7.0, about 6.0 to about 6.5, about 6.0 to about 6.9, about 6.2 to about 6.75, or about 6.0 to about 6.75.

Pharmaceutical compositions typically should be sterile and stable under the conditions of manufacture and storage. Formulations of therapeutic and diagnostic agents may be prepared by mixing with acceptable carriers, excipients, or stabilizers in the form of, e.g., lyophilized powders, slurries, aqueous solutions, suspensions, microemulsions, dispersions, liposomes, or other ordered structure suitable to high antibody concentration (see, e.g., Hardman, et al. (2001) *Goodman and Gilman's The Pharmacological Basis of Therapeutics*, McGraw-Hill, New York, N.Y.; Gennaro (2000) *Remington: The Science and Practice of Pharmacy*, Lippincott, Williams, and Wilkins, New York, N.Y.; Avis, et al. (eds.) (1993) *Pharmaceutical Dosage Forms: Parenteral Medications*, Marcel Dekker, NY; Lieberman, et al. (eds.) (1990) *Pharmaceutical Dosage Forms: Tablets*, Marcel Dekker, NY; Lieberman, et al. (eds.) (1990) *Pharmaceutical Dosage Forms: Disperse Systems*, Marcel Dekker, NY; Weiner and Kotkoskie (2000) *Excipient Toxicity and Safety*, Marcel Dekker, Inc., New York, N.Y.).

Sterile injectable solutions can be prepared by incorporating the active compound (i.e., antibody or antigen binding protein) in the required therapeutically effective amount in an appropriate solvent with one or a combination of ingredients, as required, followed by filtered sterilization. Generally, dispersions are prepared by incorporating the active compound into a sterile vehicle that contains a basic dispersion medium and the required other ingredients. In the case of sterile powders for the preparation of sterile injectable solutions, the useful methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

In one embodiment, anti-CMV antibodies of the present invention or fragments thereof are diluted to an appropriate concentration in a sodium acetate solution pH 5-6, and NaCl or sucrose is added for tonicity. Additional agents, such as polysorbate 20 or polysorbate 80, may be added to enhance stability.

Toxicity and therapeutic efficacy of the antigen binding protein compositions, administered alone or in combination with another agent, can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index ($LD_{50}/ED_{50}$). In particular aspects, antigen binding proteins exhibiting high therapeutic indices are desirable. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration.

In a further embodiment, a composition comprising an antigen binding protein disclosed herein is administered to a subject in accordance with the Physicians' Desk Reference 2003 (Thomson Healthcare; 57th edition (Nov. 1, 2002)).

The mode of administration can vary. Suitable routes of administration include oral, rectal, transmucosal, intestinal, parenteral; intramuscular, subcutaneous, intradermal, intrathecal, direct intraventricular, intravenous, intraperitoneal, intranasal, intraocular, inhalation, insufflation, topical, cutaneous, transdermal, or intra-arterial.

In particular embodiments, the anti-CMV antigen binding protein can be administered by an invasive route such as by injection. In further embodiments of the invention, an anti-CMV antigen binding protein, or pharmaceutical composition thereof, is administered intravenously, subcutaneously, intramuscularly, intraarterially, intra-articularly (e.g. in arthritis joints), intratumorally, or by inhalation, aerosol delivery. Administration by non-invasive routes (e.g., orally; for example, in a pill, capsule or tablet) is also within the scope of the present invention.

Compositions can be administered with medical devices known in the art. For example, a pharmaceutical composition of the invention can be administered by injection with a hypodermic needle, including, e.g., a prefilled syringe or autoinjector.

The pharmaceutical compositions disclosed herein may also be administered with a needleless hypodermic injection device; such as the devices disclosed in U.S. Pat. Nos. 6,620,135; 6,096,002; 5,399,163; 5,383,851; 5,312,335; 5,064,413; 4,941,880; 4,790,824 or 4,596,556.

The pharmaceutical compositions disclosed herein may also be administered by infusion. Examples of well-known implants and modules form administering pharmaceutical compositions include: U.S. Pat. No. 4,487,603, which discloses an implantable micro-infusion pump for dispensing medication at a controlled rate; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments. Many other such implants, delivery systems, and modules are well known to those skilled in the art.

The administration regimen depends on several factors, including the serum or tissue turnover rate of the therapeutic antigen binding protein, the level of symptoms, the immunogenicity of the therapeutic antigen binding protein, and the accessibility of the target cells in the biological matrix. Preferably, the administration regimen delivers sufficient therapeutic antigen binding protein to effect improvement in the target disease state, while simultaneously minimizing undesired side effects. Accordingly, the amount of biologic delivered depends in part on the particular therapeutic antigen binding protein and the severity of the condition being treated. Guidance in selecting appropriate doses of therapeutic antigen binding proteins is available (see, e.g., Wawrzynczak (1996) *Antibody Therapy*, Bios Scientific Pub. Ltd, Oxfordshire, UK; Kresina (ed.) (1991)*Monoclonal Antibodies, Cytokines and Arthritis*, Marcel Dekker, New York, N.Y.; Bach (ed.) (1993) *Monoclonal Antibodies and Peptide Therapy in Autoimmune Diseases*, Marcel Dekker, New York, N.Y.; Baert et al., 2003, *New Engl. J. Med.* 348:601-608; Milgrom et al., 1999, *New Engl. J. Med.* 341:1966-1973; Slamon et al., 2001, *New Engl. J. Med.* 344:783-792; Beniaminovitz et al., 2000, *New Engl. J. Med.* 342:613-619; Ghosh et al., 2003, *New Engl. J. Med.* 348: 24-32; Lipsky et al., 2000, *New Engl. J. Med.* 343:1594-1602).

Determination of the appropriate dose is made by the clinician, e.g., using parameters or factors known or suspected in the art to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced. In general, it is desirable that a biologic that will be used is derived from or designed from the same species as the animal targeted for treatment, thereby minimizing any immune response to the reagent. In the case of human subjects, for example, chimeric, humanized and fully human antigen binding proteins are desirable.

Antigen binding proteins disclosed herein may be provided by continuous infusion, or by doses administered, e.g., daily, 1-7 times per week, weekly, bi-weekly, monthly, bimonthly, quarterly, semiannually, annually etc. Doses may be provided, e.g., intravenously, subcutaneously, topically, orally, nasally, rectally, intramuscular, intracerebrally, intraspinally, or by inhalation. A total weekly dose is generally at least 0.05 µg/kg body weight, more generally at least 0.2 µg/kg, 0.5 µg/kg, 1 µg/kg, 10 µg/kg, 100 µg/kg, 0.25 mg/kg, 1.0 mg/kg, 2.0 mg/kg, 5.0 mg/ml, 10 mg/kg, 25 mg/kg, 50 mg/kg or more (see, e.g., Yang et al., 2003, *New Engl. J. Med.* 349:427-434; Herold et al., 2002, *New Engl. J. Med.* 346:1692-1698; Liu et al., 1999, *J. Neurol. Neurosurg. Psych.* 67:451-456; Portielje et al., 2003, *Cancer Immunol. Immunother.* 52:133-144). Doses may also be provided to achieve a pre-determined target concentration of anti-CMV antigen binding proteins in the subject's serum, such as 0.1, 0.3, 1, 3, 10, 30, 100, 300 µg/ml or more. In other embodiments, an anti-CMV antigen binding protein of the present invention is administered subcutaneously or intravenously, on a weekly, biweekly, "every 4 weeks," monthly, bimonthly, or quarterly basis at 10, 20, 50, 80, 100, 200, 500, 1000 or 2500 mg/subject.

As used herein, "inhibit" or "treat" or "treatment" includes a postponement of development of the symptoms associated with CMV infection and/or a reduction in the severity of the symptoms of CMV infection. The terms further include ameliorating existing uncontrolled or unwanted symptoms, preventing additional symptoms, and ameliorating or preventing the underlying causes of such symptoms. Thus, the terms denote that a beneficial result has been conferred on a vertebrate subject with a CMV infection or with the potential to develop such an infection.

As used herein, the terms "therapeutically effective amount", "therapeutically effective dose" and "effective amount" refer to an amount of an anti-CMV antigen binding protein of the invention that, when administered alone or in combination with an additional therapeutic agent to a cell, tissue, or subject, is effective to cause a measurable improvement in one or more symptoms of a CMV infection or condition or the progression of such an infection. A therapeutically effective dose further refers to that amount of the antigen binding protein sufficient to result in at least partial amelioration of symptoms, e.g., treatment, healing, prevention or amelioration of the relevant medical condition, or an increase in rate of treatment, healing, prevention or amelioration of such conditions. When applied to an individual active ingredient administered alone, a therapeutically effective dose refers to that ingredient alone. When applied to a combination, a therapeutically effective dose refers to combined amounts of the active ingredients that result in the therapeutic effect, whether administered in combination, serially or simultaneously. An effective amount of a therapeutic will result in an improvement of a diagnostic measure or parameter by at least 10%; usually by at least 20%; preferably at least about 30%; more preferably at least 40%, and most preferably by at least 50%. An effective amount can also result in an improvement in a subjective measure in cases where subjective measures are used to assess disease severity. In some embodiments of the invention, an effective amount is an amount sufficient to inhibit CMV replication.

Kits

Also included in the invention are kits including a container comprising an antigen binding protein, antibody or pharmaceutical composition of the invention. The term "container" as used herein refers to a man-made container for holding, storing, or transporting the antigen binding protein, antibody or pharmaceutical composition of the invention, including vials, syringes, cartridges, ampoules, and bottles. Containers can be formed of any material that is suitable for storing pharmaceutical or biologic preparations, i.e. materials that are sterile and non-reactive with the preparation such as glass. The glass container should meet the compendial requirements, e.g. the criteria as defined by the US and European Pharmacopeias (USP and EP) for glass used in pharmaceutical packaging The kits can include one or more other elements including: instructions for use; other reagents, e.g., a label, a therapeutic agent, or an agent useful for chelating, or otherwise coupling, an antibody to a label or therapeutic agent, or other materials for preparing the antibody for administration; pharmaceutically acceptable carriers; and devices or other materials for administration to a subject.

Instructions for use can include instructions for therapeutic application including suggested dosages and/or modes of administration, e.g., in a patient with a symptom of CMV infection. Other instructions can include instructions on coupling of the antibody to a chelator, a label or a therapeutic agent, or for purification of a conjugated antibody, e.g., from unreacted conjugation components.

General Methods

Standard methods in molecular biology are described Sambrook, Fritsch and Maniatis (1982 & 1989 2$^{nd}$ Edition, 2001 3$^{rd}$ Edition) *Molecular Cloning, A Laboratory Manual*, Cold Spring Harbor Laboratory Press, Cold Spring Harbor, N.Y.; Sambrook and Russell (2001) *Molecular Cloning, 3$^{rd}$ ed.*, Cold Spring Harbor Laboratory Press, Cold Spring Harbor, N.Y.; Wu (1993) *Recombinant DNA*, Vol. 217, Academic Press, San Diego, Calif.). Standard methods also appear in Ausbel, et al. (2001) *Current Protocols in Molecular Biology*, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described (Coligan, et al. (2000) *Current Protocols in Protein Science*, Vol. 1, John Wiley and Sons, Inc., New York). Chemical analysis, chemical modification, post-translational modification, production of fusion proteins, glycosylation of proteins are described (see, e.g., Coligan, et al. (2000) *Current Protocols in Protein Science*, Vol. 2, John Wiley and Sons, Inc., New York; Ausubel, et al. (2001) *Current Protocols in Molecular Biology*, Vol. 3, John Wiley and Sons, Inc., NY, NY, pp. 16.0.5-16.22.17; Sigma-Aldrich, Co. (2001) *Products for Life Science Research*, St. Louis, Mo.; pp. 45-89; Amersham Pharmacia Biotech (2001) *BioDirectory*, Piscataway, N.J., pp. 384-391). Production, purification, and fragmentation of polyclonal and monoclonal antibodies are described (Coligan, et al. (2001) *Current Protocols in Immunology*, Vol. 1, John Wiley and Sons, Inc., New York; Harlow and Lane (1999) *Using Antibodies*, Cold Spring Harbor Laboratory Press, Cold Spring Harbor, N.Y.; Harlow and Lane, supra). Standard techniques for characterizing ligand/receptor interactions are available (see, e.g., Coligan, et al. (2001) *Current Protocols in Immunology*, Vol. 4, John Wiley, Inc., New York).

Monoclonal, polyclonal, and humanized antibodies can be prepared (see, e.g., Sheperd and Dean (eds.) (2000) *Monoclonal Antibodies*, Oxford Univ. Press, New York, N.Y.; Kontermann and Dubel (eds.) (2001) *Antibody Engineering*, Springer-Verlag, New York; Harlow and Lane (1988) *Antibodies A Laboratory Manual*, Cold Spring Harbor Laboratory Press, Cold Spring Harbor, N.Y., pp. 139-243; Carpenter, et al. (2000) *J. Immunol.* 165:6205; He, et al. (1998) *J. Immunol.* 160:1029; Tang et al. (1999) *J. Biol. Chem.* 274:27371-27378; Baca et al. (1997) *J. Biol. Chem.* 272:10678-10684; Chothia et al. (1989) *Nature* 342:877-883; Foote and Winter (1992) *J. Mol. Biol.* 224:487-499; U.S. Pat. No. 6,329,511).

An alternative to humanization is to use human antibody libraries displayed on phage or human antibody libraries in transgenic mice (Vaughan et al. (1996) *Nature* Biotechnol. 14:309-314; Barbas (1995) *Nature Medicine* 1:837-839; Mendez et al. (1997) *Nature Genetics* 15:146-156; Hoogenboom and Chames (2000) *Immunol. Today* 21:371-377; Barbas et al. (2001) *Phage Display: A Laboratory Manual*, Cold Spring Harbor Laboratory Press, Cold Spring Harbor, N.Y.; Kay et al. (1996) *Phage Display of Peptides and Proteins: A Laboratory Manual*, Academic Press, San Diego, Calif.; de Bruin et al. (1999) *Nature Biotechnol.* 17:397-399).

Single chain antibodies and diabodies are described (see, e.g., Malecki et al. (2002) *Proc. Natl. Acad. Sci. USA* 99:213-218; Conrath et al. (2001) *J. Biol. Chem.* 276:7346-7350; Desmyter et al. (2001) *J. Biol. Chem.* 276:26285-26290; Hudson and Kortt (1999) *J. Immunol. Methods* 231:177-189; and U.S. Pat. No. 4,946,778). Bifunctional antibodies are provided (see, e.g., Mack, et al. (1995) *Proc. Natl. Acad. Sci. USA* 92:7021-7025; Carter (2001) *J. Immunol. Methods* 248:7-15; Volkel, et al. (2001) *Protein Engineering* 14:815-823; Segal, et al. (2001) *J. Immunol. Meth-*

*ods* 248:1-6; Brennan, et al. (1985) *Science* 229:81-83; Raso, et al. (1997) *J. Biol. Chem.* 272:27623; Morrison (1985) *Science* 229:1202-1207; Traunecker, et al. (1991) *EMBO J.* 10:3655-3659; and U.S. Pat. Nos. 5,932,448, 5,532,210, and 6,129,914).

Bispecific antibodies are also provided (see, e.g., Azzoni et al. (1998) *J. Immunol.* 161:3493; Kita et al. (1999) *J. Immunol.* 162:6901; Merchant et al. (2000) *J. Biol. Chem.* 74:9115; Pandey et al. (2000) *J. Biol. Chem.* 275:38633; Zheng et al. (2001) *J. Biol Chem.* 276:12999; Propst et al. (2000) *J. Immunol.* 165:2214; Long (1999) *Ann. Rev. Immunol.* 17:875).

Purification of antigen is not necessary for the generation of antibodies. Animals can be immunized with cells bearing the antigen of interest. Splenocytes can then be isolated from the immunized animals, and the splenocytes can fused with a myeloma cell line to produce a hybridoma (see, e.g., Meyaard et al. (1997) *Immunity* 7:283-290; Wright et al. (2000) *Immunity* 13:233-242; Preston et al., supra; Kaithamana et al. (1999) *J. Immunol.* 163:5157-5164).

Antibodies can be conjugated, e.g., to small drug molecules, enzymes, liposomes, polyethylene glycol (PEG). Antibodies are useful for therapeutic, diagnostic, kit or other purposes, and include antibodies coupled, e.g., to dyes, radioisotopes, enzymes, or metals, e.g., colloidal gold (see, e.g., Le Doussal et al. (1991) *J. Immunol.* 146:169-175; Gibellini et al. (1998) *J. Immunol.* 160:3891-3898; Hsing and Bishop (1999) *J. Immunol.* 162:2804-2811; Everts et al. (2002) *J. Immunol.* 168:883-889).

Methods for flow cytometry, including fluorescence activated cell sorting (FACS), are available (see, e.g., Owens, et al. (1994) *Flow Cytometry Principles for Clinical Laboratory Practice*, John Wiley and Sons, Hoboken, N.J.; Givan (2001) *Flow Cytometry*, $2^{nd}$ ed.; Wiley-Liss, Hoboken, N.J.; Shapiro (2003) *Practical Flow Cytometry*, John Wiley and Sons, Hoboken, N.J.). Fluorescent reagents suitable for modifying nucleic acids, including nucleic acid primers and probes, polypeptides, and antibodies, for use, e.g., as diagnostic reagents, are available (Molecular Probes (2003) Catalogue, Molecular Probes, Inc., Eugene, Oreg.; Sigma-Aldrich (2003) *Catalogue*, St. Louis, Mo.).

Standard methods of histology of the immune system are described (see, e.g., Muller-Harmelink (ed.) (1986) *Human Thymus: Histopathology and Pathology*, Springer Verlag, New York, N.Y.; Hiatt, et al. (2000) *Color Atlas of Histology*, Lippincott, Williams, and Wilkins, Phila, Pa.; Louis, et al. (2002) *Basic Histology: Text and Atlas*, McGraw-Hill, New York, N.Y.).

Software packages and databases for determining, e.g., antigenic fragments, leader sequences, protein folding, functional domains, glycosylation sites, and sequence alignments, are available (see, e.g., GenBank, Vector NTI® Suite (Informax, Inc, Bethesda, Md.); GCG Wisconsin Package (Accelrys, Inc., San Diego, Calif.); DeCypher® (TimeLogic Corp., Crystal Bay, Nev.); Menne, et al. (2000) *Bioinformatics* 16: 741-742; Menne, et al. (2000) *Bioinformatics Applications Note* 16:741-742; Wren, et al. (2002) *Comput. Methods Programs Biomed.* 68:177-181; von Heijne (1983) *Eur. J. Biochem.* 133:17-21; von Heijne (1986) *Nucleic Acids Res.* 14:4683-4690).

EXAMPLES

Examples are provided below to further illustrate different features of the present invention. The examples also illustrate useful methodology for practicing the invention. These examples do not limit the claimed invention.

Example 1

Isolation of Human Memory B-Cells for Antibody Production in Culture

Antigen-specific antibodies are an essential component of host adaptive immunity to pathogens. Although antibodies in circulation are mostly produced by long-lived plasma cells residing in bone marrow, the immune memory of such adaptive immunity is preserved by antigen-specific memory B-cells in circulation. These memory B-cells harbor antigen-specific immunoglobulin sequences that encode the antigen-specific B-cell receptor (BCR), also called surface IgG (sIgG), on their cell surface. However, these memory B-cells are not producers of the antibodies. They can be activated upon their BCR ligation with the cognate antigen, and can proliferate and differentiate to plasmablast cells, hence becoming antibody-secreting cells (ASCs). The plasmablast cells only appear transiently in circulation, and some may further differentiate to become long lived plasma cells and migrate to bone marrow. Thus, although antigen-specific immunoglobulin genes can be retrieved from circulating memory B-cells, plasmablasts and plasma cells in theory, there are challenges for sampling and identifying such cells in practice (Table 5).

TABLE 5

Sources of human B cells containing antigen-specific IgG genes

| | Properties | Challenges for sampling |
|---|---|---|
| Memory B cells (CD19+, sIgG+, CD27+, sIgM−, sIgD−) | 1. circulating in peripheral blood<br>2. long lived<br>3. with antigen-specific surface IgG | 1. extremely low frequency<br>2. not producing IgG |
| Plasmablast B cells (CD19+, sIgG+, CD27+, CD38+) | 1. circulating in peripheral blood<br>2. transient with short life-span<br>3. producing IgG | 1. need specific antigen boost<br>2. only peak around day 7 post antigen boost |
| Plasma cells (CD19+, CD138+, sIgG−) | 1. residing in bone marrow<br>2. long lived<br>3. producing IgG | 1. difficult to access | sIgG: surface IgG, i.e., B cell receptor (BCR).

Figure 1B:
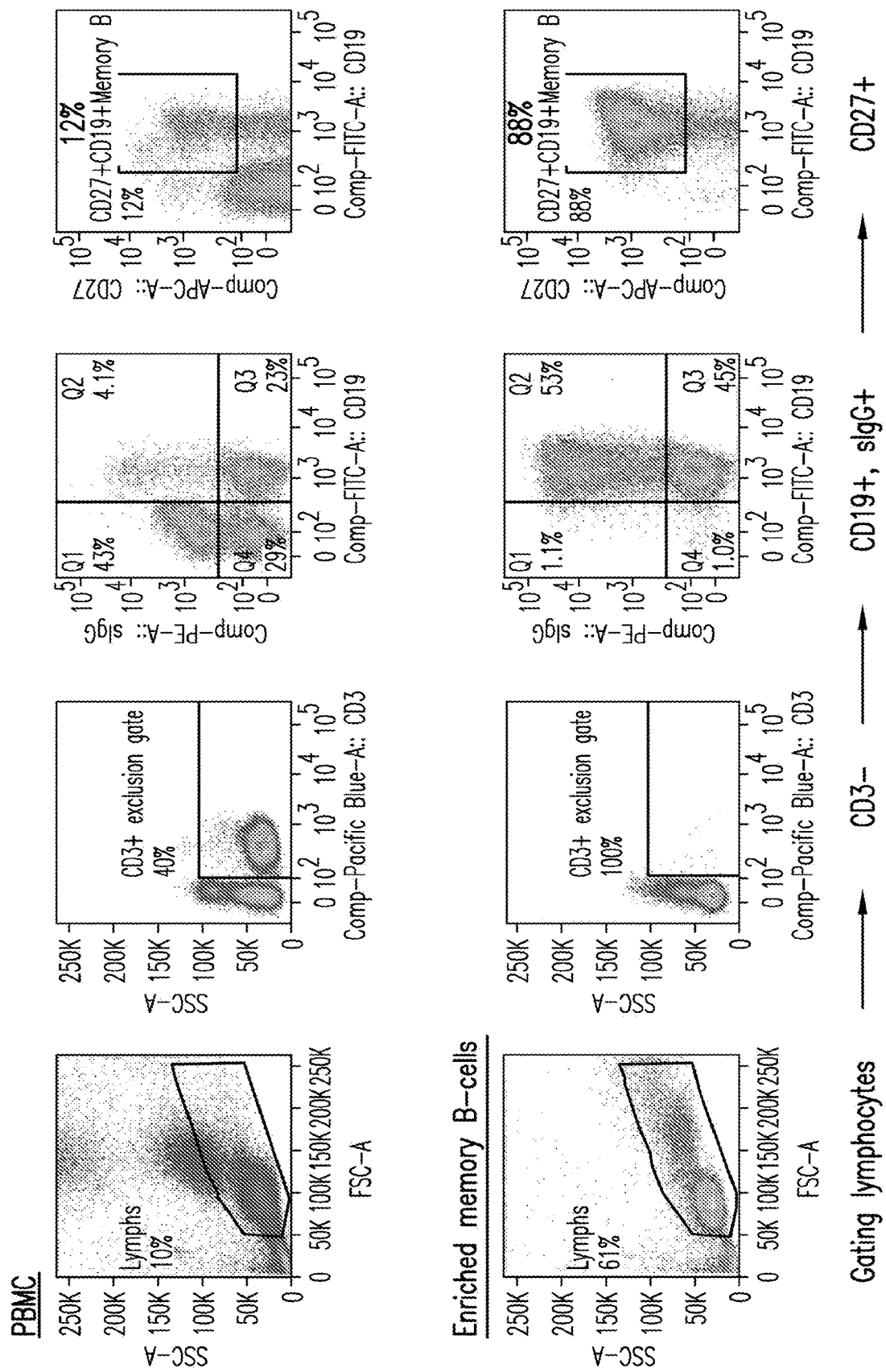
Figure 1C:
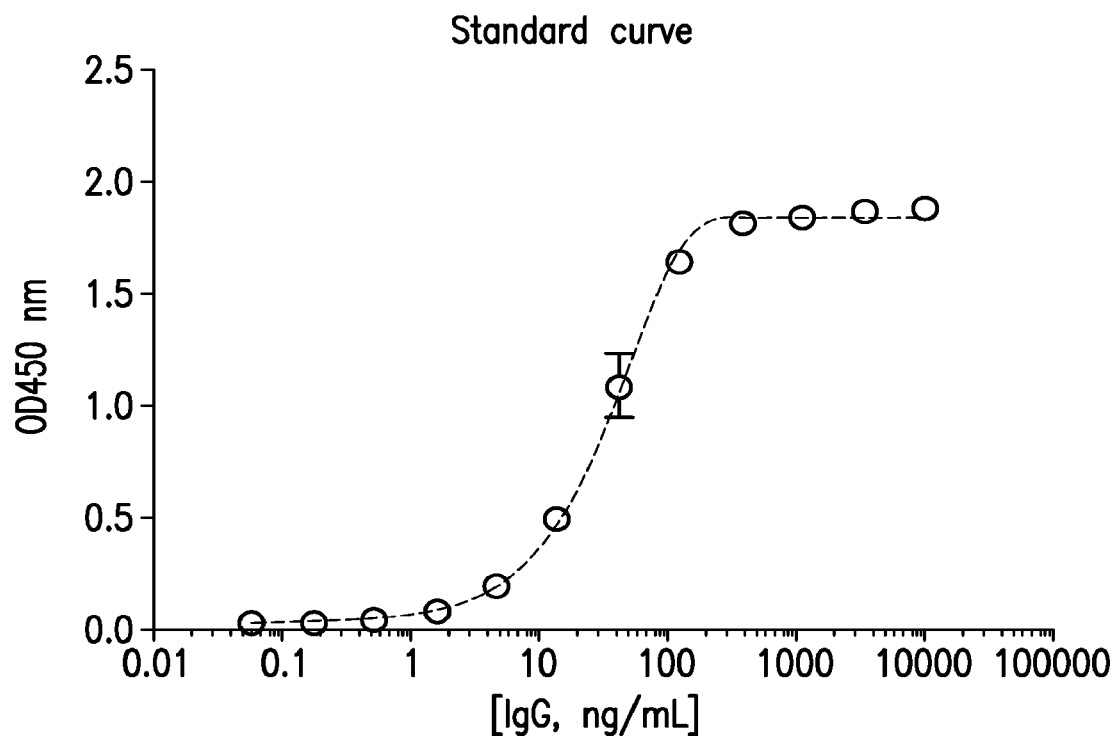
Figure 1D:
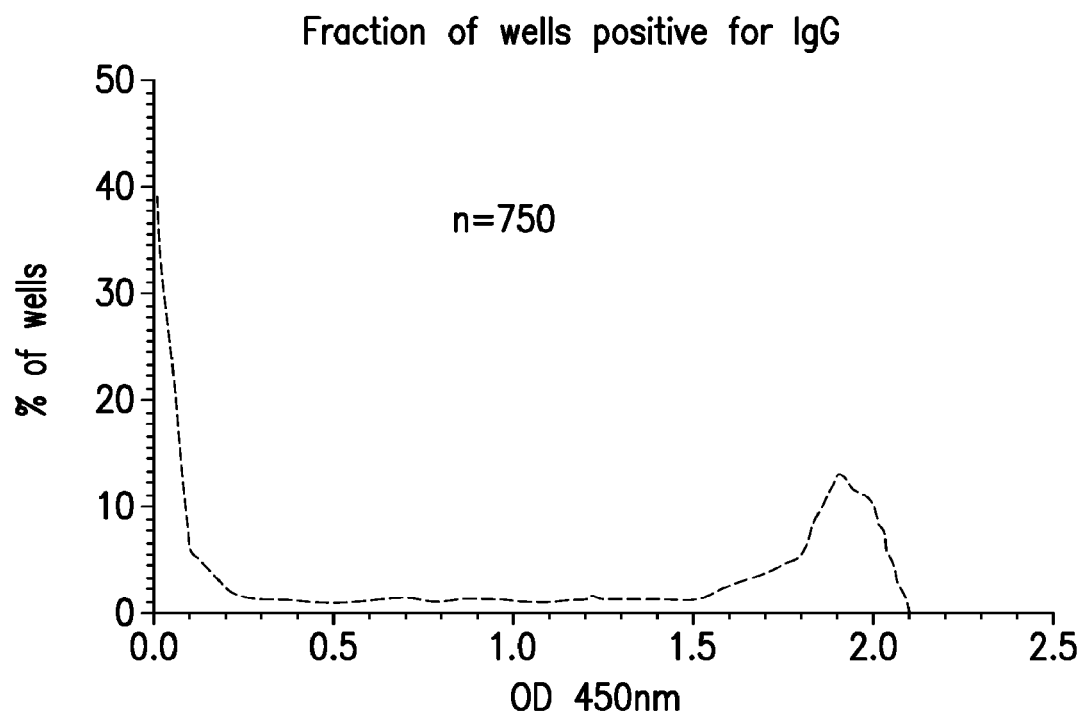

To identify human B-cells harboring immunoglobulin genes specific for CMV, one could isolate and culture memory B-cells enriched from peripheral blood and convert them to ASC, thus enabling screening process to identify the CMV-specific B-cells in culture. The culturing conditions were optimized for driving the memory B-cell differentiation and proliferation in culture. See, e.g., Amanna and Slifka, 2006, *J. Immunol Meth*, 317:175-85; Ettinger et al., 2005, *J. Immunol.* 176:7867-79; Scheid et al., 2009, *Nature*, 458:636-40; Huang et al., 2013, *Nature Protocols* 8:1907-15. To accomplish this, a feeder cell line expressing human CD40L was generated and its continuous expression was confirmed by flow cytometry (FIG. 1A). Memory B cells were isolated from fresh PBMC using a commercial kit (Miltenyi Biotec AG, Germany), designed to enrich memory B-cells through antibody-based selection of their surface markers. The enriched population was confirmed by flow cytometry, with fluorescent-conjugated mAbs for identifying combination of surface markers, including CD19+, surface IgG (sIgG)+, IgD−, IgM−, and CD27+. The purity of memory B cells was in general ~50% (FIG. 1B). The enriched memory B cells were then placed in culture at 0.5-1.5 cells/well, with a cocktail of cytokines, including IL-2 and IL-21, along with gamma-irradiated CD40L feeder cells, for 14-days. The culture supernatant was evaluated in a quantitative ELISA of human IgG (FIG. 1C). Sampling supernatant from multiple 96-well plates for human IgG production showed a binocular distribution of the cultures after 14-days: IgG production approaching 1000 ng/mL was observed in ~15-25% of the culture wells, while little IgG protection was observed in the remaining wells (FIG. 1D).

Example 2

Identification of Human Anti-CMV Antibodies by Screening of Memory B-Cell Cultures Key steps for identification of CMV-specific antibodies from human donors, including memory B-cell isolation, short-term B-cell culture and screening and isolation of immunoglobulin gene and confirmation of antibody activity are summarized in FIG. 2.

Figure 3A:
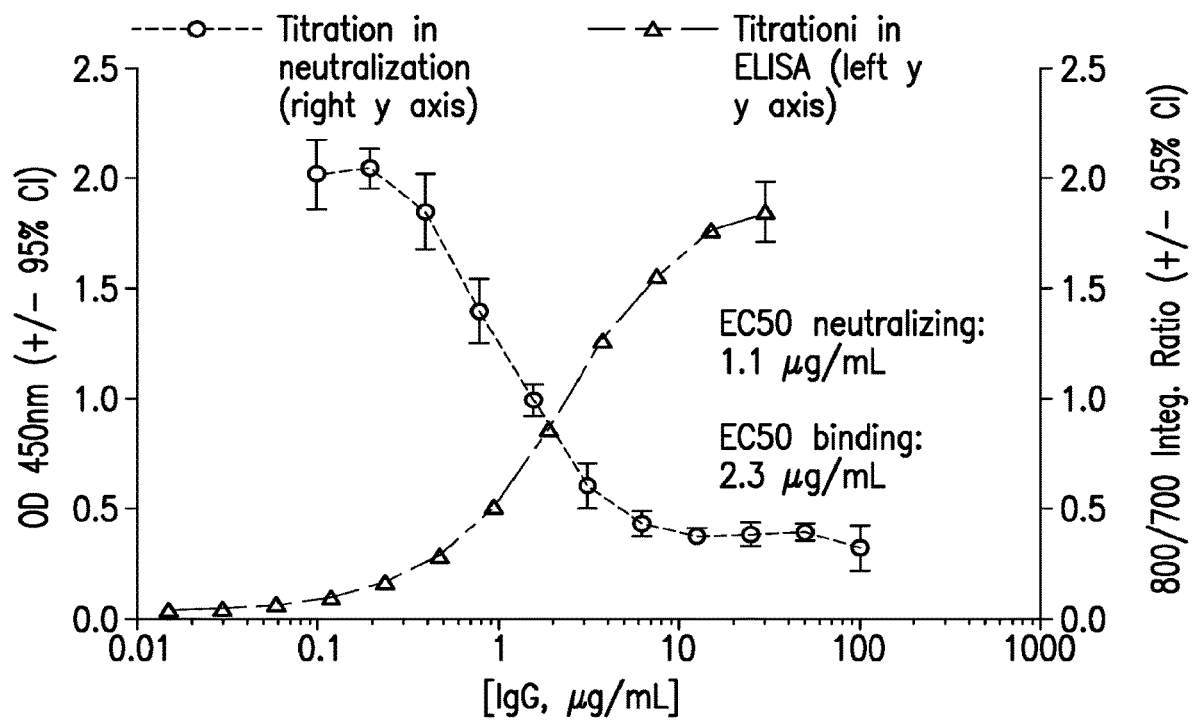
FIG. 3 shows results from assays performed to screen antibody activities towards CMV, including both a virion-binding ELISA and a viral neutralization assay (see Example 4). (A) IgG in titration was used to quantify the antibody's activities. An antibody's ability to bind CMV virion is shown as the binding signal in optical density (lefty-axis) and was proportional to IgG concentration, while the ability of the antibody to neutralize virus is shown as the reduced signal (800/700 Integrated Ratio) of viral immediate early (IE) antigen expression (right y-axis), and is inversely correlated with IgG concentration. Effective concentration to reach 50% of maximal signal in ELISA (EC50 binding) and to inhibit 50% of viral entry (EC50 neutralizing) was calculated through four-parameter curve fitting. Thus, the lower the EC50 values indicate the higher affinity or more potent neutralizing activity for the antibody. (B) For screening, a portion of conditioned medium from the B-cell culture was used in both assays. An example of screening results from donor 1, with 197 wells of B-cell culture supernatant identified as hits is shown. Antibody ability to bind virions in ELISA (x-axis) versus to neutralize virus (y-axis) is plotted. Of these, 182 antibodies showed binding activity but only 9 of these could neutralize virus. Fifteen hits show no binding activity to virions but had neutralizing activity.

Both viral neutralization and virion binding ELISA assays were utilized for screening potential antibody hits after short-term B-cell culture, as described previously. See, e.g., Tang et al., 2011, *Vaccine* 29:8350-6; Freed et al., 2013, *Proc. Natl. Sci. Acad. USA* 110:E4997-5005. The ability of an antibody to bind CMV virion in ELISA was proportional to IgG concentration, and the ability of the antibody to block virus to infect the cells, hence reduction of viral gene expression in these cells, was also correlated with IgG concentration (FIG. 3A). $EC_{50}$ neutralizing and $EC_{50}$ binding, defined as the IgG concentration required to block 50% of viral entry or reach 50% maximal binding signal, respectively, were calculated by four-parameter curve fitting. The lower $EC_{50}$ indicate more potent neutralizing activity or higher binding affinity, respectively. If a monoclonal antibody had poor binding affinity or antiviral activity, or there was no reliable curve fitting with all data points not converging to a typical sigmoid distribution, $EC_{50}$ was arbitrarily assigned a value of 100 µg/mL, indicating poor function of neutralizing or binding to virus.

As an example, B-cell culture and antibody isolation were practiced for three CMV seropositive donors. All were healthy adult volunteers with no previous history of CMV disease. Their neutralizing titers were measured at 13,500 and 6000, 1600 at the sample collection.

The enriched memory B-cells were cultured as described in Example 1, and after 14 days, about 150 µL supernatant from each culture well from each plate was transferred to a new plate, and subsequently used in screening assays for viral neutralization or virion binding in ELISA (see below). The cells in the wells were resuspended in 100 µL RNAlater® solution, and stored at −70° C.

Figure 3B:
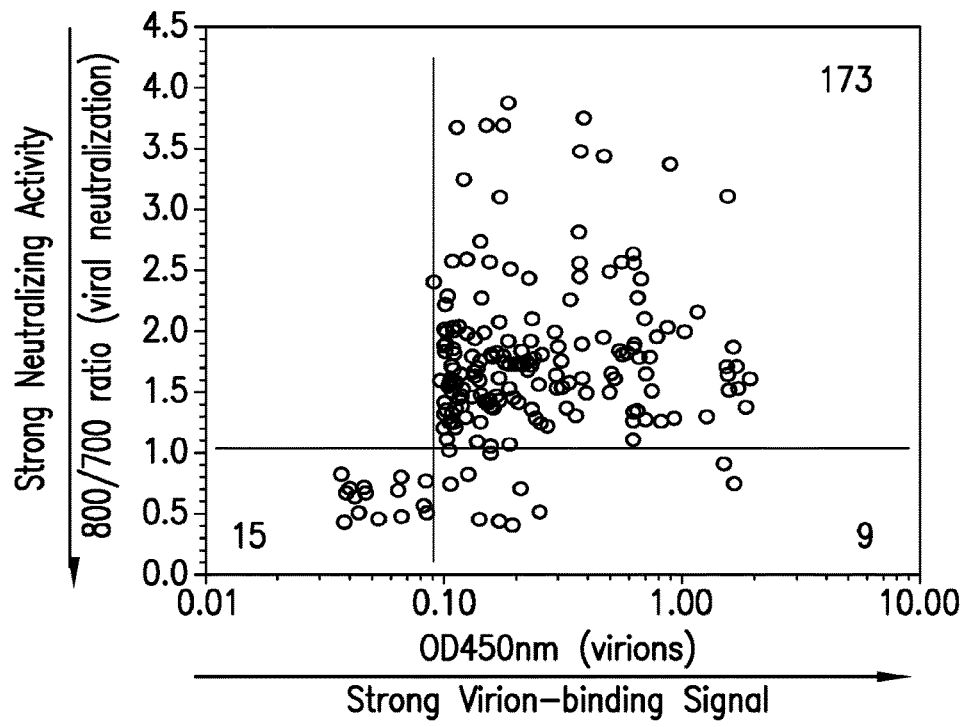

An example for donor 1 is provided in FIG. 3B. Of about 20000 culture wells screened, there were a total of 197 scored hits. Of these hits, 173 showed binding activity to virions in ELISA (OD≥0.1) but with no neutralizing activity (800/700 ratio≥1.0), while 9 hits with both binding and neutralizing activity. Interesting, there were 15 hits showing no binding activity but can neutralize virus. Overall, the neutralizing hits account for ~12% of total hits.

Example 3

Cloning of CMV-Specific Immunoglobulin Genes and Recombinant Expression of Antibodies To isolate immunoglobulin genes, total RNA was extracted from the wells of positive hits, using RNeasy Micro kit (Qiagen, Valencia, Calif.). After reverse transcription with oligo-dT and cDNA synthesis using SuperScript® III First-Strand Synthesis SuperMix kit (Invitrogen, Carlsbad, Calif.), variable region genes were amplified in one round of PCR reaction with $V_H$, $V_\kappa$, $V_\lambda$ family-leader region specific primers and Primestar® GXL polymerase (Clontech, Mountain View, Calif.). PCR products with the expected sizes were extracted using the nucleospin gel extraction kits (Macherey-Nagel, Bethlehem, Pa.), ligated into pCR2.1 TA-clone vectors (Invitrogen, Grand Island, N.Y.), and plated onto S-Gal Amp$^R$ plates for the selection of white colonies. Five colonies per antibody hit were independently picked from multiple colony pools, and each colony was sequenced from both directions using M13R and M13F sequencing primers. Primers used to amplify immunoglobulin variable domains have been described previously (Smith et al., 2009, *Nat Protocols* 4:372-384). Nucleic acid sequences of variable region genes, heavy chain (SEQ ID NOS: 64-76) and light chain (SEQ ID NOS: 77-101), are provided in Tables 7 and 8, respectively.

Immunoglobulin sequences were validated by comparison to closely matched germline V(D)J gene segments using the GenBank IgBLAST tool. Since memory B-cells were manually seeded into 96-well plates for short term culturing, it was possible that more than one B-cell in a single well which would lead to identification of multiple heavy chain or light chain sequences associated with a single antibody hit. A phylogenetic approach was used to identify the dominant cluster of one heavy/one light (1H/1L) for each antibody hit by analyzing the amino acid sequences of entire $V_H/V_L$ regions from five colonies. Since CDR3 regions best represent IgG antibody junction diversity and clonal specificity, the antibodies were analyzed based on their CDR3 length as defined by the IMGT®'s numbering system for V-domains (The International Immunogenetics Information System®, Montpellier Cedex 5, France; Lefranc, et al., IMGT® unique numbering for immunoglobulin and T cell receptor variable domains and Ig superfamily V-like domains, *Dev. Comp. Immunol.*, 27, 55-77 (2003)). The number of amino acid mutations in V region was determined by the criteria of IMGT®. For any antibody hit that multiplicity of heavy and light chains could be resolved through the 1H/1L approach, paired combinations were tested for function after recombinant expression in HEK293 cells.

Antibody variable domain genes were PCR-amplified using $V_H$, $V_\kappa$, $V_\lambda$ frame work region specific primers with 15 bp extensions homologous to the vector ends. The target fragments were isolated by gel extraction and spin-column purification. Cloning reactions were carried out using the In-Fusion® HD cloning kit (Clontech, Mountain View, Calif.). PCR products were ligated into human Igγ1, Igκ or Igλ linearized vectors containing Ig gene signal peptide sequences and the human Igγ1, Igκ or Igλ constant regions, respectively. The IgG cloning vectors were linearized by respective restriction enzyme BmtI and FspI. Stellar competent *E. coli* HST08 bacteria cells (Clontech, Mountain View, Calif.) were transformed at 42° C. with 10 µl of the ligation products. Colonies were sequenced to confirm the identity with the original PCR products. Primers used for cloning and sequencing have been described previously (Smith et al., 2009, *Nat Proto* 4:372-384).

$V_H$ and $V_L$ expression plasmids were transiently co-transfected in HEK293 suspension cells to express recombinant antibodies in 6-well plates. Conditioned media were harvested 3 to 5 days after transfection for functional assays. After confirmation with the conditional media, a total of 23 mAbs from positive recombinant antibodies in neutralization or in binding assay were selected for scale-up expression. Recombinant antibodies were purified with Protein A affinity chromatography (GE Healthcare, Pittsburgh, Pa.). Total IgG concentration was determined by Nanodrop™ (Thermo, Wilmington, Del.). All antibodies were further tested for neutralizing and binding activity to virions according to the methods in Example 4.

Example 4

Functional Characterizations of Recombinantly Expressed Antibodies

Recombinant gB protein (Sino Biologicals, Beijing China) was based on the sequence of Towne strain with its furin-cleavage site mutated and the transmembrane region deleted. See, e.g., Spaete et al., 1990, *J Virol* 64:2922-2931; Spaete, 1991, *Transplant Proc* 23(Suppl 3):90-96). Recombinant pentameric gH complex was expressed in a stable CHO cell line. Its purification and characterization were described previously. See, e.g., Loughney et al., 2015, *J. Biol. Chem.* 290:15985-15995.

Functions of antibodies were tested in ELISA for their relative binding reactivity to selected antigens. Recombinant protein gH complex or gB was immobilized at 2 µg/mL in PBS on 96-well FluoroNunc MaxiSorp™ microtiter plates at 4° C. overnight. Plates were blocked with 3% nonfat milk in PBS/0.05% Tween®20 and incubated with supernatants or purified mAbs in a titration from 0.2 to 30 µg/mL for 1 hr. Virion ELISA was performed to determine all viral antigens including gH and gB complexes. The virions were immobilized from 0.1 to 100 µg/mL in two-fold dilutions on microtiter plates at 4° C. overnight. Plates were blocked as above and then incubated with a fixed antibody concentration of 2 µg/mL. For both assays, plates were washed after antibody incubation and then detected using horseradish peroxidase (HRP) coupled with mouse anti-human IgG at a concentration of 1 µg/ml in PBS with 2 mM EDTA, 0.05% Tween®20 (Southern Biotech, Birmingham, Ala.). After incubation and washing, a fluorogenic HRP substrate, 10-acetyl-3,7-dihroxyphenoxazine (ADHP; Virolabs, Chantilly, Va.) was added to generate resorufin at a concentration proportional to the HRP concentration. Fluorescent signals with excitation at 531 nm were measured with emission at 595 nm in a plate reader (Victor III, Perkin-Elmer, Waltham, Mass.). $EC_{50}$ binding values were calculated from four-parameter curve fitting using Prism® 5.

A viral neutralization assay, based on the enumeration of ARPE-19 or MRC-5 cells expressing viral immediate early (IE) antigen 24 hours post-infection, was described previously (Tang et al., 2011, supra; Wang et al., 2011, Quantitative analysis of neutralizing antibody response to human cytomegalovirus in natural infection. *Vaccine* 29(48): 9075-9080). $EC_{50}$ neutralizing values, defined as IgG concentration required to block 50% viral entry, were calculated from four-parameter curve fitting using Prism® 5 (GraphPad® Software, San Diego, Calif.). All $EC_{50}$ values were obtained through four-parameter curve fitting, and with R-square value greater than 0.9. An arbitrary value of 100 µg/mL was assigned if there was a poor fitting.

Antibodies of 1H1L combinations were based on uniqueness of heavy and light chain sequences. If there were two or more heavy chains or light chains per original well and a unique combination of 1H1L could not be resolved, multiple combinations were tested. The functional combination was scaled up for quantitative analysis. All antibodies were tested for quantitative neutralizing ($EC_{50}$ neutralizing) and binding to virion in ELISA ($EC_{50}$ binding), as summarized in TABLE 6.

TABLE 6

Summary of functional properties for selected antibodies

| Clone ID | $EC_{50}$ Neutralizing (µg/mL) | $EC_{50}$ binding (µg/mL) |
|---|---|---|
| 1-15 | 0.0009 | Not detected |
| 1-32 | 0.02 | Not detected |
| 1-64 | 0.001 | Not detected |
| 1-85 | 0.0009 | Not detected |
| 1-103 | 0.004 | 0.2 |
| 1-125 | 0.0009 | 1.4 |
| 1-150 | 0.001 | Not detected |
| 1-175 | 0.001 | Not detected |
| 2-18 | 0.0009 | 0.09 |
| 2-25 | 0.00009 | Not detected |
| 3-7 | 0.08 | 0.07 |
| 3-16 | 0.09 | 0.1 |
| 3-25 | 0.3 | 0.04 |

Example 5

Majority of the Neutralizing Antibodies Specific to the Pentameric 2H Complex

Figure 4A:
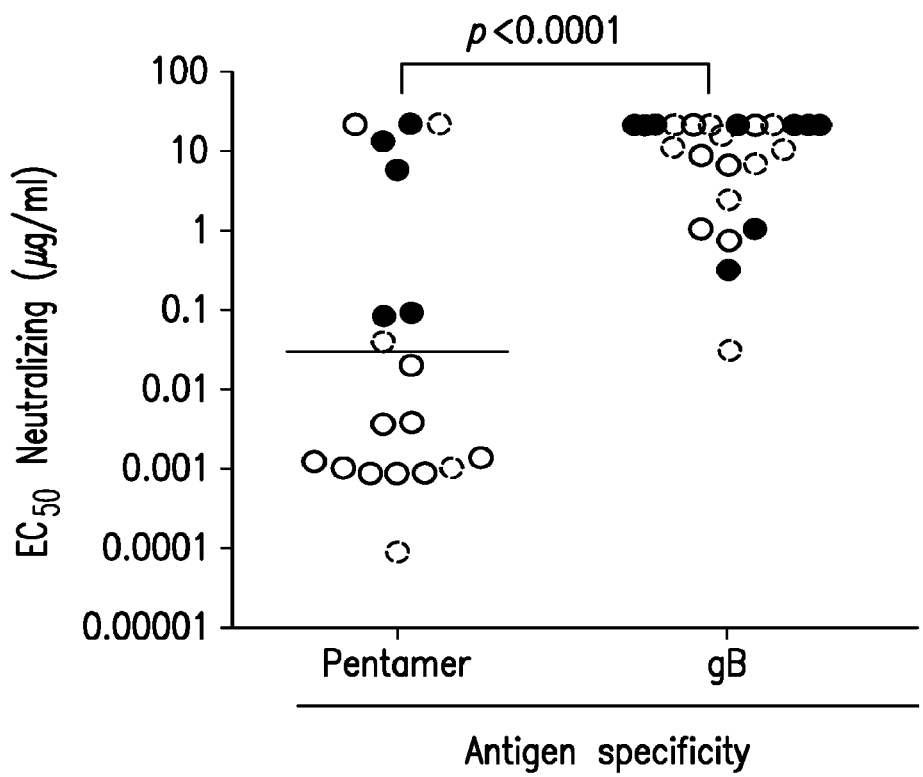
FIG. 4 shows antibodies' functional properties as neutralizing vs. binding to HCMV based on their antigen specificity to the pentamer or gB. The antibodies were tested in an ELISA assay for their reactivity to recombinant gB (Towne strain) and recombinant pentameric gH complex (Towne strain). (A) Antibodies specific for the pentameric gH complex demonstrated strong neutralizing activity in culture but mediocre to weak binding activity to virions in ELISA. (B) Antibodies of gB specificity showed poor neutralizing activity but high binding activity to virions in ELISA.
Figure 4B:
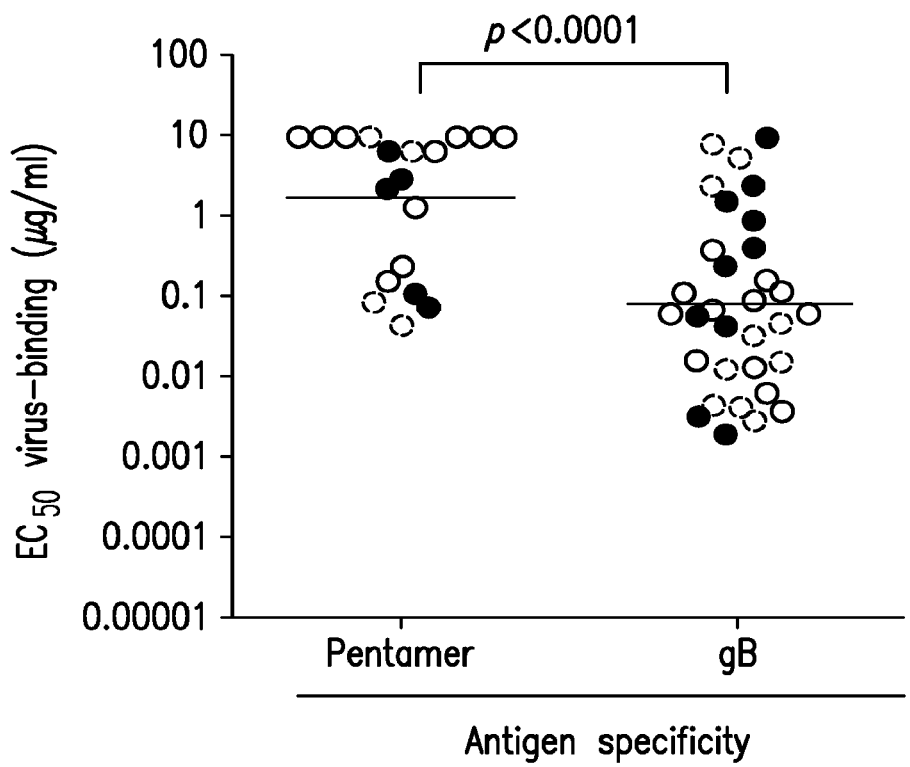

All antibodies including those listed in Table 6 were tested for their reactivity to recombinant pentameric gH complex and recombinant gB, using methods as described previously (Freed et al., 2013, Proc. Natl. Sci. Acad. USA. 110:E4997-5005). The functions of these antibodies to neutralize and bind to virus were plotted based on their antigen specificity to the pentameric gH complex vs. gB (FIG. 4): an antibody's antiviral functions was strongly associated with its specificity to the pentameric gH complex (FIG. 4A); whereas, the antibodies specific for gB was in general poorly neutralizing (FIG. 4B). The geometric means of $EC_{50}$ neutralizing for the pentamer-specific antibodies were 0.03 µg/mL, comparing to 8.5 µg/mL for the gB-specific antibodies. An opposite trend was observed for virus-binding activity, with geometric means of virus-specific $EC_{50}$ binding being 0.08 and 1.7 µg/mL for gB- and pentamer-specific antibodies, respectively (FIG. 4B). Thus, the potent neutralizing antibodies target the pentameric gH complex, not the gB, while the gB-specific antibodies have higher binding affinity to whole virions.

Example 6

Antibody's Neutralizing Activity in Human Fibroblast Cells (MRC-5 Cells)

All antibodies, including those listed in Table 6, were tested for their ability to neutralize in ARPE-19 cells, a human retinal pigment epithelial cell line. Some of the antibodies targeting the pentameric gH complex exhibited poor neutralizing activity against virus infection in human fibroblast cells, such as MRC-5 cells (FIG. 5). This is particularly true for those targeting the portion composed of pUL128-131, also designated as immunogenic region 1 (IR1; see EXAMPLE 10), as all six antibodies listed demonstrated no activity in fibroblast cells. Antibodies targeting the regions other than IR1 of the pentameric gH complex, such as 3-7 and 3-16, and antibodies targeting gB, such as 3-25, 2-48 and 2-59, have shown neutralizing activities in both cell types.

Figure 6A:
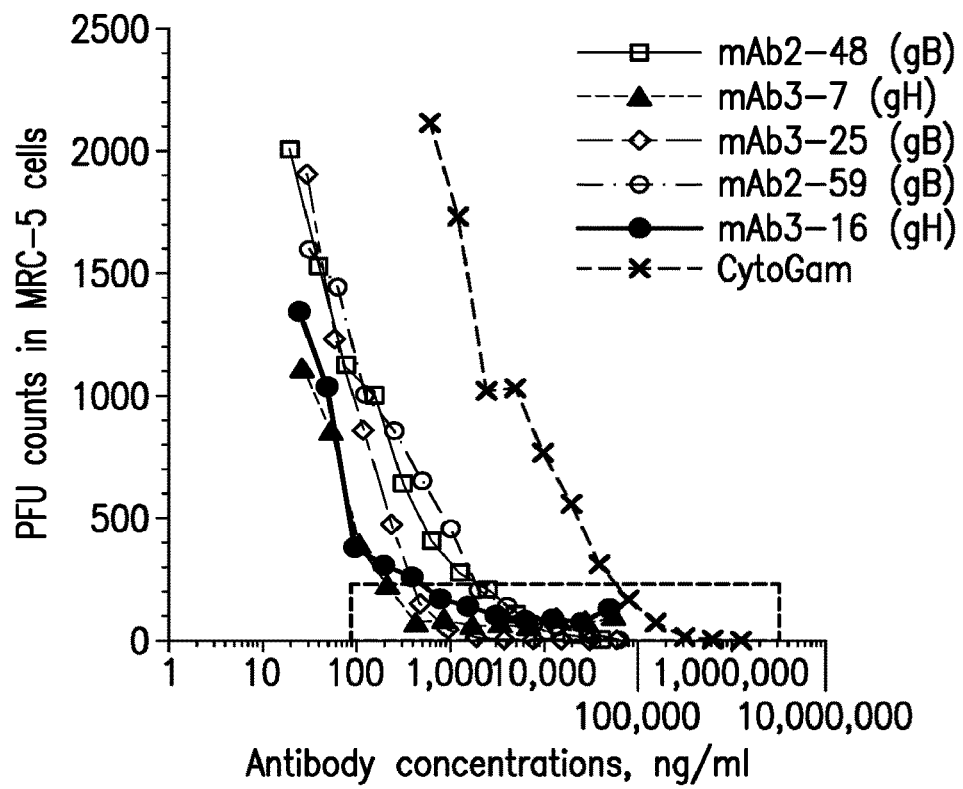
FIG. 6 shows the ability of the gB-specific antibodies, but not the antibodies to the pentameric gH complex, to achieve complete viral inhibition in MRC-5 cells. (A) The potency for the antibodies to the gH complex was comparable to that of the gB antibody. (B) The gB antibodies can eliminate all residual viral infection at the higher concentration, but not those gH antibodies.
Figure 6B:
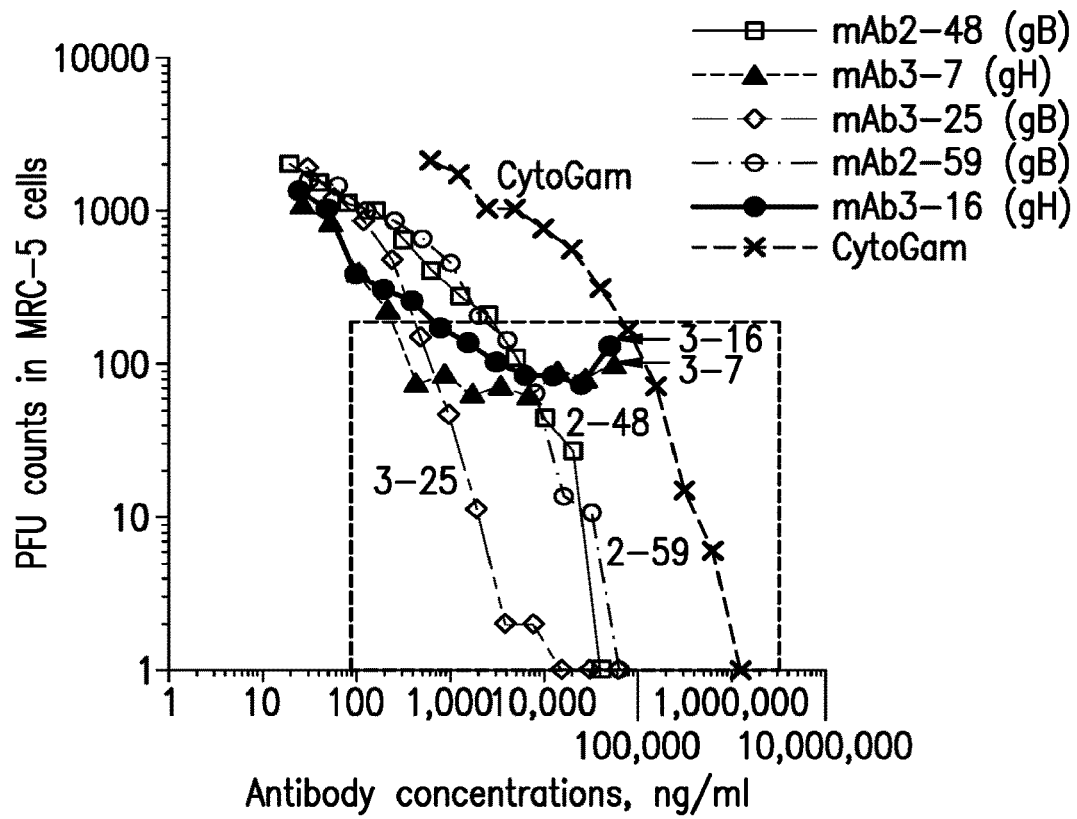

Importantly, antibodies targeting gB can achieve complete inhibition of viral entry in fibroblast cells when compared to the antibodies to the pentamer (FIGS. 6A and 6B). Antibodies 3-7 and 3-16 were potent against viral entry in fibroblast cells, but they cannot eliminate the residual 7-10% viral infection even at high concentration. In contrast, three antibodies to gB were able to achieve complete inhibition of viral entry in fibroblast cells. This result is consistent with the hypothesis that the gB is a potential fusogen for viral entry, and is absolutely required for viral infection of all cell types.

Example 7

Antibody 3-25 Recognizes a Conserved Epitope that has been Previously Reported gB-specific antibodies were evaluated in Western blot against denatured recombinant gB protein. Antibody 3-25 showed strong reactivity to the denatured gB, suggesting it likely recognized a non-conformational epitope. This epitope was mapped by using an array of 15-mer synthetic peptides with 11 amino acids overlap which encompasses the entire open reading frame of the gB (data not shown). The peptides were coated on Nunc-Immuno™ Maxisorb™ plates and the antibody 3-25 was tested for the reactivity in ELISA as detailed in Example 4. Two overlapping peptides were identified with strong signals as antigen substrates for 3-25 binding, and the epitope is confirmed to be site I of antigenic site 2 (AD-2), a highly conserved neutralizing epitope reported previously. See Meyer, Sundqvist et al., 1992, *J. Gen. Virol*, 73:2375-2383.

TABLE 7

Variable Region Gene Sequences-Heavy Chain

| Clone ID | Nucleotide Sequence | SEQ ID NO. | Amino Acid Sequence | SEQ ID NO. |
|---|---|---|---|---|
| 2-18 | GAGGTGCAACTGGTGCAGTCTGGGGGAGGCTTGGTCCAGCCTGGAGGGT CCCTGAGAGTCTCCTGTGCAGCCTCTGGATTCAGCTTCAGTGACCACGA CATGGACTGGGTCCGCCAGGCTCCAGGGAAGGGGTTTGAGTGGGTCGGC CGTAGCAGAAACAAAGATTACAGTTCCACCACAGAATATGCCGCGTCTG TGAGGGGCAGATTCACCATCTCAAGACATACTTCAGAGGATTACTGTA TCTGGAGTTGAACACCGTGAAAACCGAGGACACGGCCGTGTATTTTTGT GCTAGAGGACCTCATCACTCTGATCGGAGTGGTTATTACGGGGGAACTT TTGATATCTGGGGCCAAGGGACCATGGTCACCGTGTCCTCA | 64 | EVQLVQSGGGLVQPGGSLRVSCAASGFS FSDHDMDWVRQAPGKGFEWVGRSRNKDY SSTTEYAASVRGRFTISRHTSEDLLYLE LNTVKTEDTAVYFCARGPHHSDRSGYYG GTFDIWGQGTMVTVSS | 77 |
| 2-25 | CAAGTGCAGCTCGTGGAGTCTGGGGCTGAGGTGAAGAAGCCTGGGGCCT TAGTGAAGGTTTCCTGCAAGGCTTCTGGATACACCTTCACTAACTATGC TATACATTGGGTGCGCCAGGCCTCCGGACAAAGGCTTGAGTGGATGGGA TGGATCAACGCTGGCAGAGGTAACACAAAATATTCACAGAAGTTCCAGG GCAGAGTCACCATTACTAGGGACACATCCGCAGCACAGCCTACATGGA GCTGAGCAGTTTGAGATCTGAGGACGCGGCTGTTTATTTCTGTGCGAGA GATGAGTCAACTGGTGACTACTACTACTACATGGACGTCTGGGGCAAAG GGACCACGGTCACCGTCTCTTCA | 65 | QVQLVESGAEVKKPGALVKVSCKASGYT FTNYAIHWVRQASGQRLEWMGWINAGRG NTKYSQKFQGRVTITRDTSASTAYMELS SLRSEDAAVYFCARDESTGDYYYMDVW GKGTTVTVSS | 78 |
| 1-15 | CAGGTGCAGCTGGTGGCGTCTGGGGGAGGCTTGGTCAAGCCTGGCGGGT CCCTGAGACTCTCCTGTGCAGCCTCTGAATTCACCTTCAGTGACTACTA CATGACCTGGATCCGCCAGGCTCCAGGGAAGGGGCTGGAGTGGGTCTCG TATATTAGTAGTAGTGGTACGACCATATACTACGCCGACTCTGTGAAGG GCCGATTCACCGTCTCCAGGGACAACGCCAAGAACTCACTGTTTCTGCA AATGAACAGCCTGAGAGCCGAGGACACGGCTCTTTATTATTGTGCGAGA GACTCTTATTCGAAGTTGGTGGATATAGAGGCCATCGAAGCTTTTGATA TCTGGGGCCAAGGGACAATGGTCACCGTGTCCTCA | 66 | QVQLVASGGGLVKPGGSLRLSCAASEFT FSDYYMTWIRQAPGKGLEWVSYISSSGT TIYYADSVKGRFTVSRDNAKNSLFLQMN SLRAEDTALYYCARDSYSKLVDIEAIEA FDIWGQGTMVTVSS | 79 |
| 1-64 | CAGGTGCAGCTGGTGGCGTCTGGGGGAGGCTTGGTCAAGCCTGGCGGGT CCCTGAGACTCTCCTGTGCAGCCTCTGGATTCACCTTCAGTGACTACTA CATGACCTGGATCCGCCAGGCTCCAGGGAAGGGGCTGGAGTGGGTCTCG TATATTAGTAGTAGTGGTACGACCATATACTACGCCGACTCTGTGAAGG GCCGATTCACCGTCTCCAGGGACAACGCCAAGAACTCACTGTTTCTGCA AATGAACAGCCTGAGAGCCGAGGACACGGCTCTTTATTATTGTGCGAGA GACTCTTATTCGAAGTTGGTGGATATAGAGGCCATCGAAGCTTTTGATA TCTGGGGCCAAGGGACCATGGTCACCGTGTCCTCA | 67 | QVQLVASGGGLVKPGGSLRLSCAASGFT FSDYYMTWIRQAPGKGLEWVSYISSSGT TIYYADSVKGRFTVSRDNAKNSLFLQMN SLRAEDTALYYCARDSYSKLVDIEAIEA FDIWGQGTMVTVSS | 80 |
| 1-85 | CAGGTGCACCTGGTGGAGTCTGGGGGAGGCTTGGTCAAGCCTGGACGGT CCCTGAGACTCTCCTGTGCAGCCTCTGGATTCACCTTCAGTGACTATTA CATGGCTTGGATCCGCCAAGTTCCGGGGAAGGGGCTGGAGTGGGTTTCA TTCATTAGTAGTAGTGGTCGTACCATCTACTACGCAGACTCTGTGAAGG GCCGATTCACCATCTCCAGGGACAACGCCAAGGACTCACTGTATCTTCA AATGCACAGCCTGAGAGCCGAGGACACGGCTGTTTATTACTGTGCGAGA GATTCTTATTCGAAGTTGGTGGATATAGAGGCCATCGAGGCTTTTGATA TCTGGGGCCAGGGACCATGGTCACCGTGTCCTCA | 68 | QVHLVESGGGLVKPGRSLRLSCAASGFT FSDYYMAWIRQVPGKGLEWVSFISSSGR TIYYADSVKGRFTISRDNAKDSLYLQMH SLRAEDTAVYYCARDSYSKLVDIEAIEA FDIWGRGTMVTVSS | 81 |
| 1-125 | CAGGTGCAGCTGGTGGAATCTGGGGGAGGCTTGGTCAAGCCTGGAGGGT CCCTGAGACTCTCCTGTGCGCCAGCTGGATTCAACTTCAAAGACTACTA CATGACCTGGATCCGCCAGGCTCCAGGAAGGGGCTGGAGTGGGTTTCC TTCATTAGTAGTAGTGGTCAGACCATATACTACGCAGACTCTGTGAAGG GCCGATTCACCATCTCCAGGGACAACGCCAGGAACTCACTGTATCTGCA AATGAATAGCCTGAGAGCCGAGGACACGGCTGTTTATTACTGTGCGAGA | 69 | QVQLVESGGGLVKPGGSLRLSCAPAGFN FKDYYMTWIRQAPGKGLEWVSFISSSGQ TIYYADSVKGRFTISRDNARNSLYLQMN SLRAEDTAVYYCARDSYSKLVDIVAIEA FDLWGQGTLVSVSS | 82 |

TABLE 7-continued

Variable Region Gene Sequences-Heavy Chain

| Clone ID | Nucleotide Sequence | SEQ ID NO. | Amino Acid Sequence | SEQ ID NO. |
|---|---|---|---|---|
| | GACTCTTACTCGAAGTTGGTGGATATAGTGGCCATCGAAGCTTTTGATC TTTGGGGCCAAGGGACACTGGTCAGCGTCTCCTCA | | | |
| 1-150 | CAGGTGCAGCTGGTGGAGTCTGGGGGAGGCCTGGTCAAGCCTGGAGGGT CCCTGAGACTCTCCTGTGCAGCCTCTGGATTCAGCTTCAGTGCCTACTA CATGAGTTGGATCCGCCAGGCTCCAGGGAAGGGGCTGGAGTGGATTTCA TACATTAGTAGTAGTGGTAATACCATATACTACACAGACTCTGTGAAGG GCCGATTCACCATCGCCAGGGACAACGCCAAGAACTCACTTTATCTGCA AATGAACAGCCTGAGAGCCGAGGACACGGGTCTATATTACTGTGCGAGA GATTCTTATTCGAAGTTGGCGGACATAGAGGCCACCGAGGCTTTTGATG TCTGGGGCCAAGGGACAATGGTCGCCGTCTCTTCA | 70 | QVQLVESGGGLVKPGGSLRLSCAASGFS FSAYYMSWIRQAPGKGLEWISYISSSGN TIYYTDSVKGRFTIARDNAKNSLYLQMN SLRAEDTGLYYCARDSYSKLADIEATEA FDVWGQGTMVAVSS | 83 |
| 1-175 | CAGGTGCACCTGGTGGAGTCTGGGGGAGGCTTGGTCAAGCCTGGAGGGT CCCTGAGACTCTCCTGTGCAGCCTCTGGATTCACCTTCAGTGACTATTA CATGGCCTGGATTCGCCGCGCTCCGGGGAAGGGCCTGGAGTGGATTTCA TTCATTAGTGGCAGCGGCCGCACCCTCTACCATGCAGAGTCTGTGAAGG GCCGATTCACCGTCTCCAGGGACAACGCCAAGGACTCACTGTATCTTCA CATGCACAGCCTGAGAGACGCAGACACGGCTGTTTATTACTGTGCGAGA GATTCTTATTCGAAGTTGGTGGAAATAGAGGCCATCGAAGCCTTTGATG TCTGGGGCCGAGGGACAGTGGTCACCGTCTCCTCA | 71 | QVHLVESGGGLVKPGGSLRLSCAASGFT FSDYYMAWIRRAPGKGLEWISFISGSGR TLYHAESVKGRFTVSRDNAKDSLYLHMH SLRDADTAVYYCARDSYSKLVEIEAIEA FDVWGRGTVVTVSS | 84 |
| 1-103 | CAGCTGCAGTTGCAGGAGTCGGGCCCAGGACTGGTGAAGCCTTCGGAGA CCCTGTCCCTCACCTGCTCTGTCTCTGGTGACGCCATCAGCGGCAGCAA TTATTACTGGGGCTGGATACGCCAGCCCCCAGGGAAGGGACTGCAGTGG ATTGGGAGTATCTATCACACTGGGAGCACCTTCTACAACCCGTCATTCA GCAGTCGAGTCACCTTATCCGTAGACACGTCCAAGAACCAGTTCTCCCT GAAGCTGATCTCTGTGAACGCCGCAGACACGGCTGTGTATTATTGTGCA AGACGGATCAGGGGTTATAGTGGGACCTACGACTGGGGCCAGGGAACCC TGGTCACCGTCTCCTCA | 72 | QLQLQESGPGLVKPSETLSLTCSVSGDA ISGSNYYWGWIRQPPGKGLQWIGSIYHT GSTFYNPSFSSRVTLSVDTSKNQFSLKL ISVNAADTAVYYCARRIRGYSGTYDWGQ GTLVTVSS | 85 |
| 1-32 | CAGGTGAAGCTGGTGGAGTCGGGGGAGGCGTGGTCCAGCCTGGGAGGT CCCTGAGACTCTCATGTGCAGGCTCTGGATTCGCCTTTGATAACTACGC TATGCACTGGGTCCGCCAGGCTCCAGGCAAGGGGCTGGAGTGGGTGGCA GTCATATCACTTGAAGGAAGGAATAAATATTACGCAGGCCCCGCGAAGG GCCGGTTCTCCATTTCCAGAGACAACTCCAGAAACACAGTGCATCTGCA AATGAACAGTCTGAGACCTGAGGACACGGCTGTGTATTTCTGTGCGAGA GATATGCGTTACTATTATGATAGTAATGGTCACTATAGGAACCGATATG GCATGGACGTCTGGGGCCAAGGGACCACGGTCATCGTCTCCTCA | 73 | QVKLVESGGGVVQPGRSLRLSCAGSGFA FDNYAMHWVRQAPGKGLEWVAVISLEGR NKYYAGPAKGRFSISRDNSRNTVHLQMN SLRPEDTAVYFCARDMRYYYDSNGHYRN RYGMDVWGQGTTVIVSS | 86 |
| 3-7 | CAGGTGCAGCTGGTGCAGTCTGGAGCTGAGGTGAAGAAGCCTGGGGCCT CAGTGAAGGTCTCCTGTAAGACTTCTGGTTACACCTTTAATACTTATGC TATCAGCTGGGTGCGCCAGGCCCCTGGACAAGGGCTTGAGTGGGTGGGA TGGATCAACACTTACAGTGGAAGCACAAAGTATGCACAGAAGGTCCAGG GCAGAGTCACCATGACCACAGACACATCCACGAGCACCGCCTACATGGA GTTGAGGGGCCTGAGATCTGACGACACGGCCGTATATTACTGTGCGAGA GATGGCTACAATTGGGGTTTTCTCGACTTCTGGGGCCAGGGATCCCTGG TCACCGTCTCCTCA | 74 | QVQLVQSGAEVKKPGASVKVSCKTSGYT FNTYAISWVRQAPGQGLEWVGWINTYSG STKYAQKVQGRVTMTTDISTSTAYMELR GLRSDDTAVYYCARDGYNWGFLDFWGQG SLVTVSS | 87 |
| 3-16 | CAGGTGCAGGTGGTGCAGTCTGGAGCTGAGGTGAAGAAGCCTGGGGCCT CAGTGATGGTCTCCTGCAAGACTTCTGGTTACAGATTTACCATATATAG TATCGCCTGGATGCGCCAGGCCCCGGGACAAGGGCTTGAGTGGATGGGG TCGATCAACACTTACAATGGCAATACAAAGTATGCAGAGAAGTTCCAGG GCAGAGTCACCATGAGTAGAGACACATCCACGAGCACAGCCTACATGGA GGTGAGGAGCCTGGGATCTGCCGACACGGCCATGTATTACTGTGCGAGA GACGCAGAGAACTGGGGATTTTTTGACGACTGGGGCCAGGGGACCCTGG TCACCGTCTCCTCA | 75 | QVQVVQSGAEVKKPGASVMVSCKTSGYR FTIYSIAWMRQAPGQGLEWMGSINTYNG NTKYAEKFQGRVTMSRDTSTSTAYMEVR SLGSADTAMYYCARDAENWGFFDDWGQG TLVTVSS | 88 |
| 3-25 | CAGGTGCAGCTGGTGGAGTCTGGGGGAGGCGTGGTCCAGCCTGGAAGGT CCCTGAGACTCTCCTGTGCAGCCTCTGGATTCACCTTCAGTAACCATGG TCTACACTGGGTCCGCCAGCCTCCAGGCAAGGGGCTGGAGTGGGTGGCA GTTGTATCAAAAGATGGAACCAATGAACACTACGCAGACTCCGTGAGGG GCCGGTTCACCATCTCCAGAGACAATTCCAAGAACACGTTGTATCTGCT AATGAAGAGCCTCAGACTTGAGGACACGGCTGTATATTATTGTGCGAGA GAAGGGTATTGTGGGGATGATCGCTGCTACTCCGGACAGCCTGACTACT GGGGCCAGGGAATCCTGGTCACCGTCTCCTCA | 76 | QVQLVESGGGVVQPGRSLRLSCAASGFT FSNHGLHWVRQPPGKGLEWVAVVSKDGT NEHYADSVRGRFTISRDNSKNTLYLLMK SLRLEDTAVYYCAREGYCGDDRCYSGQP DYWGQGILVTVSS | 89 |

TABLE 8

Variable Region Gene Sequences-Light Chain

| Clone ID | Nucleotide Sequence | SEQ ID NO. | Amino Acid Sequence | SEQ ID NO. |
|---|---|---|---|---|
| 2-18 | GACATCCAGATGACCCAGTCTCCATCTTCCGTGTCTGCATCTGTAGGCGA CAGAGTCATCATCACTTGTCGGGCGAGTCAGGGTATTAGCAGCTGGTTAG CCTGGTATCAGCAGAAACCAGGGAGAGCCCCGAGGCTCCTGATCTATGAT GCCTCCACTTTGGAAAGTGGGGTCCCATCAAGGTTCAGCGGCAGAGGATC TGGGACAGAATTCACTCTCACCATCAACAGCCTGCAGCCTGAAGATTTTG CAACTTACTATTGTCAACAGGGTAACATGTTCCCGCTCACTTTCGGCGGA GGGACCAAGGTGGAAATCAAA | 90 | DIQMTQSPSSVSASVGDRVIITCRA SQGISSWLAWYQQKPGRAPRLLIYD ASTLESGVPSRFSGRGSGTEFTLTI NSLQPEDFATYYCQQGNMFPLTFGG GTKVEIK | 102 |
| 2-25 | TCCTATGAGCTGACTCAGCCACCCTCAGTGTCCGTGTCCCCAGGACAGAC AGCCAGCATCACCTGCTCTGGAGATAGATTGGACGATAAATATGCTTCCT GGTATCAGCAGAAGCCAGGCCAGTCCCCTGTCCTGGTCATCTATCAAGAT AACAAGAGGCCCTCAGGGATCCCTGAGCGATTCTCTGGCTCCAACTCTGG GAACACTGCCACTCTGACCATCAGCGGGACCCAGGCTATGGATGAGGCTG ACTATTATTGTCAGGCGTGGGACAGCGACACGTATGTCTTCGGAACTGGG ACCAAGGTCACCGTCCTA | 91 | SYELTQPPSVSVSPGQTASITCSGD RLDDKYASWYQQKAGQSPVLVIYQD NKRPSGIPERFSGSNSGNTATLTIS GTQAMDEADYYCQAWDSDTYVFGTG TKVTVL | 103 |
| 1-15 | TCCTATGAGCTGACTCAGCCACCCTCAGTGTCAGTGGGCCCGGGAAGGAC GGCCAGGATTACCTGTGGGGCAAACAACATTGGAAGTAAAAGTGTGCACT GGTACCAACAGAGGCCTGGCCAGGCCCCTGTCCTGGTCATCTCTTTTGAT ACCGACCGGCCCTCAGGGATCCCTGAGCGATTCTCTGGCTCCAACTCTGG GAACACGGCCACCCTGACCATCAGCAGGGTCGAAGCCGGGGATGAGGCCG ACTATTTCTGTCAGGTGTGGGATCGTACTAGTGATCATGTGGTGTTCGGC GGAGGGACCAAGCTGACCGTCCTA | 92 | SYELTQPPSVSVGPGRTARITCGAN NIGSKSVHWYQQRPGQAPVLVISFD TDRPSGIPERFSGSNSGNTATLTIS RVEAGDEADYFCQVWDRTSDHVVFG GGTKLTVL | 104 |
| 1-64 | TCCTATGAGCTGACTCAGCCACCCTCAGTGTCAGTGGGCCCGGGAAGGAC GGCCAGGATTACCTGTGGGGCAAACAACATTGGAAGTAAAAGTGTGCACT GGTACCAACAGAGGCCTGGCCAGGCCCCTGTCCTGGTCATCTCTTTTGAT ACCGACCGGCCCTCAGGGATCCCTGAGCGATTCTCTGGCTCCAACTCTGG GAACACGGCCACCCTGACCATCAGCAGGGTCGAAGCCGGGGATGAGGCCG ACTATTTCTGTCAGGTGTGGGATCGTACTAGTGATCATGTGGTGTTCGGC GGAGGGACCAAGCTGACCGTCCTA | 92 | SYELTQPPSVSVGPGRTARITCGAN NIGSKSVHWYQQRPGQAPVLVISFD TDRPSGIPERFSGSNSGNTATLTIS RVEAGDEADYFCQVWDRTSDHVVFG GGTKLTVL | 104 |
| 1-85 | TCCTATGAGCTGGCTCAGCCACCCTCAGTGTCAGTGGCCCCAGGAAAGAC GGCCACGATTGCCTGTGGGGGAGACAATATTGGAGGTAAAAGTGTGCACT GGTACCTTCAGAAGGCAGGCCAGGCCCCTGTATTGGTCATTTCTTATGAC AGCGACCGGCCCTCAGGGATCCCTGAGCGATTCTCTGGCTCCAACTCTGG GAACACGGCCACCCTGACCATCAGCAGGGTCGAAGCCGGTGATGAGGCCG ACTATTTCTGTCAGGTGTGGGATCGTCATGGTGATCATGTGGTCTTCGGC GGAGGGACCAAGCTGACCGTCCTA | 93 | SYELAQPPSVSVAPGKTATIACGGD NIGGKSVHWYLQKAGQAPVLVISYD SDRPSGIPERFSGSNSGNTATLTIS RVEAGDEADYFCQVWDRHGDHVVFG GGTKLTVL | 105 |
| 1-125 | TCCTATGAGCTGACTCAACCACCCTCAGTGTCAGTGGCCCCAGGAAAAAT GGCCAGGATTACCTGTGGCGGAGACAACATTGGAAGTAAAAGTGTGCACT GGTACCAGCAGAGGCCAGGCCAGGCCCCTGTCCTGGTCATCCGTTTTGAT ACCGACCGGCCCTCACGGATCCCTGAGCGATTCTCTGGCTCCAACTCAGG GAACACGGCCACCCTGGCCATCAGCAGGGTCGAAGCCGGGGATGAGGCCG ACTATTACTGTCAGGTGTGGGATTCTAGTAGTGCTCGTTTGGTGTTCGGC GGAGGGACCAAGCTGACCGTCCTA | 94 | SYELTQPPSVSVAPGKMARITCGGD NIGSKSVHWYQQRPGQAPVLVIRFD TDRPSRIPERFSGSNSGNTATLAIS RVEAGDEADYYCQVWDSSSARLVFG GGTKLTVL | 106 |
| 1-150 | TCCTATGAGCTGACTCAGCCTCCCTCAGTGTCAGTGGCCCCAGGAAAGAC GGCCAGGATTACTTGTGGGGGAAACAACATTGGAAGTAAGAGTGTGCACT GGTACCAGCAGAAGCCAGGCCAGGCCCCTGTCATGGTCATCTATTATGAT AGCGACCGGCCCTCAGGGATCCCTGAGCGATTCTCTGGCTCCAACTCTGG GAACACGGCCACTCTGACCATCAGCAGGGTCGAAGCCGGGGATGAGGCCG ACTATTACTGTCAGGTGTGGGATAGTGGTAGTGATCGTGTGGTATTCGGC GGAGGGACCAAGCTGACCGTCCTA | 95 | SYELTQPPSVSVAPGKTARITCGGN NIGSKSVHWYQQKPGQAPVMVIYYD SDRPSGIPERFSGSNSGNTATLTIS RVEAGDEADYYCQVWDSGSDRVVFG GGTKLTVL | 107 |
| 1-175 | TCCTATGAGCTGGCTCAGCCACCCTCAGTGTCAGTGGCCCCAGGAAAGCC GGCCAGGATTGCCTGTGGGGGAGACAACATTGGAGGTAAAAGTGTGCACT GGTACCTTCAGAAGGCAGGCCAGGCCCCTGTCCTGGTCATGTCTTATGAC AGCGACCGGCCCTCAGGGATCCCTGAGCGATTCTCTGGCTCCAACTCTGG CAACACGGCCACCCTGACCATCAGCAGGGTCGAAGCCGGTGAAGGCGG ACTATTTCTGTCAGGTGTGGGATCGTCAAACTGATCATGTGGTCTTCGGC GGAGGGACCAAGCTGACCGTCCTA | 96 | SYELAQPPSVSVAPGKPARIACGGD NIGGKSVHWYLQKAGQAPVLVMSYD SDRPSGIPERFSGSNSGNTATLTIS RVEAGDEGDYFCQVWDRQTDHVVFG GGTKLTVL | 108 |
| 1-103 | GACATCCAGTTGACCCAGTCTCCGTCCTTCCTGTCTGCATCTGTAGGCGA CAGAGTCACCATCACTTGCCGGGCCAGTCAGGACATAAGCAGTTATGTAG CCTGGTATCAGCAAAAACCAGGGAATGCCCCTAAGCTCCTGATCTCTTCT GCATCCACTTTGCCAAGTGGGGTCCCGTCAAGGTTCAGCGGCAGTAGATC TGGGACAGACTTCACTCTCACAATCAGCAGCCTGCAGCCTGAAGATTTTG CAACTTATTACTGTCAACAACTTAATAATTTCGGCCCTGGGACTACAGTG GATATCAAA | 97 | DIQLTQSPSFLSASVGDRVTITCRA SQDISSYVAWYQQKPGNAPKLLISS ASTLPSGVPSRFSGSRSGTDFTLTI SSLQPEDFATYYCQQLNNFGPGTTV DIK | 109 |
| 1-32 | GACATCCAGATGACCCAATCTCCATCCTCCCTGTCTGCGTCTGTAGGAGA CAGCGTCACCATCACTTGCCAGGCGAGTCAGGACATTAATCAGTTTGTAA | 98 | DIQMTQSPSSLSASVGDSVTITCQA SQDINQFVSWYQQKPGKPPKLLIYD | 110 |

TABLE 8-continued

Variable Region Gene Sequences-Light Chain

| Clone ID | Nucleotide Sequence | SEQ ID NO. | Amino Acid Sequence | SEQ ID NO. |
|---|---|---|---|---|
| | GTTGGTATCAACAGAAACCAGGGAAACCCCCTAAACTCCTGATCTACGAT GCTTCCAATTTGGAGTCAGGCGTCCCATCAAGGTTCAGTGGAAGTGGATC TGGGACACATTTTACTTTCACCATCAGCAGCCTGCAGCCCGACGATATTG CGACATATTACTGTCAGCAATATGAAAATCTATTCACTTTCGGCCCTGGG ACCAAAGTGGATATCAAA | | ASNLESGVPSRFSGSGSGTHFTFTI SSLQPDDIATYYCQQYENLFTFGPG TKVDIK | |
| 3-7 | GACATCCAGATGACCCAGTCTCCATCCTCCCTGTCTGCATCTGTAGGAGA CAGAGTCACCATCACTTGCCGGGCGAGTCAGGGCATTAGCAATTATTTAG CCTGGTATCAGCAAAAACCGGGGAAACTTCCTAAGCTCCTGATCTATGCT GCATCCACGTTGCAATCAGGGGTCCCATCTCGGTTCAGTGGCAGTGGATC TGGGACAGATTTCACTCTCACCATCAGCAGCCTGCAGCCTGAAGATGTTG CAAGTTATTACTGTCAAAAGTATAACAGTGCCCCTCTCACTTTCGGCCCT GGGACCAAAGTGGATATCAAA | 99 | DIQMTQSPSSLSASVGDRVTITCRA SQGISNYLAWYQQKPGKLPKLLIYA ASTLQSGVPSRFSGSGSGTDFTLTI SSLQPEDVASYYCQKYNSAPLTFGP GTKVDIK | 111 |
| 3-16 | GAAATTGTGTTGACGCAGTCTCCAGGCACTGTGTCTTTGTCTCCCGGGGA AAGAGTCACCCTCTCCTGCAGGGCCAGTCAGAGTGTCGGCAGACACTTAG CCTGGTACCAGCAGAAACCTGGCCAGCCTCCCAGGCTCCTCATCTATGGT GCATCTACCAGGGCCACTGGCGTCCCAGACAGGTTCAGTGGCAGTGGGTC TGAGACAGAGTTCACTCTCGCCATCAGCAGCCTGCAGTCTGAAGATTTTG CACTTTATTACTGTCAACAATATAATACCTGGCCGTACACTTTTGGCCAG GGGACCAAGCTGGAGATCAAA | 100 | EIVLTQSPGTVSLSPGERVTLSCRA SQSVGRHLAWYQQKPGQPPRLLIYG ASTRATGVPDRFSGSGSETEFTLAI SSLQSEDFALYYCQQYNTWPYTFGQ GTKLEIK | 112 |
| 3-25 | GAAATTGTGTTGACACAGTTTCCAGCCACCCTGTCTTTGTCTCCAGGAGA AAGAGCCACCCTCTCCTGCAGGGCCAGTCAGAGTGTTGGCAGGTACTTGG CCTGGTACCAACAGAAACCTGGCCAGGCTCCCAGGCTCCTCATCTATGAT TCATCCAACAGGGCCACTGGCGTCCCAGCCAGGTTCAGTGGCAGTGGGTC TGGGACAGACTTCACTCTCTCCATCAGCAGCCTGGAGCCTGAAGATTTTG CAGTGTATTTCTGTCAACAGCGTAGCCACTGGCCTCCGCTCACTTTCGGC GGAGGGACCAAGGTGGAAATCAAA | 101 | EIVLTQFPATLSLSPGERATLSCRA SQSVGRYLAWYQQKPGQAPRLLIYD SSNRATGVPARFSGSGSGTDFTLSI SSLEPEDFAVYFCQQRSHWPPLTFG GGTKVEIK | 113 |

Example 8

Biochemical Properties of the Antibodies to the Pentameric 2H Complex

To better understand the antigenic structure of the pentameric gH complex, we characterized a collection of pentamer-specific antibodies (Table 9). Since the pentameric gH complex is composed of five proteins, with the gH/gL as the membrane-bound anchor for the domain formed by pUL128-131, an antibody's specificity to the pentamer vs. the gH/gL dimer could provide the information on its epitope location on the pentamer. If an antibody binds to gH/gL and also the pentamer, its epitope is likely located gH/gL portion of the complex. If an antibody reacts only to the pentamer, its epitope likely is located on the pUL128-131 portion of the complex. Moreover, if the antibody can react to any viral protein of the pentameric gH complex in Western blot analysis, it would suggest that this mAb recognized a nonconformational epitope. Nonconformational epitopes can be mapped using synthetic overlapping peptides as shown in Example 7.

As shown in Table 9 below, seven antibodies were specific to pUL128-131, while nine to the gH/gL scaffold. Four antibodies recognized a viral protein of 125 KDa in Western blot analysis (data not shown), corresponding to the molecular weight of the full length gH. Thus, these antibodies most likely targeting the epitopes at the very N-terminus of gH specifically to AD169rev virus, and the epitopes were not conserved in the recombinant gH/gL or the pentamer which were based on Towne strain sequences.

TABLE 9

Summary of 20 anti-HCMV neutralizing antibodies

| | Ab | Origin | Binding to Towne derived gH/gL | Binding to Towne derived Pentamer | Western Blot (AD169rev as antigen) |
|---|---|---|---|---|---|
| 1 | 2-25 | H | − | + | − |
| 2 | 2-18 | H | − | + | − |
| 3 | 1-85 | H | − | + | − |
| 4 | 1-150 | H | − | + | − |
| 5 | 1-103 | H | − | + | − |
| 6 | 57.4 | R | − | + | − |
| 7 | 276.1 | R | − | + | − |
| 8 | 1-32 | H | + | + | − |
| 9 | 70.7 | R | + | + | − |
| 10 | 124.4 | R | + | + | − |
| 11 | 270.7 | R | + | + | − |
| 12 | 316.2 | R | + | + | − |
| 13 | 324.4 | R | + | + | − |
| 14 | 3-7 | H | + | + | − |
| 15 | 3-15 | H | + | + | − |
| 16 | 3-16 | H | + | + | − |
| 17 | 15.1 | R | − | − | + |
| 18 | 58.5 | R | − | − | + |
| 19 | 223.4 | R | − | − | + |
| 20 | 347.3 | R | − | − | + |

H: antibodies isolated from healthy human individuals with natural CMV infection
R: antibodies isolated from a rabbit immunized with AD169rev vaccine (see Freed et al., 2013, Proc. Natl. Acad. Sci. USA 110: E4997-E5005)

Example 9

Identification of the N-Terminal Linear Epitope of gH

To further map the epitopes, two peptides corresponding to amino acids 26 to 43 of the gH from the AD169 and Towne strains, respectively, were synthesized. Rabbit antibodies, 15.1, 58.5, 223.4, and 347.3, previously shown to neutralize AD169rev (see Freed et al., 2013, Proc. Natl. Acad. Sci. USA 110:E4997-E5005) were tested for reactivity to these peptides in ELISA as detailed in Example 4.

The rabbit antibodies 15.1, 58.5, 223.4, and 347.3 showed strong binding to the AD169 gH peptide but not to the Towne peptide, confirming that this group of antibodies recognizes the linear epitope of AD169 gH (amino acids 26-43) (data not shown).

Example 10

Identification of Seven Conformational Epitopes (Sites) of 2H

To map the immunogenic sites of the gH antibodies, biolayer interferometry was used to compare the bindings between each pair of antibodies. A competition assay was performed on an Octet® HTX using NTA Biosensors (ForteBio, Menlo Park, Calif.). Antibodies were diluted to 15 μg/mL in PBS and were placed into 384 tilted-bottom microplates. All biosensors were rehydrated with PBS for at least 10 minutes, loaded with recombinant HIS-tagged pentamer at 5 μg/mL in PBS for 900 seconds, then washed in PBS for 60 seconds. A group of 16 biosensors were then loaded for 2000 seconds with either PBS as control or a first antibody (antibody 1) at 15 μg/mL to achieve saturation. The biosensors were then washed in PBS for 60 seconds, transferred to wells containing 16 different second antibodies (antibody 2) to allow 1500 seconds of total binding time. The decrease of the second antibody association in the presence of the first antibody was normalized by the total binding in the absence of the first antibody (PBS control) in order to calculate the percent of competition. If the binding of the second antibody is reduced by ≥70% compared to that without the first antibody, the two antibodies are considered competing. A negative signal indicated that the second antibody binding increased in the presence of the first antibody. This could be caused by the synergetic binding between two independent epitopes or irrelevant antibody-antibody interaction.

The results are shown in Table 10.

and 276.1, site 5 by 1-32, site 6 by rabbit antibodies 70.7, 124.4, 270.7, 316.2, and 324.4, and site 7 by 3-7, 3-15, and 3-16.

No competition is observed between site 1, 2, 3, 4, 6, and 7, suggesting these are non-overlapping immunogenic sites. Site 5 partially overlaps with site 6. Interestingly, the binding of site 5 antibody 1-32 significantly blocks the binding of site 6 antibodies 70.7, 270.7 and 316.2, but not 124.4 and 324.4, suggesting there are subtle epitope differences within site 6. Overall, the pentamer as an antigen is highly immunogenic and it exposes multiple neutralizing epitopes.

Example 11

Positioning Antigenic Sites Based on Electromicroscopy Analysis

Electromicroscopy (EM) analysis was applied to visualize the contact point for each antibody with the pentameric gH complex. Each sample of the recombinant antigen with or without Fab fragment cleaved from the antibody was applied to a layer of continuous carbon supported by nitro-cellulose on a 400-mesh copper grid and stained with uranyl formate. EM was performed using an FEI Tecnai T12 electron microscope, operated at 120 keV equipped with an FRI Eagle 4 k×4 k CCD camera. After identifying at low magnification the suitable target areas for imaging, high magnification images were acquired in tilt pairs (0°, 60°) at a nominal magnification of 67,000×. The images were acquired at a nominal under focus of −2 μm to −1 μm and electron doses of ~25-30 e/$A^2$.

Individual particles were selected using automated picking protocols on both untilted and tilted images. Auto alignment was used to match particles across the tilted image pairs. A reference-free alignment strategy based on the XMIPP processing package was used to separate these particles into classes. RCT geometry was used to reconstruct the 3D structures. The nominal resolution of the 3D maps is ~35-40 Å according to the $FSC_{0.5}$ resolution criterion. The Chimera visualization package was used to produce the surface renderings and to fit X-ray models into the EM maps.

TABLE 10

Summary of pair-wise antibody inhibitions

| Pair-wise | | S1 | | S2 | S3 | S4 | | S5 | S6 | | | | S7 | | |
|---|---|---|---|---|---|---|---|---|---|---|---|---|---|---|---|
| inhibition (%) | | 2-25 | 2-18 | 1-85 | 1-150 | 1-103 | 57.4 | 276.1 | 1-32 | 70.7 | 124.4 | 270.7 | 316.2 | 324.4 | 3-7 | 3-15 | 3-16 |
| Antibody 1 | 2-25 | 104 | 87 | 7 | −17 | −4 | 15 | −25 | 2 | 29 | 1 | −10 | −1 | −4 | 9 | 10 | 6 |
| | 2-18 | 117 | 97 | 10 | 12 | 8 | 8 | −31 | −1 | 6 | −11 | −6 | 3 | −1 | 16 | 15 | 17 |
| | 1-85 | −4 | 14 | 87 | 117 | 27 | 29 | −2 | 16 | 36 | 24 | 27 | 29 | 17 | 27 | 33 | 37 |
| | 1-150 | −22 | −10 | 61 | 104 | 26 | −19 | −12 | −11 | −32 | −22 | −29 | −22 | −12 | 0 | 6 | 2 |
| | 1-103 | −20 | −10 | 6 | −49 | 89 | −4 | −2 | −12 | −31 | −22 | −35 | −28 | −19 | −12 | −7 | −38 |
| | 57.4 | −13 | 14 | 26 | 12 | 29 | 93 | 82 | 41 | 35 | 25 | 17 | 19 | 22 | 8 | 10 | 13 |
| | 276.1 | −32 | −17 | 6 | −17 | 1 | 84 | 92 | 7 | 15 | −5 | −14 | −1 | −7 | 0 | −4 | 3 |
| | 1-32 | −33 | −1 | 18 | 4 | 15 | 57 | −11 | 91 | 87 | 7 | 97 | 78 | 6 | 8 | 7 | 10 |
| | 70.7 | 43 | 36 | 31 | 35 | 23 | 35 | 30 | 64 | 84 | 76 | 99 | 89 | 94 | 27 | 26 | 25 |
| | 124.4 | −2 | 7 | 18 | 6 | 9 | 13 | 4 | 20 | 82 | 94 | 97 | 79 | 96 | 11 | 10 | 8 |
| | 270.7 | 40 | 32 | 26 | 33 | 13 | 28 | 18 | 57 | 72 | 70 | 95 | 78 | 97 | 24 | 23 | 17 |
| | 316.2 | 9 | 23 | 26 | 31 | 20 | 12 | 5 | 59 | 82 | 87 | 109 | 92 | 103 | 18 | 18 | 19 |
| | 324.4 | 43 | 24 | 26 | 37 | 24 | 35 | 30 | 32 | 76 | 78 | 93 | 80 | 94 | 24 | 27 | 29 |
| | 3-7 | 44 | 51 | 35 | −6 | 27 | 20 | 12 | 10 | 38 | 35 | 16 | 21 | 14 | 91 | 102 | 97 |
| | 3-15 | −2 | −12 | 10 | −29 | 7 | 6 | 14 | 1 | −1 | −11 | −3 | 3 | 5 | 81 | 97 | 86 |
| | 3-16 | −21 | −17 | 16 | −22 | 6 | 11 | 18 | −5 | 2 | −1 | −1 | −7 | −5 | 79 | 95 | 88 |

The competition results reveal seven distinct immunogenic sites: site 1 recognized by 2-25 and 2-18, site 2 by 1-85 and 1-150, site 3 by 1-103, site 4 by rabbit antibodies 57.4

Figure 7A:
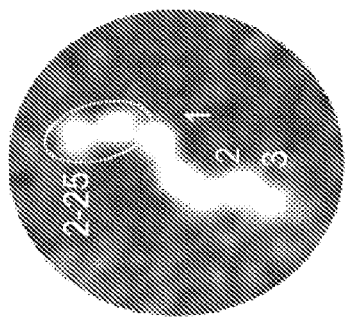
FIG. 7 shows two-dimensional (2D) class averages of the pentameric gH complex, (gH/gL)₂ homodimer, and their complexes with Fab as labeled. (A) EM image of the pentameric gH complex with three domains labeled. (B) The image of a head-to-head dimer of gH/gL complex with domains 2 and 3 as labeled. (C, D) Fab270.7 in complex with (gH/gL)₂ dimer or the pentamer. (E, F, G, H, and I) Fab as indicated in complex with the pentamer. (J) Fab3-16 in complex with (gH/gL)₂ dimer.
Figure 7B:
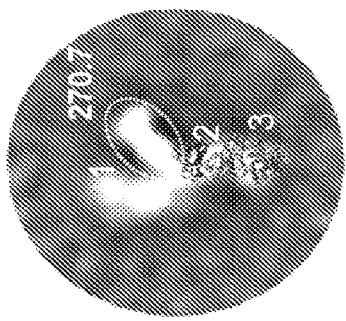
Figure 7C:
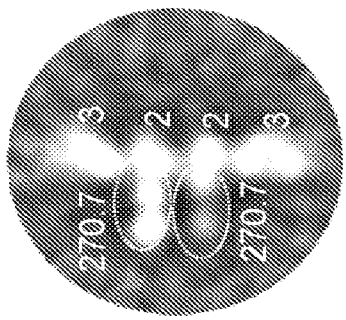
Figure 7D:
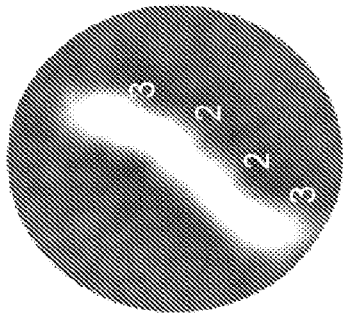
Figure 7E:
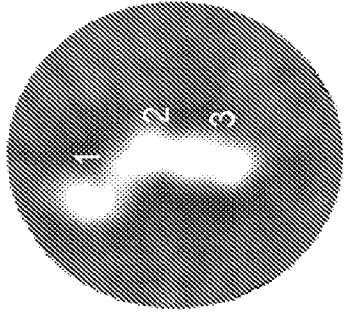
Figure 7F:
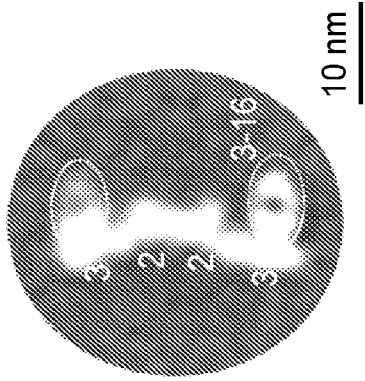
Figure 7G:
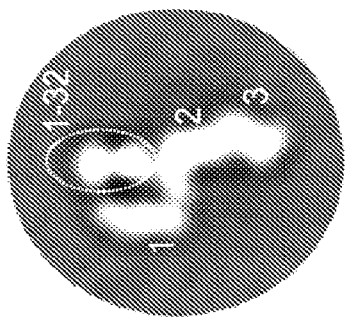
Figure 7H:
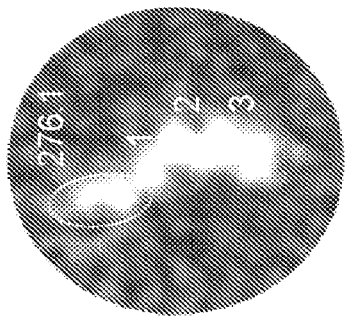

Negative-staining EM 2D class averages illustrate that the free pentamer contains a curved and loosely connected module 1, a smaller inner module 2 (~4 nm length) and a bigger outer module 3 (~7 nm length) (FIG. 7A). The identity of each module is revealed by comparing the binding of Fab 270.7 to either gH/gL or pentamer. Recombinant soluble gH/gL exists predominantly as (gH/gL)$_2$ homodimer, joined by two gL proteins at Cys 144 (FIG. 7B). EM shows that Fab 270.7, appearing as a characteristic 5 nm double-ring, binds (gH/gL)$_2$ at the inner module composed of gL and the N-terminus of gH (FIG. 7C). FIG. 7D shows that Fab 270.7 binds module 2 of the pentamer, suggesting that module 2 is composed of gL and the N-terminus of gH. The structure of EBV gH/gL, which shares 27% sequence homology with HCMV, could be overlaid onto the EM image of the pentamer. The C-terminus of gH fits nicely and only to module 3. This leaves module 1 which is comprised of pUL128-131. Interestingly, Fab 270.7 binds the pentamer at a ~120° angle against the long axis of the gH/gL stalk and ~90° angle to (gH/gL)$_2$. Apparently, Fab 270.7 needs to approach (gH/gL)$_2$ at a different angle in order to spatially accommodate two Fabs binding to one (gH/gL)$_2$ homodimer.

Figure 7I:
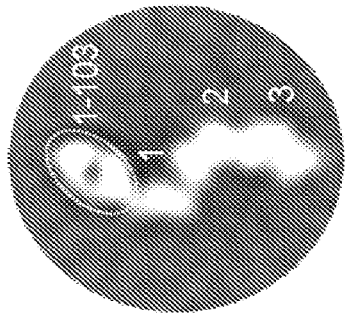
Figure 7J:
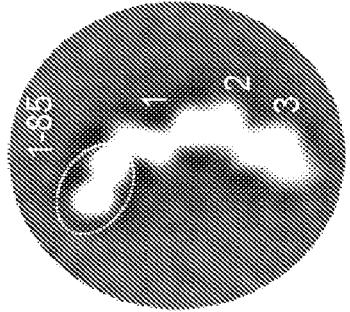

The identification of the three modules of the pentamer facilitated the construction of the spatial map for each immunogenic site on the pentamer. The 2D class averages show that site 1-4 antibodies are directed at the tip of module 1 which comprises pUL128-131 (FIGS. 7E-H). This is consistent with the observation that site 1-4 antibodies bind to pentamer only and not gH/gL (Table 9). Site 5 antibody 1-32 targets the tip of module 2 (FIG. 7I) while site 6 antibody 270.7 targets the side of module 2 (FIG. 7D). Site 7 antibody targets the side of module 3 (FIG. 7J). Since module 2 and 3 are preserved in gH/gL, the 2D images are consistent with the observation that site 5-7 antibodies bind to both pentamer and gH/gL (Table 9).

Figure 8:
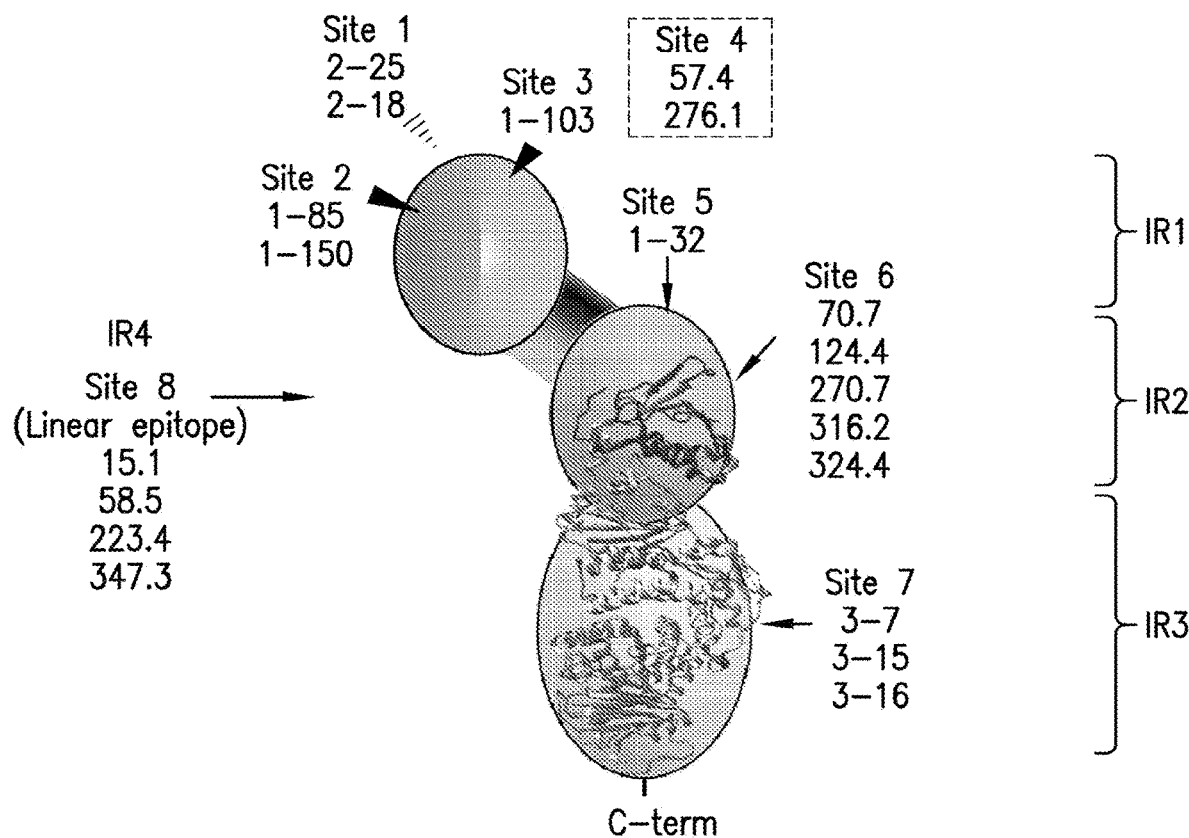
FIG. 8 shows the immunological map for the pentameric gH complex based on antibody mapping and 2D EM analysis. Four immunologenic region (IR) and the eight immunogenic sites along with the representative antibodies are marked. The EBV gH/gL structure is overlaid to IR2 and IR3 domains.

In summary, a total of four immunogenic regions (IR) can be derived from peptide mapping, pair-wise antibody competition, and EM epitope mapping (FIG. 8). IR1 is composed of pUL128, 130, and 131, showing as module 1 in the pentamer EM 2D averages. Four non-overlapping conformational immunogenic sites (sites 1-4) are identified in IR1. A visual comparison with the EM 2D averages published by Ciferri et al. suggests there are likely more sites in IR1. See Ciferri et al., 2015, PLOS Pathogens 11:e1005230. IR2 is composed of gL and the N-terminus of gH, showing as module 2 in the pentamer EM 2D averages. Two partially overlapping conformational immunogenic sites are identified in IR2 (sites 5 and 6). IR3, showing as module 3 in the pentamer 2D averages, consists of the C-terminus of gH and has one conformational immunogenic site (site 7). IR4 resides in the first 40 amino acids of gH and has one linear immunogenic site (site 8).

Example 12

Conservation of Immunogenic Sites Among Different HCMV Strains

Figure 9:
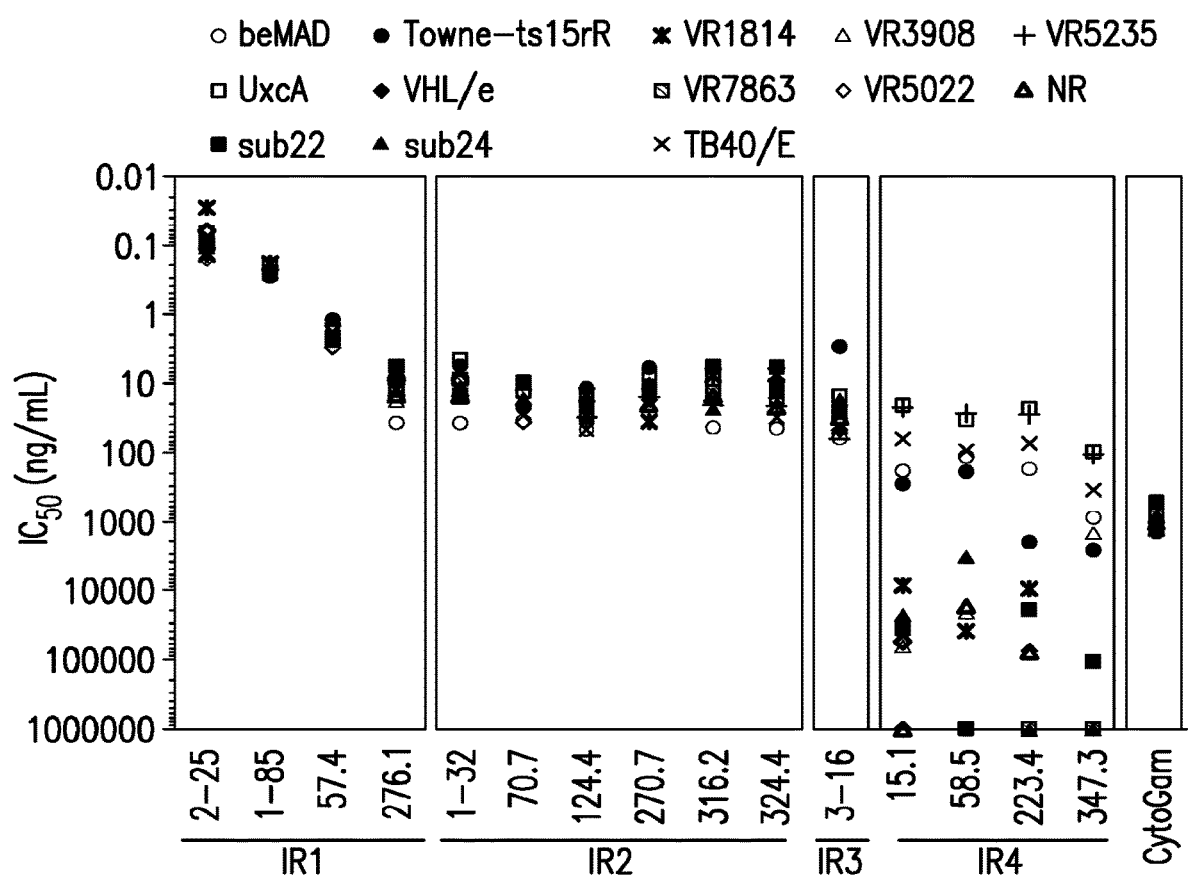
FIG. 9 shows the breadth of antibody neutralization activities across clinical isolates in APRE-19 cells. The antiviral potency is shown on y-axis as IC₅₀ (antibody concentration to achieve 50% inhibition of viral infection). Two laboratory strains are beMAD (AD169 derived) and Towne-ts15rR (Towne derived). Eleven clinical isolates were cultured adapted in ARPE-19 cells.

With the eight immunogenic sites identified, we next determined whether these sites were conserved among different HCMV strains. The neutralization potencies of the antibodies were tested against two lab strains (AD169rev and Towne-ts15rR) and 11 clinical isolates in ARPE-19 cells (FIG. 9). IR1-3 antibodies neutralized all HCMV strains tested, demonstrating broad virus coverage. In contrast, IR4 antibodies showed variable potencies against different strains, with higher potencies against AD169-like strains than Towne-like stains, consistent with the rabbit vaccination source of AD169rev.

Example 13

Inhibition of Viral Infection in ARPE-19 and MRC-5

HCMV has a broad cell tropism with different entry mechanisms in different cell types. A study was undertaken to investigate how these viral entries could be impacted by antibody bindings at different IR. The neutralization potencies of these 20 antibodies was tested in both ARPE-19 and MRC-5 cells and summarized the data in Table 11.

TABLE 11

Summary of antibody neutralization potencies in ARPE-19 and MRC-5 in correlation with the four IRs of the soluble pentamer.

| Immunogenic Region | Immunogenic Sites | Antibody | IC50 in ARPE-19 (ng/mL) | IC50 in MRC-5 (ng/mL) |
|---|---|---|---|---|
| Conformational antibodies | | | | |
| IR1 | Site 1 | 2-25 | 0.08 | — |
|  |  | 2-18 | 0.18 | — |
|  | Site 2 | 1-85 | 0.13 | — |
|  |  | 1-150 | 0.31 | 260 |
|  | Site 3 | 1-103 | 0.88 | — |
|  | Site 4 | 57.4 | 10 | — |
|  |  | 276.1 | 10 | — |
| IR2 | Site 5 | 1-32 | 0.82 | — |
|  | Site 6 | 70.7 | 10 | 66 |
|  |  | 124.4 | 12 | 50 |
|  |  | 270.7 | 8.8 | 44 |
|  |  | 316.2 | 12 | 42 |
|  |  | 324.4 | 16 | 27 |
| IR3 | Site 7 | 3-7 | 9.5 | 19 |
|  |  | 3-15 | 13 | 22 |
|  |  | 3-16 | 17 | 37 |
| Linear-epitope antibodies | | | | |
| IR4 | Site 8 | 15.1 | 31 | — |
|  |  | 58.5 | 29 | — |
|  |  | 223.4 | 38 | — |
|  |  | 347.3 | 620 | — |

As expected, the most potent ARPE-19 neutralizers, from both human and rabbit, target IR1. However, IR1 antibodies do not inhibit viral entry in MRC-5 cells. IR2 and IR3 antibodies, with the exception of 1-32, inhibit viral entry in both ARPE-19 and MRC-5 cells although ~100-fold less potent than IR1 in ARPE-19 cells. The fact that IR2 and IR3 inhibit viral entry in both ARPE-19 and MRC-5 cells with similar potencies suggests that IR2 and IR3 are involved in a common viral entry mechanism such as gB activation independent of cell tropism. 1-32 is a unique antibody that targets IR2 but does not inhibit viral entry to fibroblasts. The 3D density map shows that Fab 1-32 is directed at module 2 at a ~180° angle against the gH/gL stalk, significantly different from other gH/gL binders such as 124.4 and 270.7. This binding epitope may be unique to the pentamer or the angle may preclude 1-32 from interfering the gB activation. IR4 antibodies in this study inhibit viral entry in APRE-19 cells only. These IR4 antibodies are apparently different from the AP86 binding sera reported by Urban et al. (1992, J. Virol. 66:1303-1311) that bind to the gH N-terminal linear epitope and neutralize fibroblasts.

Example 14

Germline of CMV Antibody Sequences

Upon encountering an antigen such as in primary HCMV infection, naïve B-cells undergo extensive in vivo maturation to improve the antibodies' binding and neutralizing activities. The maturation process centers on mutations in the CDR regions, but mutations in the frame regions can occur. Mutations in the frame regions may or may not contribute to the improved properties of the antibodies. Therefore, IgG genes recovered from single memory B-cells of an infected individual donor may bear mutations in the IgG frame regions as a result of B-cell maturation that are specific to the host (the donor). An antibody with these unique mutations would differ from any canonical antibodies in the database such as the IMGT© database not only for its unique CDR regions, but also the mutations in the frame regions. Although these mutations in the frame regions could be important for its improved functions such as binding and neutralization in the donor, they could be a liability for developing such an antibody as a drug. The risk can be presented as the poor expression of the molecule in the cell cultures for IgG production. Risk also exists that much deviation from the canonical sequences may induce immune rejection of the antibody, also known as anti-drug antibody response when used in the clinic use.

IgG variable sequence was recovered through RT PCR of cultured single B-cells, and the sequence was compared to the original human IgG germ line sequences at "IMGT®, the international ImMunoGeneTics information System®. Non-canonical sequence was corrected based on the human IgG germline sequences in the IMGT® information system as hereby referred as "germlining". For antibodies 1-85, 2-18, and 3-25, the germlined sequences for both heavy and light chains are provided as an example (Table 12 (variable domain)). Germlining in some cases (e.g., 1-85 and 2-18, data not shown) has improved IgG production in transient transfected cell cultures, and germlined antibodies preserved antiviral functional properties when compared to their respective parental antibodies (data not shown).

Example 15

Mutations Engineered to Extend IgG1 Half-Life

The triple mutation M252Y/S254T/T256E, commonly referred as YTE mutation, in IgG1 Fc region can improve the antibody's affinity for neonatal Fc receptor binding and improve antibody's half-life, both in cynolmogus macaques and humans. See Dall'Acqua et al., 2006, J. Biol. Chem. 281:23514-23524. The YTE mutations are introduced into anti-CMV antibodies, for the purpose of extending its half-life. For antibodies 1-85, 2-18, and 3-25, the germlined sequences with YTE are provided as an example (Table 13 (full length)).

TABLE 12

Variable region sequences of selected germlined antibodies

| Clone ID | Nucleotide Sequence | SEQ ID NO. | Amino Acid Sequence | SEQ ID NO. |
|---|---|---|---|---|
| Germ-lined 2-18 IgG1 Heavy Chain | GAGGTGCAGCTGGTGGAGTCTGGAGGAGGACTGGTGCAGCCAGGAGGCTCCCTGAGG CTGTCTTGCGCCGCCAGCGGCTTCTCCTTTTCTGACCACGATATGGACTGGGTGCGC CAGGCACCTGGCAAGGGCCTGGAGTGGGTGGGCCGGAGCAGAAACAAGGATTACAGC TCCACCACAGAGTATGCGAGCCTCCGTGAGGGGCCGCTTCACCATCTCTCGGGACGAT AGCAAGAACTCCCTGTACCTGCAGATGAACAGCCTGAAGACCGAGGACACAGCCGTG TACTATTGTGCCAGAGGCCCCCACCACTCTGATAGAAGCGGCTACTATGGCGGCACA TTTGACATCTGGGGCCAGGGCACAATGGTGACAGTGTCTAGC | 114 | EVQLVESGGGLVQPGGSLRL SCAASGFSFSDHDMDWVRQA PGKGLEWVGRSRNKDYSSTT EYAASVRGRFTISRDDSKNS LYLQMNSLKTEDTAVYYCAR GPHHSDRSGYYGGTFDIWGQ GTMVTVSS | 115 |
| Germ-lined 2-18 IgG1 Light Chain | GACATCCAGATGACACAGTCTCCTAGCTCCGTGAGCGCCTCCGTGGGCGATAGGGTG ACCATCACATGCAGAGCCTCCCAGGGCATCTCTAGCTGGCTGGCCTGGTATCAGCAG AAGCCCGGCAAGGCCCCTAAGCTGCTGATCTATGACGCCTCTACCCTGGAGAGCGGC GTGCCCTCCCGGTTCTCTGGCAGCGGCTCCGGCACAGACTTTACCCTGACAATCTCC TCTCTGCAGCCAGAGGATTTCGCCACCTACTATTGTCAGCAGGGCAACATGTTCCCC CTGACCTTTGGCGGCGGCACAAAGGTGGAGATCAAG | 116 | DIQMTQSPSSVSASVGDRVT ITCRASQGISSWLAWYQQKP GKAPKLLIYDASTLESGVPS RFSGSGSGTDFTLTISSLQP EDFATYYCQQGNMFPLTFGG GTKVEIK | 117 |
| Germ-lined 1-85 IgG1 Heavy Chain | CAGGTGCAGCTGGTGGAGTCCGGAGGAGGACTGGTGAAGCCAGGAGGCTCCCTGAGG CTGTCTTGCGCCGCCAGCGGCTTCACCTTTAGCGACTACTATATGGCCTGGATCAGA CAGGCACCTGGCAAGGGCCTGGAGTGGGTGTCCTTCATCAGCTCCTCTGGCAGAACC ATCTACTATGCCGACTCTGTGAAGGGCCGGTTTACAATCTCCAGAGATAACGCCAAG AACAGCCTGTACCTGCAGATGAACAGCCTGAGGGCCGAGGACACAGCCGTGTACTAT TGTGCCCGGGACTCTTATAGCAAGCTGGTGGATATCGAGGCCATCGAGGCCTTCGAT ATCTGGGGCAGAGGCACAATGGTGACCGTGAGCAGC | 118 | QVQLVESGGGLVKPGGSLRL SCAASGFTFSDYYMAWIRQA PGKGLEWVSFISSSGRTIYY ADSVKGRFTISRDNAKNSLY LQMNSLRAEDTAVYYCARDS YSKLVDIEAIEAFDIWGRGT MVTVSS | 119 |
| Germ-lined 1-85 IgG1 Light Chain | AGCTACGTGCTGACACAGCCACCTAGCGTGTCCGTGGCACCAGGCAAGACAGCAAGG ATCACCTGCGGCGGCGACAACATCGGCTCTAAGAGCGTGCACTGGTATCAGCAGAAG CCAGGACAGGCACCCGTGCTGGTCATCTACTATGACTCCGATCGGCCTTCTGGCATC CCAGAGAGATTCTCCGGCTCTAACAGCGGCAATACCGCCACACTGACCATCTCCAGG GTGGAGGCAGGCGACGAGGCAGATTACTTCTGTCAAGTGTGGGACCGCCACGGCGAT CACGTGGTGTTTGGCGGCGGCACAAAGCTGACCGTGCTG | 120 | SYVLTQPPSVSVAPGKTARI TCGGDNIGSKSVHWYQQKPG QAPVLVIYYDSDRPSGIPER FSGSNSGNTATLTISRVEAG DEADYFCQVWDRHGDHVVFG GGTKLTVL | 121 |
| Germ-lined 3-25 IgG1 Heavy Chain | CAGGTGCAGCTGGTGGAGAGCGGAGGAGGAGTGGTGCAGCCAGGCAGGTCTCTGAGG CTGAGCTGCGCCGCCTCCGGCTTCACCTTTTCCAACCACGGCCTGCACTGGGTGCGG CAGGCACCTGGCAAGGGCCTGGAGTGGGTGGCAGTGGTGTCCAAGGACGGCACAAAT GAGCACTACGCCGATTCTGTGCGGGGCAGATTCACCATCTCTAGGGACAACAGCAAG AATACACTGTATCTGCAGATGAACTCTCTGCGCGCCGAGGATACCGCCGTGTACTAT TGTGCCCGGGAGGGCTACTGCGGCGACGATAGATGTTACAGCGGACAGCCAGACTAT TGGGGACAGGGCACCCTGGTGACCGTGAGCAGC | 122 | QVQLVESGGGVVQPGRSLRL SCAASGFTFSNHGLHWVRQA PGKGLEWVAVVSKDGTNEHY ADSVRGRFTISRDNSKNTLY LQMNSLRAEDTAVYYCAREG YCGDDRCYSGQPDYWGQGTL VTVSS | 123 |
| Germ-lined 3-25 | GAGATCGTGCTGACCCAGTCTCCTGCCACACTGTCCCTGTCTCCAGGAGAGAGGGCC ACCCTGAGCTGCAGAGCCAGCCAGTCCGTGGGCAGATACCTGGCCTGGTATCAGCAG AAGCCAGGACAGGCACCAAGGCTGCTGATCTACGACAGCTCCAACAGGGCAACCGGC | 124 | EIVLTQSPATLSLSPGERAT LSCRASQSVGRYLAWYQQKP GQAPRLLIYDSSNRATGVPA | 125 |

TABLE 12-continued

Variable region sequences of selected germlined antibodies

| Clone ID | Nucleotide Sequence | SEQ ID NO. | Amino Acid Sequence | SEQ ID NO. |
|---|---|---|---|---|
| Light Chain | GTGCCCGCACGCTTCTCTGGCAGCGGCTCCGGCACAGACTTTACCCTGACAATCTCT AGCCTGGAGCCTGAGGATTTCGCCGTGTACTATTGTCAGCAGCGGTCCCACTGGCCA CCTCTGACCTTTGGCGGAGGCACAAAGGTGGAGATCAAG | | RFSGSGSGTDFTLTISSLEP EDFAVYYCQQRSHWPPLTFG GGTKVEIK | |

TABLE 13

Representative Full Length Sequences (Germlined without and with YTE mutations)

| Clone ID | Nucleotide Sequence | SEQ ID NO. | Amino Acid Sequence | SEQ ID NO. |
|---|---|---|---|---|
| Germlined 2-18 IgG1 Heavy Chain | GAGGTGCAGCTGGTGGAGTCTGGAGGAGGACTGGTGCAGCCAGGAGGCTCCCTGAGG CTGTCTTGCGCCGCCAGCGGCTTCTCCTTTTCTGACCACGATATGGACTGGGTGCGC CAGGCACCTGGCAAGGGCCTGGAGTGGGTGGGCCGGAGCAGAAACAAGGATTACAGC TCCACCACAGAGTATGCAGCCTCCGTGAGGGGCCGCTTCACCATCTCTCGGGACGAT AGCAAGAACTCCCTGTACCTGCAGATGAACAGCCTGAAGACCGAGGACACAGCCGTG TACTATTGTGCCAGAGGCCCCCACCACTCTGATAGAAGCGGCTACTATGGCGGCACA TTTGACATCTGGGGCCAGGGCACAATGGTGACAGTGTCTAGCGCATCCACCAAGGGC CCATCTGTCTTCCCCCTGGCCCCATCCTCCAAGAGCACCTCTGGCGGCACAGCTGCC CTGGGCTGCCTGGTGAAGGACTACTTCCCTGAGCCTGTGACAGTGTCTTGGAACTCT GGCGCCCTGACCAGCGGCGTGCACACCTTCCCTGCTGTGCTCCAGTCCTCTGGCCTG TACTCCCTGAGCAGCGTGGTGACAGTGCCATCCAGCAGCCTGGGCACCCAGACCTAC ATCTGCAATGTGAACCACAAGCCCAGCAACACCAAGGTGGACAAGCGGGTGGAGCCC AAGTCCTGCGACAAGACCCACACCTGCCCCCCATGCCCCGCCCCTGAGCTGCTGGGC GGCCCATCTGTCTTCCTGTTCCCCCCAAGCCCAAGGACACCCTGATGATCTCCCGG ACCCCCGAGGTGACCTGTGTGGTGGTGGATGTGAGCCATGAGGACCCCGAGGTGAAG TTCAACTGGTATGTGGATGGCGTGGAGGTGCACAACGCCAAGACCAAGCCCCGGGAG GAGCAGTACAACAGCACCTACCGGGTGTGCAGTGCTGCACGTGCCATCAGGAC TGGCTGAATGGCAAGGAGTACAAGTGCAAGGTGTCCAACAAGGCCCTGCCTGCCCCC ATTGAGAAGACCATCTCCAAGGCCAAGGGCCAGCCCCGGGAGCCCCAGGTCTACACC CTGCCCCCCTCCCGGGAGGAGATGACCAAGAACCAGGTGAGCCTGACCTGCCTGGTG AAGGGCTTCTACCCCAGCGACATTGCTGTGGAGTGGGAGAGCAACGGCCAGCCTGAG AACAACTACAAGACCACCCCCCCTGTGCTGGACTCTGATGGCTCCTTCTTCCTGTAC AGCAAGCTGACAGTGGACAAGAGCCGGTGGCAGCAGGGCAATGTCTTCTCCTGCTCT GTGATGCATGAGGCCCTGCACAACCACTACACCCAGAAGAGCCTGTCCCTGTCCCCC GGCAAG | 126 | EVQLVESGGGLVQPGGSLRL SCAASGFGFSDHDMDWVRQA PGKGLEWVGRSRNKDYSSTT EYAASVRGRFTISRDDSKNS LYLQMNSLKTEDTAVYYCAR GPHHSDRSGYYGGTFDIWGQ GTMVTVSSASTKGPSVFPLA PSSKSTSGGTAALGCLVKDY FPEPVTVSWNSGALTSGVHT FPAVLQSSGLYSLSSVVTVP SSSLGTQTYICNVNHKPSNT KVDKRVEPKSCDKTHTCPPC PAPELLGGPSVFLFPPKPKD TLMISRTPEVTCVVVDVSHE DPEVKFNWYVDGVEVHNAKT KPREEQYNSTYRVVSVLTVL HQDWLNGKEYKCKVSNKALP APIEKTISKAKGQPREPQVY TLPPSREEMTKNQVSLTCLV KGFYPSDIAVEWESNGQPEN NYKTTPPVLDSDGSFFLYSK LTVDKSRWQQGNVFSCSVMH EALHNHYTQKSLSLSPGK | 127 |
| Germlined 2-18 IgG1 Light Chain | GACATCCAGATGACACAGTCTCCTAGCTCCGTGAGCGCCTCCGTGGGCGATAGGGTG ACCATCACATGCAGAGCCTCCCAGGGCATCTCTAGCTGGCTGGCCTGGTATCAGCAG AAGCCCGGCAAGGCCCCTAAGCTGCTGATCTATGACGCCTCTACCCTGGAGAGCGGC GTGCCCTCCCGGTTCTCTGGCAGCGGCTCCGGCACAGACTTTACCCTGACAATCTCC TCTCTGCAGCCAGAGGATTCGCCACCTACTATTGTCAGCAGGGCAACATGTTCCCC CTGACCTTTGGCGGCGGCACAAAGGTGGAGATCAAGCGTACGGTGGCTGCACCATCT GTCTTCATCTTCCCGCCATCTGATGAGCAGTTGAAATCTGGAACTGCCTCTGTTGTG TGCCTGCTGAATAACTTCTATCCCAGAGAGGCCAAAGTACAGTGGAAGGTGGATAAC GCCCTCCAATCGGGTAACTCCCAGGAGAGTGTCACAGAGCAGGACAGCAAGGACAGC ACCTACAGCCTCAGCAGCACCCTGACGCTGAGCAAAGCAGACTACGAGAAACACAAA GTCTACGCCTGCGAAGTCACCCATCAGGGCCTGAGCTCGCCCGTCACAAAGAGCTTC AACAGGGGAGAGTGT | 128 | DIQMTQSPSSVSASVGDRVT ITCRASQGISSWLAWYQQKP GKAPKLLIYDASTLESGVPS RFSGSGSGTDFTLTISSLQP EDFATYYCQQGNMFPLTFGG GTKVEIKRTVAAPSVFIFPP SDEQLKSGTASVVCLLNNFY PREAKVQWKVDNALQSGNSQ ESVTEQDSKDSTYSLSSTLT LSKADYEKHKVYACEVTHQG LSSPVTKSFNRGEC | 129 |
| Germlined 2-18 IgG1 Heavy Chain + YTE | ATGGAGTGGAGCTGGGTGTTTCTGTTCTTCCTCAGCGTGACCACCGGCGTGCATTCC GAGGTGCAGCTGGTGGAGTCCGGAGGAGGACTCGTGCAGCCCGGAGGTTCTCTGAGG CTCAGCTGTGCTGCCTCCGGATTCTCCTTCAGCGACCACGATGATGGGGTGCGGCAG CAGGCTCCCGGAAAAGGCCTGGAGTGGGTCGGCAGGAGCAGGAACAAGGACTATTCC AGCACCACCGAATACGCCGCCAGCGTGAGGGGCAGGTTCACCATCTCCAGGGATGAC AGCAAGAACTCCCTGTACCTGCAGATGAACAGCCTGAAGACCGAAGACACCGCCGTG TACTATTGCGCCCGGGGCCCTCACCATTCCGACCGGAGCGGCTATTACGGCGGCACC TTCGACATTTGGGGCCAGGGAACAATGGTCACCGTGTCCAGCGCTAGCACCAAGGGC CCTAGCGTGTTTCCCCTGGCTCCTAGCTCCAAGAGCACCAGCGGAGGCACAGCCGCT CTGGGATGCCTGGTCAAAGACTACTTCCCCGAGCCCGTCACAGTCAGCTGGAACTCC GGAGCCCTGACCTCCGGCGTCCATACCTTCCCTGCTGTCCTGCAGTCCTCGGGACTC TACTCCCTGAGCTCCGTGGTCACAGTGCCTAGCTCCAGCCTCGGAACCCAGACATAC ATCTGCAACGTGAACCACAAGCCTTCCAACACCAAGGTCGACAAGAAGGTGGAGCCT AAGTCCTGCGACAAACCCACACCTGCCCTCCTTGCCCTGCTCCTGAACTGCTGGGC GGCCCTTCCGTGTTCCTGTTCCCCCCTAAACCTAAGGACACCCTGATGATCACCCGG ACCCCCGAGGTGACATGCGTGGTGGTCGACGTGTCCCACGAGGACCCCGAGGTGAAG TTCAACTGGTATGTCGATGGCGTGGAGGTCCACAACGCCAAGACCAAACCCAGGGAA GAGCAGTACAACTCCACCTACCGGGTGGTCAGCGTGCTGACCGTGCTGCACCAGGAC TGGCTGAATGGCAAGGAGTACAAGTGCAAGGTCAGCAATAAAGCCCTGCCCGCCCCT ATCGAGAAGACAATCTCCAAGGCCAAGGGACAGCCCCGGGAACCCCAGGTGTATACC | 130 | MEWSWVFLFFLSVTTGVHSE VQLVESGGGLVQPGGSLRLS CAASGFSFSDHDMDWVRQAP GKGLEWVGRSRNKDYSSTTE YAASVRGRFTISRDDSKNSL YLQMNSLKTEDTAVYYCARG PHHSDRSGYYGGTFDIWGQG TMVTVSSASTKGPSVFPLAP SSKSTSGGTAALGCLVKDYF PEPVTVSWNSGALTSGVHTF PAVLQSSGLYSLSSVVTVPS SSLGTQTYICNVNHKPSNTK VDKKVEPKSCDKTHTCPPCP APELLGGPSVFLFPPKPKDT LyItRePEVTCVVVDVSHED PEVKFNWYVDGVEVHNAKTK PREEQYNSTYRVVSVLTVLH QDWLNGKEYKCKVSNKALPA PIEKTISKAKGQPREPQVYT LPPSRDELTKNQVSLTCLVK | 131 |

TABLE 13-continued

Representative Full Length Sequences (Germlined without and with YTE mutations)

| Clone ID | Nucleotide Sequence | SEQ ID NO. | Amino Acid Sequence | SEQ ID NO. |
|---|---|---|---|---|
| | CTGCCCCCTCCCGGGATGAACTGACCAAAAACCAGGTCAGCCTGACCTGTCTGGTC AAAGGCTTCTACCCCTCCGACATCGCTGTGGAATGGGAGAGCAATGGCCAGCCTGAG AACAACTATAAGACCACCCCTCCCGTGCTCGACAGCGATGGCTCCTTCTTTCTCTAC AGCAAGCTGACCGTGGATAAGTCCCGGTGGCAACAGGGCAACGTGTTCAGCTGCTCC GTCATGCATGAGGCCCTGCACAATCACTACACCCAGAAGAGCCTGTCCCTGTCCCCC GGCAAGTGA | | GFYPSDIAVEWESNGQPENN YKTTPPVLDSDGSFFLYSKL TVDKSRWQQGNVFSCSVMHE ALHNHYTQKSLSLSPGK | |
| Germ-lined 2-18 IgG1 Light Chain + YTE | ATGAGCGTGCCCACACAGGTGCTCGGCCTGCTGCTGCTGTGGCTGACCGACGCCAGG TGCGACATCCAGATGACCCAGTCCCCTTCCTCCGTGTCCGCTTCCGTGGGCGATAGG GTGACAATCACCTGCAGGGCCAGCCAGGGCATCTCCAGCTGGCTGGCCTGGTACCAG CAGAAGCCCGGCAAGGCCCCCAAGCTGCTGATCTACGACGCCAGCACACTGGAGAGC GGCGTGCCCTCCCGGTTCAGCGGTTCTGGCAGCGGAACAGACTTCACCCTGACCATT TCCTCCCTGCAGCCCGAGGACTTCGCCACCTACTACTGCCAGCAGGGCAACATGTTC CCTCTGACCTTCGGAGGCGGCACAAAGGTGGAGATCAAGCGGACCGTCGCCGCTCCC TCCGTGTTCATCTTCCCCCCCTCCGATGAGCAGCTCAAGTCCGGCACCGCTAGCGTG GTGTGCCTGCTGAACAACTTCTACCCCCGGGAGGCCAAGGTGCAGTGGAAGGTCGAC AACGCCCTGCAGTCCGGCAACAGCCAGGAGAGCGTGACCGAGCAGGACTCCAAGGAC TCCACCTACTCCCTCTCCTCCACCCTGACCCTGTCCAAGGCCGACTACGAGAAGCAC AAAGTGTACGCCTGCGAAGTGACCCACCAGGGCCTGAGCTCCCCCGTGACAAAGTCC TTCAACAGGGGCGAGTGTTGA | 132 | MSVPTQVLGLLLLWLTDARC DIQMTQSPSSVSASVGDRVT ITCRASQGISSWLAWYQQKP GKAPKLLIYDASTLESGVPS RFSGSGSGTDFTLTISSLQP EDFATYYCQQGNMFPLTFGG GTKVEIKRTVAAPSVFIFPP SDEQLKSGTASVVCLLNNFY PREAKVQWKVDNALQSGNSQ ESVTEQDSKDSTYSLSSTLT LSKADYEKHKVYACEVTHQG LSSPVTKSFNRGEC | 133 |
| Germ-lined 1-85 IgG1 Heavy Chain | CAGGTGCAGCTGGTGGAGTCCGGAGGAGGACTGGTGAAGCCAGGAGGCTCCCTGAGG CTGTCTTGCGCCGCTAGCGGCTTCACCTTTAGCGACTACTATATGGCCTGGATCAGA CAGGCACCTGGCAAGGGCTTGGAGTGGGTGTCCTTCATCAGCTCCTCTGGCAGAACC ATCTACTATGCCGACTCTGTGAAGGGCCGGTTTACAATCTCCAGAGATAACGCCAAG AACAGCCTGTACCTGCAGATGAACAGCCTGAGGGCCGAGGACACAGCCGTGTACTAT TGTGCCCGCGACTCTTATAGCAAGCTGGTGGATATCGAGGCCATCGAGGCCTTCGAT ATCTGGGGCAGAGGCACAATGGTGACCGTGAGCAGCGCATCCAACCAAGGGCCATCT GTCTTCCCCCTGGCCCCATCCTCCAAGAGCACCTCTGGCGGCACAGCTGCCCTGGGC TGCCTGGTGAAGGACTACTTCCCTGAGCCTGTGACAGTGTCCTGGAACTCTGGCGCC CTGACCAGCGGCGTGCACACCTTCCCTGCTGTGCTCCAGTCCTCTGGCCTGTACTCC CTGAGCAGCGTGGTGACAGTGCCATCCAGCAGCCTGGGCACCCAGACCTACATCTGC AATGTGAACCACAAGCCCAGCAACACCAAGGTGGACAAGCGGGTGGAGCCCAAGTCC TGTGACAAGACCCACACCTGCCCCCATGCCCCGCCCCTGAGCTGCTGGGCGGCCCA TCTGTCTTCCTGTTCCCCCCAACCCAAGGACACCCTGATGATCTCCCCGGACCCCC GAGGTGACCTGTGTGGTGGTGGATGTGAGCCATGAGGACCCCGAGGTGAAGTTCAAC TGGTATGTGGATGGCGTGGAGGTGCACAACGCCAAGACCAAGCCCCGGGAGGAGCAG TACAACAGCACCTACCGGGTGGTGAGCGTGCTGACAGTGCTGCATCAGGACTGGCTG AATGGCAAGGAGTACAAGTGCAAGGTGTCCAACAAGGCCCTGCCTGCCCCCATTGAG AAGACCATCTCCAAGGCCAAGGGCCAGCCCCGGGAGCCCCAGGTCTACACCCTGCCC CCCTCCCGGGAGGAGATGACCAAGAACCAGGTGAGCCTGACCTGCCTGGTGAAGGGC TTCTACCCCAGCGACATTGCTGTGGAGTGGGAGAGCAACGGCCAGCCTGAGAACAAC TACAAGACCACCCCCCCTGTGCTGGACTCTGATGGCTCCTTCTTCCTGTACAGCAAG CTGACAGTGGACAAGAGCCGGTGGCAGCAGGGCAATGTCTTCTCCTGCTCTGTGATG CATGAGGCCCTGCACAACCACTACACCCAGAAGAGCCTGTCCCTGTCCCCGGCAAG | 134 | QVQLVESGGGLVKPGGSLRL SCAASGFTFSDYYMAWIRQA PGKGLEWVSFISSSGRTIYY ADSVKGRFTISRDNAKNSLY LQMNSLRAEDTAVYYCARDS YSKLVDIEAIEAFDIWGRGT MVTVSSASTKGPSVFPLAPS SKSTSGGTAALGCLVKDYFP EPVTVSWNSGALTSGVHTFP AVLQSSGLYSLSSVVTVPSS SLGTQTYICNVNHKPSNTKV DKRVEPKSCDKTHTCPPCPA PELLGGPSVFLFPPKPKDTL MISRTPEVTCVVVDVSHEDP EVKFNWYVDGVEVHNAKTKP REEQYNSTYRVVSVLTVLHQ DWLNGKEYKCKVSNKALPAP IEKTISKAKGQPREPQVYTL PPSREEMTKNQVSLTCLVKG FYPSDIAVEWESNGQPENNY KTTPPVLDSDGSFFLYSKLT VDKSRWQQGNVFSCSVMHEA LHNHYTQKSLSLSPGK | 135 |
| Germ-lined 1-85 IgG1 Light Chain | AGCTACGTGCTGACACAGCCACCTAGCGTGTCCGTGGCACCAGGCAAGACAGCAAGG ATCACCTGCGGCGGCGACAATATCGGCTCTAAGAGCGTGCACTGGTATCAGCAGAAG CCAGGACAGGCACCCGTGCTGGTCATCTACTATGACTCCGATCGGCCTTCTGGCATC CCAGAGAGATTCTCCGGCTCTAACAGCGGCAATACCGCCACACTGACCATCTCCAGG GTGGAGGCAGGCGACGAGGCAGATTACTTCTGTCAAGTGTGGGACCGCCACGGCGAT CACGTGGTGTTTGGCGGCGGCACAAAGCTGACCGTGCTGCAGCCCAAGGCCAACCCC ACCGTGACCCTGTTCCCCCCATCTTCTGAGGAGCTGCAAGCCAACAAGGCTACCCTG GTGTGCCTGATCTCTGACTTCTACCCTGGCGCTGTGACAGTGGCCTGGAAGGCTGAT GGCTCTCCTGTGAAGGCTGGCGTGGAGACCACCAAGCCATCTAAGCAGTCTAACAAC AAGTATGCTGCCTCTTCTTACCTGTCTCTGACCCCTGAGCAGTGGAAGAGCCACCGG TCTTACTCTTGCCAGGTGACCCATGAGGGCTCTACAGTGGAGAAGACAGTGGCCCCC ACAGAGTGCTCT | 136 | SYVLTQPPSVSVAPGKTARI TCGGDNIGSKSVHWYQQKPG QAPVLVIYYDSDRPSGIPER FSGSNSGNTATLTISRVEAG DEADYFCQVWDRHGDHVVFG GGTKLTVLQPKANPTVTLFP PSSEELQANKATLVCLISDF YPGAVTVAWKADGSPVKAGV ETTKPSKQSNNKYAASSYLS LTPEQWKSHRSYSCQVTHEG STVEKTVAPTECS | 137 |
| Germ-lined 1-85 IgG1 Heavy Chain + YTE | ATGGAATGGTCCTGGGTGTTCCTGTTCTTTCTGAGCGTCACCACCGGCGTGCACAGC GAGGTGCAACTGGTGGAGAGCGGCGGAGGCCTGGTGAAACCTGGCGGTTCTCTGAGG CTGTCCTGTGCTGCCAGCGGCTTCACCTTCTCCGACTATTACATGGCCTGGATTCGG CAGGCTCCTGGCAAGGGCCTGGAATGGGTGTCCTTCATCTCCAGCAGCGGCCGGACA ATCTATTATGCCGACTCCGTGAAGGGCCGGTTTACCATCTCCAGGGATAACGCCAAG AACTCCCTGTACCTGCAGATGAACTCTCTGAGGGCTGAAGACACAGCTGTGTATTAC TGCGCTCGGGACAGCTACAGCAAGCTGGTGGATATCGAGGCCATCGAAGCCTTCGAT ATTTGGGGCAGGGGAACAATGGTGACCGTGAGCTCCGCTTCCACCAAGGGACCCAGC GTGTTCCCTCTGGCTCCAGCTCCAAGTCCACCAGCGGAGGCACCGCTGCTCTGGGA TGTCTGGTGAAGGACTACTTTCCCGAACCTGTGACAGTGTCCTGGAACAGCGGAGCT CTGACCAGCGGAGTCCACACCTTCCCCGCTGTGCTGCAGTCCTCCGGCCTGTACAGC CTGAGCAGCGTGGTGACCGTGCCTTCAGCTCCTCTGGCACCCAGACCTACATCTGC AATGTGAATCACAAGCCCAGCAACACCAAGGTGGATAAGAAGGTCGAGCCTAAGAGC TGCGACAAGACCCACACATGCCCTCCTTGTCCTGCTCCTGAGCTGCTGGGAGGCCCT AGCGTCTTCCTCTTCCCCAAACCCAAGGATACCCTCTACATCACCCGGGAGCCC | 138 | MEWSWVFLFFLSVTTGVHSe VQLVESGGGLVKPGGSLRLS CAASGFTFSDYYMAWIRQAP GKGLEWVSFISSSGRTIYYA DSVKGRFTISRDNAKNSLYL QMNSLRAEDTAVYYCARDSY SKLVDIEAIEAFDIWGRGTM VTVSSASTKGPSVFPLAPSS KSTSGGTAALGCLVKDYFPE PVTVSWNSGALTSGVHTFPA VLQSSGLYSLSSVVTVPSSS LGTQTYICNVNHKPSNTKVD KKVEPKSCDKTHTCPPCPAP ELLGGPSVFLFPPKPKDTLy ItRePEVTCVVVDVSHEDPE | 139 |

TABLE 13-continued

Representative Full Length Sequences (Germlined without and with YTE mutations)

| Clone ID | Nucleotide Sequence | SEQ ID NO. | Amino Acid Sequence | SEQ ID NO. |
|---|---|---|---|---|
| | GAAGTGACCTGCGTGGTGGTGGACGTGTCCCACGAAGATCCTGAAGTCAAGTTCAAC TGGTACGTGGATGGCGTCGAGGTGCACAACGCCAAAACCAAACCCCGGGAGGAACAG TATAACAGCACCTACCGGGTCGTGAGCGTGCTGACCGTGCTGCACCAGGATTGGCTG AATGGCAAGGAGTACAAGTGCAAGGTGTCCAACAAAGCCCTGCCCGCTCCCATCGAG AAGACAATCTCCAAGGCCAAAGGCCAGCCTCGGGAACCCCAGGTGTATACCCTGCCC CCCAGCAGGGACGAACTGACCAAAAACCAGGTGAGCCTGACCTGCCTGGTGAAGGGA TTCTACCCTAGCGATATCGCCGTGGAATGGGAGAGCAATGGACAGCCTGAGAACAAC TACAAAACCACCCCCCCTGTGCTCGACTCCGATGGTTCTTTCTTCCTGTACAGCAAA CTGACCGTGGACAAGAGCCGGTGGCAGCAGGGCAACGTGTTTTCCTGCAGCGTGATG CATGAGGCTCTGCACAACCATTACACCCAGAAGAGCCTGAGCCTGTCCCCTGGCAAG TGA | | VKFNWYVDGVEVHNAKTKPR EEQYNSTYRVVSVLTVLHQD WLNGKEYKCKVSNKALPAPI EKTISKAKGQPREPQVYTLP PSRDELTKNQVSLTCLVKGF YPSDIAVEWESNGQPENNYK TTPPVLDSDGSFFLYSKLTV DKSRWQQGNVFSCSVMHEAL HNHYTQKSLSLSPGK | |
| Germ-lined 1-85 IgG1 Light Chain + YTE | ATGTCCGTGCCCACACAGGTGCTGGGCCTGCTGCTGCTGTGGCTGACCGATGCCAGG TGCTCCTACGTGCTGACCCAGCCTCCTTCCGTGTCCGTGGCTCCTGGCAAGACAGCT ACGGATCACCTGCGGCGGCGACAACATCGGCAGCAAGAGCGTGCACTGGTATCAGCAG AAGCCCGGCCAGGCCCCTGTGCTGGTGATCTACTACGATTCCGACCGGCCTAGCGGC ATCCCCGAGAGGTTCAGCGGCTCCAACTCCGGCAACACCGCCACACTGACCATCTCC CGGGTGGAGGCCGGAGATGAGGCTGACTACTTCTGCCAGGTGTGGGACAGGCATGGC GATCACGTGGGTTTCGGCGGCGGCACCAAGCTGACAGTGCTGGGACAGCCTAAGGCC CCTTCCGTGACCCTGTTCCCCCCTAGCTCCGAGGAGCTGCAGGCCAACAAGGCC ACCCTGGTGTGTCTCATCAGCGACTTCTACCCCGGCGCTGTGACCGTGGCCTGGAAG GCTGACAGCTCCCCCGTGAAGGCTGGCGTGGAGACCACAACCCCCTCCAAGCAGTCC AACAATAAGTACGCCGCAGCTCCTACCTGTCCCTGACCCCCGAGCAGTGGAAGAGC CACCGGTCCTACAGCTGCCAGGTGACCCACGAAGGCTCCACCGTGGAGAAGACCGTG GCCCCTACCGAGTGCAGCTGA | 140 | MSVPTQVLGLLLLWLTDARC SYELAQPPSVSVAPGKTATI ACGGDNIGGKSVHWYLQKAG QAPVLVISYDSDRPSGIPER FSGSNSGNTATLTISRVEAG DEADYFCQVWDRHGDHVVFG GGTKLTVLGQPKAAPSVTLF PPSSEELQANKATLVCLISD FYPGAVTVAWKADSSPVKAG VETTTPSKQSNNKYAASSYL SLTPEQWKSHRSYSCQVTHE GSTVEKTVAPTECS | 141 |
| Germ-lined 3-25 Heavy Chain | CAGGTGCAGCTGGTGGAGAGCGGAGGAGGAGTGGTGCAGCCAGGCAGGTCTCTGAGG CTGAGCTGCGCCGCCTCCGGCTTCACCTTTTCCAACCACGGCCTGCACTGGGTGCGG CAGGCACCTGGCAAGGGCCTGGAGTGGGTGGCAGTGGTGTCAAGGACGGCACAAAT GAGCACTACGCCGATTCTGTGCGGGGCAGATTCACCATCTCTAGGGACAACAGCAAG AATACACTGTATCTGCAGATGAACTCTCTGCGCGCCGAGGATACCGCCGTGTACTAT TGTGCCCGGGAGGGCTACTGCGGCGACGATAGGTGTTACTCCGGACAGCCAGACTAT TGGGGACAGGGCACCCTGGTGACCGTGAGCAGCGCCATCCACCAAGGGCCCATCTGTC TTCCCCCTGGCCCCATCCTCCAAGAGCACCTCTGGCGGCACAGCTGCCCTGGGCTGC CTGGTGAAGGACTACTTCCCTGAGCCTGTGACAGTGTCCTGGAACTCTGGCGCCCTG ACCAGCGGCGTACACCTTCCCTGCTGTGCTCCAGTCCTCTGGCCTGTACTCCCTG AGCAGCGTGGTGACAGTGCCCTCATCCAGCAGCCTGGGCACCCAGACCTACATCTGCAAT GTGAACCACAAGCCCAGCAACACCAAGGTGGACAAGCGGGTGGAGCCCAAGTCCTGT GACAAGACCCACACCTGCCCCCCATGCCCCGCCCCTGAGCTGCTGGGCGGACCATCT GTCTTCCTGTTCCCCCCCAAGCCCAAGGACACCCTGATGATCTCCCGGACCCCTGAG GTGACCTGTGTGGTGGTGGATGTGAGCCATGAGGACCCCGAGGTGAAGTTCAACTGG TATGTGGATGGCGTGGAGGTGCACAACGCCAAGACCAAGCCCCGGGAGGAGCAGTAC AACAGCACCTACCGGGTGGTGAGCGTGCTGACAGTGCTGCATCAGGACTGGCTGAAT GGCAAGGAGTACAAGTGCAAGGTGTCCAACAAAGCCCTGCCTGCCCCCATTGAAGAG AAGACCATCTCCAAGGCCAAGGGCCAGCCCCGGGAGCCCCAGGTCTACACCCTGCCCCCC TCCCGGGAGGAGATGACCAAGAACCAGGTGAGCCTGACCTGCCTGGTGAAGGGCTTC TACCCCAGCGACATTGCTGTGGAGTGGGAGAGCAACGGCCAGCCTGAGAACAACTAC AAGACCACCCCCCCTGTGCTGGACTCTGATGGCTCCTTCTTCCTGTACAGCAAGCTG ACAGTGGACAAGAGCCGGTGGCAGCAGGGCAATGTCTTCTCCTGCTCTGTGATGCAT GAGGCCCTGCACAACCACTACACCCAGAAGAGCCTGTCCCTGTCCCCGGCAAG | 142 | QVQLVESGGGVVQPGRSLRL SCAASGFTFSNHGLHWVRQA PGKGLEWVAVVSKDGTNEHY ADSVRGRFTISRDNSKNTLY LQMNSLRAEDTAVYYCAREG YCGDDRCYSGQPDYWGQGTL VTVSSASTKGPSVFPLAPSS KSTSGGTAALGCLVKDYFPE PVTVSWNSGALTSGVHTFPA VLQSSGLYSLSSVVTVPSSS LGTQTYICNVNHKPSNTKVD KRVEPKSCDKTHTCPPCPAP ELLGGPSVFLFPPKPKDTLM ISRTPEVTCVVVDVSHEDPE VKFNWYVDGVEVHNAKTKPR EEQYNSTYRVVSVLTVLHQD WLNGKEYKCKVSNKALPAPI EKTISKAKGQPREPQVYTLP PSREEMTKNQVSLTCLVKGF YPSDIAVEWESNGQPEENNYK TTPPVLDSDGSFFLYSKLTV DKSRWQQGNVFSCSVMHEAL HNHYTQKSLSLSPGK | 143 |
| Germ-lined 3-25 Light Chain | GAGATCGTGCTGACCCAGTCTCCTGCCACACTGTCCCTGTCTCCAGGAGAGAGGGCC ACCCTGAGCTGCAGAGCCAGCCAGTCCGTGGGCAGATACCTGGCCTGGTATCAGCAG AAGCCAGGACAGGCACCCAAGGCTGCTGATCTACGACAGCTCCAACAGGGCAACCGGC GTGCCCGCACGCTTCTCTGGCAGCGGCTCCGGCACAGACTTTACCCTGACAATCTCT AGCCTGGAGCCTGAGGATTTCGCCGTGTACTATTGTGTCAGCAGCGGTCCCACTGGCA CCTCTGCCCCTTTGGCGGAGGCCAAAGGTGAGGATCGTACGGTGCTGCACCA TCTGTCTTCATCTTCCCGCCATCTGATGAGCAGTTGAAATCTGGAACTGCCTCTGTT GTGTGCCTGCTGAATAACTTCTATCCCAGAGAGGCCAAAGTACAGTGGAAGGTGGAT AACGCCCTCCAATCGGGTAACTCCCAGGAGAGTGTCACAGAGCAGGACAGCAAGGAC AGCACCTACAGCCTCAGCAGCACCCTGACGCTGAGCAAAGCAGACTACGAGAAACAC AAAGTCTACGCCTGCGAAGTCACCCATCAGGGCCTGAGCTCGCCCGTCACAAAGAGC TTCAACAGGGGAGAGTGT | 144 | EIVLTQSPATLSLSPGERAT LSCRASQSVGRYLAWYQQKP GQAPRLLIYDSSNRATGVPA RFSGSGSGTDFTLTISSLEP EDFAVYYCQQRSHWPPLTFG GGTKVEIKRTVAAPSVFIFP PSDEQLKSGTASVVCLLNNF YPREAKVQWKVDNALQSGNS QESVTEQDSKDSTYSLSSTL TLSKADYEKHKVYACEVTHQ GLSSPVTKSFNRGEC | 145 |
| Germ-lined 3-25 Heavy Chain + YTE | ATGGAATGGAGCTGGGTGTTCCTGTTCTTCCTGAGCGTCACCACCGGCGTGCACTCC GAAGTGCAGCTGGTGGAATCCGGCGGCGGAGTCGTGCAACCCGGCAGGTCCCTGAGG CTGAGCTGCGCTGCCTCCGGCTTCACCTTCTCCAACCATGGCCTGCACTGGGTGAGG CAAGCTCCCGGAAAGGGCCTGGAGTGGGTGGCTGTCGTGTCCAAGGACGGAACCAAC GAACACTACGCCGACTCCGTGAGGGGAAGGTTCACAATCAGCCGGGACAACAGCAAG AACACACTCTATCTGCAGATGAACAGCCTGCGGGCCGAGGACACAGCCGTCTACTAC TGCGCCCGGGAAGGATACTGCGGCGACGATAGGTGTTACTCCGGCCAGCCTGACTAC TGGGGACAGGGCACCCTGGTGACCGTGAGCAGCGCTTCCACCAAGGGCCCCAGCGTG TTCCCTCTGGCTCCCAGCAGCAAATCCACCAGCGGAGGCACAGCTGCCCTCGGATGC CTCGTCAAGGACTATTTTCCCGAGCCCGTGACCGTCTCCTGGAACTCTGGCGCCCTG | 146 | MEWSWVFLFFLSVTTGVHSe VQLVESGGGVVQPGRSLRL SCAASGFTFSNHGLHWVRQA PGKGLEWVAVVSKDGTNEHYA DSVRGRFTISRDNSKNTLYL QMNSLRAEDTAVYYCAREGY CGDDRCYSGQPDYWGQGTLV TVSSASTKGPSVFPLAPSS STSGGTAALGCLVKDYFPEP VTVSWNSGALTSGVHTFPAV | 147 |

TABLE 13-continued

Representative Full Length Sequences (Germlined without and with YTE mutations)

| Clone ID | Nucleotide Sequence | SEQ ID NO. | Amino Acid Sequence | SEQ ID NO. |
|---|---|---|---|---|
| | ACAAGCGGCGTGCACACATTCCCCGCTGTGCTGCAGAGCAGCGGACTGTATTCCCTG TCCAGCGTCGTGACCGTCCCTTCCTCCAGCCTGGGAACACAGACCTACATCTGCAAC GTGAACCACAAGCCCTCCAATACAAAGGTGGACAAGAAGGTGGAGCCCAAGAGCTGT GACAAAACCCATACCTGCCCTCCTTGCCCTGCTCCCGAACTGCTGGGAGGACCCTCC GTCTTTCTGTTCCCCCCAAAACCCAAGGACACCCTCTACATTACCAGGGAGCCCGAG GTGACCTGCGTGGTCGTGGATGTGAGCCACGAAGATCCTGAGGTGAAGTTCAATTGG TACGTGGACGGCGTCGAGGTGCACAACGCCAAGACCAAGCCTCGGGAAGAGCAGTAC AACTCCACATACAGGGTGGTGTCCGTCCTGACCGTCCTGCACCAGGACTGGCTCAAC GGCAAGGAGTACAAGTGCAAGGTGAGCAACAAGGCCCTCCCCGCTCCTATCGAGAAG ACCATCTCCAAGGCCAAAGGACAGCCCCGGGAGCCCCAAGTGTACACCCTGCCTCCT TCCCGGGATGAGCTGACCAAGAACCAAGTCTCCCTGACCTGCCTCGTGAAAGGCTTC TACCCTAGCGATATCGCTGTGGAATGGGAGTCCAACGGCCAGCCCGAGAATAACTAC AAGACAACCCCTCCCGTGCTGGACTCCGACGGCAGCTTCTTCCTGTACAGCAAGCTG ACCGTGGACAAAAGCAGGTGGCAGCAGGGAAACGTGTTCCTGCTCCGTCATGCAC GAGGCCCTGCACAACCACTATACCCAGAAGTCCCTGAGCCTGTCCCCCGGCAAGTGA | | LQSSGLYSLSSVVTVPSSSL GTQTYICNVNHKPSNTKVDK KVEPKSCDKTHTCPPCPAPE LLGGPSVFLFPPKPKDTLyI tRePEVTCVVVDVSHEDPEV KFNWYVDGVEVHNAKTKPRE EQYNSTYRVVSVLTVLHQDW LNGKEYKCKVSNKALPAPIE KTISKAKGQPREPQVYTLPP SRDELTKNQVSLTCLVKGFY PSDIAVEWESNGQPENNYKT TPPVLDSDGSFFLYSKLTVD KSRWQQGNVFSCSVMHEALH NHYTQKSLSLSPGK | |
| Germ- lined 3-25 Light Chain + YTE | ATGTCCGTGCCCACCCAGGTGCTGGGACTGCTGCTGCTGTGGCTGACCGACGCCAGG TGCGAGATCGTGCTGACCCAGAGCCCTGCTACACTGTCCCTGAGCCCCGGCGAGAGG GCTACACTGAGCTGTAGGGCTAGCCAGTCCGTGGGACGGTACCTGGCCTGGTACCAG CAAAAACCCGGACAGGCCCCCCGGCTGCTGATTTACGATAGCAGCAACAGGGCCACC AGGTTCTCCGGTTCTGGCAGCGGCACCGACTTTACCCTGACAATC TCCTCCCTGGAGCCCGAGGACTTCGCCGTGTACTACTGCCAGCAGAGGTCCCATTGG CCTCCTCTGACCTTCGGCGGCGGCACCAAGGTGGAGATCAAGAGGACCGTGGCCGCC CCCTCCGTGTTCATCTTTCCCCCCTCCGACGAGCAGCTGAAGAGCGGCACCGCTAGC GTGGTGTGCCTGCTGAACAACTTCTACCCCAGGGAGGCCAAGGTGCAGTGGAAGGTG GACAACGCTCTGCAGTCCGGCAACAGCCAGGAGAGCGTGACCGAGCAGGACAGCAAG GACTCCACCTACTCCCTGAGCAGCACCCTGACCCTGTCCAAAGCCGACTACGAGAAG CACAAGGTGTACGCTTGCGAGGTGACCCACCAGGGCCTGTCCAGCCCTGTGACCAAA TCCTTCAACAGGGGCGAGTGCTGA | 148 | MSVPTQVLGLLLLWLTDARC EIVLTQSPATLSLSPGERAT LSCRASQSVGRYLAWYQQKP GQAPRLLIYDSSNRATGVPA RFSGSGSGTDFTLTISSLEP EDFAVYYCQQRSHWPPLTFG GGTKVEIKRTVAAPSVFIFP PSDEQLKSGTASVVCLLNNF YPREAKVQWKVDNALQSGNS QESVTEQDSKDSTYSLSSTL TLSKADYEKHKVYACEVTHQ GLSSPVTKSFNRGEC | 149 |

What is claimed is:

1. An antibody or antigen binding fragment thereof that binds to human cytomegalovirus (CMV), wherein the antibody or antigen binding fragment is isolated or recombinant and comprises:
(A) an antibody or antigen binding fragment that binds to the pentameric gH complex site 1 selected from the group consisting of:
(1) a heavy chain variable domain complementary determining region (CDR) 1 comprising the amino acid sequence of SEQ ID NO: 1, a heavy chain variable domain CDR2 comprising the amino acid sequence of SEQ ID NO: 2, and a heavy chain variable domain CDR3 comprising the amino acid sequence of SEQ ID NO: 3; and a light chain variable domain CDR1 comprising the amino acid sequence of SEQ ID NO: 4, a light chain variable domain CDR2 comprising the amino acid sequence of SEQ ID NO: 5, and a light chain variable domain CDR3 comprising the amino acid sequence of SEQ ID NO: 6,
(2) a heavy chain variable domain complementary determining region (CDR) 1 comprising the amino acid sequence of SEQ ID NO: 7, a heavy chain variable domain CDR2 comprising the amino acid sequence of SEQ ID NO: 8, and a heavy chain variable domain CDR3 comprising the amino acid sequence of SEQ ID NO: 9; and a light chain variable domain CDR1 comprising the amino acid sequence of SEQ ID NO: 10, a light chain variable domain CDR2 comprising the amino acid sequence of SEQ ID NO: 11, and a light chain variable domain CDR3 comprising the amino acid sequence of SEQ ID NO: 12, and
(B) a M252Y/S254T/T256E mutation.

2. The antibody or antigen binding fragment of claim 1, wherein the antibody or antigen binding fragment comprises:
a heavy chain variable domain CDR1 comprising the amino acid sequence of SEQ ID NO: 7, a heavy chain variable domain CDR2 comprising the amino acid sequence of SEQ ID NO: 8, a heavy chain variable domain CDR3 comprising the amino acid sequence of SEQ TD NO: 9, a light chain variable domain CDR1 comprising the amino acid sequence of SEQ ID NO: 10, a light chain variable domain CDR2 comprising the amino acid sequence of SEQ TD NO: 11, and a light chain variable domain CDR3 comprising the amino acid sequence of SEQ ID NO: 12.

3. The antibody or antigen binding fragment of claim 1, wherein the antibody or antigen binding fragment comprises:
an antibody or antigen binding fragment comprising: a heavy chain variable domain CDR1 comprising the amino acid sequence of SEQ ID NO: 1, a heavy chain variable domain CDR2 comprising the amino acid sequence of SEQ ID NO: 2, a heavy chain variable domain CDR3 comprising the amino acid sequence of SEQ ID NO: 3, a light chain variable domain CDR1 comprising the amino acid sequence of SEQ ID NO: 4, a light chain variable domain CDR2 comprising the amino acid sequence of SEQ ID NO: 5, and a light chain variable domain CDR3 comprising the amino acid sequence of SEQ ID NO: 6.

4. The antibody or antigen binding fragment of claim 1, comprising a variable heavy chain comprising the amino acid sequence of SEQ ID NO: 119 and a variable light chain comprising the amino acid sequence of SEQ ID NO: 121.

5. The antibody or antigen binding fragment of claim 4, wherein the heavy chain comprises the amino acid sequence of SEQ ID NO: 135 or SEQ ID NO: 139 and the light chain comprises the amino acid sequence of SEQ ID NO: 137 or SEQ ID NO: 141.

6. The antibody or antigen binding fragment of claim 5, comprising a variable heavy chain comprising the amino acid sequence of SEQ ID NO: 123 and a variable light chain comprising the amino acid sequence of SEQ ID NO: 125.

7. The antibody or antigen binding fragment of claim 1, wherein the heavy chain comprises the amino acid sequence of SEQ ID NO: 143 or SEQ ID NO: 147 and the light chain comprises the amino acid sequence of SEQ ID NO: 145 or SEQ ID NO: 149.

8. An isolated nucleic acid encoding an antibody or antigen binding fragment of claim 1.

9. The isolated nucleic acid molecule of claim 8, wherein the nucleic acid molecule comprises a sequence of nucleotides as set forth in any of SEQ ID NOS: 64 to 76 or SEQ ID NOS: 90 to 101.

10. The isolated nucleic acid molecule of claim 8, wherein the nucleic acid molecule comprises a sequence of nucleotides as set forth in any of SEQ ID NOS: 114, 116, 118, 120, 122, or 124.

11. The isolated nucleic acid molecule of claim 8, wherein the nucleic acid molecule comprises a sequence of nucleotides as set forth in any of SEQ ID NOS: 126, 128, 130, 132, 134, 136, 138, 140, 142, 144, 146, or 148.

12. An expression vector comprising the isolated nucleic acid of claim 8 operably linked to a promoter.

13. An isolated host cell comprising the expression vector of claim 12.

14. A pharmaceutical composition comprising the antibody or antigen binding fragment of claim 1 and a pharmaceutically acceptable carrier or diluent.

15. A method of treating a CMV infection in a subject comprising administering to a subject in need thereof an effective amount of the antibody or antigen binding fragment of claim 1.

16. A method of conferring passive immunity to a CMV infection in a patient, the method comprising administering to the patient one or more antibodies or antigen binding fragments according to claim 1.

17. A method of producing an antibody or antigen binding fragment:
  (a) culturing a host cell comprising a polynucleotide encoding the heavy chain and/or the light chain of any one of the antibodies or antigen binding fragments of claim 1 under conditions wherein the polynucleotide is expressed; and
  (b) optionally, recovering the antibody or antigen binding fragment from the host cell and/or culture medium.

* * * * *

SEQUENCE LISTING

<160> NUMBER OF SEQ ID NOS: 149

<210> SEQ ID NO 1
<211> LENGTH: 8
<212> TYPE: PRT
<213> ORGANISM: Homo sapiens

<400> SEQUENCE: 1

Gly Phe Ser Phe Ser Asp His Asp
1               5

<210> SEQ ID NO 2
<211> LENGTH: 10
<212> TYPE: PRT
<213> ORGANISM: Homo sapiens

<400> SEQUENCE: 2

Ser Arg Asn Lys Asp Tyr Ser Ser Thr Thr
1               5                   10

<210> SEQ ID NO 3
<211> LENGTH: 19
<212> TYPE: PRT
<213> ORGANISM: Homo sapiens

<400> SEQUENCE: 3

Ala Arg Gly Pro His His Ser Asp Arg Ser Gly Tyr Tyr Gly Gly Thr
1               5                   10                  15

Phe Asp Ile

```
<210> SEQ ID NO 4
<211> LENGTH: 6
<212> TYPE: PRT
<213> ORGANISM: Homo sapiens

<400> SEQUENCE: 4

Gln Gly Ile Ser Ser Trp
1               5

<210> SEQ ID NO 5
<211> LENGTH: 3
<212> TYPE: PRT
<213> ORGANISM: Homo sapiens

<400> SEQUENCE: 5

Asp Ala Ser
1

<210> SEQ ID NO 6
<211> LENGTH: 9
<212> TYPE: PRT
<213> ORGANISM: Homo sapiens

<400> SEQUENCE: 6

Gln Gln Gly Asn Met Phe Pro Leu Thr
1               5

<210> SEQ ID NO 7
<211> LENGTH: 8
<212> TYPE: PRT
<213> ORGANISM: Homo sapiens

<400> SEQUENCE: 7

Gly Tyr Thr Phe Thr Asn Tyr Ala
1               5

<210> SEQ ID NO 8
<211> LENGTH: 8
<212> TYPE: PRT
<213> ORGANISM: Homo sapiens

<400> SEQUENCE: 8

Ile Asn Ala Gly Arg Gly Asn Thr
1               5

<210> SEQ ID NO 9
<211> LENGTH: 15
<212> TYPE: PRT
<213> ORGANISM: Homo sapiens

<400> SEQUENCE: 9

Ala Arg Asp Glu Ser Thr Gly Asp Tyr Tyr Tyr Met Asp Val
1               5                   10                  15

<210> SEQ ID NO 10
<211> LENGTH: 6
<212> TYPE: PRT
<213> ORGANISM: Homo sapiens

<400> SEQUENCE: 10

Arg Leu Asp Asp Lys Tyr
1               5

<210> SEQ ID NO 11
<211> LENGTH: 3
```

<212> TYPE: PRT
<213> ORGANISM: Homo sapiens

<400> SEQUENCE: 11

Gln Asp Asn
1

<210> SEQ ID NO 12
<211> LENGTH: 9
<212> TYPE: PRT
<213> ORGANISM: Homo sapiens

<400> SEQUENCE: 12

Gln Ala Trp Asp Ser Asp Thr Tyr Val
1               5

<210> SEQ ID NO 13
<211> LENGTH: 8
<212> TYPE: PRT
<213> ORGANISM: Homo sapiens

<400> SEQUENCE: 13

Glu Phe Thr Phe Ser Asp Tyr Tyr
1               5

<210> SEQ ID NO 14
<211> LENGTH: 8
<212> TYPE: PRT
<213> ORGANISM: Homo sapiens

<400> SEQUENCE: 14

Ile Ser Ser Ser Gly Thr Thr Ile
1               5

<210> SEQ ID NO 15
<211> LENGTH: 19
<212> TYPE: PRT
<213> ORGANISM: Homo sapiens

<400> SEQUENCE: 15

Ala Arg Asp Ser Tyr Ser Lys Leu Val Asp Ile Glu Ala Ile Glu Ala
1               5                   10                  15

Phe Asp Ile

<210> SEQ ID NO 16
<211> LENGTH: 6
<212> TYPE: PRT
<213> ORGANISM: Homo sapiens

<400> SEQUENCE: 16

Asn Ile Gly Ser Lys Ser
1               5

<210> SEQ ID NO 17
<211> LENGTH: 3
<212> TYPE: PRT
<213> ORGANISM: Homo sapiens

<400> SEQUENCE: 17

Phe Asp Thr
1

<210> SEQ ID NO 18
<211> LENGTH: 11

```
<212> TYPE: PRT
<213> ORGANISM: Homo sapiens

<400> SEQUENCE: 18

Gln Val Trp Asp Arg Thr Ser Asp His Val Val
1               5                   10

<210> SEQ ID NO 19
<211> LENGTH: 8
<212> TYPE: PRT
<213> ORGANISM: Homo sapiens

<400> SEQUENCE: 19

Gly Phe Thr Phe Ser Asp Tyr Tyr
1               5

<210> SEQ ID NO 20
<211> LENGTH: 8
<212> TYPE: PRT
<213> ORGANISM: Homo sapiens

<400> SEQUENCE: 20

Ile Ser Ser Ser Gly Arg Thr Ile
1               5

<210> SEQ ID NO 21
<211> LENGTH: 6
<212> TYPE: PRT
<213> ORGANISM: Homo sapiens

<400> SEQUENCE: 21

Asn Ile Gly Gly Lys Ser
1               5

<210> SEQ ID NO 22
<211> LENGTH: 3
<212> TYPE: PRT
<213> ORGANISM: Homo sapiens

<400> SEQUENCE: 22

Tyr Asp Ser
1

<210> SEQ ID NO 23
<211> LENGTH: 11
<212> TYPE: PRT
<213> ORGANISM: Homo sapiens

<400> SEQUENCE: 23

Gln Val Trp Asp Arg His Gly Asp His Val Val
1               5                   10

<210> SEQ ID NO 24
<211> LENGTH: 8
<212> TYPE: PRT
<213> ORGANISM: Homo sapiens

<400> SEQUENCE: 24

Gly Phe Asn Phe Lys Asp Tyr Tyr
1               5

<210> SEQ ID NO 25
<211> LENGTH: 8
<212> TYPE: PRT
<213> ORGANISM: Homo sapiens
```

<400> SEQUENCE: 25

Ile Ser Ser Ser Gly Gln Thr Ile
1               5

<210> SEQ ID NO 26
<211> LENGTH: 19
<212> TYPE: PRT
<213> ORGANISM: Homo sapiens

<400> SEQUENCE: 26

Ala Arg Asp Ser Tyr Ser Lys Leu Val Asp Ile Val Ala Ile Glu Ala
1               5                   10                  15

Phe Asp Leu

<210> SEQ ID NO 27
<211> LENGTH: 11
<212> TYPE: PRT
<213> ORGANISM: Homo sapiens

<400> SEQUENCE: 27

Gln Val Trp Asp Ser Ser Ser Ala Arg Leu Val
1               5                   10

<210> SEQ ID NO 28
<211> LENGTH: 8
<212> TYPE: PRT
<213> ORGANISM: Homo sapiens

<400> SEQUENCE: 28

Gly Phe Ser Phe Ser Ala Tyr Tyr
1               5

<210> SEQ ID NO 29
<211> LENGTH: 8
<212> TYPE: PRT
<213> ORGANISM: Homo sapiens

<400> SEQUENCE: 29

Ile Ser Ser Ser Gly Asn Thr Ile
1               5

<210> SEQ ID NO 30
<211> LENGTH: 19
<212> TYPE: PRT
<213> ORGANISM: Homo sapiens

<400> SEQUENCE: 30

Ala Arg Asp Ser Tyr Ser Lys Leu Ala Asp Ile Glu Ala Thr Glu Ala
1               5                   10                  15

Phe Asp Val

<210> SEQ ID NO 31
<211> LENGTH: 11
<212> TYPE: PRT
<213> ORGANISM: Homo sapiens

<400> SEQUENCE: 31

Gln Val Trp Asp Ser Gly Ser Asp Arg Val Val
1               5                   10

<210> SEQ ID NO 32
<211> LENGTH: 8

```
<212> TYPE: PRT
<213> ORGANISM: Homo sapiens

<400> SEQUENCE: 32

Ile Ser Gly Ser Gly Arg Thr Leu
1               5

<210> SEQ ID NO 33
<211> LENGTH: 19
<212> TYPE: PRT
<213> ORGANISM: Homo sapiens

<400> SEQUENCE: 33

Ala Arg Asp Ser Tyr Ser Lys Leu Val Glu Ile Glu Ala Ile Glu Ala
1               5                   10                  15

Phe Asp Val

<210> SEQ ID NO 34
<211> LENGTH: 11
<212> TYPE: PRT
<213> ORGANISM: Homo sapiens

<400> SEQUENCE: 34

Gln Val Trp Asp Arg Gln Thr Asp His Val Val
1               5                   10

<210> SEQ ID NO 35
<211> LENGTH: 10
<212> TYPE: PRT
<213> ORGANISM: Homo sapiens

<400> SEQUENCE: 35

Gly Asp Ala Ile Ser Gly Ser Asn Tyr Tyr
1               5                   10

<210> SEQ ID NO 36
<211> LENGTH: 7
<212> TYPE: PRT
<213> ORGANISM: Homo sapiens

<400> SEQUENCE: 36

Ile Tyr His Thr Gly Ser Thr
1               5

<210> SEQ ID NO 37
<211> LENGTH: 12
<212> TYPE: PRT
<213> ORGANISM: Homo sapiens

<400> SEQUENCE: 37

Ala Arg Arg Ile Arg Gly Tyr Ser Gly Thr Tyr Asp
1               5                   10

<210> SEQ ID NO 38
<211> LENGTH: 6
<212> TYPE: PRT
<213> ORGANISM: Homo sapiens

<400> SEQUENCE: 38

Gln Asp Ile Ser Ser Tyr
1               5

<210> SEQ ID NO 39
<211> LENGTH: 3
```

<212> TYPE: PRT
<213> ORGANISM: Homo sapiens

<400> SEQUENCE: 39

Ser Ala Ser
1

<210> SEQ ID NO 40
<211> LENGTH: 5
<212> TYPE: PRT
<213> ORGANISM: Homo sapiens

<400> SEQUENCE: 40

Gln Gln Leu Asn Asn
1               5

<210> SEQ ID NO 41
<211> LENGTH: 8
<212> TYPE: PRT
<213> ORGANISM: Homo sapiens

<400> SEQUENCE: 41

Gly Phe Ala Phe Asp Asn Tyr Ala
1               5

<210> SEQ ID NO 42
<211> LENGTH: 8
<212> TYPE: PRT
<213> ORGANISM: Homo sapiens

<400> SEQUENCE: 42

Ile Ser Leu Glu Gly Arg Asn Lys
1               5

<210> SEQ ID NO 43
<211> LENGTH: 22
<212> TYPE: PRT
<213> ORGANISM: Homo sapiens

<400> SEQUENCE: 43

Ala Arg Asp Met Arg Tyr Tyr Tyr Asp Ser Asn Gly His Tyr Arg Asn
1               5                   10                  15

Arg Tyr Gly Met Asp Val
            20

<210> SEQ ID NO 44
<211> LENGTH: 6
<212> TYPE: PRT
<213> ORGANISM: Homo sapiens

<400> SEQUENCE: 44

Gln Asp Ile Asn Gln Phe
1               5

<210> SEQ ID NO 45
<211> LENGTH: 8
<212> TYPE: PRT
<213> ORGANISM: Homo sapiens

<400> SEQUENCE: 45

Gln Gln Tyr Glu Asn Leu Phe Thr
1               5

<210> SEQ ID NO 46

```
<211> LENGTH: 8
<212> TYPE: PRT
<213> ORGANISM: Homo sapiens

<400> SEQUENCE: 46

Gly Tyr Thr Phe Asn Thr Tyr Ala
1               5

<210> SEQ ID NO 47
<211> LENGTH: 8
<212> TYPE: PRT
<213> ORGANISM: Homo sapiens

<400> SEQUENCE: 47

Ile Asn Thr Tyr Ser Gly Ser Thr
1               5

<210> SEQ ID NO 48
<211> LENGTH: 12
<212> TYPE: PRT
<213> ORGANISM: Homo sapiens

<400> SEQUENCE: 48

Ala Arg Asp Gly Tyr Asn Trp Gly Phe Leu Asp Phe
1               5                   10

<210> SEQ ID NO 49
<211> LENGTH: 6
<212> TYPE: PRT
<213> ORGANISM: Homo sapiens

<400> SEQUENCE: 49

Gln Gly Ile Ser Asn Tyr
1               5

<210> SEQ ID NO 50
<211> LENGTH: 3
<212> TYPE: PRT
<213> ORGANISM: Homo sapiens

<400> SEQUENCE: 50

Ala Ala Ser
1

<210> SEQ ID NO 51
<211> LENGTH: 9
<212> TYPE: PRT
<213> ORGANISM: Homo sapiens

<400> SEQUENCE: 51

Gln Lys Tyr Asn Ser Ala Pro Leu Thr
1               5

<210> SEQ ID NO 52
<211> LENGTH: 8
<212> TYPE: PRT
<213> ORGANISM: Homo sapiens

<400> SEQUENCE: 52

Gly Tyr Arg Phe Thr Ile Tyr Ser
1               5

<210> SEQ ID NO 53
<211> LENGTH: 8
<212> TYPE: PRT
```

<213> ORGANISM: Homo sapiens

<400> SEQUENCE: 53

Ile Asn Thr Tyr Asn Gly Asn Thr
1               5

<210> SEQ ID NO 54
<211> LENGTH: 12
<212> TYPE: PRT
<213> ORGANISM: Homo sapiens

<400> SEQUENCE: 54

Ala Arg Asp Ala Glu Asn Trp Gly Phe Phe Asp Asp
1               5                   10

<210> SEQ ID NO 55
<211> LENGTH: 6
<212> TYPE: PRT
<213> ORGANISM: Homo sapiens

<400> SEQUENCE: 55

Gln Ser Val Gly Arg His
1               5

<210> SEQ ID NO 56
<211> LENGTH: 3
<212> TYPE: PRT
<213> ORGANISM: Homo sapiens

<400> SEQUENCE: 56

Gly Ala Ser
1

<210> SEQ ID NO 57
<211> LENGTH: 9
<212> TYPE: PRT
<213> ORGANISM: Homo sapiens

<400> SEQUENCE: 57

Gln Gln Tyr Asn Thr Trp Pro Tyr Thr
1               5

<210> SEQ ID NO 58
<211> LENGTH: 8
<212> TYPE: PRT
<213> ORGANISM: Homo sapiens

<400> SEQUENCE: 58

Gly Phe Thr Phe Ser Asn His Gly
1               5

<210> SEQ ID NO 59
<211> LENGTH: 8
<212> TYPE: PRT
<213> ORGANISM: Homo sapiens

<400> SEQUENCE: 59

Val Ser Lys Asp Gly Thr Asn Glu
1               5

<210> SEQ ID NO 60
<211> LENGTH: 18
<212> TYPE: PRT
<213> ORGANISM: Homo sapiens

<400> SEQUENCE: 60

Ala Arg Glu Gly Tyr Cys Gly Asp Asp Arg Cys Tyr Ser Gly Gln Pro
1               5                   10                  15

Asp Tyr

<210> SEQ ID NO 61
<211> LENGTH: 6
<212> TYPE: PRT
<213> ORGANISM: Homo sapiens

<400> SEQUENCE: 61

Gln Ser Val Gly Arg Tyr
1               5

<210> SEQ ID NO 62
<211> LENGTH: 3
<212> TYPE: PRT
<213> ORGANISM: Homo sapiens

<400> SEQUENCE: 62

Asp Ser Ser
1

<210> SEQ ID NO 63
<211> LENGTH: 10
<212> TYPE: PRT
<213> ORGANISM: Homo sapiens

<400> SEQUENCE: 63

Gln Gln Arg Ser His Trp Pro Pro Leu Thr
1               5                   10

<210> SEQ ID NO 64
<211> LENGTH: 384
<212> TYPE: DNA
<213> ORGANISM: Homo sapiens

<400> SEQUENCE: 64
gaggtgcaac tggtgcagtc tgggggaggc ttggtccagc ctggagggtc cctgagagtc       60
tcctgtgcag cctctggatt cagcttcagt gaccacgaca tggactgggt ccgccaggct      120
ccagggaagg ggtttgagtg ggtcggccgt agcagaaaca agattacag ttccaccaca       180 gaatatgccg cgtctgtgag gggcagattc accatctcaa gacatacttc agaggattta      240
ctgtatctgg agttgaacac cgtgaaaacc gaggacacgg ccgtgtattt ttgtgctaga      300
ggacctcatc actctgatcg gagtggttat tacggggaa cttttgatat ctggggccaa       360
gggaccatgg tcaccgtgtc ctca                                             384

<210> SEQ ID NO 65
<211> LENGTH: 366
<212> TYPE: DNA
<213> ORGANISM: Homo sapiens

<400> SEQUENCE: 65
caagtgcagc tcgtggagtc tgggctgag gtgaagaagc tggggcctt agtgaaggtt        60 tcctgcaagg cttctggata caccttcact aactatgcta cattgggt gcgccaggcc       120 tccggacaaa ggcttgagtg gatgggatgg atcaacgctg gcagaggtaa cacaaaatat     180
tcacagaagt tccagggcag agtcaccatt actaggaca catccgcgag cacagcctac      240
atggagctga gcagtttgag atctgaggac gcggctgttt atttctgtgc gagagatgag     300

```
tcaactggtg actactacta ctacatggac gtctggggca agggaccac ggtcaccgtc    360 tcttca                                                              366

<210> SEQ ID NO 66
<211> LENGTH: 378
<212> TYPE: DNA
<213> ORGANISM: Homo sapiens

<400> SEQUENCE: 66
caggtgcagc tggtggcgtc tgggggaggc ttggtcaagc ctggcgggtc cctgagactc    60
tcctgtgcag cctctgaatt caccttcagt gactactaca tgacctggat ccgccaggct   120
ccagggaagg ggctggagtg ggtctcgtat attagtagta gtggtacgac catatactac   180
gccgactctg tgaagggccg attcaccgtc tccagggaca cgccaagaa ctcactgttt    240 ctgcaaatga acagcctgag agccgaggac acggctcttt attattgtgc gagagactct   300
tattcgaagt tggtggatat agaggccatc gaagcttttg atatctgggg ccaagggaca   360
atggtcaccg tgtcctca                                                 378

<210> SEQ ID NO 67
<211> LENGTH: 378
<212> TYPE: DNA
<213> ORGANISM: Homo sapiens

<400> SEQUENCE: 67
caggtgcagc tggtggcgtc tgggggaggc ttggtcaagc ctggcgggtc cctgagactc    60
tcctgtgcag cctctggatt caccttcagt gactactaca tgacctggat ccgccaggct   120
ccagggaagg ggctggagtg ggtctcgtat attagtagta gtggtacgac catatactac   180
gccgactctg tgaagggccg attcaccgtc tccagggaca cgccaagaa ctcactgttt    240 ctgcaaatga acagcctgag agccgaggac acggctcttt attattgtgc gagagactct   300
tattcgaagt tggtggatat agaggccatc gaagcttttg atatctgggg ccaagggacc   360
atggtcaccg tgtcctca                                                 378

<210> SEQ ID NO 68
<211> LENGTH: 378
<212> TYPE: DNA
<213> ORGANISM: Homo sapiens

<400> SEQUENCE: 68
caggtgcacc tggtggagtc tgggggaggc ttggtcaagc ctggacggtc cctgagactc    60
tcctgtgcag cctctggatt caccttcagt gactattaca tggcttggat ccgccaagtt   120
ccggggaagg ggctggagtg ggtttcattc attagtagta gtggtcgtac catctactac   180
gcagactctg tgaagggccg attcaccatc tccagggaca cgccaagga ctcactgtat    240 cttcaaatgc acagcctgag agccgaggac acggctgttt attactgtgc gagagattct   300
tattcgaagt tggtggatat agaggccatc gaggcttttg atatctgggg ccgagggacc   360
atggtcaccg tgtcctca                                                 378

<210> SEQ ID NO 69
<211> LENGTH: 378
<212> TYPE: DNA
<213> ORGANISM: Homo sapiens

<400> SEQUENCE: 69
```

```
caggtgcagc tggtggaatc tgggggaggc ttggtcaagc ctggagggtc cctgagactc    60
tcctgtgcgc cagctggatt caacttcaaa gactactaca tgacctggat ccgccaggct   120
ccaggaaagg ggctggagtg ggtttccttc atcagtagta gtggtcagac catatactac   180
gcagactctg tgaagggccg attcaccatc tccaggaca acgccaggaa ctcactgtat    240
ctgcaaatga atagcctgag agccgaggac acggctgttt attactgtgc gagagactct   300
tactcgaagt tggtggatat agtggccatc gaagcttttg atctttgggg ccaagggaca   360
ctggtcagcg tctcctca                                                 378
```

```
<210> SEQ ID NO 70
<211> LENGTH: 378
<212> TYPE: DNA
<213> ORGANISM: Homo sapiens

<400> SEQUENCE: 70
```

```
caggtgcagc tggtggagtc tgggggaggc ctggtcaagc ctggagggtc cctgagactc    60
tcctgtgcag cctctggatt cagcttcagt gcctactaca tgagttggat ccgccaggct   120
ccagggaagg ggctggagtg gatttcatac attagtagta gtggtaatac catatactac   180
acagactctg tgaagggccg attcaccatc gccaggaca acgccaagaa ctcactttat    240
ctgcaaatga acagcctgag agccgaggac acgggtctat attactgtgc gagagattct   300
tattcgaagt tggcggacat agaggccacc gaggcttttg atgtctgggg ccaagggaca   360
atggtcgccg tctcttca                                                 378
```

```
<210> SEQ ID NO 71
<211> LENGTH: 378
<212> TYPE: DNA
<213> ORGANISM: Homo sapiens

<400> SEQUENCE: 71
```

```
caggtgcacc tggtggagtc tgggggaggc ttggtcaagc ctggagggtc cctgagactc    60
tcctgtgcag cctctggatt caccttcagt gactattaca tggcctggat tcgccgcgct   120
ccggggaagg gcctggagtg gatttcattc attagtggca gcggccgcac cctctaccat   180
gcagagtctg tgaagggccg attcaccgtc tccagggaca acgccaagga ctcactgtat   240
cttcacatgc acagcctgag agacgcagac acggctgttt attactgtgc gagagattct   300
tattcgaagt tggtggaaat agaggccatc gaagcctttg atgtctgggg ccgagggaca   360
gtggtcaccg tctcctca                                                 378
```

```
<210> SEQ ID NO 72
<211> LENGTH: 360
<212> TYPE: DNA
<213> ORGANISM: Homo sapiens

<400> SEQUENCE: 72
```

```
cagctgcagt tgcaggagtc gggcccagga ctggtgaagc cttcggagac cctgtccctc    60
acctgctctg tctctggtga cgccatcagc ggcagcaatt attactgggg ctggatacgc   120
cagcccccag ggaagggact gcagtggatt gggagtatct atcacactgg gagcaccttc   180
tacaacccgt cattcagcag tcgagtcacc ttatccgtag acacgtccaa gaaccagttc   240
tccctgaagc tgatctctgt gaacgccgca gacacggctg tgtattattg tgcaagacgg   300
atcaggggtt atagtgggac ctacgactgg ggccaggaa ccctggtcac cgtctcctca   360
```

-continued

<210> SEQ ID NO 73
<211> LENGTH: 387
<212> TYPE: DNA
<213> ORGANISM: Homo sapiens

<400> SEQUENCE: 73

| | | | | | | |
|---|---|---|---|---|---|---|
| caggtgaagc | tggtggagtc | gggggggaggc | gtggtccagc | ctgggaggtc | cctgagactc | 60 |
| tcatgtgcag | gctctggatt | cgcctttgat | aactacgcta | tgcactgggt | ccgccaggct | 120 |
| ccaggcaagg | ggctggagtg | ggtggcagtc | atatcacttg | aaggaaggaa | taaatattac | 180 |
| gcaggccccg | cgaagggccg | gttctccatt | tccagagaca | actccagaaa | cacagtgcat | 240 |
| ctgcaaatga | acagtctgag | acctgaggac | acggctgtgt | atttctgtgc | gagagatatg | 300 |
| cgttactatt | atgatagtaa | tggtcactat | aggaaccgat | atggcatgga | cgtctggggc | 360 |
| caagggacca | cggtcatcgt | ctcctca | | | | 387 |

<210> SEQ ID NO 74
<211> LENGTH: 357
<212> TYPE: DNA
<213> ORGANISM: Homo sapiens

<400> SEQUENCE: 74

| | | | | | | |
|---|---|---|---|---|---|---|
| caggtgcagc | tggtgcagtc | tggagctgag | gtgaagaagc | ctggggcctc | agtgaaggtc | 60 |
| tcctgtaaga | cttctggtta | cacctttaat | acttatgcta | tcagctgggt | gcgccaggcc | 120 |
| cctggacaag | ggcttgagtg | ggtgggatgg | atcaacactt | acagtggaag | cacaaagtat | 180 |
| gcacagaagg | tccagggcag | agtcaccatg | accacagaca | catccacgag | caccgcctac | 240 |
| atggagttga | ggggcctgag | atctgacgac | acggccgtat | attactgtgc | gagagatggc | 300 |
| tacaattggg | gttttctcga | cttctggggc | cagggatccc | tggtcaccgt | ctcctca | 357 |

<210> SEQ ID NO 75
<211> LENGTH: 357
<212> TYPE: DNA
<213> ORGANISM: Homo sapiens

<400> SEQUENCE: 75

| | | | | | | |
|---|---|---|---|---|---|---|
| caggtgcagg | tggtgcagtc | tggagctgag | gtgaagaagc | ctggggcctc | agtgatggtc | 60 |
| tcctgcaaga | cttctggtta | cagatttacc | atatatagta | tcgcctggat | gcgccaggcc | 120 |
| ccgggacaag | ggcttgagtg | gatggggtcg | atcaacactt | acaatggcaa | tacaaagtat | 180 |
| gcagagaagt | tccagggcag | agtcaccatg | agtagagaca | catccacgag | cacagcctac | 240 |
| atggaggtga | ggagcctggg | atctgccgac | acggccatgt | attactgtgc | gagagacgca | 300 |
| gagaactggg | gattttttga | cgactggggc | caggggaccc | tggtcaccgt | ctcctca | 357 |

<210> SEQ ID NO 76
<211> LENGTH: 375
<212> TYPE: DNA
<213> ORGANISM: Homo sapiens

<400> SEQUENCE: 76

| | | | | | | |
|---|---|---|---|---|---|---|
| caggtgcagc | tggtggagtc | tgggggaggc | gtggtccagc | ctggaaggtc | cctgagactc | 60 |
| tcctgtgcag | cctctggatt | caccttcagt | aaccatggtc | tacactgggt | ccgccagcct | 120 |
| ccaggcaagg | ggctggagtg | ggtggcagtt | gtatcaaaag | atggaaccaa | tgaacactac | 180 |
| gcagactccg | tgaggggccg | gttcaccatc | tccagagaca | attccaagaa | cacgttgtat | 240 |
| ctgctaatga | agagcctcag | acttgaggac | acggctgtat | attattgtgc | gagagaaggg | 300 |

```
tattgtgggg atgatcgctg ctactccgga cagcctgact actggggcca gggaatcctg    360
gtcaccgtct cctca                                                     375
```

<210> SEQ ID NO 77
<211> LENGTH: 128
<212> TYPE: PRT
<213> ORGANISM: Homo sapiens

<400> SEQUENCE: 77

Glu Val Gln Leu Val Gln Ser Gly Gly Gly Leu Val Gln Pro Gly Gly
1               5                   10                  15

Ser Leu Arg Val Ser Cys Ala Ala Ser Gly Phe Ser Phe Ser Asp His
            20                  25                  30

Asp Met Asp Trp Val Arg Gln Ala Pro Gly Lys Gly Phe Glu Trp Val
        35                  40                  45

Gly Arg Ser Arg Asn Lys Asp Tyr Ser Ser Thr Thr Glu Tyr Ala Ala
    50                  55                  60

Ser Val Arg Gly Arg Phe Thr Ile Ser Arg His Thr Ser Glu Asp Leu
65                  70                  75                  80

Leu Tyr Leu Glu Leu Asn Thr Val Lys Thr Glu Asp Thr Ala Val Tyr
                85                  90                  95

Phe Cys Ala Arg Gly Pro His His Ser Asp Arg Ser Gly Tyr Tyr Gly
            100                 105                 110

Gly Thr Phe Asp Ile Trp Gly Gln Gly Thr Met Val Thr Val Ser Ser
        115                 120                 125

<210> SEQ ID NO 78
<211> LENGTH: 122
<212> TYPE: PRT
<213> ORGANISM: Homo sapiens

<400> SEQUENCE: 78

Gln Val Gln Leu Val Glu Ser Gly Ala Glu Val Lys Lys Pro Gly Ala
1               5                   10                  15

Leu Val Lys Val Ser Cys Lys Ala Ser Gly Tyr Thr Phe Thr Asn Tyr
            20                  25                  30

Ala Ile His Trp Val Arg Gln Ala Ser Gly Gln Arg Leu Glu Trp Met
        35                  40                  45

Gly Trp Ile Asn Ala Gly Arg Gly Asn Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Ala Ala Val Tyr Phe Cys
                85                  90                  95

Ala Arg Asp Glu Ser Thr Gly Asp Tyr Tyr Tyr Tyr Met Asp Val Trp
            100                 105                 110

Gly Lys Gly Thr Thr Val Thr Val Ser Ser
        115                 120

<210> SEQ ID NO 79
<211> LENGTH: 126
<212> TYPE: PRT
<213> ORGANISM: Homo sapiens

<400> SEQUENCE: 79

Gln Val Gln Leu Val Ala Ser Gly Gly Gly Leu Val Lys Pro Gly Gly
1               5                   10                  15

```
Ser Leu Arg Leu Ser Cys Ala Ala Ser Glu Phe Thr Phe Ser Asp Tyr
            20                  25                  30

Tyr Met Thr Trp Ile Arg Gln Ala Pro Gly Lys Gly Leu Glu Trp Val
            35                  40                  45

Ser Tyr Ile Ser Ser Ser Gly Thr Thr Ile Tyr Tyr Ala Asp Ser Val
 50                  55                  60

Lys Gly Arg Phe Thr Val Ser Arg Asp Asn Ala Lys Asn Ser Leu Phe
 65                  70                  75                  80

Leu Gln Met Asn Ser Leu Arg Ala Glu Asp Thr Ala Leu Tyr Tyr Cys
                 85                  90                  95

Ala Arg Asp Ser Tyr Ser Lys Leu Val Asp Ile Glu Ala Ile Glu Ala
                100                 105                 110

Phe Asp Ile Trp Gly Gln Gly Thr Met Val Thr Val Ser Ser
            115                 120                 125

<210> SEQ ID NO 80
<211> LENGTH: 126
<212> TYPE: PRT
<213> ORGANISM: Homo sapiens

<400> SEQUENCE: 80

Gln Val Gln Leu Val Ala Ser Gly Gly Gly Leu Val Lys Pro Gly Gly
 1               5                  10                  15

Ser Leu Arg Leu Ser Cys Ala Ala Ser Gly Phe Thr Phe Ser Asp Tyr
            20                  25                  30

Tyr Met Thr Trp Ile Arg Gln Ala Pro Gly Lys Gly Leu Glu Trp Val
            35                  40                  45

Ser Tyr Ile Ser Ser Ser Gly Thr Thr Ile Tyr Tyr Ala Asp Ser Val
 50                  55                  60

Lys Gly Arg Phe Thr Val Ser Arg Asp Asn Ala Lys Asn Ser Leu Phe
 65                  70                  75                  80

Leu Gln Met Asn Ser Leu Arg Ala Glu Asp Thr Ala Leu Tyr Tyr Cys
                 85                  90                  95

Ala Arg Asp Ser Tyr Ser Lys Leu Val Asp Ile Glu Ala Ile Glu Ala
                100                 105                 110

Phe Asp Ile Trp Gly Gln Gly Thr Met Val Thr Val Ser Ser
            115                 120                 125

<210> SEQ ID NO 81
<211> LENGTH: 126
<212> TYPE: PRT
<213> ORGANISM: Homo sapiens

<400> SEQUENCE: 81

Gln Val His Leu Val Glu Ser Gly Gly Gly Leu Val Lys Pro Gly Arg
 1               5                  10                  15

Ser Leu Arg Leu Ser Cys Ala Ala Ser Gly Phe Thr Phe Ser Asp Tyr
            20                  25                  30

Tyr Met Ala Trp Ile Arg Gln Val Pro Gly Lys Gly Leu Glu Trp Val
            35                  40                  45

Ser Phe Ile Ser Ser Ser Gly Arg Thr Ile Tyr Tyr Ala Asp Ser Val
 50                  55                  60

Lys Gly Arg Phe Thr Ile Ser Arg Asp Asn Ala Lys Asp Ser Leu Tyr
 65                  70                  75                  80

Leu Gln Met His Ser Leu Arg Ala Glu Asp Thr Ala Val Tyr Tyr Cys
                 85                  90                  95
```

```
Ala Arg Asp Ser Tyr Ser Lys Leu Val Asp Ile Glu Ala Ile Glu Ala
            100                 105                 110

Phe Asp Ile Trp Gly Arg Gly Thr Met Val Thr Val Ser Ser
        115                 120                 125

<210> SEQ ID NO 82
<211> LENGTH: 126
<212> TYPE: PRT
<213> ORGANISM: Homo sapiens

<400> SEQUENCE: 82

Gln Val Gln Leu Val Glu Ser Gly Gly Gly Leu Val Lys Pro Gly Gly
1               5                   10                  15

Ser Leu Arg Leu Ser Cys Ala Pro Ala Gly Phe Asn Phe Lys Asp Tyr
            20                  25                  30

Tyr Met Thr Trp Ile Arg Gln Ala Pro Gly Lys Gly Leu Glu Trp Val
        35                  40                  45

Ser Phe Ile Ser Ser Ser Gly Gln Thr Ile Tyr Tyr Ala Asp Ser Val
    50                  55                  60

Lys Gly Arg Phe Thr Ile Ser Arg Asp Asn Ala Arg Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Tyr Ser Lys Leu Val Asp Ile Val Ala Ile Glu Ala
            100                 105                 110

Phe Asp Leu Trp Gly Gln Gly Thr Leu Val Ser Val Ser Ser
        115                 120                 125

<210> SEQ ID NO 83
<211> LENGTH: 126
<212> TYPE: PRT
<213> ORGANISM: Homo sapiens

<400> SEQUENCE: 83

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Ser Phe Ser Ala Tyr
            20                  25                  30

Tyr Met Ser Trp Ile Arg Gln Ala Pro Gly Lys Gly Leu Glu Trp Ile
        35                  40                  45

Ser Tyr Ile Ser Ser Ser Gly Asn Thr Ile Tyr Tyr Thr Asp Ser Val
    50                  55                  60

Lys Gly Arg Phe Thr Ile Ala Arg Asp Asn Ala Lys Asn Ser Leu Tyr
65                  70                  75                  80

Leu Gln Met Asn Ser Leu Arg Ala Glu Asp Thr Gly Leu Tyr Tyr Cys
                85                  90                  95

Ala Arg Asp Ser Tyr Ser Lys Leu Ala Asp Ile Glu Ala Thr Glu Ala
            100                 105                 110

Phe Asp Val Trp Gly Gln Gly Thr Met Val Ala Val Ser Ser
        115                 120                 125

<210> SEQ ID NO 84
<211> LENGTH: 126
<212> TYPE: PRT
<213> ORGANISM: Homo sapiens

<400> SEQUENCE: 84

Gln Val His Leu Val Glu Ser Gly Gly Gly Leu Val Lys Pro Gly Gly
```

```
                1               5                   10                  15
                Ser Leu Arg Leu Ser Cys Ala Ala Ser Gly Phe Thr Phe Ser Asp Tyr
                            20                  25                  30

Tyr Met Ala Trp Ile Arg Arg Ala Pro Gly Lys Gly Leu Glu Trp Ile
                            35                  40                  45

Ser Phe Ile Ser Gly Ser Gly Arg Thr Leu Tyr His Ala Glu Ser Val
                            50                  55                  60

Lys Gly Arg Phe Thr Val Ser Arg Asp Asn Ala Lys Asp Ser Leu Tyr
                65                          70                  75                  80

Leu His Met His Ser Leu Arg Asp Ala Asp Thr Ala Val Tyr Tyr Cys
                            85                  90                  95

Ala Arg Asp Ser Tyr Ser Lys Leu Val Glu Ile Glu Ala Ile Glu Ala
                            100                 105                 110

Phe Asp Val Trp Gly Arg Gly Thr Val Val Thr Val Ser Ser
                            115                 120                 125

<210> SEQ ID NO 85
<211> LENGTH: 120
<212> TYPE: PRT
<213> ORGANISM: Homo sapiens

<400> SEQUENCE: 85

Gln Leu Gln Leu Gln Glu Ser Gly Pro Gly Leu Val Lys Pro Ser Glu
1               5                   10                  15

Thr Leu Ser Leu Thr Cys Ser Val Ser Gly Asp Ala Ile Ser Gly Ser
            20                  25                  30

Asn Tyr Tyr Trp Gly Trp Ile Arg Gln Pro Pro Gly Lys Gly Leu Gln
            35                  40                  45

Trp Ile Gly Ser Ile Tyr His Thr Gly Ser Thr Phe Tyr Asn Pro Ser
            50                  55                  60

Phe Ser Ser Arg Val Thr Leu Ser Val Asp Thr Ser Lys Asn Gln Phe
65                          70                  75                  80

Ser Leu Lys Leu Ile Ser Val Asn Ala Ala Asp Thr Ala Val Tyr Tyr
            85                  90                  95

Cys Ala Arg Arg Ile Arg Gly Tyr Ser Gly Thr Tyr Asp Trp Gly Gln
            100                 105                 110

Gly Thr Leu Val Thr Val Ser Ser
            115                 120

<210> SEQ ID NO 86
<211> LENGTH: 129
<212> TYPE: PRT
<213> ORGANISM: Homo sapiens

<400> SEQUENCE: 86

Gln Val Lys Leu Val Glu Ser Gly Gly Val Val Gln Pro Gly Arg
1               5                   10                  15

Ser Leu Arg Leu Ser Cys Ala Gly Ser Gly Phe Ala Phe Asp Asn Tyr
            20                  25                  30

Ala Met His Trp Val Arg Gln Ala Pro Gly Lys Gly Leu Glu Trp Val
            35                  40                  45

Ala Val Ile Ser Leu Glu Gly Arg Asn Lys Tyr Tyr Ala Gly Pro Ala
            50                  55                  60

Lys Gly Arg Phe Ser Ile Ser Arg Asp Asn Ser Arg Asn Thr Val His
65                          70                  75                  80

Leu Gln Met Asn Ser Leu Arg Pro Glu Asp Thr Ala Val Tyr Phe Cys
```

-continued

```
                    85                  90                  95
Ala Arg Asp Met Arg Tyr Tyr Tyr Asp Ser Asn Gly His Tyr Arg Asn
                100                 105                 110
Arg Tyr Gly Met Asp Val Trp Gly Gln Gly Thr Thr Val Ile Val Ser
            115                 120                 125
Ser

<210> SEQ ID NO 87
<211> LENGTH: 119
<212> TYPE: PRT
<213> ORGANISM: Homo sapiens

<400> SEQUENCE: 87

Gln Val Gln Leu Val Gln Ser Gly Ala Glu Val Lys Lys Pro Gly Ala
1               5                   10                  15
Ser Val Lys Val Ser Cys Lys Thr Ser Gly Tyr Thr Phe Asn Thr Tyr
                20                  25                  30
Ala Ile Ser Trp Val Arg Gln Ala Pro Gly Gln Gly Leu Glu Trp Val
            35                  40                  45
Gly Trp Ile Asn Thr Tyr Ser Gly Ser Thr Lys Tyr Ala Gln Lys Val
        50                  55                  60
Gln Gly Arg Val Thr Met Thr Thr Asp Thr Ser Thr Ser Thr Ala Tyr
65                  70                  75                  80
Met Glu Leu Arg Gly Leu Arg Ser Asp Asp Thr Ala Val Tyr Tyr Cys
                85                  90                  95
Ala Arg Asp Gly Tyr Asn Trp Gly Phe Leu Asp Phe Trp Gly Gln Gly
                100                 105                 110
Ser Leu Val Thr Val Ser Ser
            115

<210> SEQ ID NO 88
<211> LENGTH: 119
<212> TYPE: PRT
<213> ORGANISM: Homo sapiens

<400> SEQUENCE: 88

Gln Val Gln Val Val Gln Ser Gly Ala Glu Val Lys Lys Pro Gly Ala
1               5                   10                  15
Ser Val Met Val Ser Cys Lys Thr Ser Gly Tyr Arg Phe Thr Ile Tyr
                20                  25                  30
Ser Ile Ala Trp Met Arg Gln Ala Pro Gly Gln Gly Leu Glu Trp Met
            35                  40                  45
Gly Ser Ile Asn Thr Tyr Asn Gly Asn Thr Lys Tyr Ala Glu Lys Phe
        50                  55                  60
Gln Gly Arg Val Thr Met Ser Arg Asp Thr Ser Thr Ser Thr Ala Tyr
65                  70                  75                  80
Met Glu Val Arg Ser Leu Gly Ser Ala Asp Thr Ala Met Tyr Tyr Cys
                85                  90                  95
Ala Arg Asp Ala Glu Asn Trp Gly Phe Phe Asp Asp Trp Gly Gln Gly
                100                 105                 110
Thr Leu Val Thr Val Ser Ser
            115

<210> SEQ ID NO 89
<211> LENGTH: 125
<212> TYPE: PRT
<213> ORGANISM: Homo sapiens
```

<400> SEQUENCE: 89

| Gln | Val | Gln | Leu | Val | Glu | Ser | Gly | Gly | Gly | Val | Val | Gln | Pro | Gly | Arg |
| 1 | | | | 5 | | | | | 10 | | | | | 15 | |

| Ser | Leu | Arg | Leu | Ser | Cys | Ala | Ala | Ser | Gly | Phe | Thr | Phe | Ser | Asn | His |
| | | | 20 | | | | | 25 | | | | | 30 | | |

| Gly | Leu | His | Trp | Val | Arg | Gln | Pro | Pro | Gly | Lys | Gly | Leu | Glu | Trp | Val |
| | | 35 | | | | | 40 | | | | | 45 | | | |

| Ala | Val | Val | Ser | Lys | Asp | Gly | Thr | Asn | Glu | His | Tyr | Ala | Asp | Ser | Val |
| | 50 | | | | | 55 | | | | | 60 | | | | |

| Arg | Gly | Arg | Phe | Thr | Ile | Ser | Arg | Asp | Asn | Ser | Lys | Asn | Thr | Leu | Tyr |
| 65 | | | | | 70 | | | | | 75 | | | | | 80 |

| Leu | Leu | Met | Lys | Ser | Leu | Arg | Leu | Glu | Asp | Thr | Ala | Val | Tyr | Tyr | Cys |
| | | | | 85 | | | | | 90 | | | | | 95 | |

| Ala | Arg | Glu | Gly | Tyr | Cys | Gly | Asp | Asp | Arg | Cys | Tyr | Ser | Gly | Gln | Pro |
| | | | 100 | | | | | 105 | | | | | 110 | | |

| Asp | Tyr | Trp | Gly | Gln | Gly | Ile | Leu | Val | Thr | Val | Ser | Ser |
| | | 115 | | | | | 120 | | | | | 125 |

<210> SEQ ID NO 90
<211> LENGTH: 321
<212> TYPE: DNA
<213> ORGANISM: Homo sapiens

<400> SEQUENCE: 90

```
gacatccaga tgacccagtc tccatcttcc gtgtctgcat ctgtaggcga cagagtcatc    60
atcacttgtc gggcgagtca gggtattagc agctggttag cctggtatca gcagaaacca   120
gggagagccc cgaggctcct gatctatgat gcctccactt tggaaagtgg ggtcccatca   180
aggttcagcg gcagaggatc tgggacagaa ttcactctca ccatcaacag cctgcagcct   240
gaagattttg caacttacta ttgtcaacag ggtaacatgt tcccgctcac tttcggcgga   300
gggaccaagg tggaaatcaa a                                              321
```

<210> SEQ ID NO 91
<211> LENGTH: 318
<212> TYPE: DNA
<213> ORGANISM: Homo sapiens

<400> SEQUENCE: 91

```
tcctatgagc tgactcagcc accctcagtg tccgtgtccc caggacagac agccagcatc    60
acctgctctg gagatagatt ggacgataaa tatgcttcct ggtatcagca gaaggcaggc   120
cagtcccctg tcctggtcat ctatcaagat aacaagaggc cctcagggat ccctgagcga   180
ttctctggct ccaactctgg gaacactgcc actctgacca tcagcgggac ccaggctatg   240
gatgaggctg actattattg tcaggcgtgg gacagcgaca cgtatgtctt cggaactggg   300
accaaggtca ccgtccta                                                  318
```

<210> SEQ ID NO 92
<211> LENGTH: 324
<212> TYPE: DNA
<213> ORGANISM: Homo sapiens

<400> SEQUENCE: 92

```
tcctatgagc tgactcagcc accctcagtg tcagtgggcc cgggaaggac ggccaggatt    60
acctgtgggg caaacaacat tggaagtaaa agtgtgcact ggtaccaaca gaggcctggc   120
```

```
caggcccctg tcctggtcat ctcttttgat accgaccggc cctcagggat ccctgagcga    180
ttctctggct ccaactctgg gaacacggcc accctgacca tcagcagggt cgaagccggg    240
gatgaggccg actatttctg tcaggtgtgg gatcgtacta gtgatcatgt ggtgttcggc    300
ggagggacca agctgaccgt ccta                                           324
```

<210> SEQ ID NO 93
<211> LENGTH: 324
<212> TYPE: DNA
<213> ORGANISM: Homo sapiens

<400> SEQUENCE: 93

```
tcctatgagc tggctcagcc accctcagtg tcagtggccc caggaaagac ggccacgatt    60
gcctgtgggg gagacaatat tggaggtaaa agtgtgcact ggtaccttca gaaggcaggc    120
caggcccctg tattggtcat ttcttatgac agcgaccggc cctcagggat ccctgagcga    180
ttctctggct ccaactctgg gaacacggcc accctgacca tcagcagggt cgaagccggt    240
gatgaggccg actatttctg tcaggtgtgg gatcgtcatg gtgatcatgt ggtcttcggc    300
ggagggacca agctgaccgt ccta                                           324
```

<210> SEQ ID NO 94
<211> LENGTH: 324
<212> TYPE: DNA
<213> ORGANISM: Homo sapiens

<400> SEQUENCE: 94

```
tcctatgagc tgactcaacc accctcagtg tcagtggccc caggaaaaat ggccaggatt    60
acctgtggcg agacaacat tggaagtaaa agtgtgcact ggtaccagca gaggccaggc    120
caggcccctg tcctggtcat ccgttttgat accgaccggc cctcacgat ccctgagcga    180 ttctctggct ccaactcagg gaacacggcc accctggcca tcagcagggt cgaagccggg    240
gatgaggccg actattactg tcaggtgtgg gattctagta gtgctcgttt ggtgttcggc    300
ggagggacca agctgaccgt ccta                                           324
```

<210> SEQ ID NO 95
<211> LENGTH: 324
<212> TYPE: DNA
<213> ORGANISM: Homo sapiens

<400> SEQUENCE: 95

```
tcctatgagc tgactcagcc tccctcagtg tcagtggccc caggaaagac ggccaggatt    60
acttgtgggg gaaacaacat tggaagtaag agtgtgcact ggtaccagca gaagccaggc    120
caggcccctg tcatggtcat ctattatgat agcgaccggc cctcagggat ccctgagcga    180
ttctctggct ccaactctgg gaacacggcc actctgacca tcagcagggt cgaagccggg    240
gatgaggccg actattactg tcaggtgtgg gatagtggta gtgatcgtgt ggtattcggc    300
ggagggacca agctgaccgt ccta                                           324
```

<210> SEQ ID NO 96
<211> LENGTH: 324
<212> TYPE: DNA
<213> ORGANISM: Homo sapiens

<400> SEQUENCE: 96

```
tcctatgagc tggctcagcc accctcagtg tcagtggccc caggaaagcc ggccaggatt    60
gcctgtgggg gagacaacat tggaggtaaa agtgtgcact ggtaccttca gaaggcaggc    120
```

```
caggcccctg tcctggtcat gtcttatgac agcgaccggc cctcagggat ccctgagcga    180
ttctctggct ccaactctgg caacacggcc accctgacca tcagcagggt cgaagccggt    240
gatgaaggcg actatttctg tcaggtgtgg gatcgtcaaa ctgatcatgt ggtcttcggc    300
ggagggacca agctgaccgt ccta                                           324

<210> SEQ ID NO 97
<211> LENGTH: 309
<212> TYPE: DNA
<213> ORGANISM: Homo sapiens

<400> SEQUENCE: 97
gacatccagt tgacccagtc tccgtccttc ctgtctgcat ctgtaggcga cagagtcacc     60
atcacttgcc gggccagtca ggacataagc agttatgtag cctggtatca gcaaaaacca    120
gggaatgccc ctaagctcct gatctcttct gcatccactt tgccaagtgg ggtcccgtca    180
aggttcagcg gcagtagatc tgggacagac ttcactctca caatcagcag cctgcagcct    240
gaagattttg caacttatta ctgtcaacaa cttaataatt tcggccctgg gactacagtg    300
gatatcaaa                                                            309

<210> SEQ ID NO 98
<211> LENGTH: 318
<212> TYPE: DNA
<213> ORGANISM: Homo sapiens

<400> SEQUENCE: 98
gacatccaga tgacccaatc tccatcctcc ctgtctgcgt ctgtaggaga cagcgtcacc     60
atcacttgcc aggcgagtca ggacattaat cagtttgtaa gttggtatca acagaaacca    120
gggaaacccc ctaaactcct gatctacgat gcttccaatt tggagtcagg cgtcccatca    180
aggttcagtg gaagtggatc tgggacacat tttacttttca ccatcagcag cctgcagccc    240
gacgatattg cgacatatta ctgtcagcaa tatgaaaatc tattcacttt cggccctggg    300
accaaagtgg atatcaaa                                                  318

<210> SEQ ID NO 99
<211> LENGTH: 321
<212> TYPE: DNA
<213> ORGANISM: Homo sapiens

<400> SEQUENCE: 99
gacatccaga tgacccagtc tccatcctcc ctgtctgcat ctgtaggaga cagagtcacc     60
atcacttgcc gggcgagtca gggcattagc aattatttag cctggtatca gcaaaaaccg    120
gggaaacttc ctaagctcct gatctatgct gcatccacgt tgcaatcagg ggtcccatct    180
cggttcagtg gcagtggatc tgggacagat ttcactctca ccatcagcag cctgcagcct    240
gaagatgttg caagttatta ctgtcaaaag tataacagtg cccctctcac tttcggccct    300
gggaccaaag tggatatcaa a                                              321

<210> SEQ ID NO 100
<211> LENGTH: 321
<212> TYPE: DNA
<213> ORGANISM: Homo sapiens

<400> SEQUENCE: 100
gaaattgtgt tgacgcagtc tccaggcact gtgtctttgt ctcccgggga aagagtcacc     60
```
ctctcctgca gggccagtca gagtgtcggc agacacttag cctggtacca gcagaaacct    120
ggccagcctc ccaggctcct catctatggt gcatctacca gggccactgg cgtcccagac    180
aggttcagtg gcagtgggtc tgagacagag ttcactctcg ccatcagcag cctgcagtct    240
gaagattttg cactttatta ctgtcaacaa tataatacct ggccgtacac ttttggccag    300
gggaccaagc tggagatcaa a                                              321

<210> SEQ ID NO 101
<211> LENGTH: 324
<212> TYPE: DNA
<213> ORGANISM: Homo sapiens

<400> SEQUENCE: 101
gaaattgtgt tgacacagtt tccagccacc ctgtctttgt ctccaggaga aagagccacc     60
ctctcctgca gggccagtca gagtgttggc aggtacttgg cctggtacca acagaaacct    120
ggccaggctc ccaggctcct catctatgat tcatccaaca gggccactgg cgtcccagcc    180
aggttcagtg gcagtgggtc tgggacagac ttcactctct ccatcagcag cctggagcct    240
gaagattttg cagtgtattt ctgtcaacag cgtagccact ggcctccgct cactttcggc    300
ggagggacca aggtggaaat caaa                                            324

<210> SEQ ID NO 102
<211> LENGTH: 107
<212> TYPE: PRT
<213> ORGANISM: Homo sapiens

<400> SEQUENCE: 102

Asp Ile Gln Met Thr Gln Ser Pro Ser Ser Val Ser Ala Ser Val Gly
1               5                   10                  15

Asp Arg Val Ile Ile Thr Cys Arg Ala Ser Gln Gly Ile Ser Ser Trp
            20                  25                  30

Leu Ala Trp Tyr Gln Gln Lys Pro Gly Arg Ala Pro Arg Leu Leu Ile
        35                  40                  45

Tyr Asp Ala Ser Thr Leu Glu Ser Gly Val Pro Ser Arg Phe Ser Gly
    50                  55                  60

Arg Gly Ser Gly Thr Glu Phe Thr Leu Thr Ile Asn Ser Leu Gln Pro
65                  70                  75                  80

Glu Asp Phe Ala Thr Tyr Tyr Cys Gln Gln Gly Asn Met Phe Pro Leu
                85                  90                  95

Thr Phe Gly Gly Gly Thr Lys Val Glu Ile Lys
            100                 105

<210> SEQ ID NO 103
<211> LENGTH: 106
<212> TYPE: PRT
<213> ORGANISM: Homo sapiens

<400> SEQUENCE: 103

Ser Tyr Glu Leu Thr Gln Pro Pro Ser Val Ser Val Ser Pro Gly Gln
1               5                   10                  15

Thr Ala Ser Ile Thr Cys Ser Gly Asp Arg Leu Asp Asp Lys Tyr Ala
            20                  25                  30

Ser Trp Tyr Gln Gln Lys Ala Gly Gln Ser Pro Val Leu Val Ile Tyr
        35                  40                  45

Gln Asp Asn Lys Arg Pro Ser Gly Ile Pro Glu Arg Phe Ser Gly Ser
    50                  55                  60

```
Asn Ser Gly Asn Thr Ala Thr Leu Thr Ile Ser Gly Thr Gln Ala Met
 65                  70                  75                  80

Asp Glu Ala Asp Tyr Tyr Cys Gln Ala Trp Asp Ser Asp Thr Tyr Val
                 85                  90                  95

Phe Gly Thr Gly Thr Lys Val Thr Val Leu
                100                 105

<210> SEQ ID NO 104
<211> LENGTH: 108
<212> TYPE: PRT
<213> ORGANISM: Homo sapiens

<400> SEQUENCE: 104

Ser Tyr Glu Leu Thr Gln Pro Pro Ser Val Ser Val Gly Pro Gly Arg
  1               5                  10                  15

Thr Ala Arg Ile Thr Cys Gly Ala Asn Asn Ile Gly Ser Lys Ser Val
                 20                  25                  30

His Trp Tyr Gln Gln Arg Pro Gly Gln Ala Pro Val Leu Val Ile Ser
             35                  40                  45

Phe Asp Thr Asp Arg Pro Ser Gly Ile Pro Glu Arg Phe Ser Gly Ser
         50                  55                  60

Asn Ser Gly Asn Thr Ala Thr Leu Thr Ile Ser Arg Val Glu Ala Gly
 65                  70                  75                  80

Asp Glu Ala Asp Tyr Phe Cys Gln Val Trp Asp Arg Thr Ser Asp His
                 85                  90                  95

Val Val Phe Gly Gly Gly Thr Lys Leu Thr Val Leu
                100                 105

<210> SEQ ID NO 105
<211> LENGTH: 108
<212> TYPE: PRT
<213> ORGANISM: Homo sapiens

<400> SEQUENCE: 105

Ser Tyr Glu Leu Ala Gln Pro Pro Ser Val Ser Val Ala Pro Gly Lys
  1               5                  10                  15

Thr Ala Thr Ile Ala Cys Gly Gly Asp Asn Ile Gly Gly Lys Ser Val
                 20                  25                  30

His Trp Tyr Leu Gln Lys Ala Gly Gln Ala Pro Val Leu Val Ile Ser
             35                  40                  45

Tyr Asp Ser Asp Arg Pro Ser Gly Ile Pro Glu Arg Phe Ser Gly Ser
         50                  55                  60

Asn Ser Gly Asn Thr Ala Thr Leu Thr Ile Ser Arg Val Glu Ala Gly
 65                  70                  75                  80

Asp Glu Ala Asp Tyr Phe Cys Gln Val Trp Asp Arg His Gly Asp His
                 85                  90                  95

Val Val Phe Gly Gly Gly Thr Lys Leu Thr Val Leu
                100                 105

<210> SEQ ID NO 106
<211> LENGTH: 108
<212> TYPE: PRT
<213> ORGANISM: Homo sapiens

<400> SEQUENCE: 106

Ser Tyr Glu Leu Thr Gln Pro Pro Ser Val Ser Val Ala Pro Gly Lys
  1               5                  10                  15

Met Ala Arg Ile Thr Cys Gly Gly Asp Asn Ile Gly Ser Lys Ser Val
```

```
                    20                  25                  30

His Trp Tyr Gln Gln Arg Pro Gly Gln Ala Pro Val Leu Val Ile Arg
            35                  40                  45

Phe Asp Thr Asp Arg Pro Ser Arg Ile Pro Glu Arg Phe Ser Gly Ser
        50                  55                  60

Asn Ser Gly Asn Thr Ala Thr Leu Ala Ile Ser Arg Val Glu Ala Gly
65                  70                  75                  80

Asp Glu Ala Asp Tyr Tyr Cys Gln Val Trp Asp Ser Ser Ser Ala Arg
                85                  90                  95

Leu Val Phe Gly Gly Gly Thr Lys Leu Thr Val Leu
            100                 105

<210> SEQ ID NO 107
<211> LENGTH: 108
<212> TYPE: PRT
<213> ORGANISM: Homo sapiens

<400> SEQUENCE: 107

Ser Tyr Glu Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Met Val Ile Tyr
            35                  40                  45

Tyr Asp Ser Asp Arg Pro Ser Gly Ile Pro Glu Arg Phe Ser Gly Ser
        50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Gly Ser Asp Arg
                85                  90                  95

Val Val Phe Gly Gly Gly Thr Lys Leu Thr Val Leu
            100                 105

<210> SEQ ID NO 108
<211> LENGTH: 108
<212> TYPE: PRT
<213> ORGANISM: Homo sapiens

<400> SEQUENCE: 108

Ser Tyr Glu Leu Ala Gln Pro Pro Ser Val Ser Val Ala Pro Gly Lys
1               5                   10                  15

Pro Ala Arg Ile Ala Cys Gly Gly Asp Asn Ile Gly Gly Lys Ser Val
            20                  25                  30

His Trp Tyr Leu Gln Lys Ala Gly Gln Ala Pro Val Leu Val Met Ser
            35                  40                  45

Tyr Asp Ser Asp Arg Pro Ser Gly Ile Pro Glu Arg Phe Ser Gly Ser
        50                  55                  60

Asn Ser Gly Asn Thr Ala Thr Leu Thr Ile Ser Arg Val Glu Ala Gly
65                  70                  75                  80

Asp Glu Gly Asp Tyr Phe Cys Gln Val Trp Asp Arg Gln Thr Asp His
                85                  90                  95

Val Val Phe Gly Gly Gly Thr Lys Leu Thr Val Leu
            100                 105

<210> SEQ ID NO 109
<211> LENGTH: 103
<212> TYPE: PRT
```

<213> ORGANISM: Homo sapiens

<400> SEQUENCE: 109

Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Asp Ile Ser Ser Tyr
            20                  25                  30

Val Ala Trp Tyr Gln Gln Lys Pro Gly Asn Ala Pro Lys Leu Leu Ile
        35                  40                  45

Ser Ser Ala Ser Thr Leu Pro Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Leu Asn Asn Phe Gly Pro
                85                  90                  95

Gly Thr Thr Val Asp Ile Lys
            100

<210> SEQ ID NO 110
<211> LENGTH: 106
<212> TYPE: PRT
<213> ORGANISM: Homo sapiens

<400> SEQUENCE: 110

Asp Ile Gln Met Thr Gln Ser Pro Ser Ser Leu Ser Ala Ser Val Gly
1               5                   10                  15

Asp Ser Val Thr Ile Thr Cys Gln Ala Ser Gln Asp Ile Asn Gln Phe
            20                  25                  30

Val Ser Trp Tyr Gln Gln Lys Pro Gly Lys Pro Pro Lys Leu Leu Ile
        35                  40                  45

Tyr Asp Ala Ser Asn Leu Glu Ser Gly Val Pro Ser Arg Phe Ser Gly
    50                  55                  60

Ser Gly Ser Gly Thr His Phe Thr Phe Thr Ile Ser Ser Leu Gln Pro
65                  70                  75                  80

Asp Asp Ile Ala Thr Tyr Tyr Cys Gln Gln Tyr Glu Asn Leu Phe Thr
                85                  90                  95

Phe Gly Pro Gly Thr Lys Val Asp Ile Lys
            100                 105

<210> SEQ ID NO 111
<211> LENGTH: 107
<212> TYPE: PRT
<213> ORGANISM: Homo sapiens

<400> SEQUENCE: 111

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Leu Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Ser Tyr Tyr Cys Gln Lys Tyr Asn Ser Ala Pro Leu
                85                  90                  95

Thr Phe Gly Pro Gly Thr Lys Val Asp Ile Lys
              100                 105

<210> SEQ ID NO 112
<211> LENGTH: 107
<212> TYPE: PRT
<213> ORGANISM: Homo sapiens

<400> SEQUENCE: 112

Glu Ile Val Leu Thr Gln Ser Pro Gly Thr Val Ser Leu Ser Pro Gly
1               5                   10                  15

Glu Arg Val Thr Leu Ser Cys Arg Ala Ser Gln Ser Val Gly Arg His
            20                  25                  30

Leu Ala Trp Tyr Gln Gln Lys Pro Gly Gln Pro Pro Arg Leu Leu Ile
        35                  40                  45

Tyr Gly Ala Ser Thr Arg Ala Thr Gly Val Pro Asp Arg Phe Ser Gly
    50                  55                  60

Ser Gly Ser Glu Thr Glu Phe Thr Leu Ala Ile Ser Ser Leu Gln Ser
65                  70                  75                  80

Glu Asp Phe Ala Leu Tyr Tyr Cys Gln Gln Tyr Asn Thr Trp Pro Tyr
                85                  90                  95

Thr Phe Gly Gln Gly Thr Lys Leu Glu Ile Lys
              100                 105

<210> SEQ ID NO 113
<211> LENGTH: 108
<212> TYPE: PRT
<213> ORGANISM: Homo sapiens

<400> SEQUENCE: 113

Glu Ile Val Leu Thr Gln Phe Pro Ala Thr Leu Ser Leu Ser Pro Gly
1               5                   10                  15

Glu Arg Ala Thr Leu Ser Cys Arg Ala Ser Gln Ser Val Gly Arg Tyr
            20                  25                  30

Leu Ala Trp Tyr Gln Gln Lys Pro Gly Gln Ala Pro Arg Leu Leu Ile
        35                  40                  45

Tyr Asp Ser Ser Asn Arg Ala Thr Gly Val Pro Ala Arg Phe Ser Gly
    50                  55                  60

Ser Gly Ser Gly Thr Asp Phe Thr Leu Ser Ile Ser Ser Leu Glu Pro
65                  70                  75                  80

Glu Asp Phe Ala Val Tyr Phe Cys Gln Gln Arg Ser His Trp Pro Pro
                85                  90                  95

Leu Thr Phe Gly Gly Gly Thr Lys Val Glu Ile Lys
              100                 105

<210> SEQ ID NO 114
<211> LENGTH: 384
<212> TYPE: DNA
<213> ORGANISM: Artificial Sequence
<220> FEATURE:
<223> OTHER INFORMATION: GERMLINED 2-18 IgG1 HEAVY CHAIN

<400> SEQUENCE: 114
gaggtgcagc tggtggagtc tgaggaggga ctggtgcagc caggaggctc cctgaggctg      60
tcttgcgccg ccagcggctt ctccttttct gaccacgata tggactgggt cgccaggca     120 cctggcaagg gcctggagtg ggtgggccgg agcagaaaca aggattacag ctccaccaca     180
gagtatgcag cctccgtgag gggccgcttc accatctctc gggacgatag caagaactcc     240

```
ctgtacctgc agatgaacag cctgaagacc gaggacacag ccgtgtacta ttgtgccaga    300
ggcccccacc actctgatag aagcggctac tatggcggca catttgacat ctggggccag    360
ggcacaatgg tgacagtgtc tagc                                           384
```

<210> SEQ ID NO 115
<211> LENGTH: 128
<212> TYPE: PRT
<213> ORGANISM: Artificial Sequence
<220> FEATURE:
<223> OTHER INFORMATION: GERMLINED 2-18 IgG1 HEAVY CHAIN

<400> SEQUENCE: 115

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Asp His
            20                  25                  30

Asp Met Asp Trp Val Arg Gln Ala Pro Gly Lys Gly Leu Glu Trp Val
        35                  40                  45

Gly Arg Ser Arg Asn Lys Asp Tyr Ser Ser Thr Thr Glu Tyr Ala Ala
    50                  55                  60

Ser Val Arg Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Gly Pro His His Ser Asp Arg Ser Gly Tyr Tyr Gly
            100                 105                 110

Gly Thr Phe Asp Ile Trp Gly Gln Gly Thr Met Val Thr Val Ser Ser
        115                 120                 125
```

<210> SEQ ID NO 116
<211> LENGTH: 321
<212> TYPE: DNA
<213> ORGANISM: Artificial Sequence
<220> FEATURE:
<223> OTHER INFORMATION: GERMLINED 2-18 IgG1 LIGHT CHAIN

<400> SEQUENCE: 116

```
gacatccaga tgacacagtc tcctagctcc gtgagcgcct ccgtgggcga tagggtgacc    60
atcacatgca gagcctccca gggcatctct agctggctgg cctggtatca gcagaagccc   120
ggcaaggccc ctaagctgct gatctatgac gcctctaccc tggagagcgg cgtgccctcc   180
cggttctctg gcagcggctc cggcacagac tttaccctga caatctcctc tctgcagcca   240
gaggatttcg ccacctacta ttgtcagcag ggcaacatgt tccccctgac ctttggcggc   300
ggcacaaagg tggagatcaa g                                             321
```

<210> SEQ ID NO 117
<211> LENGTH: 107
<212> TYPE: PRT
<213> ORGANISM: Artificial Sequence
<220> FEATURE:
<223> OTHER INFORMATION: GERMLINED 2-18 IgG1 LIGHT CHAIN

<400> SEQUENCE: 117

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30
```

```
Leu Ala Trp Tyr Gln Gln Lys Pro Gly Lys Ala Pro Lys Leu Leu Ile
            35                  40                  45

Tyr Asp Ala Ser Thr Leu Glu Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Asn Met Phe Pro Leu
                 85                  90                  95

Thr Phe Gly Gly Gly Thr Lys Val Glu Ile Lys
                100                 105
```

<210> SEQ ID NO 118
<211> LENGTH: 378
<212> TYPE: DNA
<213> ORGANISM: Artificial Sequence
<220> FEATURE:
<223> OTHER INFORMATION: GERMLINED 1-85 IgG1 HEAVY CHAIN

<400> SEQUENCE: 118

```
caggtgcagc tggtggagtc cggaggagga ctggtgaagc caggaggctc cctgagactg     60
tcttgcgccg ccagcggctt cacctttagc gactactata tggcctggat cagacaggca    120
cctggcaagg gcctggagtg ggtgtccttc atcagctcct ctggcagaac catctactat    180
gccgactctg tgaagggccg gtttacaatc tccagagata cgccaagaa cagcctgtac    240
ctgcagatga acagcctgag ggccgaggac acagccgtgt actattgtgc cgcgactct    300
tatagcaagc tggtggatat cgaggccatc gaggccttcg atatctgggg cagaggcaca    360
atggtgaccg tgagcagc                                                  378
```

<210> SEQ ID NO 119
<211> LENGTH: 126
<212> TYPE: PRT
<213> ORGANISM: Artificial Sequence
<220> FEATURE:
<223> OTHER INFORMATION: GERMLINED 1-85 IgG1 HEAVY CHAIN

<400> SEQUENCE: 119

```
Gln Val Gln Leu Val Glu Ser Gly Gly Gly Leu Val Lys Pro Gly Gly
  1               5                  10                  15

Ser Leu Arg Leu Ser Cys Ala Ala Ser Gly Phe Thr Phe Ser Asp Tyr
             20                  25                  30

Tyr Met Ala Trp Ile Arg Gln Ala Pro Gly Lys Gly Leu Glu Trp Val
            35                  40                  45

Ser Phe Ile Ser Ser Ser Gly Arg Thr Ile Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Ser Tyr Ser Lys Leu Val Asp Ile Glu Ala Ile Glu Ala
                100                 105                 110

Phe Asp Ile Trp Gly Arg Gly Thr Met Val Thr Val Ser Ser
            115                 120                 125
```

<210> SEQ ID NO 120
<211> LENGTH: 324
<212> TYPE: DNA
<213> ORGANISM: Artificial Sequence
<220> FEATURE:

<223> OTHER INFORMATION: GERMLINED 1-85 IgG1 LIGHT CHAIN

<400> SEQUENCE: 120

```
agctacgtgc tgacacagcc acctagcgtg tccgtggcac caggcaagac agcaaggatc    60
acctgcggcg cgacaacat cggctctaag agcgtgcact ggtatcagca gaagccagga   120
caggcacccg tgctggtcat ctactatgac tccgatcggc cttctggcat cccagagaga   180
ttctccggct ctaacagcgg caataccgcc acactgacca tctccagggt ggaggcaggc   240
gacgaggcag attacttctg tcaagtgtgg gaccgccacg gcgatcacgt ggtgtttggc   300
ggcggcacaa agctgaccgt gctg                                         324
```

<210> SEQ ID NO 121
<211> LENGTH: 108
<212> TYPE: PRT
<213> ORGANISM: Artificial Sequence
<220> FEATURE:
<223> OTHER INFORMATION: GERMLINED 1-85 IgG1 LIGHT CHAIN

<400> SEQUENCE: 121

```
Ser Tyr Val Leu Thr Gln Pro Pro Ser Val Ser Val Ala Pro Gly Lys
1               5                   10                  15
Thr Ala Arg Ile Thr Cys Gly Gly Asp Asn Ile Gly Ser Lys Ser Val
            20                  25                  30
His Trp Tyr Gln Gln Lys Pro Gly Gln Ala Pro Val Leu Val Ile Tyr
        35                  40                  45
Tyr Asp Ser Asp Arg Pro Ser Gly Ile Pro Glu Arg Phe Ser Gly Ser
    50                  55                  60
Asn Ser Gly Asn Thr Ala Thr Leu Thr Ile Ser Arg Val Glu Ala Gly
65                  70                  75                  80
Asp Glu Ala Asp Tyr Phe Cys Gln Val Trp Asp Arg His Gly Asp His
                85                  90                  95
Val Val Phe Gly Gly Gly Thr Lys Leu Thr Val Leu
            100                 105
```

<210> SEQ ID NO 122
<211> LENGTH: 375
<212> TYPE: DNA
<213> ORGANISM: Artificial Sequence
<220> FEATURE:
<223> OTHER INFORMATION: GERMLINED 3-25 HEAVY CHAIN

<400> SEQUENCE: 122

```
caggtgcagc tggtggagag cggaggagga gtggtgcagc caggcaggtc tctgaggctg    60
agctgcgccg cctccggctt caccttttcc aaccacggcc tgcactgggt gcggcaggca   120
cctggcaagg gcctggagtg gtggcagtg gtgtccaagg acggcacaaa tgagcactac   180
gccgattctg tgcggggcag attcaccatc tctaggaca acagcaagaa tacactgtat   240
ctgcagatga actctctgcg cgccgaggat accgccgtgt actattgtgc ccgggagggc   300
tactgcggcg acgatagatg ttacagcgga cagccagact attggggaca gggcaccctg   360
gtgaccgtga gcagc                                                   375
```

<210> SEQ ID NO 123
<211> LENGTH: 125
<212> TYPE: PRT
<213> ORGANISM: Artificial Sequence
<220> FEATURE:
<223> OTHER INFORMATION: GERMLINED 3-25 HEAVY CHAIN

<400> SEQUENCE: 123

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Asn His
            20                  25                  30

Gly Leu His Trp Val Arg Gln Ala Pro Gly Lys Gly Leu Glu Trp Val
        35                  40                  45

Ala Val Val Ser Lys Asp Gly Thr Asn Glu His Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Tyr Cys Gly Asp Asp Arg Cys Tyr Ser Gly Gln Pro
            100                 105                 110

Asp Tyr Trp Gly Gln Gly Thr Leu Val Thr Val Ser Ser
        115                 120                 125

<210> SEQ ID NO 124
<211> LENGTH: 324
<212> TYPE: DNA
<213> ORGANISM: Artificial Sequence
<220> FEATURE:
<223> OTHER INFORMATION: GERMLINED 3-25 LIGHT CHAIN

<400> SEQUENCE: 124
gagatcgtgc tgacccagtc tcctgccaca ctgtccctgt ctccaggaga gagggccacc     60
ctgagctgca gagccagcca gtccgtgggc agatacctgg cctggtatca gcagaagcca    120
ggacaggcac caaggctgct gatctacgac agctccaaca gggcaaccgg cgtgcccgca    180
cgcttctctg gcagcggctc cggcacagac tttaccctga caatctctag cctggagcct    240
gaggatttcg ccgtgtacta ttgtcagcag cggtcccact ggccaccttct gacctttggc    300
ggaggcacaa aggtggagat caag                                            324

<210> SEQ ID NO 125
<211> LENGTH: 108
<212> TYPE: PRT
<213> ORGANISM: Artificial Sequence
<220> FEATURE:
<223> OTHER INFORMATION: GERMLINED 3-25 LIGHT CHAIN

<400> SEQUENCE: 125

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Gly Arg Tyr
            20                  25                  30

Leu Ala Trp Tyr Gln Gln Lys Pro Gly Gln Ala Pro Arg Leu Leu Ile
        35                  40                  45

Tyr Asp Ser Ser Asn Arg Ala Thr Gly Val Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser His Trp Pro Pro
                85                  90                  95

Leu Thr Phe Gly Gly Gly Thr Lys Val Glu Ile Lys
            100                 105

<210> SEQ ID NO 126
<211> LENGTH: 1374
<212> TYPE: DNA
<213> ORGANISM: Artificial Sequence
<220> FEATURE:
<223> OTHER INFORMATION: GERMLINED 2-18 IgG1 HEAVY CHAIN

<400> SEQUENCE: 126

| | |
|---|---|
| gaggtgcagc tggtggagtc tggaggagga ctggtgcagc caggaggctc cctgaggctg | 60 |
| tcttgcgccg ccagcggctt ctccttttct gaccacgata tggactgggt gcgccaggca | 120 |
| cctggcaagg gcctggagtg ggtgggccgg agcagaaaca aggattacag ctccaccaca | 180 |
| gagtatgcag cctccgtgag gggccgcttc accatctctc gggacgatag caagaactcc | 240 |
| ctgtacctgc agatgaacag cctgaagacc gaggacacag ccgtgtacta ttgtgccaga | 300 |
| ggcccccacc actctgatag aagcggctac tatgcggca catttgacat ctggggccag | 360 |
| ggcacaatgg tgacagtgtc tagcgcatcc accaagggcc catctgtctt ccccctggcc | 420 |
| ccatcctcca gagcaccctc tggcggcaca gctgccctgg gctgcctggt gaaggactac | 480 |
| ttccctgagc ctgtgacagt gtcctggaac tctggcgccc tgaccagcgg cgtgcacacc | 540 |
| ttccctgctg tgctccagtc ctctggcctg tactccctga gcagcgtggt gacagtgcca | 600 |
| tccagcagcc tgggcaccca gacctacatc tgcaatgtga accacaagcc cagcaacacc | 660 |
| aaggtggaca gcggggtgga gcccaagtcc tgtgacaaga cccacacctg ccccccatgc | 720 |
| cccgcccctg agctgctggg cggcccatct gtcttcctgt tccccccaa gcccaaggac | 780 |
| accctgatga tctcccggac ccccgaggtg acctgtgtgg tggtggatgt gagccatgag | 840 |
| gaccccgagg tgaagttcaa ctggtatgtg gatggcgtgg aggtgcacaa cgccaagacc | 900 |
| aagcccnggg aggagcagta caacagcacc taccgggtgg tgagcgtgct gacagtgctg | 960 |
| catcaggact ggctgaatgg caaggagtac aagtgcaagg tgtccaacaa ggccctgcct | 1020 |
| gcccccattg agaagaccat ctccaaggcc aagggccagc ccgggagcc ccaggtctac | 1080 |
| accctgcccc cctcccggga ggagatgacc aagaaccagg tgagcctgac ctgcctggtg | 1140 |
| aagggcttct accccagcga cattgctgtg gagtgggaga gcaacggcca gcctgagaac | 1200 |
| aactacaaga ccaccccccc tgtgctggac tctgatggct ccttcttcct gtacagcaag | 1260 |
| ctgacagtgg acaagagccg gtggcagcag ggcaatgtct tctcctgctc tgtgatgcat | 1320 |
| gaggccctgc acaaccacta cacccagaag agcctgtccc tgtcccccgg caag | 1374 |

<210> SEQ ID NO 127
<211> LENGTH: 458
<212> TYPE: PRT
<213> ORGANISM: Artificial Sequence
<220> FEATURE:
<223> OTHER INFORMATION: GERMLINED 2-18 IgG1 HEAVY CHAIN

<400> SEQUENCE: 127

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Asp His
            20                  25                  30

Asp Met Asp Trp Val Arg Gln Ala Pro Gly Lys Gly Leu Glu Trp Val
        35                  40                  45

Gly Arg Ser Arg Asn Lys Asp Tyr Ser Ser Thr Thr Glu Tyr Ala Ala
    50                  55                  60

Ser Val Arg Gly Arg Phe Thr Ile Ser Arg Asp Asp Ser Lys Asn Ser

```
            65                  70                  75                  80
Leu Tyr Leu Gln Met Asn Ser Leu Lys Thr Glu Asp Thr Ala Val Tyr
                85                  90                  95

Tyr Cys Ala Arg Gly Pro His His Ser Asp Arg Ser Gly Tyr Tyr Gly
                100                 105                 110

Gly Thr Phe Asp Ile Trp Gly Gln Gly Thr Met Val Thr Val Ser Ser
                115                 120                 125

Ala Ser Thr Lys Gly Pro Ser Val Phe Pro Leu Ala Pro Ser Ser Lys
            130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                    165                 170                 175

Gly Val His Thr Phe Pro Ala Val Leu Gln Ser Ser Gly Leu Tyr Ser
                180                 185                 190

Leu Ser Ser Val Val Thr Val Pro Ser Ser Ser Leu Gly Thr Gln Thr
                195                 200                 205

Tyr Ile Cys Asn Val Asn His Lys Pro Ser Asn Thr Lys Val Asp Lys
            210                 215                 220

Arg Val Glu Pro Lys Ser Cys Asp Lys Thr His Thr Cys Pro Pro Cys
225                 230                 235                 240

Pro Ala Pro Glu Leu Leu Gly Gly Pro Ser Val Phe Leu Phe Pro Pro
                    245                 250                 255

Lys Pro Lys Asp Thr Leu Met Ile Ser Arg Thr Pro Glu Val Thr Cys
                260                 265                 270

Val Val Val Asp Val Ser His Glu Asp Pro Glu Val Lys Phe Asn Trp
                275                 280                 285

Tyr Val Asp Gly Val Glu Val His Asn Ala Lys Thr Lys Pro Arg Glu
            290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                    325                 330                 335

Lys Ala Leu Pro Ala Pro Ile Glu Lys Thr Ile Ser Lys Ala Lys Gly
                340                 345                 350

Gln Pro Arg Glu Pro Gln Val Tyr Thr Leu Pro Pro Ser Arg Glu Glu
                355                 360                 365

Met Thr Lys Asn Gln Val Ser Leu Thr Cys Leu Val Lys Gly Phe Tyr
            370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                    405                 410                 415

Leu Tyr Ser Lys Leu Thr Val Asp Lys Ser Arg Trp Gln Gln Gly Asn
                420                 425                 430

Val Phe Ser Cys Ser Val Met His Glu Ala Leu His Asn His Tyr Thr
                435                 440                 445

Gln Lys Ser Leu Ser Leu Ser Pro Gly Lys
        450                 455

<210> SEQ ID NO 128
<211> LENGTH: 642
<212> TYPE: DNA
<213> ORGANISM: Artificial Sequence
```

```
<220> FEATURE:
<223> OTHER INFORMATION: GERMLINED 2-18 IgG1 LIGHT CHAIN

<400> SEQUENCE: 128
gacatccaga tgacacagtc tcctagctcc gtgagcgcct ccgtgggcga tagggtgacc      60
atcacatgca gagcctccca gggcatctct agctggctgg cctggtatca gcagaagccc     120
ggcaaggccc ctaagctgct gatctatgac gcctctaccc tggagagcgg cgtgccctcc     180
cggttctctg gcagcggctc cggcacagac tttaccctga caatctcctc tctgcagcca     240
gaggatttcg ccacctacta ttgtcagcag ggcaacatgt tccccctgac ctttggcggc     300
ggcacaaagg tggagatcaa agtacggtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga gaaacacaaa gtctacgcct gcgaagtcac ccatcagggc     600
ctgagctcgc ccgtcacaaa gagcttcaac aggggagagt gt                        642

<210> SEQ ID NO 129
<211> LENGTH: 214
<212> TYPE: PRT
<213> ORGANISM: Artificial Sequence
<220> FEATURE:
<223> OTHER INFORMATION: GERMLINED 2-18 IgG1 LIGHT CHAIN

<400> SEQUENCE: 129

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Thr Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asn Met Phe Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 130
<211> LENGTH: 1434
<212> TYPE: DNA
<213> ORGANISM: Artificial Sequence
<220> FEATURE:
<223> OTHER INFORMATION: GERMLINED 2-18 IgG1 HEAVY CHAIN + YTE

<400> SEQUENCE: 130

```
atggagtgga gctgggtgtt tctgttcttc ctcagcgtga ccaccggcgt gcattccgag      60
gtgcagctgg tggagtccgg aggaggactc gtgcagcccg aggttctct gaggctcagc     120
tgtgctgcct ccggattctc cttcagcgac acgacatgg attgggtgcg gcaggctccc     180
ggaaaaggcc tggagtgggt cggcaggagc aggaacaagg actattccag caccaccgaa     240
tacgccgcca gcgtgagggg caggttcacc atctccaggg atgacagcaa gaactccctg     300
tacctgcaga tgaacagcct gaagaccgaa gacaccgccg tgtactattg cgcccggggc     360
cctcaccatt ccgaccggag cggctattac ggcggcacct tcgacatttg gggccaggga     420
acaatggtca ccgtgtccag cgctagcacc aaggccccta cgtgttccc cctggctcct     480
agctccaaga gcaccagcgg aggcacagcc gctctgggat gcctggtcaa agactacttc     540
cccgagcccg tcacagtcag ctggaactcc ggagccctga cctccggcgt ccatacctc     600
cccgctgtgc tgcagagctc cggcctgtac tccctgagct ccgtggtcac agtgcctagc     660
tccagcctcg gaacccagac atacatctgc aacgtgaacc acaagccctc caacaccaag     720
gtcgacaaga aggtggagcc taagtcctgc gacaaaaccc acacctgccc tccttgccct     780
gctcctgaac tgctgggcgg ccttccgtg ttcctgttcc ccctaaaacc taaggacacc     840
ctgtacatca cccggagcc cgaggtgaca tgcgtggtgg tggacgtgtc ccacgaggac     900
cccgaggtga agttcaactg gtatgtcgat ggcgtggagg tccacaacgc caagaccaaa     960
cccagggaag agcagtacaa ctccacctac cgggtggtca gcgtgctgac cgtgctgcac    1020
caggactggc tgaatggcaa ggagtacaag tgcaaggtca gcaataaagc cctgcccgcc    1080
cctatcgaga agacaatctc caaggccaag ggacagccca gggaaccca ggtgtatacc    1140
ctgccccccct cccgggatga actgaccaaa aaccaggtca gcctgacctg tctggtcaaa    1200
ggcttctacc cctccgacat cgctgtggaa tgggagagca atggccagcc tgagaacaac    1260
tataagacca cccctcccgt gctcgacagc gatggctcct tctttctcta cagcaagctg    1320
accgtggata agtcccggtg gcaacagggc aacgtgttca gctgctccgt catgcatgag    1380
gccctgcaca tcactacac ccagaagagc ctgtccctgt ccccggcaa gtga            1434
```

<210> SEQ ID NO 131
<211> LENGTH: 477
<212> TYPE: PRT
<213> ORGANISM: Artificial Sequence
<220> FEATURE:
<223> OTHER INFORMATION: GERMLINED 2-18 IgG1 HEAVY CHAIN + YTE

<400> SEQUENCE: 131

```
Met Glu Trp Ser Trp Val Phe Leu Phe Phe Leu Ser Val Thr Thr Gly
1               5                  10                  15

Val His Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Ser Phe
        35                  40                  45

Ser Asp His Asp Met Asp Trp Val Arg Gln Ala Pro Gly Lys Gly Leu
    50                  55                  60
```

```
Glu Trp Val Gly Arg Ser Arg Asn Lys Asp Tyr Ser Thr Thr Glu
65                  70                  75                  80

Tyr Ala Ala Ser Val Arg Gly Arg Phe Thr Ile Ser Arg Asp Asp Ser
                85                  90                  95

Lys Asn Ser Leu Tyr Leu Gln Met Asn Ser Leu Lys Thr Glu Asp Thr
            100                 105                 110

Ala Val Tyr Tyr Cys Ala Arg Gly Pro His His Ser Asp Arg Ser Gly
            115                 120                 125

Tyr Tyr Gly Gly Thr Phe Asp Ile Trp Gly Gln Gly Thr Met Val Thr
        130                 135                 140

Val Ser Ser Ala Ser Thr Lys Gly Pro Ser Val Phe Pro Leu Ala Pro
145                 150                 155                 160

Ser Ser Lys Ser Thr Ser Gly Gly Thr Ala Ala Leu Gly Cys Leu Val
                165                 170                 175

Lys Asp Tyr Phe Pro Glu Pro Val Thr Val Ser Trp Asn Ser Gly Ala
            180                 185                 190

Leu Thr Ser Gly Val His Thr Phe Pro Ala Val Leu Gln Ser Ser Gly
        195                 200                 205

Leu Tyr Ser Leu Ser Ser Val Val Thr Val Pro Ser Ser Ser Leu Gly
    210                 215                 220

Thr Gln Thr Tyr Ile Cys Asn Val Asn His Lys Pro Ser Asn Thr Lys
225                 230                 235                 240

Val Asp Lys Lys Val Glu Pro Lys Ser Cys Asp Lys Thr His Thr Cys
                245                 250                 255

Pro Pro Cys Pro Ala Pro Glu Leu Leu Gly Gly Pro Ser Val Phe Leu
            260                 265                 270

Phe Pro Pro Lys Pro Lys Asp Thr Leu Tyr Ile Thr Arg Glu Pro Glu
        275                 280                 285

Val Thr Cys Val Val Val Asp Val Ser His Glu Asp Pro Glu Val Lys
    290                 295                 300

Phe Asn Trp Tyr Val Asp Gly Val Glu Val His Asn Ala Lys Thr Lys
305                 310                 315                 320

Pro Arg Glu Glu Gln Tyr Asn Ser Thr Tyr Arg Val Val Ser Val Leu
                325                 330                 335

Thr Val Leu His Gln Asp Trp Leu Asn Gly Lys Glu Tyr Lys Cys Lys
            340                 345                 350

Val Ser Asn Lys Ala Leu Pro Ala Pro Ile Glu Lys Thr Ile Ser Lys
        355                 360                 365

Ala Lys Gly Gln Pro Arg Glu Pro Gln Val Tyr Thr Leu Pro Pro Ser
    370                 375                 380

Arg Asp Glu Leu Thr Lys Asn Gln Val Ser Leu Thr Cys Leu Val Lys
385                 390                 395                 400

Gly Phe Tyr Pro Ser Asp Ile Ala Val Glu Trp Glu Ser Asn Gly Gln
                405                 410                 415

Pro Glu Asn Asn Tyr Lys Thr Thr Pro Pro Val Leu Asp Ser Asp Gly
            420                 425                 430

Ser Phe Phe Leu Tyr Ser Lys Leu Thr Val Asp Lys Ser Arg Trp Gln
        435                 440                 445

Gln Gly Asn Val Phe Ser Cys Ser Val Met His Glu Ala Leu His Asn
    450                 455                 460

His Tyr Thr Gln Lys Ser Leu Ser Leu Ser Pro Gly Lys
465                 470                 475
```

<210> SEQ ID NO 132
<211> LENGTH: 705
<212> TYPE: DNA
<213> ORGANISM: Artificial Sequence
<220> FEATURE:
<223> OTHER INFORMATION: GERMLINED 2-18 IgG1 LIGHT CHAIN + YTE

<400> SEQUENCE: 132

```
atgagcgtgc ccacacaggt gctcggcctg ctgctgctgt ggctgaccga cgccaggtgc    60
gacatccaga tgacccagtc cccttcctcc gtgtccgctt ccgtgggcga tagggtgaca   120
atcacctgca gggccagcca gggcatctcc agctggctgg cctggtacca gcagaagccc   180
ggcaaggccc ccaagctgct gatctacgac gccagcacac tggagagcgg cgtgccttcc   240
cggttcagcg gttctggcag cggaacagac ttcaccctga ccatttcctc cctgcagccc   300
gaggacttcg ccacctacta ctgccagcag ggcaacatgt tccctctgac cttcggaggc   360
ggcacaaagg tggagatcaa gcggaccgtc gccgctccct ccgtgttcat cttccccccc   420
tccgatgagc agctcaagtc cggcaccgct agcgtggtgt gcctgctgaa caacttctac   480
ccccgggagg ccaaggtgca gtggaaggtc gacaacgccc tgcagtccgg caacagccag   540
gagagcgtga ccgagcagga ctccaaggac tccacctact ccctctcctc caccctgacc   600
ctgtccaagg ccgactacga gaagcacaaa gtgtacgcct gcgaagtgac ccaccagggc   660
ctgagctccc ccgtgacaaa gtccttcaac agggcgagt gttga             705
```

<210> SEQ ID NO 133
<211> LENGTH: 234
<212> TYPE: PRT
<213> ORGANISM: Artificial Sequence
<220> FEATURE:
<223> OTHER INFORMATION: GERMLINED 2-18 IgG1 LIGHT CHAIN + YTE

<400> SEQUENCE: 133

```
Met Ser Val Pro Thr Gln Val Leu Gly Leu Leu Leu Leu Trp Leu Thr
1               5                   10                  15

Asp Ala Arg Cys Asp Ile Gln Met Thr Gln Ser Pro Ser Ser Val Ser
            20                  25                  30

Ala Ser Val Gly Asp Arg Val Thr Ile Thr Cys Arg Ala Ser Gln Gly
        35                  40                  45

Ile Ser Ser Trp Leu Ala Trp Tyr Gln Gln Lys Pro Gly Lys Ala Pro
    50                  55                  60

Lys Leu Leu Ile Tyr Asp Ala Ser Thr Leu Glu Ser Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Gln Gln Gly Asn
            100                 105                 110

Met Phe Pro Leu Thr Phe Gly Gly Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190
```

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 134
<211> LENGTH: 1368
<212> TYPE: DNA
<213> ORGANISM: Artificial Sequence
<220> FEATURE:
<223> OTHER INFORMATION: GERMLINED 1-85 IgG1 HEAVY CHAIN

<400> SEQUENCE: 134

| | | | | | | |
|---|---|---|---|---|---|---|
| caggtgcagc | tggtggagtc | cggaggagga | ctggtgaagc | caggaggctc | cctgaggctg | 60 |
| tcttgcgccg | ccagcggctt | cacctttagc | gactactata | tggcctggat | cagacaggca | 120 |
| cctggcaagg | gcctggagtg | ggtgtccttc | atcagctcct | ctggcagaac | catctactat | 180 |
| gccgactctg | tgaagggccg | gtttacaatc | tccagagata | acgccaagaa | cagcctgtac | 240 |
| ctgcagatga | acagcctgag | ggccgaggac | acagccgtgt | actattgtgc | ccgcgactct | 300 |
| tatagcaagc | tggtggatat | cgaggccatc | gaggccttcg | atatctgggg | cagaggcaca | 360 |
| atggtgaccg | tgagcagcgc | atccaccaag | ggcccatctg | tcttccccct | ggccccatcc | 420 |
| tccaagagca | cctctggcgg | cacagctgcc | ctgggctgcc | tggtgaagga | ctacttccct | 480 |
| gagcctgtga | cagtgtcctg | gaactctggc | gccctgacca | gcggcgtgca | caccttccct | 540 |
| gctgtgctcc | agtcctctgg | cctgtactcc | ctgagcagcg | tggtgacagt | gccatccagc | 600 |
| agcctgggca | cccagaccta | catctgcaat | gtgaaccaca | agcccagcaa | caccaaggtg | 660 |
| gacaagcggg | tggagcccaa | gtcctgtgac | aagacccaca | cctgcccccc | atgccccgcc | 720 |
| cctgagctgc | tgggcggccc | atctgtcttc | ctgttccccc | caagcccaa | ggacaccctg | 780 |
| atgatctccc | ggaccccccga | ggtgacctgt | gtggtggtgg | atgtgagcca | tgaggacccc | 840 |
| gaggtgaagt | tcaactggta | tgtggatggc | gtggaggtgc | acaacgccaa | gaccaagccc | 900 |
| cgggaggagc | agtacaacag | cacctaccgg | gtggtgagcg | tgctgacagt | gctgcatcag | 960 |
| gactggctga | atggcaagga | gtacaagtgc | aaggtgtcca | acaaggccct | gcctgccccc | 1020 |
| attgagaaga | ccatctccaa | ggccaagggc | cagccccggg | agccccaggt | ctacaccctg | 1080 |
| cccccctccc | gggaggagat | gaccaagaac | caggtgagcc | tgacctgcct | ggtgaagggc | 1140 |
| ttctacccca | gcgacattgc | tgtggagtgg | gagagcaacg | gccagcctga | gaacaactac | 1200 |
| aagaccaccc | cccctgtgct | ggactctgat | ggctccttct | tcctgtacag | caagctgaca | 1260 |
| gtggacaaga | gccggtggca | gcagggcaat | gtcttctcct | gctctgtgat | gcatgaggcc | 1320 |
| ctgcacaacc | actacaccca | gaagagcctg | tccctgtccc | ccggcaag | | 1368 |

<210> SEQ ID NO 135
<211> LENGTH: 456
<212> TYPE: PRT
<213> ORGANISM: Artificial Sequence
<220> FEATURE:
<223> OTHER INFORMATION: GERMLINED 1-85 IgG1 HEAVY CHAIN

<400> SEQUENCE: 135

Gln Val Gln Leu Val Glu Ser Gly Gly Gly Leu Val Lys Pro Gly Gly
1               5                   10                  15

```
Ser Leu Arg Leu Ser Cys Ala Ala Ser Gly Phe Thr Phe Ser Asp Tyr
         20                  25                  30
Tyr Met Ala Trp Ile Arg Gln Ala Pro Gly Lys Gly Leu Glu Trp Val
             35                  40                  45
Ser Phe Ile Ser Ser Ser Gly Arg Thr Ile Tyr Tyr Ala Asp Ser Val
 50                  55                  60
Lys Gly Arg Phe Thr Ile Ser Arg Asp Asn Ala Lys Asn Ser Leu Tyr
 65                  70                  75                  80
Leu Gln Met Asn Ser Leu Arg Ala Glu Asp Thr Ala Val Tyr Tyr Cys
                 85                  90                  95
Ala Arg Asp Ser Tyr Ser Lys Leu Val Asp Ile Glu Ala Ile Glu Ala
            100                 105                 110
Phe Asp Ile Trp Gly Arg Gly Thr Met Val Thr Val Ser Ser Ala Ser
        115                 120                 125
Thr Lys Gly Pro Ser Val Phe Pro Leu Ala Pro Ser Ser Lys Ser Thr
    130                 135                 140
Ser Gly Gly Thr Ala Ala Leu Gly Cys Leu Val Lys Asp Tyr Phe Pro
145                 150                 155                 160
Glu Pro Val Thr Val Ser Trp Asn Ser Gly Ala Leu Thr Ser Gly Val
                165                 170                 175
His Thr Phe Pro Ala Val Leu Gln Ser Ser Gly Leu Tyr Ser Leu Ser
            180                 185                 190
Ser Val Val Thr Val Pro Ser Ser Ser Leu Gly Thr Gln Thr Tyr Ile
        195                 200                 205
Cys Asn Val Asn His Lys Pro Ser Asn Thr Lys Val Asp Lys Arg Val
    210                 215                 220
Glu Pro Lys Ser Cys Asp Lys Thr His Thr Cys Pro Pro Cys Pro Ala
225                 230                 235                 240
Pro Glu Leu Leu Gly Gly Pro Ser Val Phe Leu Phe Pro Pro Lys Pro
                245                 250                 255
Lys Asp Thr Leu Met Ile Ser Arg Thr Pro Glu Val Thr Cys Val Val
            260                 265                 270
Val Asp Val Ser His Glu Asp Pro Glu Val Lys Phe Asn Trp Tyr Val
        275                 280                 285
Asp Gly Val Glu Val His Asn Ala Lys Thr Lys Pro Arg Glu Glu Gln
    290                 295                 300
Tyr Asn Ser Thr Tyr Arg Val Val Ser Val Leu Thr Val Leu His Gln
305                 310                 315                 320
Asp Trp Leu Asn Gly Lys Glu Tyr Lys Cys Lys Val Ser Asn Lys Ala
                325                 330                 335
Leu Pro Ala Pro Ile Glu Lys Thr Ile Ser Lys Ala Lys Gly Gln Pro
            340                 345                 350
Arg Glu Pro Gln Val Tyr Thr Leu Pro Pro Ser Arg Glu Glu Met Thr
        355                 360                 365
Lys Asn Gln Val Ser Leu Thr Cys Leu Val Lys Gly Phe Tyr Pro Ser
    370                 375                 380
Asp Ile Ala Val Glu Trp Glu Ser Asn Gly Gln Pro Glu Asn Asn Tyr
385                 390                 395                 400
Lys Thr Thr Pro Pro Val Leu Asp Ser Asp Gly Ser Phe Phe Leu Tyr
                405                 410                 415
Ser Lys Leu Thr Val Asp Lys Ser Arg Trp Gln Gln Gly Asn Val Phe
            420                 425                 430
Ser Cys Ser Val Met His Glu Ala Leu His Asn His Tyr Thr Gln Lys
```

<210> SEQ ID NO 136
<211> LENGTH: 639
<212> TYPE: DNA
<213> ORGANISM: Artificial Sequence
<220> FEATURE:
<223> OTHER INFORMATION: GERMLINED 1-85 IgG1 LIGHT CHAIN

<400> SEQUENCE: 136

```
agctacgtgc tgacacagcc acctagcgtg tccgtggcac caggcaagac agcaaggatc    60
acctgcggcg gcgacaacat cggctctaag agcgtgcact ggtatcagca gaagccagga   120
caggcacccg tgctggtcat ctactatgac tccgatcggc cttctggcat cccagagaga   180
ttctccggct ctaacagcgg caataccgcc acactgacca tctccagggt ggaggcaggc   240
gacgaggcag attacttctg tcaagtgtgg gaccgccacg gcgatcacgt ggtgtttggc   300
ggcggcacaa agctgaccgt gctgcagccc aaggccaacc ccaccgtgac cctgttcccc   360
ccatcttctg aggagctgca agccaacaag gccaccctgg tgtgcctgat ctctgacttc   420
taccctggcg ctgtgacagt ggcctggaag gctgatggct ctcctgtgaa ggctggcgtg   480
gagaccacca gccatctaa gcagtctaac aacaagtatg ctgcctcttc ttacctgtct   540
ctgaccctg agcagtggaa gagccaccgg tcttactctt gccaggtgac ccatgagggc   600
tctacagtgg agaagacagt ggccccaca gagtgctct                          639
```

<210> SEQ ID NO 137
<211> LENGTH: 213
<212> TYPE: PRT
<213> ORGANISM: Artificial Sequence
<220> FEATURE:
<223> OTHER INFORMATION: GERMLINED 1-85 IgG1 LIGHT CHAIN

<400> SEQUENCE: 137

```
Ser Tyr Val Leu Thr Gln Pro Pro Ser Val Ser Val Ala Pro Gly Lys
  1               5                  10                  15

Thr Ala Arg Ile Thr Cys Gly Gly Asp Asn Ile Gly Ser Lys Ser Val
                 20                  25                  30

His Trp Tyr Gln Gln Lys Pro Gly Gln Ala Pro Val Leu Val Ile Tyr
             35                  40                  45

Tyr Asp Ser Asp Arg Pro Ser Gly Ile Pro Glu Arg Phe Ser Gly Ser
         50                  55                  60

Asn Ser Gly Asn Thr Ala Thr Leu Thr Ile Ser Arg Val Glu Ala Gly
 65                  70                  75                  80

Asp Glu Ala Asp Tyr Phe Cys Gln Val Trp Asp Arg His Gly Asp His
                 85                  90                  95

Val Val Phe Gly Gly Gly Thr Lys Leu Thr Val Leu Gln Pro Lys Ala
            100                 105                 110

Asn Pro Thr Val Thr Leu Phe Pro Pro Ser Ser Glu Glu Leu Gln Ala
        115                 120                 125

Asn Lys Ala Thr Leu Val Cys Leu Ile Ser Asp Phe Tyr Pro Gly Ala
    130                 135                 140

Val Thr Val Ala Trp Lys Ala Asp Gly Ser Pro Val Lys Ala Gly Val
145                 150                 155                 160

Glu Thr Thr Lys Pro Ser Lys Gln Ser Asn Asn Lys Tyr Ala Ala Ser
                165                 170                 175
```

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Thr Glu Cys Ser
    210

<210> SEQ ID NO 138
<211> LENGTH: 1428
<212> TYPE: DNA
<213> ORGANISM: Artificial Sequence
<220> FEATURE:
<223> OTHER INFORMATION: GERMLINED 1-85 IgG1 HEAVY CHAIN + YTE

<400> SEQUENCE: 138

| | |
|---|---|
| atggaatggt cctgggtgtt cctgttcttt ctgagcgtca ccaccggcgt gcacagcgag | 60 |
| gtgcaactgg tggagagcgg cggaggcctg gtgaaacctg gcggttctct gaggctgtcc | 120 |
| tgtgctgcca gcggcttcac cttctccgac tattacatgg cctggattcg gcaggctcct | 180 |
| ggcaagggcc tggaatgggt gtccttcatc tccagcagcg gccggacaat ctattatgcc | 240 |
| gactccgtga agggccggtt taccatctcc agggataacg ccaagaactc cctgtacctg | 300 |
| cagatgaact ctctgagggc tgaagacaca gctgtgtatt actgcgctcg ggacagctac | 360 |
| agcaagctgt ggatatcga ggccatcgaa gccttcgata tttggggcag gggaaccatg | 420 |
| gtgaccgtga gctccgcttc caccaaggga cccagcgtgt tccctctggc tcctagctcc | 480 |
| aagtccacca gcggaggcac cgctgctctg ggatgtctgg tgaaagacta ctttcccgag | 540 |
| cctgtcacag tgtcctggaa cagcggagcc ctgaccagcg gagtccacac cttcccgct | 600 |
| gtgctgcagt cctccggcct gtacagcctg agcagcgtgg tgaccgtgcc ttccagctcc | 660 |
| ctcggcaccc agacctacat ctgcaatgtg aatcacaagc ccagcaacac caaggtggat | 720 |
| aagaaggtcg agcctaagag ctgcgacaag acccacacat gccctccttg tcctgctcct | 780 |
| gagctgctgg gaggccctag cgtcttcctc ttccctccca acccaaggga taccctctac | 840 |
| atcacccggg agcccgaagt gacctgcgtg gtggtggacg tgtcccacga agatcctgaa | 900 |
| gtcaagttca actggtacgt ggatggcgtc gaggtgcaca cgccaaaac caaaccccgg | 960 |
| gaggaacagt ataacagcac ctaccgggtc gtgagcgtgc tgaccgtgct gcaccaggat | 1020 |
| tggctgaatg gcaaggagta caagtgcaag gtgtccaaca agccctgcc cgctcccatc | 1080 |
| gagaagacaa tctccaaggc caaaggccag cctcgggaac cccaggtgta tcccctcccc | 1140 |
| cccagcaggg acgaactgac caaaaccag gtgagcctga cctgcctggt gaagggattc | 1200 |
| taccctagcg atatcgccgt ggaatgggag agcaatggac agcctgagaa caactacaaa | 1260 |
| accaccccc ctgtgctcga ctccgatggt tctttcttcc tgtacagcaa actgaccgtg | 1320 |
| gacaagagcc ggtggcagca gggcaacgtg ttttcctgca gcgtgatgca tgaggctctg | 1380 |
| cacaaccatt acacccagaa gagcctgagc ctgtcccctg gcaagtga | 1428 |

<210> SEQ ID NO 139
<211> LENGTH: 475
<212> TYPE: PRT
<213> ORGANISM: Artificial Sequence
<220> FEATURE:
<223> OTHER INFORMATION: GERMLINED 1-85 IgG1 HEAVY CHAIN + YTE

<400> SEQUENCE: 139

Met Glu Trp Ser Trp Val Phe Leu Phe Phe Leu Ser Val Thr Thr Gly

-continued

```
1               5                   10                  15
Val His Ser Glu Val Gln Leu Val Glu Ser Gly Gly Gly Leu Val Lys
                20                  25                  30
Pro Gly Gly Ser Leu Arg Leu Ser Cys Ala Ala Ser Gly Phe Thr Phe
                35                  40                  45
Ser Asp Tyr Tyr Met Ala Trp Ile Arg Gln Ala Pro Gly Lys Gly Leu
    50                  55                  60
Glu Trp Val Ser Phe Ile Ser Ser Ser Gly Arg Thr Ile Tyr Tyr Ala
65                  70                  75                  80
Asp Ser Val Lys Gly Arg Phe Thr Ile Ser Arg Asp Asn Ala Lys Asn
                85                  90                  95
Ser Leu Tyr Leu Gln Met Asn Ser Leu Arg Ala Glu Asp Thr Ala Val
                100                 105                 110
Tyr Tyr Cys Ala Arg Asp Ser Tyr Ser Lys Leu Val Asp Ile Glu Ala
                115                 120                 125
Ile Glu Ala Phe Asp Ile Trp Gly Arg Gly Thr Met Val Thr Val Ser
                130                 135                 140
Ser Ala Ser Thr Lys Gly Pro Ser Val Phe Pro Leu Ala Pro Ser Ser
145                 150                 155                 160
Lys Ser Thr Ser Gly Gly Thr Ala Ala Leu Gly Cys Leu Val Lys Asp
                165                 170                 175
Tyr Phe Pro Glu Pro Val Thr Val Ser Trp Asn Ser Gly Ala Leu Thr
                180                 185                 190
Ser Gly Val His Thr Phe Pro Ala Val Leu Gln Ser Ser Gly Leu Tyr
                195                 200                 205
Ser Leu Ser Ser Val Val Thr Val Pro Ser Ser Ser Leu Gly Thr Gln
    210                 215                 220
Thr Tyr Ile Cys Asn Val Asn His Lys Pro Ser Asn Thr Lys Val Asp
225                 230                 235                 240
Lys Lys Val Glu Pro Lys Ser Cys Asp Lys Thr His Thr Cys Pro Pro
                245                 250                 255
Cys Pro Ala Pro Glu Leu Leu Gly Gly Pro Ser Val Phe Leu Phe Pro
                260                 265                 270
Pro Lys Pro Lys Asp Thr Leu Tyr Ile Thr Arg Glu Pro Glu Val Thr
                275                 280                 285
Cys Val Val Val Asp Val Ser His Glu Asp Pro Glu Val Lys Phe Asn
                290                 295                 300
Trp Tyr Val Asp Gly Val Glu Val His Asn Ala Lys Thr Lys Pro Arg
305                 310                 315                 320
Glu Glu Gln Tyr Asn Ser Thr Tyr Arg Val Val Ser Val Leu Thr Val
                325                 330                 335
Leu His Gln Asp Trp Leu Asn Gly Lys Glu Tyr Lys Cys Lys Val Ser
                340                 345                 350
Asn Lys Ala Leu Pro Ala Pro Ile Glu Lys Thr Ile Ser Lys Ala Lys
                355                 360                 365
Gly Gln Pro Arg Glu Pro Gln Val Tyr Thr Leu Pro Pro Ser Arg Asp
                370                 375                 380
Glu Leu Thr Lys Asn Gln Val Ser Leu Thr Cys Leu Val Lys Gly Phe
385                 390                 395                 400
Tyr Pro Ser Asp Ile Ala Val Glu Trp Glu Ser Asn Gly Gln Pro Glu
                405                 410                 415
Asn Asn Tyr Lys Thr Thr Pro Pro Val Leu Asp Ser Asp Gly Ser Phe
                420                 425                 430
```

Phe Leu Tyr Ser Lys Leu Thr Val Asp Lys Ser Arg Trp Gln Gln Gly
            435                 440                 445

Asn Val Phe Ser Cys Ser Val Met His Glu Ala Leu His Asn His Tyr
        450                 455                 460

Thr Gln Lys Ser Leu Ser Leu Ser Pro Gly Lys
465                 470                 475

<210> SEQ ID NO 140
<211> LENGTH: 705
<212> TYPE: DNA
<213> ORGANISM: Artificial Sequence
<220> FEATURE:
<223> OTHER INFORMATION: GERMLINED 1-85 IgG1 LIGHT CHAIN + YTE

<400> SEQUENCE: 140

```
atgtccgtgc ccacacaggt gctgggcctg ctgctgctgt ggctgaccga tgccaggtgc    60
tcctacgtgc tgacccagcc tccttccgtg tccgtggctc ctggcaagac agctaggatc   120
acctgcggcg gcgacaacat cggcagcaag agcgtgcact ggtatcaaca gaagcccggc   180
caggcccctg tgctggtgat ctactacgat tccgaccggc ctagcggcat ccccgagagg   240
ttcagcggct ccaactccgg caacaccgcc acactgacca tctcccgggt ggaggccgga   300
gatgaggctg actacttctg ccaggtgtgg acaggcatg gcgatcacgt ggtgttcggc   360
ggcggcacca agctgacagt gctgggacag cctaaggccg ctcccctcgt gaccctgttc   420
cccctagct ccgaggagct gcaggccaac aaggccaccc tggtgtgtct catcagcgac   480
ttctacccccg cgctgtgac cgtggcctgg aaggctgaca gctcccccgt gaaggctggc   540
gtggagacca accccccctc aagcagtcc aacaataagt acgccgccag ctcctacctg   600
tccctgaccc ccgagcagtg gaagagccac cggtcctaca gctgccaggt gacccacgaa   660
ggctccaccg tggagaagac cgtggcccct accgagtgca gctga              705
```

<210> SEQ ID NO 141
<211> LENGTH: 234
<212> TYPE: PRT
<213> ORGANISM: Artificial Sequence
<220> FEATURE:
<223> OTHER INFORMATION: GERMLINED 1-85 IgG1 LIGHT CHAIN + YTE

<400> SEQUENCE: 141

Met Ser Val Pro Thr Gln Val Leu Gly Leu Leu Leu Leu Trp Leu Thr
1               5                   10                  15

Asp Ala Arg Cys Ser Tyr Glu Leu Ala Gln Pro Pro Ser Val Ser Val
            20                  25                  30

Ala Pro Gly Lys Thr Ala Thr Ile Ala Cys Gly Gly Asp Asn Ile Gly
        35                  40                  45

Gly Lys Ser Val His Trp Tyr Leu Gln Lys Ala Gly Gln Ala Pro Val
    50                  55                  60

Leu Val Ile Ser Tyr Asp Ser Asp Arg Pro Ser Gly Ile Pro Glu Arg
65                  70                  75                  80

Phe Ser Gly Ser Asn Ser Gly Asn Thr Ala Thr Leu Thr Ile Ser Arg
                85                  90                  95

Val Glu Ala Gly Asp Glu Ala Asp Tyr Phe Cys Gln Val Trp Asp Arg
            100                 105                 110

His Gly Asp His Val Val Phe Gly Gly Gly Thr Lys Leu Thr Val Leu
        115                 120                 125

Gly Gln Pro Lys Ala Ala Pro Ser Val Thr Leu Phe Pro Pro Ser Ser

```
                    130              135                 140
Glu Glu Leu Gln Ala Asn Lys Ala Thr Leu Val Cys Leu Ile Ser Asp
145                 150                 155                 160

Phe Tyr Pro Gly Ala Val Thr Val Ala Trp Lys Ala Asp Ser Ser Pro
                165                 170                 175

Val Lys Ala Gly Val Glu Thr Thr Thr Pro Ser Lys Gln Ser Asn Asn
                180                 185                 190

Lys Tyr Ala Ala Ser Ser Tyr Leu Ser Leu Thr Pro Glu Gln Trp Lys
                195                 200                 205

Ser His Arg Ser Tyr Ser Cys Gln Val Thr His Glu Gly Ser Thr Val
                210                 215                 220

Glu Lys Thr Val Ala Pro Thr Glu Cys Ser
225                 230
```

<210> SEQ ID NO 142
<211> LENGTH: 1365
<212> TYPE: DNA
<213> ORGANISM: Artificial Sequence
<220> FEATURE:
<223> OTHER INFORMATION: GERMLINED 3-25 HEAVY CHAIN

<400> SEQUENCE: 142

```
caggtgcagc tggtggagag cggaggagga gtggtgcagc aggcaggtc tctgaggctg      60
agctgcgccg cctccggctt cacctttcc aaccacggcc tgcactgggt gcggcaggca     120
cctggcaagg gcctggagtg ggtggcagtg gtgtccaagg acggcacaaa tgagcactac    180
gccgattctg tgcggggcag attcaccatc tctaggaca acagcaagaa tacactgtat    240
ctgcagatga actctctgcg cgccgaggat accgccgtgt actattgtgc ccgggagggc    300
tactgcggcg acgatagatg ttacagcgga cagccagact attggggaca gggcaccctg    360
gtgaccgtga gcagcgcatc caccaagggc ccatctgtct tccccctggc ccatcctcc    420
aagagcacct ctggcggcac agctgccctg ggctgcctgg tgaaggacta cttccctgag    480
cctgtgacag tgtcctggaa ctctggcgcc ctgaccagcg gcgtgcacac cttccctgct    540
gtgctccagt cctctggcct gtactccctg agcagcgtgg tgacagtgcc atccagcagc    600
ctgggcaccc agacctacat ctgcaatgtg aaccacaagc ccagcaacac caaggtggac    660
aagcgggtgg agcccaagtc ctgtgacaag cccacacct gccccccatg ccccgccct    720
gagctgctgg gcggcccatc tgtcttcctg ttccccccca gcccaagga caccctgatg    780
atctcccgga cccccgaggt gacctgtgtg gtggtggatg tgagccatga ggaccccgag    840
gtgaagttca actggtatgt ggatggcgtg gaggtgcaca acgccaagac caagccccgg    900
gaggagcagt acaacagcac ctaccgggtg gtgagcgtgc tgacagtgct gcatcaggac    960
tggctgaatg gcaaggagta caagtgcaag gtgtccaaca aggccctgcc tgccccatt    1020
gagaagacca tctccaaggc caagggccag ccccgggagc cccaggtcta caccctgccc    1080
ccctcccggg aggagatgac caagaaccag gtgagcctga cctgcctggt gaagggcttc    1140
taccccagcg acattgctgt ggagtgggag agcaacggcc agcctgagaa caactacaag    1200
accacccccc ctgtgctgga ctctgatggc tccttcttcc tgtacagcaa gctgacagtg    1260
gacaagagcc ggtggcagca gggcaatgtc ttctcctgct ctgtgatgca tgaggccctg    1320
cacaaccact acacccagaa gagcctgtcc ctgtcccccg gcaag                   1365
```

<210> SEQ ID NO 143
<211> LENGTH: 455

<212> TYPE: PRT
<213> ORGANISM: Artificial Sequence
<220> FEATURE:
<223> OTHER INFORMATION: GERMLINED 3-25 HEAVY CHAIN

<400> SEQUENCE: 143

| | | | | | | | | | | | | | | |
|---|---|---|---|---|---|---|---|---|---|---|---|---|---|---|
| Gln | Val | Gln | Leu | Val | Glu | Ser | Gly | Gly | Gly | Val | Val | Gln | Pro | Gly | Arg |
| 1 | | | | 5 | | | | | 10 | | | | | 15 | |
| Ser | Leu | Arg | Leu | Ser | Cys | Ala | Ala | Ser | Gly | Phe | Thr | Phe | Ser | Asn | His |
| | | | 20 | | | | | 25 | | | | | 30 | | |
| Gly | Leu | His | Trp | Val | Arg | Gln | Ala | Pro | Gly | Lys | Gly | Leu | Glu | Trp | Val |
| | | 35 | | | | | 40 | | | | | 45 | | | |
| Ala | Val | Val | Ser | Lys | Asp | Gly | Thr | Asn | Glu | His | Tyr | Ala | Asp | Ser | Val |
| 50 | | | | | 55 | | | | | 60 | | | | | |
| Arg | Gly | Arg | Phe | Thr | Ile | Ser | Arg | Asp | Asn | Ser | Lys | Asn | Thr | Leu | Tyr |
| 65 | | | | 70 | | | | | 75 | | | | | 80 | |
| Leu | Gln | Met | Asn | Ser | Leu | Arg | Ala | Glu | Asp | Thr | Ala | Val | Tyr | Tyr | Cys |
| | | | | 85 | | | | | 90 | | | | | 95 | |
| Ala | Arg | Glu | Gly | Tyr | Cys | Gly | Asp | Asp | Arg | Cys | Tyr | Ser | Gly | Gln | Pro |
| | | | 100 | | | | | 105 | | | | | 110 | | |
| Asp | Tyr | Trp | Gly | Gln | Gly | Thr | Leu | Val | Thr | Val | Ser | Ser | Ala | Ser | Thr |
| | | | 115 | | | | | 120 | | | | | 125 | | |
| Lys | Gly | Pro | Ser | Val | Phe | Pro | Leu | Ala | Pro | Ser | Ser | Lys | Ser | Thr | Ser |
| 130 | | | | | 135 | | | | | 140 | | | | | |
| Gly | Gly | Thr | Ala | Ala | Leu | Gly | Cys | Leu | Val | Lys | Asp | Tyr | Phe | Pro | Glu |
| 145 | | | | | 150 | | | | | 155 | | | | | 160 |
| Pro | Val | Thr | Val | Ser | Trp | Asn | Ser | Gly | Ala | Leu | Thr | Ser | Gly | Val | His |
| | | | | 165 | | | | | 170 | | | | | 175 | |
| Thr | Phe | Pro | Ala | Val | Leu | Gln | Ser | Ser | Gly | Leu | Tyr | Ser | Leu | Ser | Ser |
| | | | 180 | | | | | 185 | | | | | 190 | | |
| Val | Val | Thr | Val | Pro | Ser | Ser | Ser | Leu | Gly | Thr | Gln | Thr | Tyr | Ile | Cys |
| | | | 195 | | | | | 200 | | | | | 205 | | |
| Asn | Val | Asn | His | Lys | Pro | Ser | Asn | Thr | Lys | Val | Asp | Lys | Arg | Val | Glu |
| | | 210 | | | | | 215 | | | | | 220 | | | |
| Pro | Lys | Ser | Cys | Asp | Lys | Thr | His | Thr | Cys | Pro | Pro | Cys | Pro | Ala | Pro |
| 225 | | | | | 230 | | | | | 235 | | | | | 240 |
| Glu | Leu | Leu | Gly | Gly | Pro | Ser | Val | Phe | Leu | Phe | Pro | Pro | Lys | Pro | Lys |
| | | | | 245 | | | | | 250 | | | | | 255 | |
| Asp | Thr | Leu | Met | Ile | Ser | Arg | Thr | Pro | Glu | Val | Thr | Cys | Val | Val | Val |
| | | | 260 | | | | | 265 | | | | | 270 | | |
| Asp | Val | Ser | His | Glu | Asp | Pro | Glu | Val | Lys | Phe | Asn | Trp | Tyr | Val | Asp |
| | | 275 | | | | | 280 | | | | | 285 | | | |
| Gly | Val | Glu | Val | His | Asn | Ala | Lys | Thr | Lys | Pro | Arg | Glu | Glu | Gln | Tyr |
| 290 | | | | | 295 | | | | | 300 | | | | | |
| Asn | Ser | Thr | Tyr | Arg | Val | Val | Ser | Val | Leu | Thr | Val | Leu | His | Gln | Asp |
| 305 | | | | | 310 | | | | | 315 | | | | | 320 |
| Trp | Leu | Asn | Gly | Lys | Glu | Tyr | Lys | Cys | Lys | Val | Ser | Asn | Lys | Ala | Leu |
| | | | | 325 | | | | | 330 | | | | | 335 | |
| Pro | Ala | Pro | Ile | Glu | Lys | Thr | Ile | Ser | Lys | Ala | Lys | Gly | Gln | Pro | Arg |
| | | | 340 | | | | | 345 | | | | | 350 | | |
| Glu | Pro | Gln | Val | Tyr | Thr | Leu | Pro | Pro | Ser | Arg | Glu | Glu | Met | Thr | Lys |
| | | 355 | | | | | 360 | | | | | 365 | | | |
| Asn | Gln | Val | Ser | Leu | Thr | Cys | Leu | Val | Lys | Gly | Phe | Tyr | Pro | Ser | Asp |
| 370 | | | | | 375 | | | | | 380 | | | | | |

```
Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
            405                 410                 415

Lys Leu Thr Val Asp Lys Ser Arg Trp Gln Gln Gly Asn Val Phe Ser
        420                 425                 430

Cys Ser Val Met His Glu Ala Leu His Asn His Tyr Thr Gln Lys Ser
        435                 440                 445

Leu Ser Leu Ser Pro Gly Lys
    450             455
```

<210> SEQ ID NO 144
<211> LENGTH: 645
<212> TYPE: DNA
<213> ORGANISM: Artificial Sequence
<220> FEATURE:
<223> OTHER INFORMATION: GERMLINED 3-25 LIGHT CHAIN

<400> SEQUENCE: 144

```
gagatcgtgc tgacccagtc tcctgccaca ctgtccctgt ctccaggaga gagggccacc      60
ctgagctgca gagccagcca gtccgtgggc agatacctgg cctggtatca gcagaagcca     120
ggacaggcac caaggctgct gatctacgac agctccaaca gggcaaccgg cgtgcccgca     180
cgcttctctg gcagcggctc cggcacagac tttacccctga caatctctag cctggagcct    240
gaggatttcg ccgtgtacta ttgtcagcag cggtcccact ggccacctct gacctttggc     300
ggaggcacaa aggtggagat caagcgtacg gtggctgcac catctgtctt catcttcccg     360
ccatctgatg agcagttgaa atctggaact gcctctgttg tgtgcctgct gaataacttc     420
tatcccagag aggccaaagt acagtggaag gtggataacg ccctccaatc gggtaactcc     480
caggagagtg tcacagagca ggacagcaag gacagcacct acagcctcag cagcaccctg     540
acgctgagca agcagactac gagaaacaca aaagtctacg cctgcgaagt cacccatcag     600
ggcctgagct cgcccgtcac aaagagcttc aacaggggag agtgt                      645
```

<210> SEQ ID NO 145
<211> LENGTH: 215
<212> TYPE: PRT
<213> ORGANISM: Artificial Sequence
<220> FEATURE:
<223> OTHER INFORMATION: GERMLINED 3-25 LIGHT CHAIN

<400> SEQUENCE: 145

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Gly Arg Tyr
            20                  25                  30

Leu Ala Trp Tyr Gln Gln Lys Pro Gly Gln Ala Pro Arg Leu Leu Ile
        35                  40                  45

Tyr Asp Ser Ser Asn Arg Ala Thr Gly Val Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser His Trp Pro Pro
                85                  90                  95

Leu Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
```

```
                115                 120                 125
Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
210                 215

<210> SEQ ID NO 146
<211> LENGTH: 1425
<212> TYPE: DNA
<213> ORGANISM: Artificial Sequence
<220> FEATURE:
<223> OTHER INFORMATION: GERMLINED 3-25 HEAVY CHAIN + YTE

<400> SEQUENCE: 146
```

| | | | | | |
|---|---|---|---|---|---|
| atggaatgga | gctgggtgtt | cctgttcttc | ctgagcgtca | ccaccggcgt | gcactccgaa | 60 |
| gtgcagctgg | tggaatccgg | cggcggagtc | gtgcaacccg | caggtccct | gaggctgagc | 120 |
| tgcgctgcct | ccggcttcac | cttctccaac | catggcctgc | actgggtgag | gcaagctccc | 180 |
| ggaaagggcc | tggagtgggt | ggctgtcgtg | tccaaggacg | gaaccaacga | acactacgcc | 240 |
| gactccgtga | ggggaaggtt | cacaatcagc | cgggacaaca | gcaagaacac | actctatctg | 300 |
| cagatgaaca | gcctgcgggc | cgaggacaca | gccgtctact | actgcgcccg | ggaaggatac | 360 |
| tgcggcgacg | ataggtgtta | ctccggccag | cctgactact | ggggacaggg | caccctggtg | 420 |
| accgtgagca | gcgcttccac | caagggcccc | agcgtgttcc | ctctggctcc | cagcagcaaa | 480 |
| tccaccagcg | gaggcacagc | tgccctcgga | tgtctcgtga | aggactattt | ccccgagccc | 540 |
| gtgaccgtct | cctggaactc | tggcgccctg | acaagcggcg | tgcacacatt | ccccgctgtg | 600 |
| ctgcagagca | gcggactgta | ttccctgtcc | agcgtcgtga | ccgtcccttc | ctccagcctg | 660 |
| ggaacacaga | cctacatctg | caacgtgaac | cacaagccct | ccaatacaaa | ggtggacaag | 720 |
| aaggtggagc | ccaagagctg | tgacaaaacc | catacctgcc | ctccttgccc | tgctcccgaa | 780 |
| ctgctgggag | accctccgt | ctttctgttc | cccccaaac | ccaaggacac | cctctacatt | 840 |
| accagggagc | ccgaggtgac | ctgcgtggtc | gtggatgtga | gccacgaaga | tcctgaggtg | 900 |
| aagttcaatt | ggtacgtgga | cggcgtcgag | gtgcacaacg | ccaagaccaa | gcctcgggaa | 960 |
| gagcagtaca | actccacata | cagggtggtg | tccgtcctga | ccgtcctgca | ccaggactgg | 1020 |
| ctcaacggca | aggagtacaa | gtgcaaggtg | agcaacaagg | ccctcccgc | tcctatcgag | 1080 |
| aagaccatct | ccaaggccaa | aggacagccc | cgggagcccc | aagtgtacac | cctgcctcct | 1140 |
| tcccgggatg | agctgaccaa | gaaccaagtc | tccctgacct | gcctcgtgaa | aggcttctac | 1200 |
| cctagcgata | tcgctgtgga | atgggagtcc | aacggccagc | ccgagaataa | ctacaagaca | 1260 |
| acccctcccg | tgctggactc | cgacggcagc | ttcttcctgt | acagcaagct | gaccgtggac | 1320 |
| aaaagcaggt | ggcagcaggg | aaacgtgttc | tcctgctccg | tcatgcacga | ggccctgcac | 1380 |
| aaccactata | cccagaagtc | cctgagcctg | tcccccggca | agtga | | 1425 |

```
<210> SEQ ID NO 147
<211> LENGTH: 474
<212> TYPE: PRT
<213> ORGANISM: Artificial Sequence
<220> FEATURE:
<223> OTHER INFORMATION: GERMLINED 3-25 HEAVY CHAIN + YTE

<400> SEQUENCE: 147

Met Glu Trp Ser Trp Val Phe Leu Phe Phe Leu Ser Val Thr Thr Gly
1               5                   10                  15

Val His Ser Glu Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Asn His Gly Leu His Trp Val Arg Gln Ala Pro Gly Lys Gly Leu
    50                  55                  60

Glu Trp Val Ala Val Val Ser Lys Asp Gly Thr Asn Glu His Tyr Ala
65                  70                  75                  80

Asp Ser Val Arg Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Glu Gly Tyr Cys Gly Asp Asp Arg Cys Tyr Ser
        115                 120                 125

Gly Gln Pro Asp Tyr Trp Gly Gln Gly Thr Leu Val Thr Val Ser Ser
    130                 135                 140

Ala Ser Thr Lys Gly Pro Ser Val Phe Pro Leu Ala Pro Ser Ser Lys
145                 150                 155                 160

Ser Thr Ser Gly Gly Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Ser Leu Gly Thr Gln Thr
    210                 215                 220

Tyr Ile Cys Asn Val Asn His Lys Pro Ser Asn Thr Lys Val Asp Lys
225                 230                 235                 240

Lys Val Glu Pro Lys Ser Cys Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270

Lys Pro Lys Asp Thr Leu Tyr Ile Thr Arg Glu Pro Glu Val Thr Cys
        275                 280                 285

Val Val Val Asp Val Ser His Glu Asp Pro Glu Val Lys Phe Asn Trp
    290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Ala Leu Pro Ala Pro Ile Glu Lys Thr Ile Ser Lys Ala Lys Gly
        355                 360                 365

Gln Pro Arg Glu Pro Gln Val Tyr Thr Leu Pro Pro Ser Arg Asp Glu
```

-continued

```
                    370                 375                 380
Leu Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Asp Ser Asp Gly Ser Phe Phe
            420                 425                 430

Leu Tyr Ser Lys Leu Thr Val Asp Lys Ser Arg Trp Gln Gln Gly Asn
        435                 440                 445

Val Phe Ser Cys Ser Val Met His Glu Ala Leu His Asn His Tyr Thr
    450                 455                 460

Gln Lys Ser Leu Ser Leu Ser Pro Gly Lys
465                 470
```

<210> SEQ ID NO 148
<211> LENGTH: 708
<212> TYPE: DNA
<213> ORGANISM: Artificial Sequence
<220> FEATURE:
<223> OTHER INFORMATION: GERMLINED 3-25 LIGHT CHAIN + YTE

<400> SEQUENCE: 148

```
atgtccgtgc ccacccaggt gctgggactg ctgctgctgt ggctgaccga cgccaggtgc       60
gagatcgtgc tgacccagag ccctgctaca ctgtccctga gccccggcga gagggctaca      120
ctgagctgta gggctagcca gtccgtggga cggtacctgg cctggtacca gcaaaaaccc      180
ggacaggccc cccggctgct gatttacgat agcagcaaca gggccaccgg cgtgcctgct      240
aggttctccg gttctggcag cggcaccgac tttaccctga caatctcctc cctggagccc      300
gaggacttcg ccgtgtacta ctgccagcag aggtcccatt ggcctcctct gaccttcggc      360
ggcggcacca aggtggagat caagaggacc gtggccgccc cctccgtgtt catctttccc      420
ccctccgacg agcagctgaa gagcggcacc gctagcgtgg tgtgcctgct gaacaacttc      480
taccccaggg aggccaaggt gcagtggaag gtggacaacg ctctgcagtc cggcaacagc      540
caggagagcg tgaccgagca ggacagcaag gactccacct actccctgag cagcaccctg      600
accctgtcca agccgactac gagaagcac aaggtgtacg cttgcgaggt gacccaccag      660
ggcctgtcca gccctgtgac caaatccttc aacaggggcg agtgctga                  708
```

<210> SEQ ID NO 149
<211> LENGTH: 235
<212> TYPE: PRT
<213> ORGANISM: Artificial Sequence
<220> FEATURE:
<223> OTHER INFORMATION: GERMLINED 3-25 LIGHT CHAIN + YTE

<400> SEQUENCE: 149

```
Met Ser Val Pro Thr Gln Val Leu Gly Leu Leu Leu Leu Trp Leu Thr
1               5                   10                  15

Asp Ala Arg Cys Glu Ile Val Leu Thr Gln Ser Pro Ala Thr Leu Ser
            20                  25                  30

Leu Ser Pro Gly Glu Arg Ala Thr Leu Ser Cys Arg Ala Ser Gln Ser
        35                  40                  45

Val Gly Arg Tyr Leu Ala Trp Tyr Gln Gln Lys Pro Gly Gln Ala Pro
    50                  55                  60

Arg Leu Leu Ile Tyr Asp Ser Ser Asn Arg Ala Thr Gly Val Pro Ala
65                  70                  75                  80
```

-continued

```
Arg Phe Ser Gly Ser Gly Thr Asp Phe Thr Leu Thr Ile Ser
             85          90              95

Ser Leu Glu Pro Glu Asp Phe Ala Val Tyr Tyr Cys Gln Gln Arg Ser
            100             105             110

His Trp Pro Pro Leu Thr Phe Gly Gly Gly Thr Lys Val Glu Ile Lys
        115                 120             125

Arg Thr Val Ala Ala Pro Ser Val Phe Ile Phe Pro Pro Ser Asp Glu
    130             135             140

Gln Leu Lys Ser Gly Thr Ala Ser Val Val Cys Leu Leu Asn Asn Phe
145             150             155                         160

Tyr Pro Arg Glu Ala Lys Val Gln Trp Lys Val Asp Asn Ala Leu Gln
            165             170             175

Ser Gly Asn Ser Gln Glu Ser Val Thr Glu Gln Asp Ser Lys Asp Ser
            180             185             190

Thr Tyr Ser Leu Ser Ser Thr Leu Thr Leu Ser Lys Ala Asp Tyr Glu
        195             200             205

Lys His Lys Val Tyr Ala Cys Glu Val Thr His Gln Gly Leu Ser Ser
    210             215             220

Pro Val Thr Lys Ser Phe Asn Arg Gly Glu Cys
225             230             235
```